(12) United States Patent
Glinka et al.

(10) Patent No.: US 7,893,020 B2
(45) Date of Patent: *Feb. 22, 2011

(54) BACTERIAL EFFLUX PUMP INHIBITORS AND METHODS OF TREATING BACTERIAL INFECTIONS

(75) Inventors: Tomasz Glinka, Cupertino, CA (US); Keith Bostian, Atherton, CA (US); Mark Surber, San Diego, CA (US); Olga Lomovskaya, Mountain View, CA (US); Dongxu Sun, Cupertino, CA (US)

(73) Assignee: Mpex Pharmaceuticals, Inc., San Diego, CA (US)

( * ) Notice: Subject to any disclaimer, the term of this patent is extended or adjusted under 35 U.S.C. 154(b) by 99 days.

This patent is subject to a terminal disclaimer.

(21) Appl. No.: 11/134,147

(22) Filed: May 20, 2005

(65) Prior Publication Data
US 2006/0003944 A1    Jan. 5, 2006

Related U.S. Application Data

(60) Provisional application No. 60/574,014, filed on May 21, 2004.

(51) Int. Cl.
*A61K 38/00*    (2006.01)
(52) U.S. Cl. ..................................... 514/1.2
(58) Field of Classification Search ............ None
See application file for complete search history.

(56) References Cited

U.S. PATENT DOCUMENTS

| | | | |
|---|---|---|---|
| 5,883,074 A | 3/1999 | Boggs et al. | |
| 5,989,832 A | 11/1999 | Trias et al. | |
| 6,114,310 A | 9/2000 | Chamberland et al. | |
| 6,133,261 A | 10/2000 | Harris | |
| 6,204,279 B1 | 3/2001 | Leger et al. | |
| 6,245,746 B1 | 6/2001 | Chamberland et al. | |
| 6,362,229 B1 | 3/2002 | Markham et al. | |
| 6,399,629 B1 | 6/2002 | Chamberland et al. | |
| 6,436,980 B1 | 8/2002 | Leger et al. | |
| 6,777,388 B1 * | 8/2004 | Grasso et al. | 514/16 |
| 7,056,917 B2 | 6/2006 | Nakayama et al. | |

FOREIGN PATENT DOCUMENTS

| | | |
|---|---|---|
| EP | 1227084 | 7/2002 |
| WO | WO 99/37667 | 7/1999 |
| WO | WO 00/01714 | 1/2000 |

OTHER PUBLICATIONS

Renau TE, "Conformationally-restricted analogues of efflux pump inhibitors that potentiate the activity of levofloxacin in *Pseudomonas aeruginosa*," Bioorg Med Chem Lett. Aug. 18, 2003;13(16):2755-8.*
Renau et al, "Addressing the Stability of C-capped Dipeptide Efflux Pump Inhibitors that Potentiate the Activity of Levofloxacin," Bioorganic & Medicinal Chemistry Letters (2001) 663-667 (From Applicant's IDS).*
Minks et al Noninvasive Tracing of Recombinant Proteins with "Fluorophenylalanine-Fingers," Analytical Biochemistry 284, 29-34 (2000).*
Renau et al, "Conformationally-restricted analogues of efflux pump inhibitors that potentiate the activity of levofloxacin in *Pseudomonas aeruginosa*," Bioorg Med Chem Lett. Aug. 18, 2003;13(16):2755-5278.*
Renau, et al., "Addressing the stability of C-capped dipeptide efflux pump inhibitors that potentiate the activity of levofloxacin in *Pseudomonas aeruginosa*," Bioorganic & Medicinal Chem. Lett., 11(5) (2001) 663-667.
Renau, et al., "Conformationally-restricted analogues of efflux pump inhibitors that potentiate the activity of levofloxacin in *Pseudomonas aeruginosa*," Bioorganic & Medicinal Chem. Lett., 13(16) (2003) 2755-2758.
Bodor, et al., "Soft drug design: General principles and recent applications," Med. Res. Rev. 20(1) (2000) 58-101.
Renau, et al., "Addressing the stability of C-capped dipeptide efflux pump inhibitors that potentiate the activity of levofloxacin in *Pseudomonas aeruginosa*," Poster presented at 40th Interscience Conference on Antimicrobial Agents and Chemotherapy, Toronto, Canada, Sep. 17-20, 2000.
International Search Report dated Sep. 7, 2005 and Written Opinion from International Application No. PCT/US2005/017841.
Lomovskaya, et al., Efflux Pumps: Their Role in Antibacterial Drug Discovery, *Current Medicinal Chemistry*, 8, 1699-1711, 2001.

* cited by examiner

*Primary Examiner*—Cecilia Tsang
*Assistant Examiner*—Thomas S Heard
(74) *Attorney, Agent, or Firm*—Knobbe, Martens, Olson & Bear LLP.

(57) ABSTRACT

This invention relates to the field of antimicrobial agents and more specifically it relates to Efflux Pump Inhibitor (EPI) compounds to be co-administered with antimicrobial agents for the treatment of infections caused by drug resistant pathogens. The EPI compounds are soft drugs which exhibit a reduced propensity for tissue accumulation. The invention includes novel compounds useful as efflux pump inhibitors, compositions and devices comprising such efflux pump inhibitors, and therapeutic use of such compounds.

25 Claims, 15 Drawing Sheets

BACTERIAL EFFLUX PUMP INHIBITORS AND METHODS OF TREATING BACTERIAL INFECTIONS

RELATED APPLICATION

This application claims priority to U.S. Provisional Application No. 60/574,014, filed on May 21, 2004, which is incorporated herein by reference in its entirety.

BACKGROUND OF THE INVENTION

1. Field of the Invention

This invention relates to the fields of chemistry and medicine. More particular, the invention relates to novel compounds and compositions and use of compounds as therapeutic agents, including antimicrobial agents and Efflux Pump Inhibitors (EPIs).

2. Description of the Related Art

Antibiotics have been effective tools in the treatment of infectious diseases during the last half-century. From the development of antibiotic therapy to the late 1980s, there was almost complete control over bacterial infections in developed countries. However, in response to the pressure of antibiotic usage, multiple resistance mechanisms have become widespread and are threatening the clinical utility of antibacterial therapy. The increase in antibiotic resistant strains has been particularly common in major hospitals and care centers. The consequences of the increase in resistant strains include higher morbidity and mortality, longer patient hospitalization, and an increase in treatment costs.

The emergence of resistant bacterial strains is considered to be the number one infectious disease threat in hospitals and costs the U.S. Healthcare system $5 billion per year. Infections that were once treatable with antibiotics are becoming difficult and in some cases impossible to treat. As a result, 2 million people in the U.S. are infected by a bacterial pathogen while in the hospital each year, of which approximately 90,000 die, and the majority incur prolonged hospital and/or outpatient antibiotic therapy at significant pharmacoeconomic cost. More than 70% of the bacteria responsible for these infections are resistant to at least one of the antibiotics commonly used to fight them. Therefore the prevention of resistance is considered to be a high priority among infectious disease clinicians.

Resistance is not an isolated problem for specific antibiotics, but a global one affecting all antibiotics. Numerous studies have documented a strong correlation between the increased use of antibiotics and an increase in bacterial resistance, which can sometimes occur even during therapy. For example, one study documented a growth in fluoroquinolone resistance in Pseudomonas aeruginosa from 25% in 1997 to 33% in 2002. Another study reported that Pseudomonas aeruginosa resistance to fluoroquinolones increased from 29% in 1999 to 38% in 2001, with some hospitals reporting resistance rates as high as 60%. The level of fluoroquinolone use is directly correlated to the level of resistance, thus explaining the variability of resistance in different hospitals. Infections caused by resistant strains and or by strains that develop resistance during therapy limit the use of what are otherwise safe and effective fluoroquinolones as first-line therapy in hospitals.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target. There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics that would otherwise inhibit or kill the bacterial cells. Some bacteria utilize both mechanisms, combining a low permeability of the cell wall (including membranes) with an active efflux of antibiotics.

In recent years interest in efflux-mediated resistance in bacteria has been triggered by the growing amount of data implicating efflux pumps in clinical isolates. The phenomenon of antibiotic efflux was first discovered in 1980, in the context of the mechanism of tetracycline resistance in enterobacteria. Since then, it has been shown that efflux of antibiotics can be mediated by more than one pump in a single organism and that almost all antibiotics are subject to resistance by this mechanism.

Some efflux pumps selectively extrude specific antibiotics. Examples of such pumps include the Tet or CmlA transporters, which can extrude tetracycline or chloramphenicol, respectively. Other efflux pumps, so-called multi-drug resistance (MDR) pumps, extrude a variety of structurally diverse compounds. In the latter case, a single efflux system may confer resistance to multiple antibiotics with different modes of action. In this respect, bacterial MDR pumps are similar to mammalian MDR transporters. In fact, one such pump, P-glycoprotein, the first discovered MDR pump, confers multiple drug resistance on cancer cells and is considered to be one of the major reasons for tumor resistance to anti-cancer therapy. A typical example of bacterial MDR pump is MexAB-OprM from Pseudomonas aeruginosa. This pump has been shown to affect the susceptibility of the organism to almost all antibiotic classes which fluoroquinolones, β-lactams, macrolides, phenicols, tetracyclines, and oxazolidinones.

Efflux pumps in gram-positive bacteria excrete their substrates across a single cytoplasmic membrane. This is also the case for some pumps in gram-negative bacteria, and as a result their substrates are effluxed into the periplasmic space. Other efflux pumps from gram-negative bacteria efflux their substrates directly into the external medium, bypassing the periplasm and the outer membrane. These pumps are organized in complex three component structures, which traverse both inner and outer membranes. They consist of a transporter located in the cytoplasmic membrane, an outer membrane channel and a periplasmic 'linker' protein, which brings the other two components into contact. It is clearly advantageous for gram-negative bacteria to efflux drugs by bypassing the periplasm and outer membrane. In gram-negative bacteria the outer membrane significantly slows down the entry of both lipophilic and hydrophilic agents. The former, such as erythromycin and fusidic acid, are hindered by the lipopolysaccharide components of the outer leaflet of the outer membrane bilayer. Hydrophilic agents cross the outer membrane through water-filled porins whose size prevents rapid diffusion, even for small compounds such as fluoroquinolones and some β-lactams. Thus, direct efflux creates the possibility for two different mechanisms to work synergistically to provide the cell with a potent defense mechanism. Furthermore, direct efflux into the medium leads to decreased amounts of drugs not only in the cytoplasmic but also in the periplasmic space. This could explain the apparently paradoxical finding that efflux pumps protect gram-negative bacteria from β-lactam antibiotics whose target penicillin-binding proteins are found in the periplasm.

Many MDR pumps are encoded by the genes, which are normal constituents of bacterial chromosomes. In this case increased antibiotic resistance is a consequence of over-expression of these genes. Thus bacteria have the potential to develop multi-drug resistance without the acquisition of multiple specific resistance determinants. In some cases, the simultaneous operation of efflux pumps and other resistance mechanisms in the same cell results in synergistic effects.

While some genes encoding efflux pumps are not expressed in wild type cells and require induction or regulatory mutations for expression to occur, other efflux genes are expressed constitutively. As a result, wild type cells have basal level of efflux activity. This basal activity of multi-drug efflux pumps in wild type cells contribute to intrinsic antibiotic resistance, or more properly, decreased antibiotic susceptibility. This intrinsic resistance may be low enough for the bacteria to still be clinically susceptible to therapy. However, the bacteria might be even more susceptible if efflux pumps were rendered non-functional, allowing lower doses of antibiotics to be effective. To illustrate, *P. aeruginosa* laboratory-derived mutant strain PAM1626, which does not produce any measurable amounts of efflux pump is 8 to 10 fold more susceptible to levofloxacin and meropenem than the parent strain *P. aeruginosa* PAM1020, which produces the basal level of MexAB-OprM efflux pump. Were it not for efflux pumps, the spectrum of activity of many so-called 'gram-positive' antibiotics could be expanded to previously non-susceptible gram-negative species. This can be applied to 'narrow-spectrum' β-lactams, macrolides, lincosamides, streptogramins, rifamycins, fusidic acid, and oxazolidinones—all of which have a potent antibacterial effect against engineered mutants lacking efflux pumps.

It is clear that in many cases, a dramatic effect on the susceptibility of problematic pathogens would be greatly enhanced if efflux-mediated resistance were to be nullified. Two approaches to combat the adverse effects of efflux on the efficacy of antimicrobial agents can be envisioned: identification of derivatives of known antibiotics that are not effluxed and development of therapeutic agents that inhibit transport activity of efflux pumps and could be used in combination with existing antibiotics to increase their potency.

There are several examples when the first approach has been successfully reduced to practice. These examples include new fluoroquinolones, which are not affected by multidrug resistance pumps in *Staphylococcus aureus* or *Streptococcus pneumonia* or new tetracycline and macrolide derivatives, which are not recognized by the corresponding antibiotic-specific pumps. However, this approach appears to be much less successful in the case of multidrug resistance pumps from gram-negative bacteria. In gram-negative bacteria, particular restrictions are imposed on the structure of successful drugs: they must be amphiphilic in order to cross both membranes. It is this very property that makes antibiotics good substrates of multi-drug resistance efflux pumps from gram-negative bacteria. In the case of these bacteria the efflux pump inhibitory approach becomes the major strategy in improving the clinical effectiveness of existing antibacterial therapy.

SUMMARY OF THE INVENTION

One embodiment disclosed herein is a compound having the structure of Formula (II):

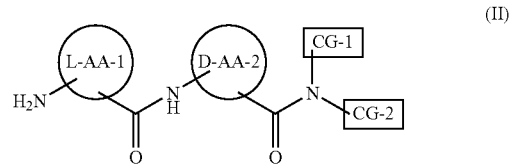

wherein:

L-AA-1 together with attached amine and carbonyl groups is a natural or artificial α-amino acid residue having an (S)-configuration, with the proviso that the a-amino functionality in the (S)-amino acid residue is not a member of a heterocyclic ring and with the proviso that the compound does not have the formula:

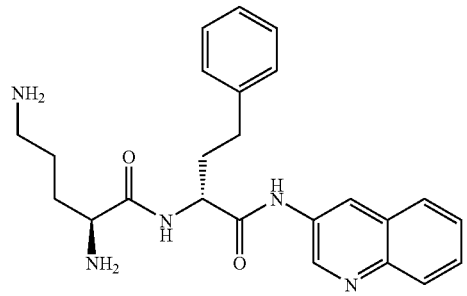

D-AA-2 together with attached amine and carbonyl groups is a natural or artificial α-amino acid residue having an (R)-configuration;

CG-1 is hydrogen or a carbon-linked capping group;

CG-2 is a carbon-linked capping group, wherein when CG-1 is a carbon-linked capping group, CG-1 and CG-2 are optionally linked together to form a 5- or 6-membered ring; and any amino groups that are not part of an amide group are optionally acylated with a natural or artificial amino acid residue having an (S)-configuration. In some embodiments, L-AA-1 comprises an amino group. In some embodiments, D-AA-2 comprises an amino group. In some embodiments, amino group is a primary amine. In some embodiments, CG-1 is hydrogen. In some embodiments, the compound comprises at least two amino groups. In some embodiments, L-AA-1 is selected from the group consisting of:

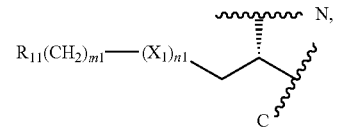

-continued

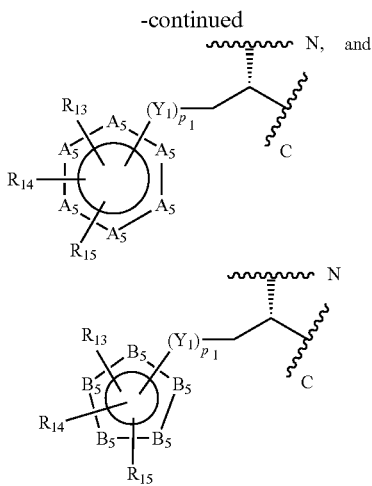

wherein:
$X_1$ is selected from the group consisting of —O— and —S—;
$m_1$ is an integer from 0 to 4;
$n_1$ is an integer from 0 to 1;
$R_{11}$ is selected from the group consisting of —$NH_2$, —NH—CH(=NH), —NH—C($CH_3$)(=NH), —CH(=NH)$NH_2$, and —NH—C(=O—NH)$NH_2$;
each $A_5$ is separately selected from the group consisting of =CH— and =N—, with the proviso that no more than four $A_5$ are =N—;
each $B_5$ is separately selected from the group consisting of =CH—, =N—, —O—, —S—, —NH—, and —N($R_6$)—, with the proviso that no more than three $B_5$ are heteroatoms;
$R_6$ is selected from the group consisting of hydrogen, $C_{1-6}$ alkyl, and $C_{3-6}$ cycloalkyl;
$R_{13}$ is selected from the group consisting of —$NH_2$, —$CH_2NH_2$, —$CH_2CH_2NH_2$, —$OCH_2CH_2NH_2$, —NH—CH(=NH), —$CH_2$NH—CH(=NH), —NH—C($CH_3$)(=NH), —$CH_2$—NH—C($CH_3$)(=NH), —C(=NH)$NH_2$, —$OCH_2$C(=NH)$NH_2$, —NH—C(=NH)$NH_2$, and —$CH_2$NH—C(=NH)$NH_2$;
$R_{14}$ and $R_{15}$ are separately selected from the group consisting of hydrogen, halogen, methyl, ethyl, hydroxyl, hydroxymethyl, methoxyl, trifluoromethyl, and trifluoromethoxyl;
$Y_1$ is selected from the group consisting of —$CH_2$—, —O—, and —S—;
$p_1$ is an integer from 0 to 1; and
the wavy line with subscript N indicates point of attachment to the amine group that is attached to L-AA-1 and the wavy line with subscript C indicates point of attachment to the carbonyl group that is attached to L-AA-1.

In some embodiments, D-AA-2 is selected from the group consisting of:

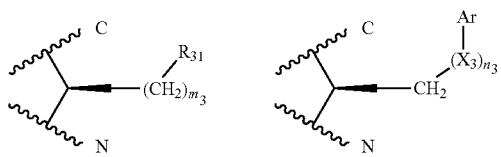

wherein:
Ar is an optionally substituted aryl or heteroaryl;
$R_{31}$ is selected from the group consisting of optionally substituted $C_{1-10}$ alkyl, $C_{1-10}$ alkenyl, $C_{1-10}$ alkynyl, and $C_{1-10}$ cycloalkyl;
$X_3$ is selected from the group consisting of —$CH_2$—, —C($CH_3$)$_2$—, —O—, and —S—;
$m_3$ is an integer from 1 to 2; and
$n_3$ is an integer from 0 to 2. In some embodiments, D-AA-1 is selected from the group consisting of:

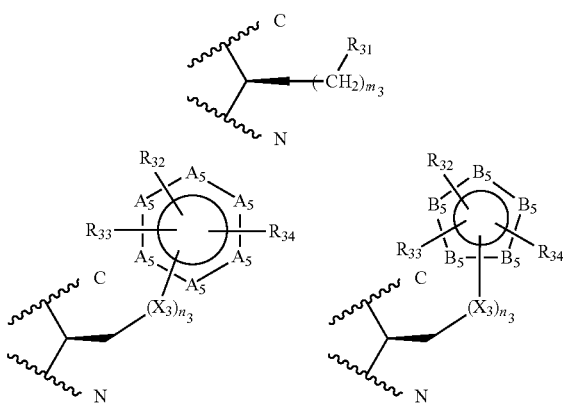

wherein:
$R_{32}$ and $R_{33}$ are separately selected from the group consisting of hydrogen, methyl, ethyl, n-propyl, isopropyl, cyclopropyl, tert-butyl, trifluoromethyl, hydroxyl, hydroxymethyl, methoxyl, trifluoromethoxyl, and halogen;
$R_{34}$ is selected from the group consisting of hydrogen, methyl, ethyl, n-propyl, isopropyl, cyclopropyl, tert-butyl, trifluoromethyl, hydroxyl, hydroxymethyl, methoxyl, trifluoromethoxyl, halogen, —$NH_2$, —$CH_2NH_2$, —$CH_2CH_2NH_2$, —$OCH_2CH_2NH_2$, —NH—CH(=NH), —$CH_2$NH—CH(=NH), —NH—C($CH_3$)(=NH), —$CH_2$—NH—C($CH_3$)(=NH), —C(=NH)$NH_2$, —$OCH_2$C(=NH)$NH_2$, —NH—C(=NH)$NH_2$, and —$CH_2$NH—C(=NH)$NH_2$;
each $A_5$ is separately selected from the group consisting of =CH— and =N—, with the proviso that no more than four $A_5$ are =N—;
each $B_5$ is separately selected from the group consisting of =CH—, =N—, —O—, —S—, —NH—, and —N($R_6$)—, with the proviso that no more than three $B_5$ are heteroatoms;
$R_6$ is selected from the group consisting of hydrogen, $C_{1-6}$ alkyl, and $C_{3-6}$ cycloalkyl; and
the wavy line with subscript N indicates point of attachment to the amino group that is attached to D-AA-2 and the wavy line with subscript C indicates point of attachment to the carbonyl group that is attached to D-AA-2.

In some embodiments, CG-1 is selected from the group consisting of hydrogen, optionally substituted $C_{1-6}$ alkyl, and optionally substituted $C_{3-7}$ cycloalkyl; and CG-2 is selected from the group consisting of:

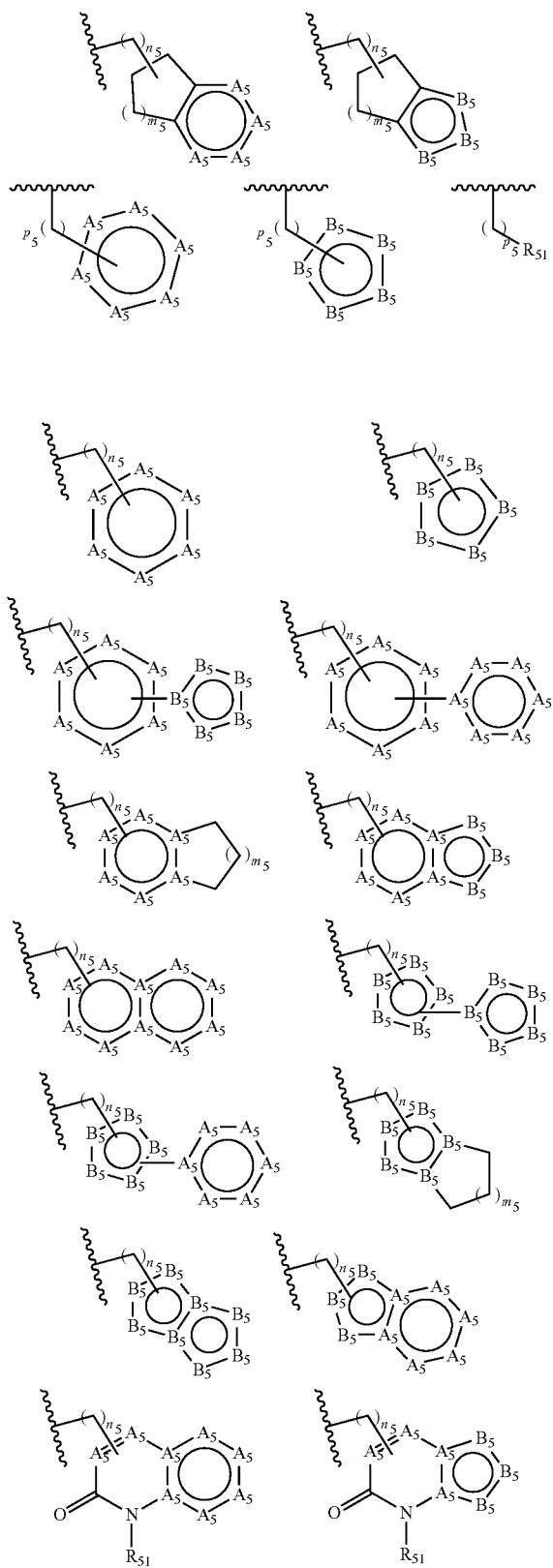

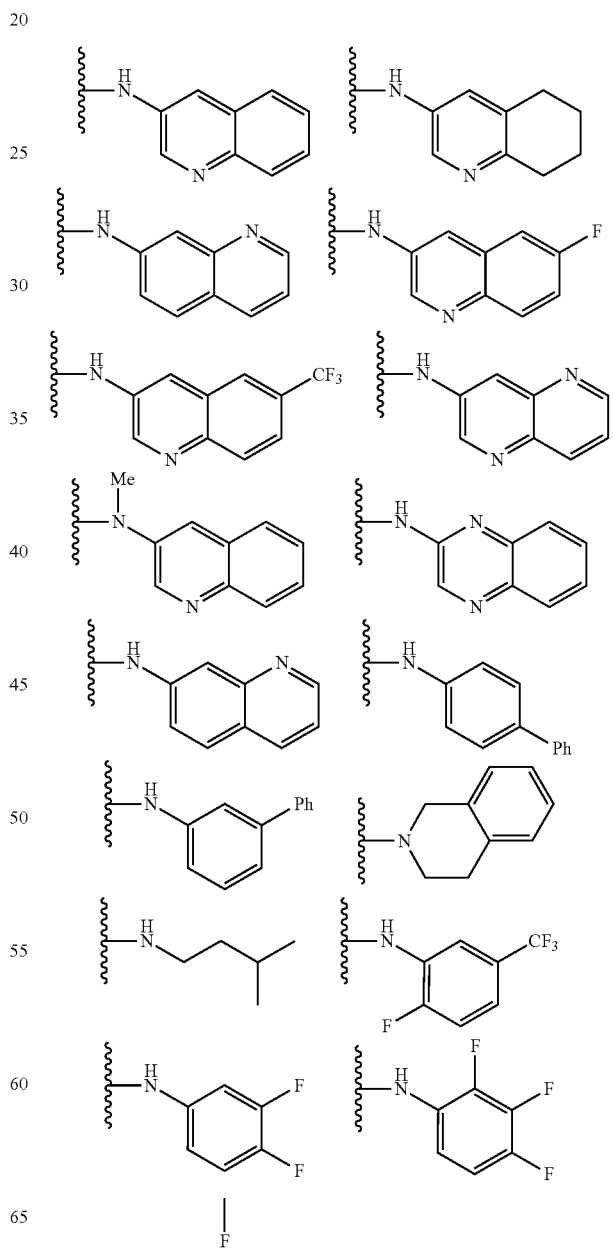

each optionally substituted with methyl, ethyl, n-propyl, isopropyl, cyclopropyl, cyclopentyl, cyclohexyl, tert-butyl, hydroxyl, methoxyl, ethoxyl, hydroxymethyl, trifluoromethyl, trifluoromethoxyl, or halogen moieties;

each $A_5$ is separately selected from the group consisting of =CH— and =N—, with the proviso that each $A_5$ containing ring contains no more than four =N— groups;

each $B_5$ is separately selected from the group consisting of —C=, —N=, —O—, —S—, —NH—, and —N($R_6$)—, with the proviso that each $B_5$ containing ring contains no more than three heteroatoms;

$R_6$ is selected from the group consisting of hydrogen, $C_{1-6}$ alkyl, and $C_{3-6}$ cycloalkyl;

$R_{51}$ is selected from the group consisting of hydrogen, methyl, ethyl, and cyclopropyl;

$m_5$ is an integer from 1 to 3;

$n_5$ is an integer from 0 to 2; and $p_5$ is an integer from 0 to 4.

In some embodiments, —N(CG-1)(CG-2) is selected from the group consisting of:

-continued
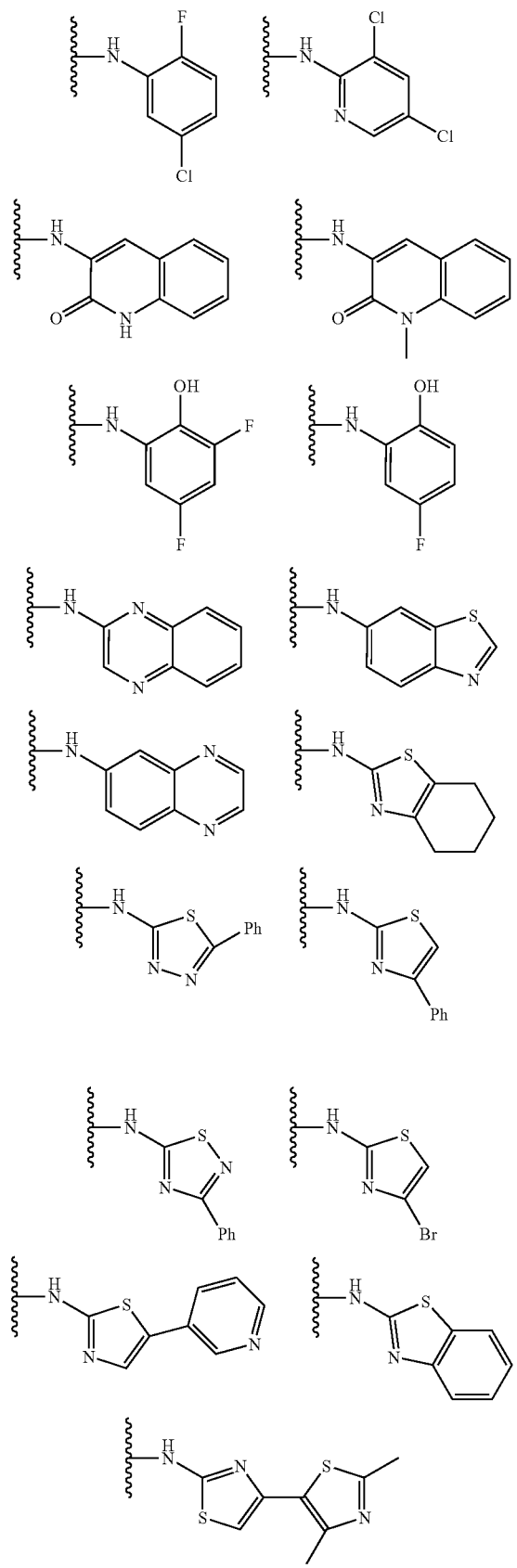
-continued
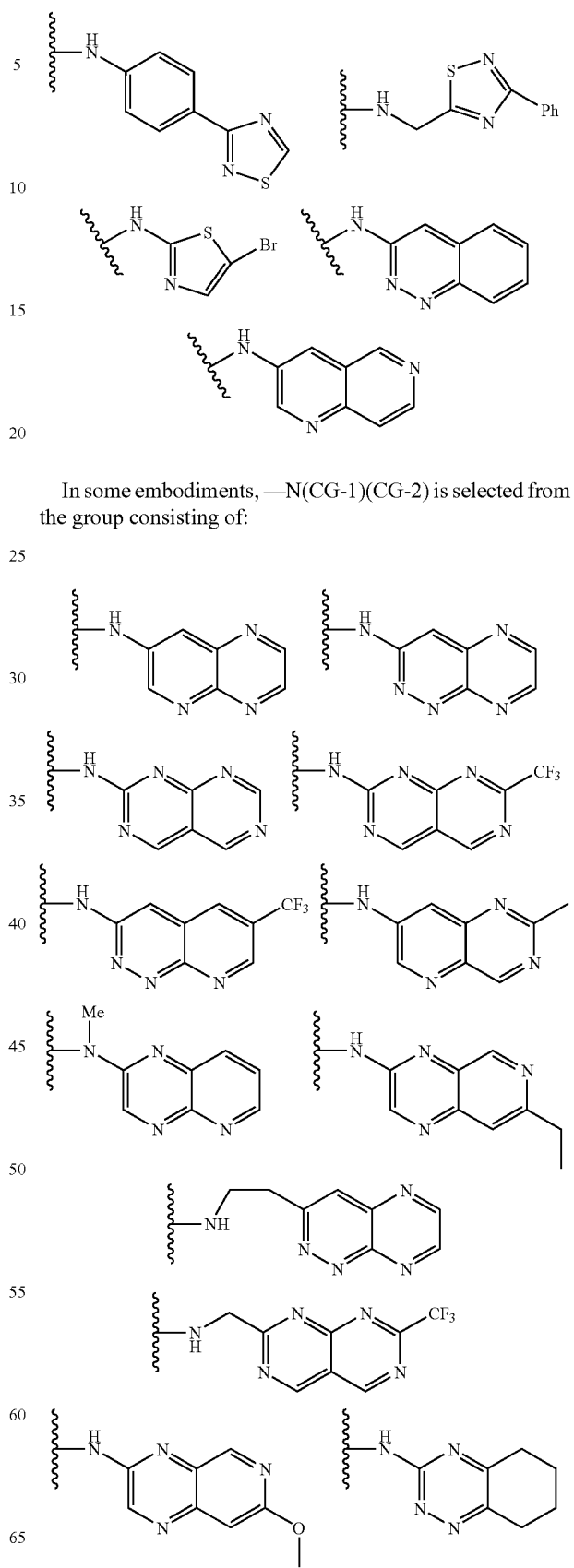
In some embodiments, —N(CG-1)(CG-2) is selected from the group consisting of:

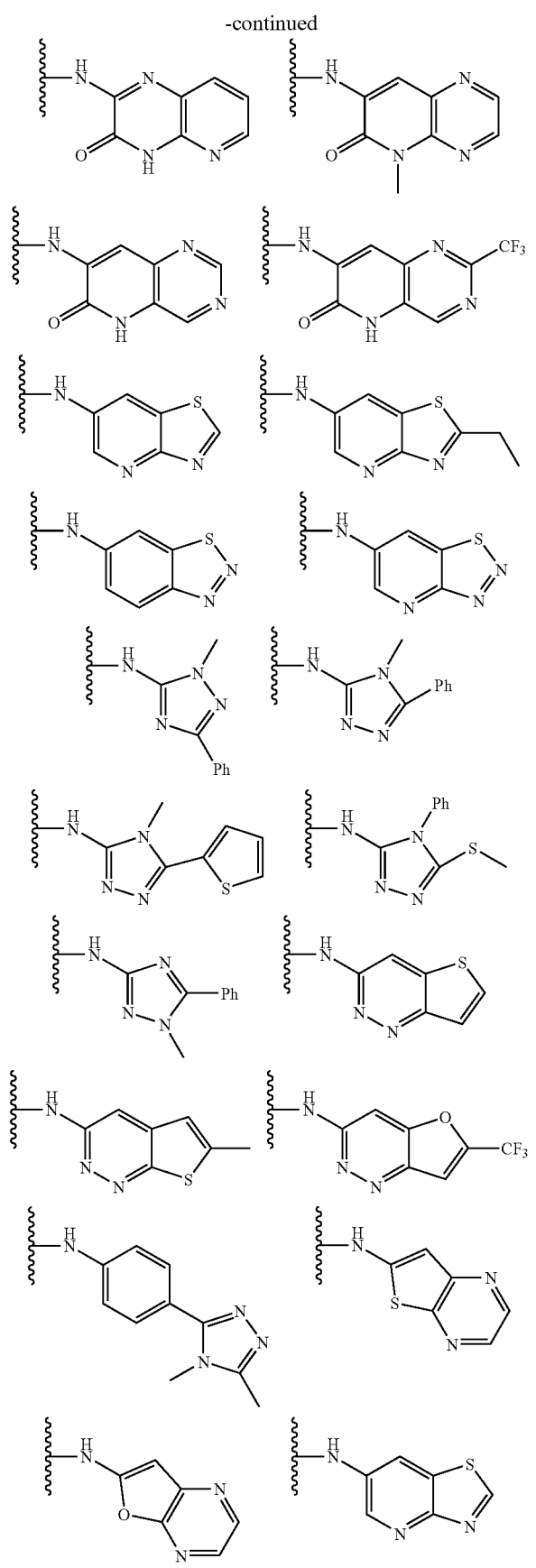
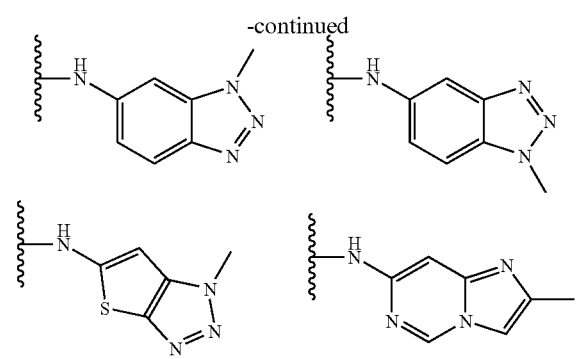

Another embodiment disclosed herein is a compound having the structure of Formula (III):

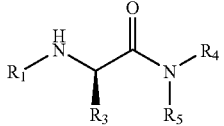

wherein:

R$_1$ is selected from the group consisting of:

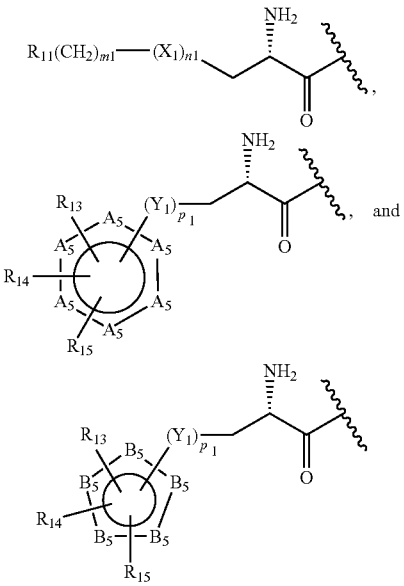

X$_1$ is selected from the group consisting of —O— and —S—;

m$_1$ is an integer from 0 to 4;

n$_1$ is an integer from 0 to 1;

R$_{11}$ is selected from the group consisting of —NH$_2$, —NH—CH(=NH), —NH—C(CH$_3$)(=NH), —CH(=NH)NH$_2$, and —NH—C(=NH)NH$_2$;

R$_{13}$ is selected from the group consisting of —NH$_2$, —CH$_2$NH$_2$, —CH$_2$CH$_2$NH$_2$, —OCH$_2$CH$_2$NH$_2$, —NH—CH(=NH), —CH$_2$NH—CH(=NH), —NH—C(CH$_3$)(=NH), —CH$_2$—NH—C(CH$_3$)(=NH), —C(=NH)NH$_2$, —OCH$_2$C(=NH)NH$_2$, —NH—C(=NH)NH$_2$, and —CH$_2$NH—C(=NH)NH$_2$;

R$_{14}$ and R$_{15}$ are separately selected from the group consisting of hydrogen, halogen, methyl, ethyl, hydroxyl, hydroxymethyl, methoxyl, trifluoromethyl, and trifluoromethoxyl;

Y$_1$ is selected from the group consisting of —CH$_2$—, —O—, and —S—;

p$_1$ is an integer from 0 to 1;

R$_3$ is selected from the group consisting of:

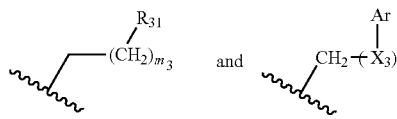

Ar is an optionally substituted aryl or heteroaryl;

X$_3$ is selected from the group consisting of —CH$_2$—, —C(CH$_3$)$_2$— —O—, and —S—;

m$_3$ is an integer from 1 to 2;

n$_3$ is an integer from 0 to 2;

R$_{31}$ is selected from the group consisting of optionally substituted C$_{1-10}$ alkyl, C$_{1-10}$ alkenyl, C$_{1-10}$ alkynyl, and C$_{1-10}$ cycloalkyl;

R$_4$ is selected from the group consisting of hydrogen, optionally substituted C$_{1-10}$ alkyl, and optionally substituted C$_{3-7}$ cycloalkyl;

R$_5$ is selected from the group consisting of:

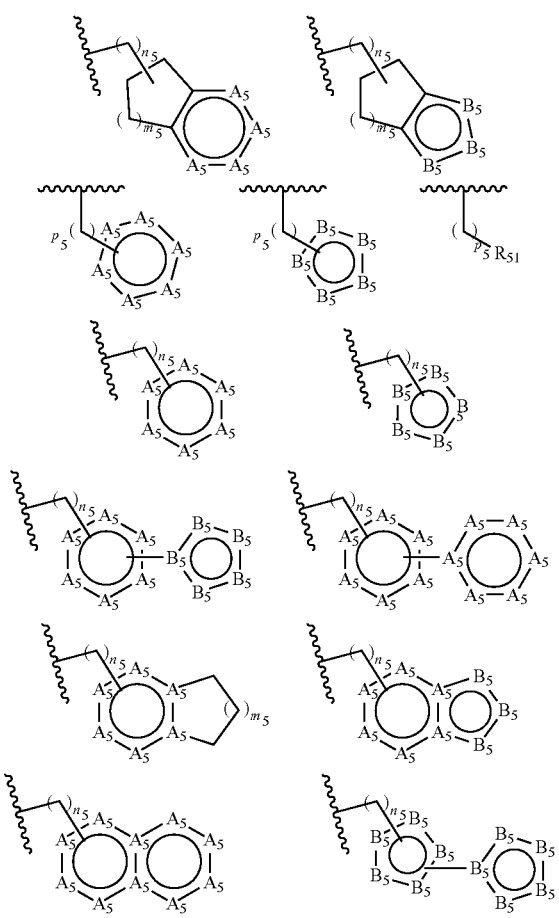

-continued

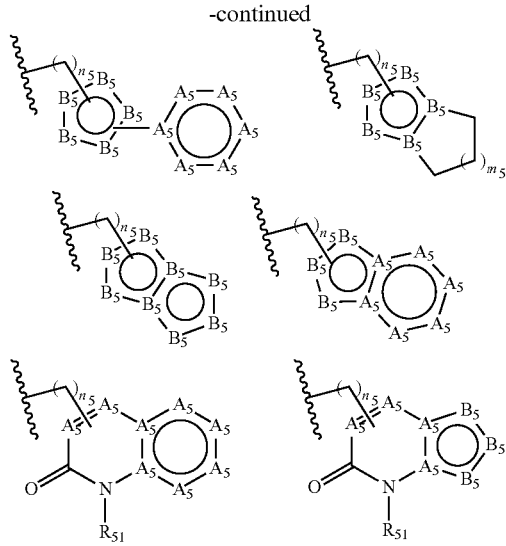

each optionally substituted with methyl, ethyl, n-propyl, isopropyl, cyclopropyl, tert-butyl, hydroxyl, methoxyl, ethoxyl, hydroxymethyl, trifluoromethyl, trifluoromethoxyl, or halogen moieties;

each A$_5$ is separately selected from the group consisting of =CH— and =N—, with the proviso that each A$_5$ containing ring contains no more than four =N— groups;

each B$_5$ is separately selected from the group consisting of —C=, —N=, —O—, —S—, —NH—, and —N(R$_6$)—, with the proviso that each B$_5$ containing ring contains no more than three heteroatoms;

R$_6$ is selected from the group consisting of hydrogen, C$_{1-6}$ alkyl, and C$_{3-6}$ cycloalkyl;

R$_{51}$ is selected from the group consisting of hydrogen, methyl, ethyl, and cyclopropyl;

m$_5$ is an integer from 1 to 3;

n$_5$ is an integer from 0 to 2;

p$_5$ is an integer from 0 to 4;

R$_4$ is optionally bound to R$_5$ to form a five-membered or six-membered heterocyclic ring; and any amino groups are optionally acylated with a natural or artificial amino acid residue having an (S)-configuration;

with the proviso that the compound does not have the formula:

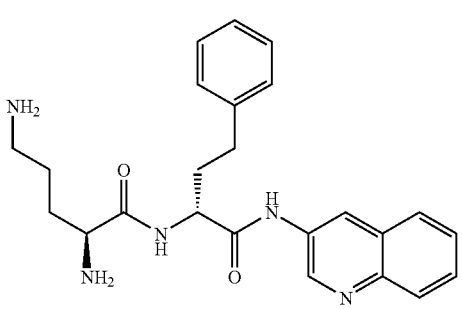

In some embodiments, R₃ is selected from the group consisting of:

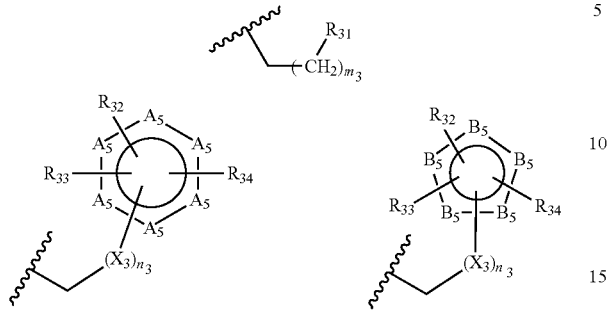

wherein:

$R_{31}$ is selected from the group consisting of ethyl, propyl, isopropyl, isobutyl, tert-butyl, cyclopropyl, cyclobutyl, cyclopentyl, and cyclohexyl;

$R_{32}$ and $R_{33}$ are separately selected from the group consisting of hydrogen, methyl, ethyl, n-propyl, isopropyl, cyclopropyl, tert-butyl, trifluoromethyl, hydroxyl, hydroxymethyl, methoxyl, trifluoromethoxyl, and halogen;

$R_{34}$ is selected from the group consisting of hydrogen, methyl, ethyl, n-propyl, isopropyl, cyclopropyl, tert-butyl, trifluoromethyl, hydroxyl, hydroxymethyl, methoxyl, trifluoromethoxyl, halogen, —NH₂, —CH₂NH₂, —CH₂CH₂NH₂, —OCH₂CH₂NH₂, —NH—CH(=NH), —CH₂NH—CH(=NH), —NH—C(CH₃)(=NH), —CH₂—NH—C(CH₃)(=NH), —C(=NH)NH₂, —OCH₂C(=NH)NH₂, —NH—C(=NH)NH₂, and —CH₂NH—C(=NH)NH₂;

$X_3$ is selected from the group consisting of —CH₂—, —C(CH₃)₂— —O—, and —S—;

$m_3$ is an integer from 1 to 2; and $n_3$ is an integer from 0 to 2.

In some embodiments, R₄ is bound to R₅ to form a five-membered or six-membered heterocyclic ring and the compound of formula III is selected from the group consisting of:

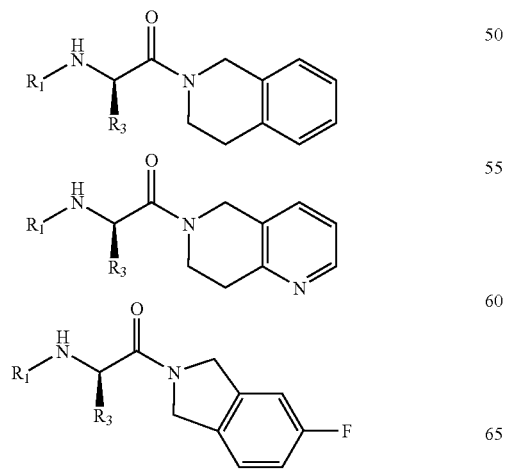

-continued

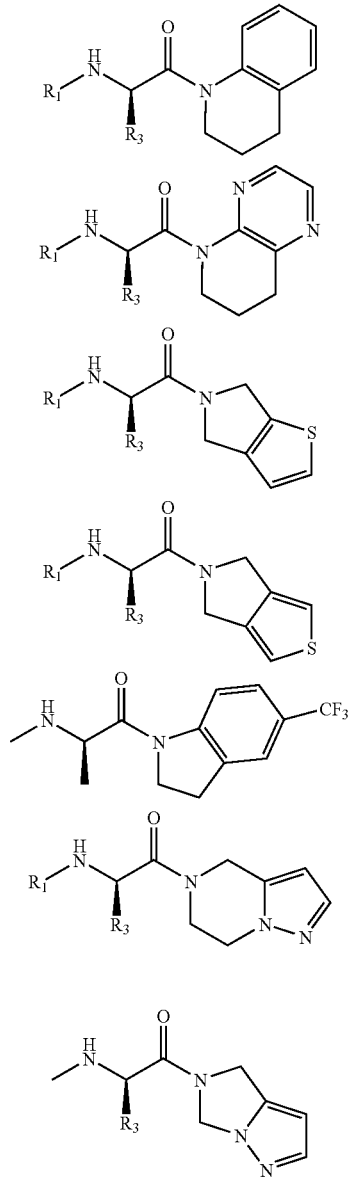

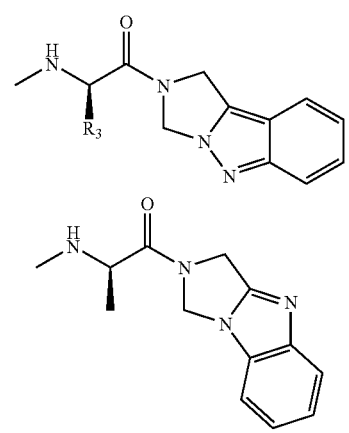

In some embodiments, —N(R$_4$)(R$_5$) is selected from the group consisting of:
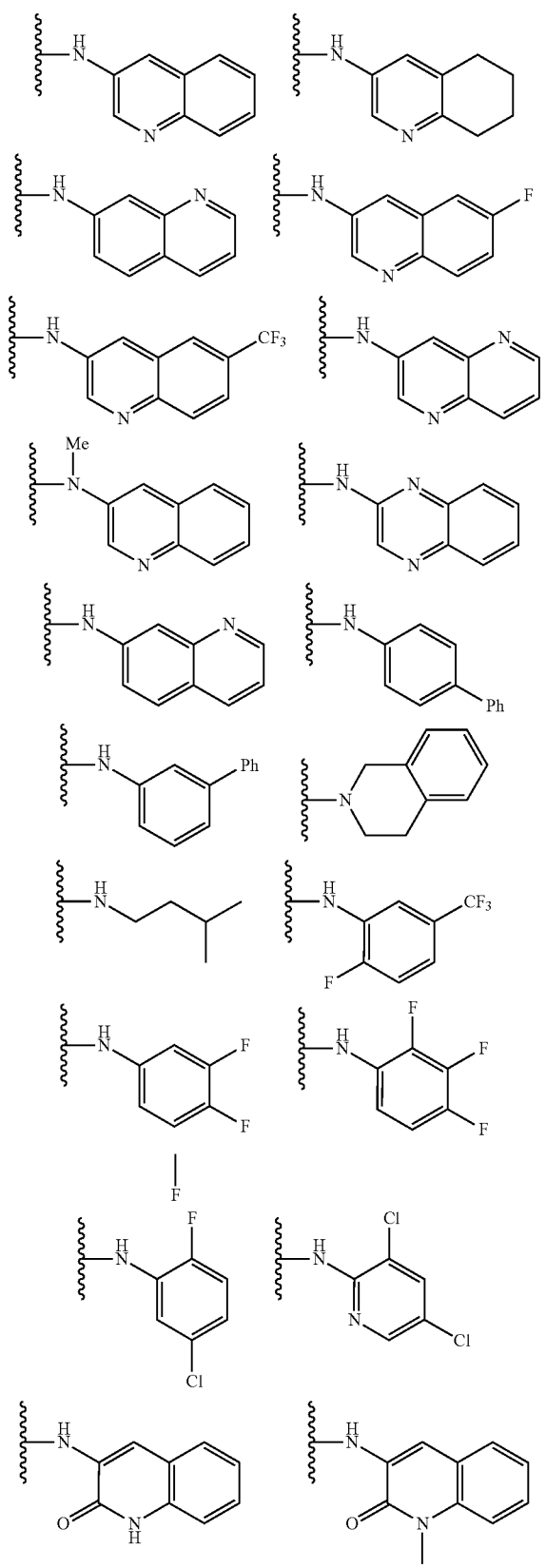
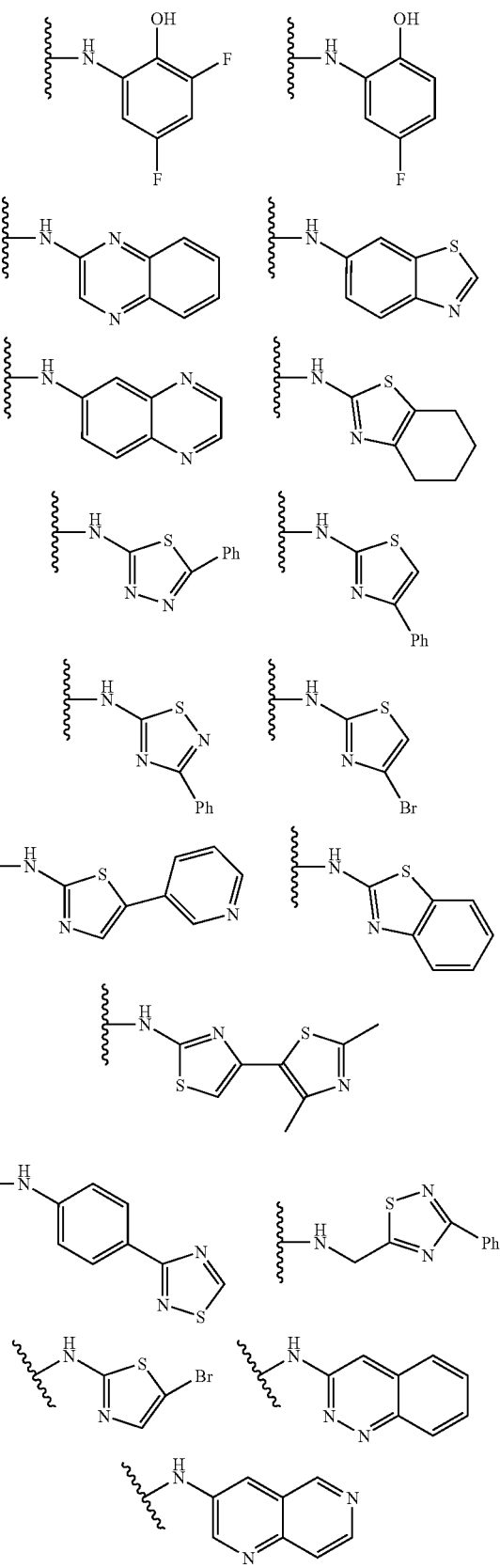

In some embodiments, the compounds described above are selected from the group consisting of:
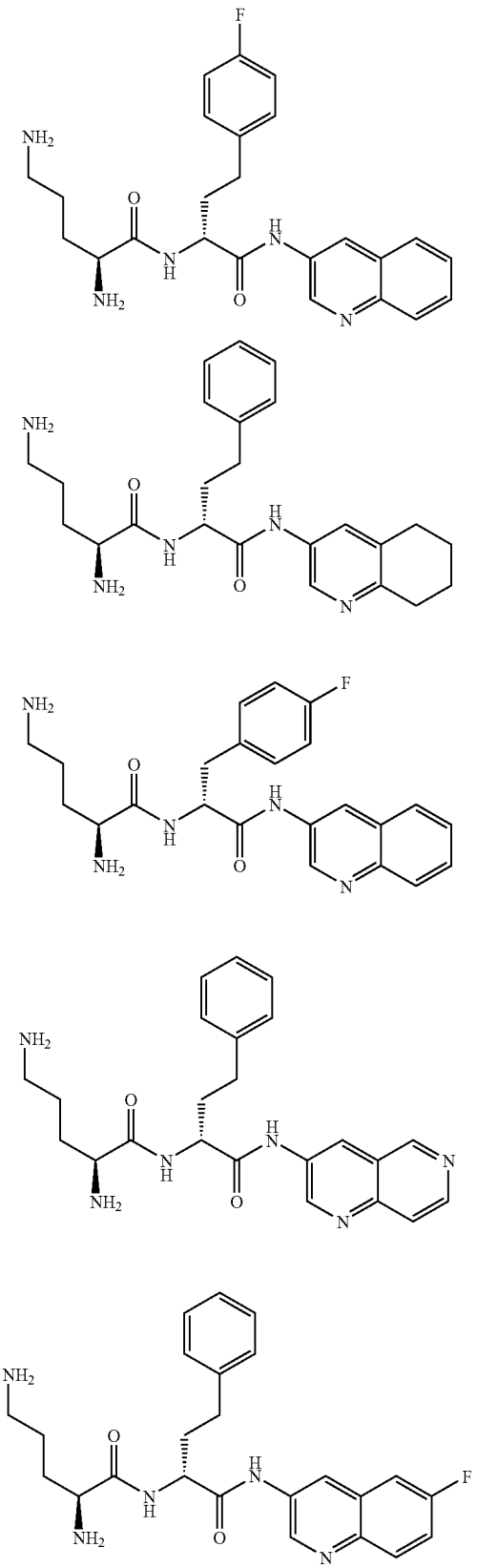
-continued
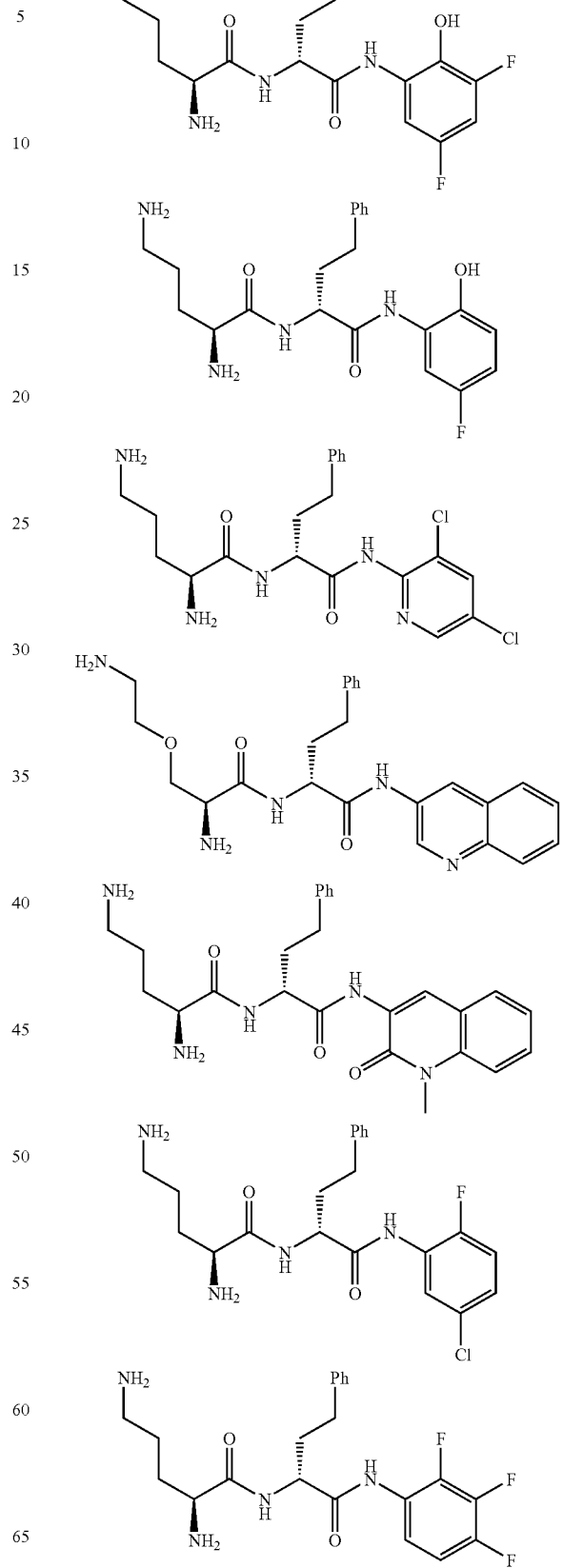

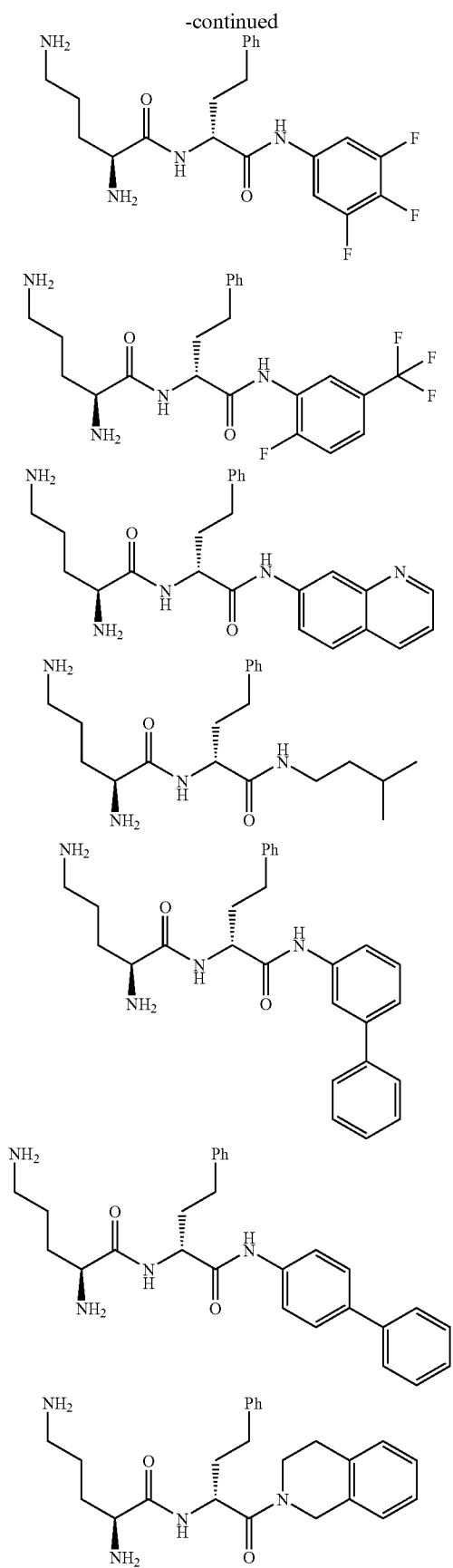
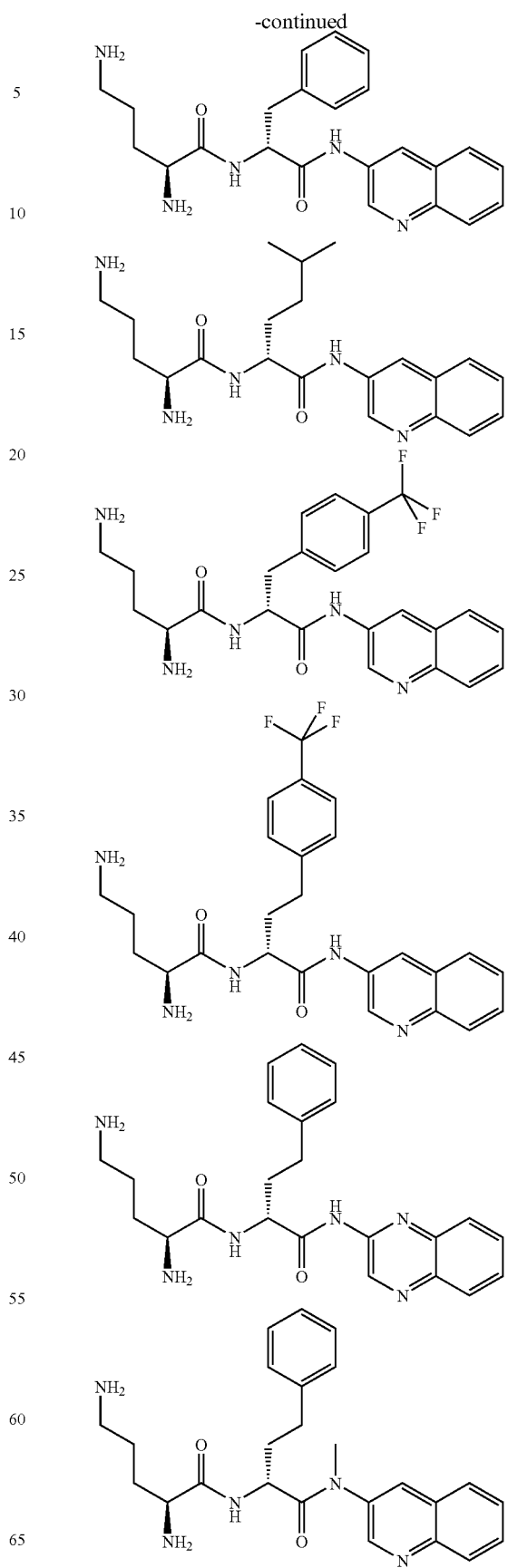

-continued
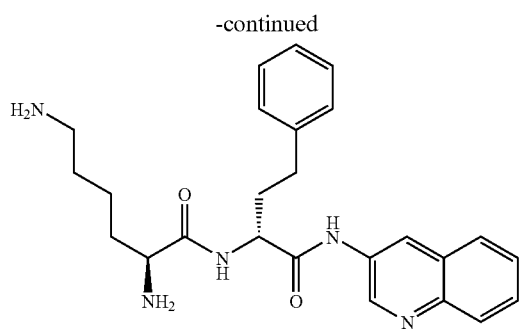
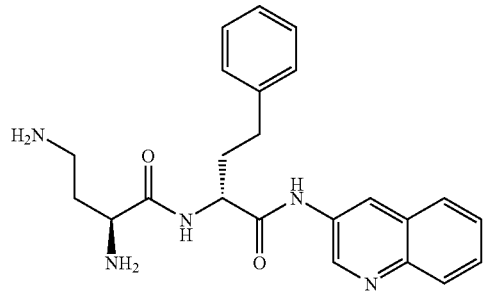
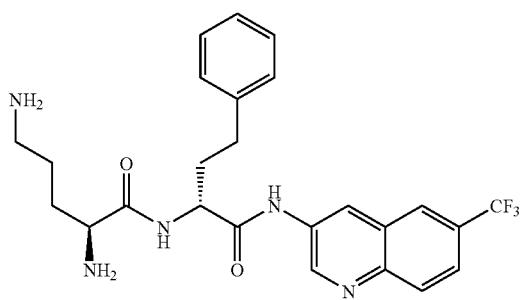
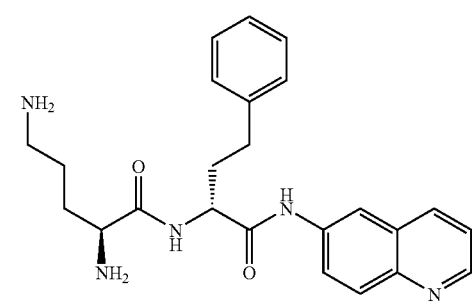
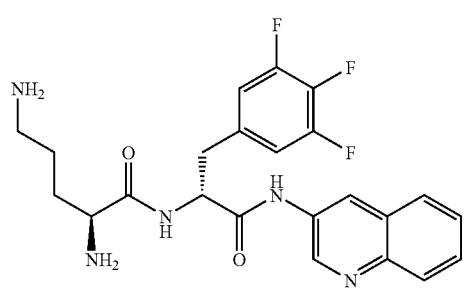
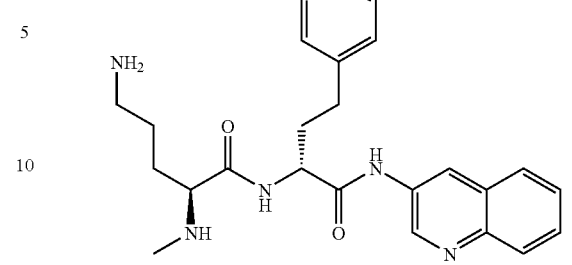
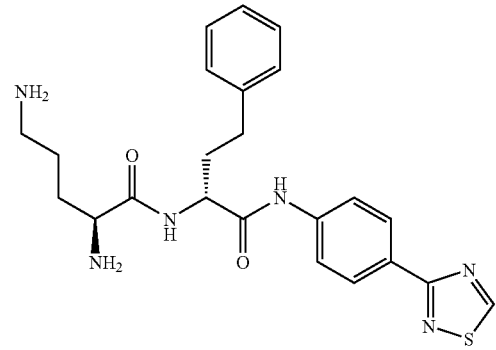
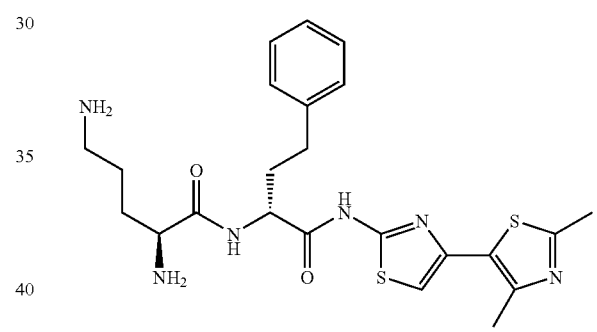
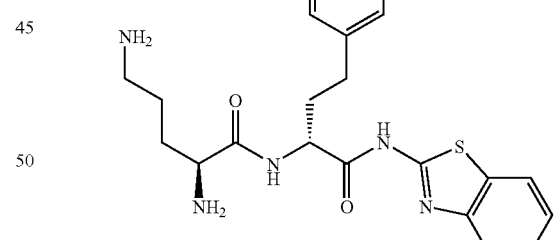
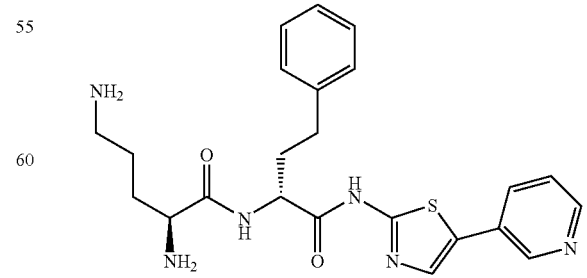

-continued
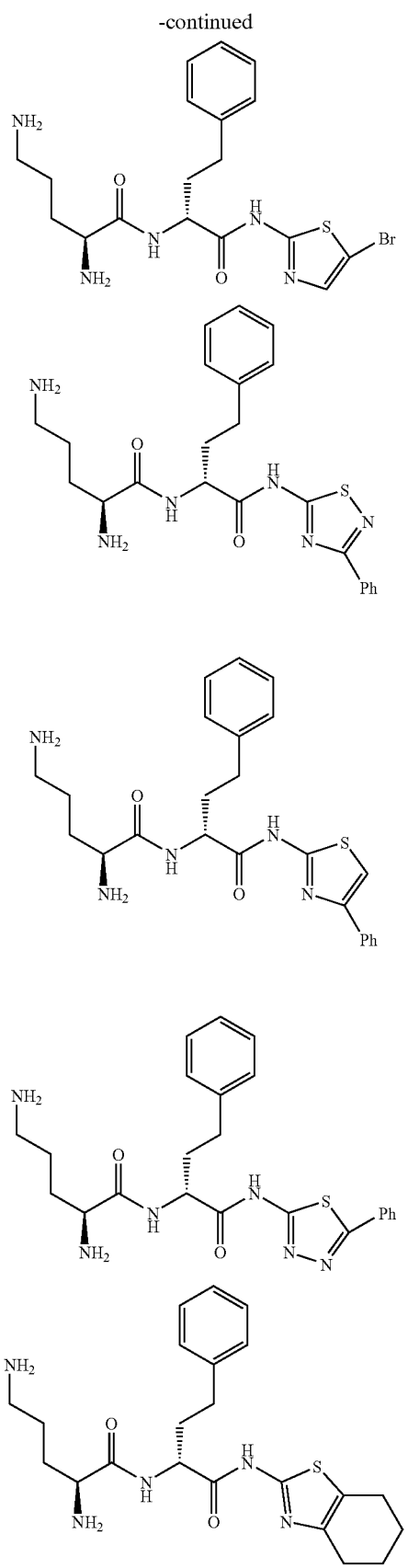
-continued
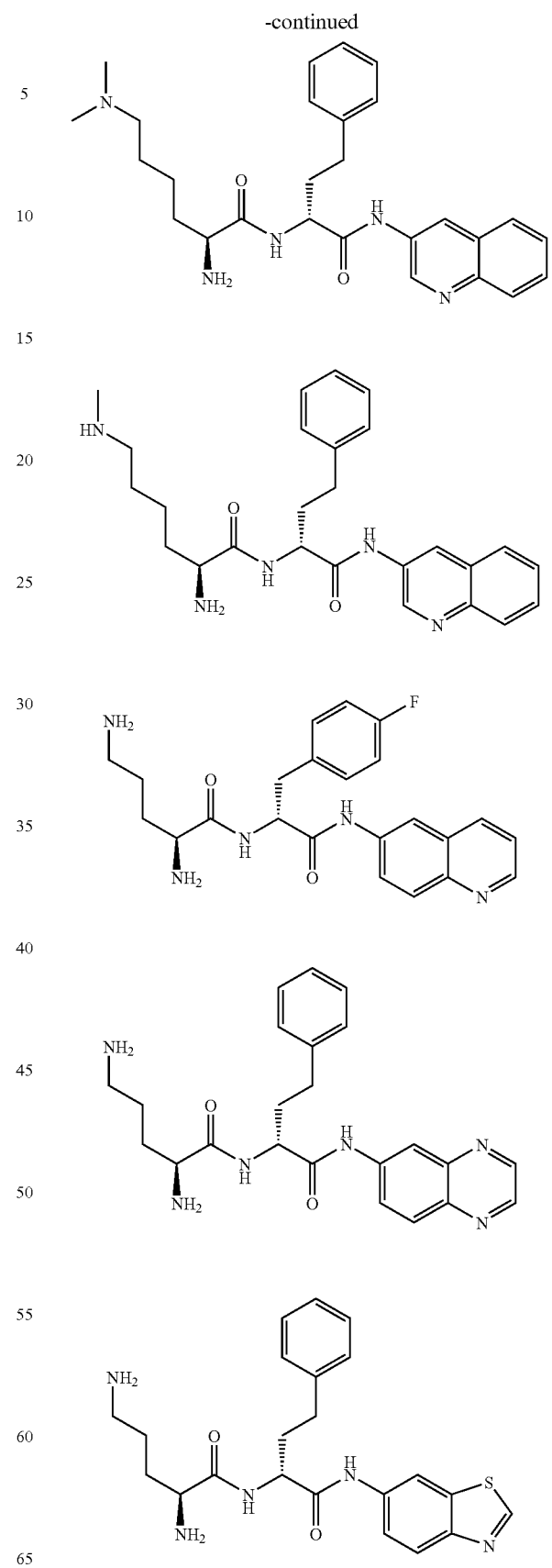

-continued

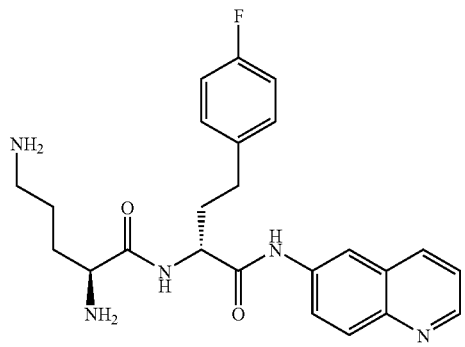

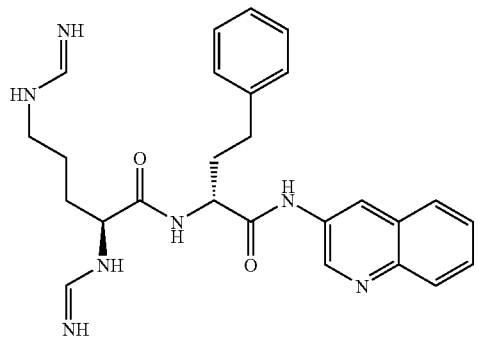

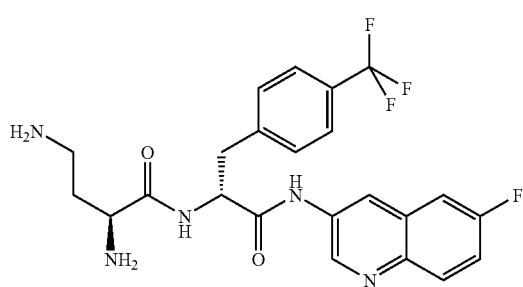

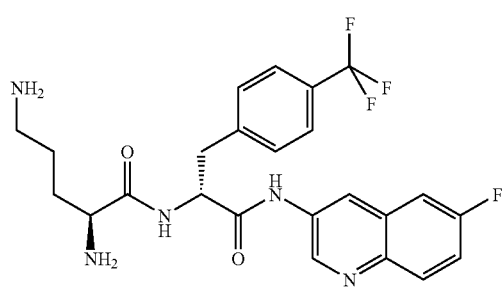

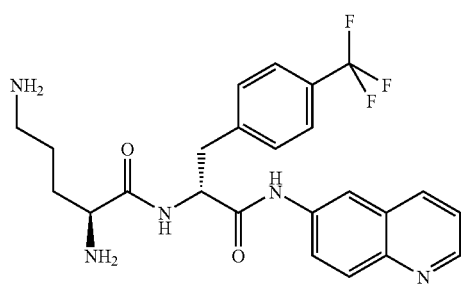

-continued

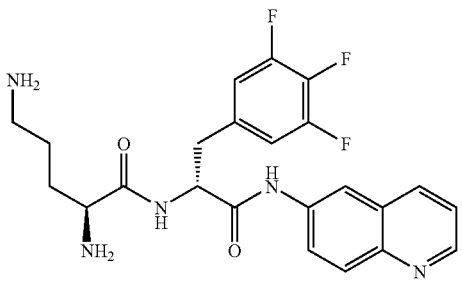

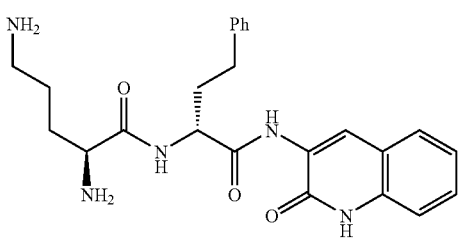

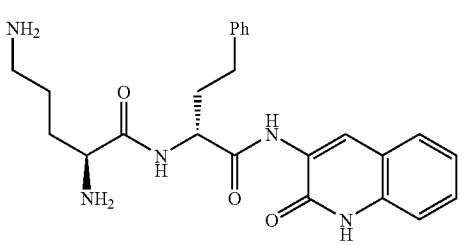

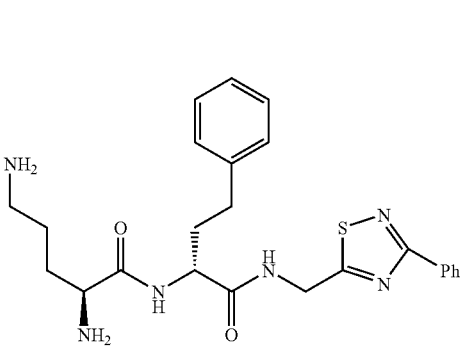

In some embodiments, the amino acid residues optionally acylating one or more amino groups in the compounds described above are selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

In some embodiments, the acylated compound is selected from the group consisting of:

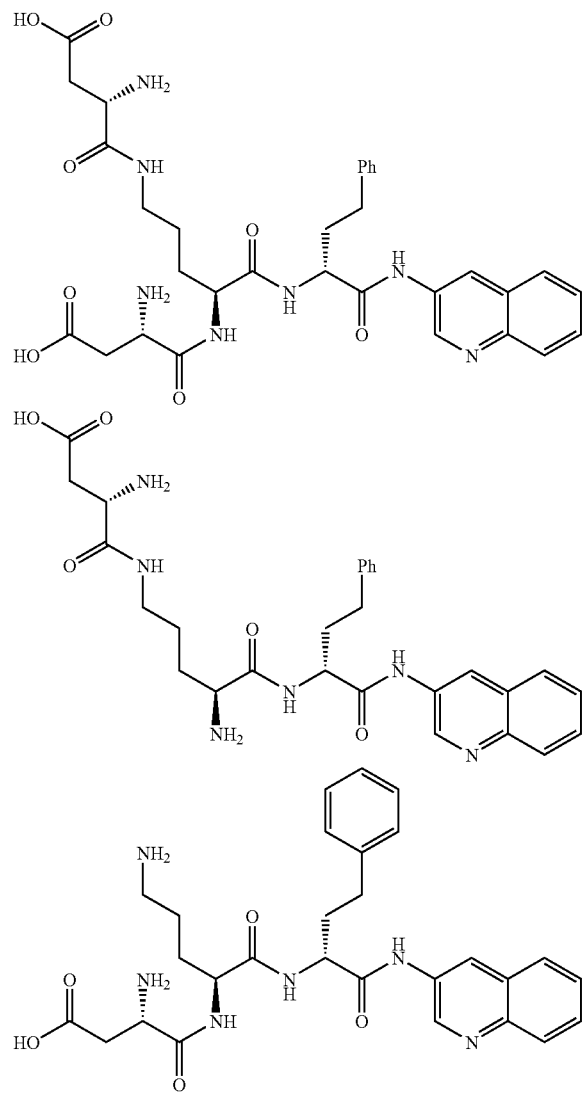

Another embodiment disclosed herein is a pharmaceutical composition comprising a compound as described above in an amount effective to inhibit an efflux pump of a microbe.

Another embodiment disclosed herein is a pharmaceutical composition, comprising a compound as described above in combination with an antimicrobial agent.

Another embodiment disclosed herein is a method of treating or preventing a microbial infection, comprising administering to a subject suffering from the microbial infection an amount effective to inhibit an efflux pump of the microbe of a compound described above.

Another embodiment disclosed herein is a method for treating or preventing growth of antimicrobial-resistant microbes, comprising contacting the microbe with a compound described above and an antimicrobial agent.

Another embodiment disclosed herein is a method for treating a subject with an efflux pump inhibitor, wherein the subject is susceptible to accumulating efflux pump inhibitors in tissue, and wherein the method comprises selecting for use in such treatment a compound of as described above.

Another embodiment disclosed herein is a method for preventing or treating a bacterial infection in a subject, wherein the bacteria causing the infection exhibit antibiotic resistance through an efflux pump mechanism, comprising administering to a subject an antibiotic to which the bacteria are resistant and administering to the subject a compound as described above in conjunction with the antibiotic, wherein the compound is selected to reduce or eliminate tissue damage due to tissue accumulation thereof.

Another embodiment disclosed herein is a compound as described above for use in treating or preventing a microbial infection.

Another embodiment disclosed herein is a compound as described above in combination with an antimicrobial agent for use in treating or preventing a microbial infection.

Another embodiment disclosed herein is a method for treating or preventing a microbial infection, comprising identifying a subject that is susceptible to accumulation in tissue of a compound of formula IIA:

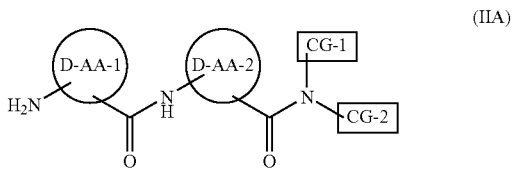

administering to the subject a compound of formula II:

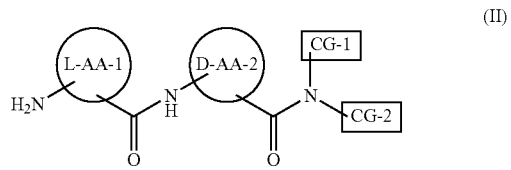

wherein:
D-AA-1 together with attached amine and carbonyl groups is a first natural or artificial α-amino acid residue having an (R)-configuration;
L-AA-1 together with attached amine and carbonyl groups is the first α-amino acid residue but having an (S)-configuration;
D-AA-2 together with attached amine and carbonyl groups is a second natural or artificial α-amino acid residue having an (R)-configuration;
CG-1 is hydrogen or a carbon-linked capping group; and
CG-2 is a carbon-linked capping group, wherein when CG-1 is a carbon-linked capping group, wherein CG-1 and CG-2 are optionally linked together to form a 5- or 6-membered ring.

In some embodiments of the above methods, the subject is a mammal. In some embodiments, the subject is a human. In some embodiments, the microbe is a bacteria. In some embodiments, the bacteria is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella*

*pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii,* and *Bacteroides splanchnicus*. In some embodiments, the antimicrobial agent is selected from the group consisting of the antimicrobial agent is a quinolone, aminoglycoside, beta-lactam, coumermycin, chloramphenical, lipopeptide, glycopeptide, glycylcycline, ketolide, macrolide, oxazolidonone, rifamycin, streptogramin, and tetracycline. In some embodiments, the antimicrobial agent is selected from the group consisting of ciprofloxacin, levofloxacin, moxifloxacin, ofloxacin, gatifloxacin, cinoxacin, gemifloxacin, norfloxacin, lomofloxacin, pefloxacin, garenoxacin, sitafloxacin, and DX-619.

Another embodiment disclosed herein is a method of identifying a compound useful for efflux pump inhibition but not accumulating significantly in tissue, comprising identifying a compound having the structure of formula IIA that is effective at inhibiting an efflux pump:

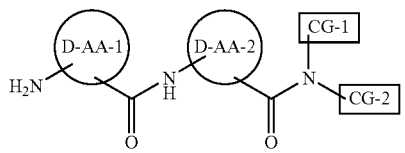

(IIA)

producing a compound of formula II:

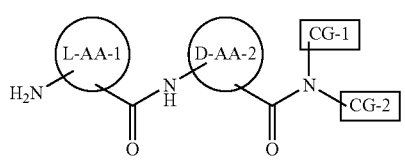

(II)

and determining whether the compound of formula II does not accumulate significantly in tissue;
wherein:
D-AA-1 together with attached amine and carbonyl groups is a first natural or artificial α-amino acid residue having an (R)-configuration;
L-AA-1 together with attached amine and carbonyl groups is the first α-amino acid residue but having an (S)-configuration;

D-AA-2 together with attached amine and carbonyl groups is a second natural or artificial α-amino acid residue having an (R)-configuration;
CG-1 is hydrogen or a carbon-linked capping group; and
CG-2 is a carbon-linked capping group, wherein when CG-1 is a carbon-linked capping group, wherein CG-1 and CG-2 are optionally linked together to form a 5- or 6-membered ring.

Another embodiment disclosed herein is a method of treating a patient by administering an efflux pump inhibitor in conjunction with an antibiotic, wherein the efflux pump inhibitor has the structure:

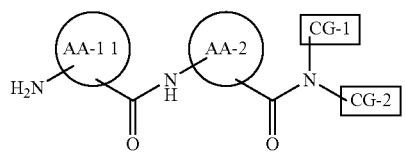

wherein AA-1 and AA-2 together with attached amine and carbonyl groups represent a natural or artificial a-amino acid residue, ascertaining whether reduced cellular accumulation of efflux pump inhibitor in the patient is desirable, and if so, selecting the efflux pump inhibitor from those efflux pump inhibitors having formula II:

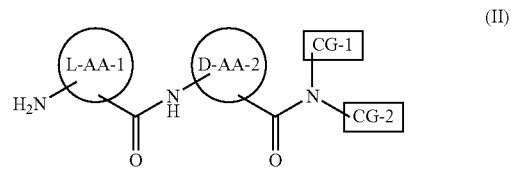

(II)

wherein:
L-AA-1 is AA-2 having an (S)-configuration;
D-AA-2 is AA-2 having an (R)-configuration;
CG-1 is hydrogen or a carbon-linked capping group; and
CG-2 is a carbon-linked capping group, wherein when CG-1 is a carbon-linked capping group, wherein CG-1 and CG-2 are optionally linked together to form a 5- or 6-membered ring.

Another embodiment disclosed herein is the use of a compound of formula II for the preparation of a medicament for treating or preventing a microbial infection without the compound accumulating significantly in tissue:

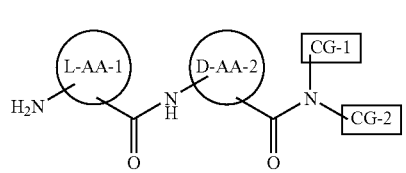

(II)

wherein:
L-AA-1 is AA-2 having an (S)-configuration;
D-AA-2 is AA-2 having an (R)-configuration;
CG-1 is hydrogen or a carbon-linked capping group; and
CG-2 is a carbon-linked capping group, wherein when CG-1 is a carbon-linked capping group, wherein CG-1 and CG-2 are optionally linked together to form a 5- or 6-membered ring.

Another embodiment disclosed herein is the use of a compound of formula II in combination with an antimicrobial agent for the preparation of a medicament for treating or preventing a microbial infection without the compound accumulating significantly in tissue:

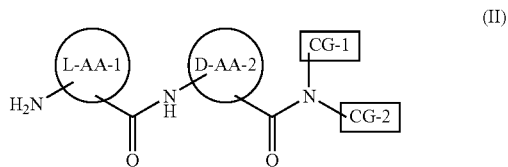

(II)

wherein:
L-AA-1 is AA-2 having an (S)-configuration;
D-AA-2 is AA-2 having an (R)-configuration;
CG-1 is hydrogen or a carbon-linked capping group; and
CG-2 is a carbon-linked capping group, wherein when CG-1 is a carbon-linked capping group, wherein CG-1 and CG-2 are optionally linked together to form a 5- or 6-membered ring.

DETAILED DESCRIPTION OF THE PREFERRED EMBODIMENT

Figure 1A:
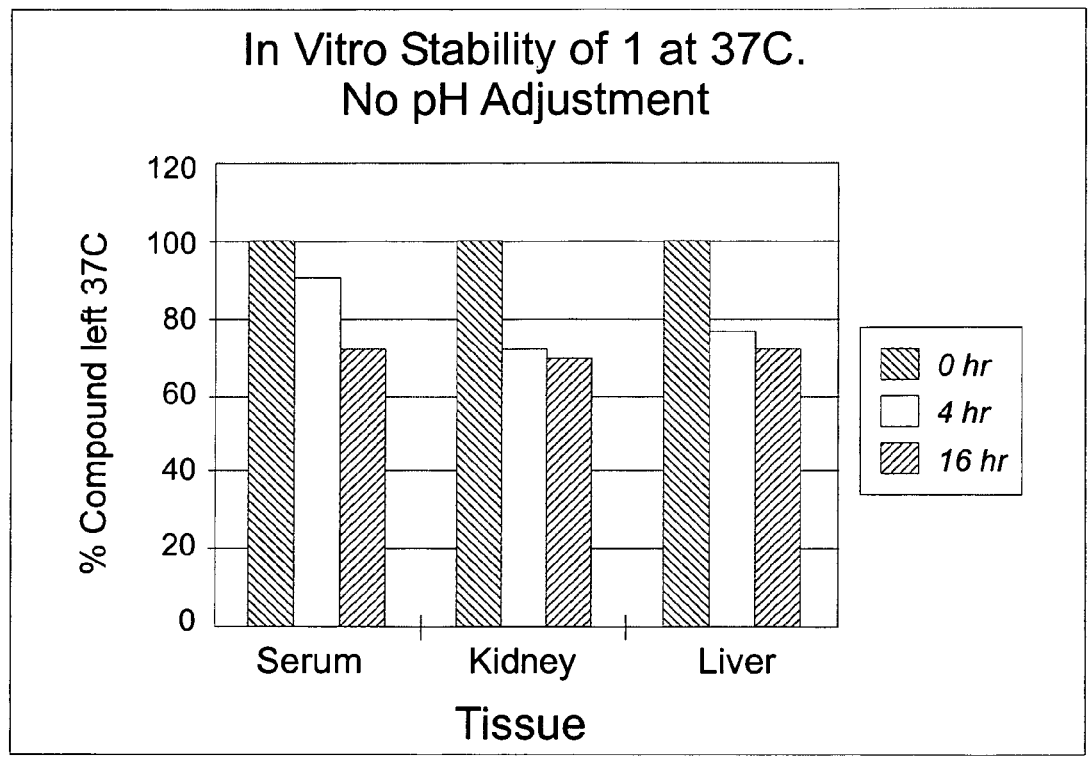
FIGS. 1A to 1C are bar graphs depicting the in vitro stability of three stereoisomers of an EPI compound in tissue homegenates.

Certain dipeptide compounds have been shown to be effective efflux pump inhibitors. For example, some EPI compounds have been shown to be effective in combination with fluoroquinolones against P. aeruginosa. See U.S. Pat. Nos. 6,114,310 and 6,245,746, which are both incorporated herein by reference in their entirety. One such compound was shown to decrease the intrinsic resistance to levofloxacin in wild-type strains (>8-fold), in strains over-expressing the efflux pumps (max 128-fold), and in clinical isolates decreasing the $MIC_{50}$ and $MIC_{90}$ (16-fold). A major beneficial consequence of the inhibition of multiple efflux pumps was shown to be a dramatic decrease in the frequency of emergence of P. aeruginosa strains with clinically relevant levels of resistance to fluoroquinolones, both in vitro and in in vivo animal models.

While certain dipeptide/diamine compounds have been shown to possess attractive microbiological profiles and significant efficacy in various animal models of infection, it is demonstrated herein that some of these compounds have a long tissue half-life and upon repeated doses accumulate in tissues (e.g., kidney, liver, and lung) to levels that induce cellular and organ damage. Previous efforts to identify analogs that avoid tissue accumulation by systematically varying physico-chemical characteristics have failed. Accordingly, in some embodiments, structural modifications of diamine EPIs are provided that result in reduced tissue accumulation and potentially reduced toxicity of these promising future therapeutic agents.

In some embodiments, diamine EPI therapeutic agents are structurally modified in such a way that they retain the desired target affinity while their propensity for accumulation in tissue is reduced due to modification of the compound observed in tissues, e.g. at the site of accumulation. In some embodiments, the modification is a degradation of the compound, such as hydrolysis. When administered to a patient suffering from a microbial infection that employs efflux pump(s) as a resistance mechanism, such drugs undergo tissue-selective degradation (i.e., tissue soft drugs) and exhibit a reduced propensity for tissue accumulation while inhibiting the activity of the resistance efflux pump(s), allowing a co-administrated antimicrobial agent to accumulate in sufficient concentration in the periplasm or cytoplasm of the infecting microbe to kill or inhibit the growth of the microbe to treat the infection. Thus, some embodiments relate to a method for treating a microbial infection whose causative microbe employs an efflux pump resistance mechanism, comprising contacting the microbial cell with a soft drug efflux pump inhibitor in combination with an antimicrobial agent. In some embodiments, the soft drug efflux pump inhibitors comprise a dipeptidic structure, as disclosed herein. In some embodiments, the dipeptidic structure includes two amino functionalities that are not part of the peptide bonds in the compound. In some embodiments, the dipeptidic structure includes absolute stereochemistry that supports the reduced tissue accumulation properties of the compound. For example, in some embodiments, the dipeptidic structure has an L,D stereochemistry, where the N-terminal amino acid has an L configuration and the C-terminal amino acid has a D configuration, which is demonstrated herein to have reduced tissue accumulation properties relative to other stereochemistries (e.g., D,D).

Another embodiment includes a method for prophylactic treatment of a mammal. In this method, a soft drug efflux pump inhibitor is administered to a mammal at risk of a microbial infection, e.g., a bacterial infection. In some embodiments, an antimicrobial agent is administered in combination with or coadministered with the soft drug efflux pump inhibitor.

Another embodiment includes a method of enhancing the antimicrobial activity of an antimicrobial agent against a microbe, in which such a microbe is contacted with a soft drug efflux pump inhibitor, and an antibacterial agent.

In still other embodiments, pharmaceutical compositions are provided that are effective for treatment of an infection of an animal, e.g., a mammal, by a microbe, such as a bacterium or a fungus. The composition includes a pharmaceutically acceptable carrier and a soft drug efflux pump inhibitor as described herein. The preferred embodiments also provide antimicrobial formulations that include an antimicrobial agent, a soft drug efflux pump inhibitor, and a carrier. In preferred embodiments, the antimicrobial agent is an antibacterial agent.

While the disclosure herein is directed primarily to compounds for treating microbial infections that employ efflux pump(s) as a resistance mechanism, it is understood that the methods herein described can be useful in producing soft drugs suitable for treatment of other indications, wherein it is desirable that the therapeutic agent exhibit a reduced propensity for tissue accumulation.

DEFINITIONS

The term "administration" or "administering" refers to a method of giving a dosage of an antimicrobial pharmaceutical composition to a vertebrate or invertebrate, including a mammal, a bird, a fish, or an amphibian, where the method is, e.g., intrarespiratory, topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics,* 8th Ed. Pergamon Press.

A "diagnostic" as used herein is a compound, method, system, or device that assists in the identification and characterization of a health or disease state. The diagnostic can be used in standard assays as is known in the art.

The term "efflux pump" refers to a protein assembly that exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump, which spans the outer membrane.

An "efflux pump inhibitor" ("EPI") is a compound that specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity.

"High throughput screening" as used herein refers to an assay that provides for multiple candidate agents or samples to be screened simultaneously. As further described below, examples of such assays include the use of microtiter plates which are especially convenient because a large number of assays can be carried out simultaneously, using small amounts of reagents and samples.

The term "subject," as used herein, refers to an organism to which the compounds disclosed herein may be administered and upon which the methods disclosed herein may practiced. In some embodiments, the subject is an animal. In some embodiments, the animal is a mammal. In some embodiments, the mammal is a human.

The term "mammal" is used in its usual biological sense. Thus, it specifically includes humans, cattle, horses, dogs, and cats, but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. The compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "multidrug resistance pump" refers to an efflux pump that is not highly specific to a particular antibiotic. The term thus includes broad substrate pumps (e.g., those that efflux a number of compounds with varying structural characteristics). These pumps are different from pumps that are highly specific for tetracyclines. Tetracycline efflux pumps are involved in specific resistance to tetracycline in bacteria. However, they do not confer resistance to other antibiotics. The genes for the tetracycline pump components are found in plasmids in Gram-negative as well as in Gram-positive bacteria.

The term "non-accumulating soft drug" refers to a drug with a structural feature allowing it to be modified in vivo, e.g. by modification including metabolism, degradation, and hydrolysis. Such soft drugs can exhibit a reduced propensity for tissue accumulation, for example, intralysosomal accumulation, intranuclear accumulation, cytoplasmic accumulation, and the like.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Solvate" refers to the compound formed by the interaction of a solvent and a soft drug, a metabolite, or salt thereof. Suitable solvates are pharmaceutically acceptable solvates including hydrates.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

By "therapeutically effective amount" or "pharmaceutically effective amount" is meant an amount of an efflux pump inhibitor, or amounts individually of an efflux pump inhibitor and an antimicrobial agent, as disclosed in the preferred embodiments, which have a therapeutic effect, which generally refers to the inhibition to some extent of the normal metabolism of microbial cells causing or contributing to a microbial infection. The doses of efflux pump inhibitor and antimicrobial agent which are useful in combination as a treatment are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective if a microbial infection existed.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a soft drug efflux pump inhibitor and an antibacterial (or antimicrobial) agent in combination (either simultaneously or serially).

Soft-Drug Mechanism

As used herein, non-accumulating soft drugs are drugs which are characterized by a predictable and controllable intracellular in vivo modification such as by metabolism, preferably intracellular hydrolytic inactivation, to non-accumulating products, preferably after they have achieved their therapeutic role.

Numerous compounds having useful therapeutic properties possess so-called lysosomotropic character. In general, such properties are displayed by molecules bearing one or more basic functionalities with (e.g., amines), such that they are highly protonated at the intralysosomal pH. Such compounds either passively permeate through the lysosomal membrane or are actively transported inside by membrane bound transport proteins. Having crossed through the membrane, the compounds encounter the acidic (pH ~5) environment of the lysosome, become highly protonated, and remain entrapped in the intralysosomal space. The accumulation of such compounds inside the lysosome can disrupt the proper functioning of the lysosomal enzymatic machinery. Such accumulation can also lead to the build-up of osmotic pressure inside the lysosome, resulting in break-up of the lysosomal membrane followed by leakage of the enzymatic content of the lysosome into the cytoplasm.

Tissues containing cells rich in lysosome vacuoles are particularly sensitive to the toxic effects of intralysosomal accumulation of basic molecules. Nephrotoxicity due to the intralysosomal accumulation of basic molecules in renal tissue is a widely documented phenomenon and has often been encountered as a serious obstacle to the development of new therapeutic agents. The sometimes unwanted accumulation of such molecules can occur inside lysosomes or other acidic vacuoles present in other organs (for example, the lung or liver) and can also produce organ toxicity.

One example of tissue accumulation occurs with the drug pentamidine. Pentamidine has been extensively studied mechanistically at the cellular level and in animals, as well as clinically in man. The most significant characteristic of these cationic compounds is their extensive accumulation in a number of body organs, most notably in the kidney and liver, resulting in frank nephrotoxic and hepatotoxic effects. The incidence of kidney toxicity with parenteral pentamidine in retrospective clinical studies in AIDS patients is above 75%.

Perfused rat kidney studies demonstrate that a combination of mechanisms (filtration, active secretion, and passive reabsorption) are involved in the renal disposition of pentamidine. Dose proportionality studies demonstrated non-linear excretion of pentamidine and significant kidney accumulation of the drug. A clear correlation was established between extent of kidney sequestration and perturbations in kidney function, most notably GFR, all consistent with observations in the rat that tubulotoxicity of pentamidine is dose-related.

Organic cations are transported in the kidney by the proximal tubule in a multi-step process involving facilitated diffusion and active cation transport. Once inside the tubular cell, intracellular sequestration can result in excessive drug concentration, either by binding to cytosolic proteins or accumulating in vesicular compartments (e.g. endosomes and lysosomes). The acidic pH of these organelles can ion-trap cationic compounds.

Other examples of drugs susceptible to tissue accumulation are aminoglycosides. It has been shown that aminoglycosides accumulate in lysosomes and inhibit lysosomal enzyme activity with concomitant nephrotoxicity.

Thus, the presence of basic functionalities, such as amino groups, within therapeutic compounds can promote unwanted and potentially toxic tissue accumulation. However, many biologically active molecules require basic functionalities (sometimes multiple basic functionalities per molecule) in order to exert their therapeutic effect through the interaction with their corresponding molecular targets. Accordingly, a general method allowing the modification of otherwise promising therapeutic agents in such a way that they retain the desired target affinity while exhibiting a reduced propensity for intralysosomal accumulation or accumulation in other tissue compartments represents an extremely useful tool aiding in the design of new therapeutic molecules and as such, is highly desirable. To this end, some embodiments provide compounds having basic functionalities, wherein the stereochemistry of the compounds has been tailored to reduce tissue accumulation.

Lysosomes are known to contain a fairly large number (about sixty) of enzymes, most of them having protease activity. Since many of such enzymes are not found in appreciable amounts outside lysosomes, the specificity of the proteolytic activity of these enzymes offers the potential for detoxification of lysosomotropic agents, provided that the lysosomotropic agent contains functionalities which can be cleaved by these enzymes. The resulting breakdown products of the lysosomotropic agent can potentially exhibit a largely reduced tendency for the disruption of the lysosomal function. The lysosomotropic agent may also not remain trapped inside the lysosome but may, like many small fragments resulting from, e.g., intralysosomal proteolysis, be removed from the lysosome by the active efflux mechanism. Certain enzymes in the lysosomes exhibit esterase activity, which can also offer the potential for detoxification of lysosomotropic agents.

An important factor in enzyme activity, such as the proteolytic activity of many of the lysosomal proteolytic enzymes is the pH required for their optimal activity. Their catalytic activity displayed at the normal lysosomal pH is often largely diminished or completely absent when the pH is increased by one or two pH units.

When the therapeutic agent, such as a drug molecule, is susceptible to the metabolic proteolytic or esterase clearance it is usually the enzymatic activity of serum, organ specific interstitial fluid, or cytosol that is responsible for the degradation of the drug molecule. Extensive degradation of the drug molecule by such enzymes can result in unacceptably high clearance and reduces the amount of drug below the therapeutically useful level. On the other hand, since the portion of the drug extracted into the lysosomes is typically quite small, the lysosomal enzymes participate only marginally in the metabolic clearance of therapeutic agents. Therefore, to use the detoxification mechanism described above, it may be desirable that the therapeutic agent molecule contains a functionality which is not sensitive to the proteolytic activity of the non-lysosomal enzymes, but which is susceptible to the enzyme or enzymes present inside the lysosome. This allows a lysosomotropic drug to exhibit a desired pharmacokinetic property, while at the same time the portion of the drug that is extracted into the lysosome undergoes detoxification by the specific activity of the lysosomal enzyme or enzymes.

While not being bound to any particular theory, it is likely that non-soft diamine EPI compounds undergo intralysosomal accumulation. The cationic character of diamine EPIs make them similar to pentamidine and aminoglycosides for which intralysosomal accumulation has been demonstrated. In contrast, it is likely that non-accumulating soft-drug EPIs disclosed herein undergo intralysosomal hydrolysis. Support for this conclusion includes: 1) serum stability and tissue-mediated hydrolysis of soft EPIs indicate that hydrolysis occurs intracellularly; 2) the presence of a peptide bond in these compounds provide susceptibility to proteolysis; 3) eukaryotic cells have 2 major systems of intracellular proteolytic activities: (a) lysosomal proteases and (b) ATP-dependent and ubiquitin-assisted proteasome peptidases in cytosol and nucleus. While many soft EPIs may lack necessary features for ubiquitinated degradation, their hydrolysis is pH-dependent indicating intralysosomal degradation. The efficiency of degradation was dramatically increased at acidic pH, which is present inside lysosomes. Lysosomes contain up to 40 acid hydrolasases that are optimally active at acidic pH and inactive at neutral pH such as is present in cytoplasm and extracellular compartments. 4) formation of the predicted product of hydrolysis of soft-EPIs is observed, both in vitro and in vivo. 5) localization of proteolytic enzymes in the soluble fraction of tissue homogenates (as opposed to membrane bound drug metabolizing P450 enzymes) suggest that they are located intralysosomally.

Because non-accumulating soft drugs are hydrolyzed intracellularly, they may undergo organ selective enzymatic hydrolysis, which is used herein to mean enzymatic hydrolysis that is observed in homogenates prepared from tissues of various organs but not in plasma. Using rodents as model organisms it was demonstrated that compounds that undergo organ-selective hydrolysis in vitro do not accumulate in tissues of these organs after administration to animals. Thus the ability to undergo organ-selective hydrolysis is advantageous if tissue accumulation in organs is expected to result in organ toxicity. In this respect organ-selective enzymatic hydrolysis might be considered as a way to limit organ-specific toxicity.

The presence of organ-selective enzymatic hydrolysis was further supported by the fact that compounds that contain potentially labile peptide bond were stable in serum but unstable in homogenates prepared from tissues of several organs (e.g., kidney, liver, and lung). The expected product of proteolytic hydrolysis of the model compound was identified after bioanalysis in tissue homogenates. The same product was also discovered in tissues of animals receiving the parent compound, indicating that the hydrolysis seen in vitro also occurs in vivo.

The principles discussed above, directed to drugs containing peptide bonds that are susceptible to organ-selective hydrolysis, can also be applied to compounds containing other chemical bonds that may be susceptible to organ-specific hydrolyzing enzymes found in intracellular compartments such as lysosomes or to compounds that may be modified by other in vivo enzymes. Accordingly, in one embodiment, a method is provided for avoiding organ-specific toxicity or accumulation of a drug in organs while administering a therapeutic compound, comprising administering a compound that is adapted to resist accumulation in one or more organs via enzymatic modification occurring at the site of accumulation. In some embodiments, the enzymatic modification is a degradation of the compound. In some embodiments, the degradation is a selective metabolism. In some embodiments, the selective metabolism is a selective enzymatic hydrolysis. In some embodiments, the organs are selected from the group consisting of kidney, liver, lung, skin, muscle, brain, pancreas, thymus, adrenal glands, thyroid, ovaries, uterus, mammary glands, spleen, heart, testes, seminal vesicles, bones, cartilage, tendons, and ligaments. In some embodiments, the site of accumulation is intracellular. In some embodiments, the site of accumulation is within the cytoplasm. In some embodiments, the site of accumulation is within an intracellular vesicle, such as but not limited to peroxisomes, endosomes, or lysosomes. In some embodiments, the selective metabolism is facilitated by enzymes, including but not limited to, oxidases or hydrolases. In some embodiments, the hydrolase is an acidic hydrolase. In some embodiments, the acidic hydrolase is a lipase, carbohydrase, nuclease, or protease. In some embodiments, the protease is a lysosomal protease.

In some embodiments, the non-accumulating soft drugs disclosed herein have the advantages of low accumulation in tissues as compared with enzymatically stable analogs and similar serum pharmacokinetics of enzymatically stable and unstable drugs resulting in comparable efficacy of the soft-drugs and there stable analogs.

Some embodiments are directed to the design and therapeutic use of soft drugs. In some embodiments, the soft drugs are modified peptide-like or ester-containing molecules which exhibit a reduced tendency to accumulate in tissue. In some embodiments, soft drug properties include a reduced tendency for accumulation in the acidic vacuole-type organelles (lysosomes, and the like), but which do not reach high concentrations inside the vacuole due to active proteolytic or esterase enzymatic degradation events occurring inside the vacuole. In the absence of such a degradation mechanism preventing the accumulation of the basic compound inside the cells, the close congeners of such non-accumulating soft drugs display accumulation that can produce organ toxicity (e.g., nephrotoxicity).

Compounds

In some embodiments, compounds having the structure of Formula II and prodrugs, pharmaceutically acceptable salts, and hydrates thereof are provided:

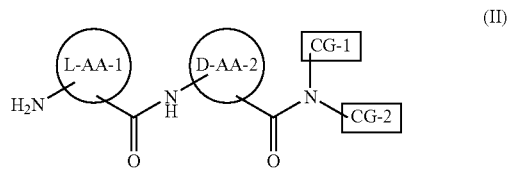

(II)

wherein:

L-AA-1 together with attached amine and carbonyl groups is a natural or artificial α-amino acid residue having an (S)-configuration, with the proviso that the a-amino functionality in the (S)-amino acid residue is not a member of a heterocyclic ring and with the proviso that the compound does not have the formula:

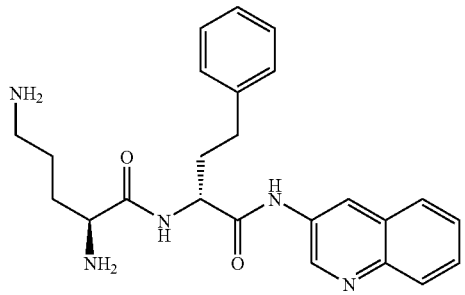

D-AA-2 together with attached amine and carbonyl groups is a natural or artificial α-amino acid residue having an (R)-configuration;

CG-1 is hydrogen or a carbon-linked capping group;

CG-2 is a carbon-linked capping group, wherein when CG-1 is a carbon-linked capping group, CG-1 and CG-2 are optionally linked together to form a 5- or 6-membered ring; and any amino groups are optionally acylated with a natural or artificial amino acid residue having an (S)-configuration.

In some embodiments, L-AA-1 and/or D-AA-2 comprise amino groups, such as primary amines. In one embodiment, the compound comprises at least two amino groups that are not part of an amide group. In one embodiment, CG-1 is hydrogen.

In one embodiment, L-AA-1 is selected from the group consisting of:

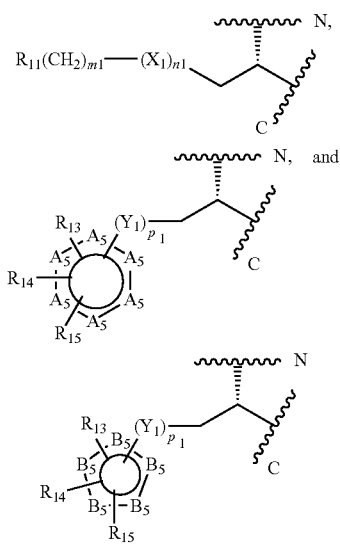

wherein:

$X_1$ is selected from the group consisting of —O— and —S—;

$m_1$ is an integer from 0 to 4;

$n_1$ is an integer from 0 to 1;

$R_{11}$ is selected from the group consisting of —NH$_2$, —NH—CH(=NH), —NH—C(CH$_3$)(=NH), —CH(=NH)NH$_2$, and —NH—C(=NH)NH$_2$;

each $A_5$ is separately selected from the group consisting of =CH— and =N—, with the proviso that no more than four $A_5$ are =N—;

each $B_5$ is separately selected from the group consisting of =CH—, =N—, —O—, —S—, —NH—, and —N(R$_6$)—, with the proviso that no more than three $B_5$ are heteroatoms;

$R_6$ is selected from the group consisting of hydrogen, $C_{1-6}$ alkyl, and $C_{3-6}$ cycloalkyl;

$R_{13}$ is selected from the group consisting of —NH$_2$, —CH$_2$NH$_2$, —CH$_2$CH$_2$NH$_2$, —OCH$_2$CH$_2$NH$_2$, —NH—CH(=NH), —CH$_2$NH—CH(=NH), —NH—C(CH$_3$)(=NH), —CH$_2$—NH—C(CH$_3$)(=NH), —C(=NH)NH$_2$, —OCH$_2$C(=NH)NH$_2$, —NH—C(=NH)NH$_2$, and —CH$_2$NH—C(=NH)NH$_2$;

$R_{14}$ and $R_{15}$ are separately selected from the group consisting of hydrogen, halogen, methyl, ethyl, hydroxyl, hydroxymethyl, methoxyl, trifluoromethyl, and trifluoromethoxyl;

$Y_1$ is selected from the group consisting of —CH$_2$—, —O—, and —S—;

$p_1$ is an integer from 0 to 1; and the wavy line with subscript N indicates point of attachment to the amine group that is attached to L-AA-1 and the wavy line with subscript C indicates point of attachment to the carbonyl group that is attached to L-AA-1.

In one embodiment, D-AA-2 is selected from the group consisting of:

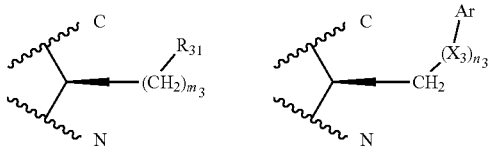

wherein:

Ar is an optionally substituted aryl or heteroaryl;

$R_{31}$ is selected from the group consisting of optionally substituted $C_{1-10}$ alkyl, $C_{1-10}$ alkenyl, $C_{1-10}$ alkynyl, and $C_{1-10}$ cycloalkyl;

$X_3$ is selected from the group consisting of —CH$_2$—, —C(CH$_3$)$_2$— —O—, and —S—;

$m_3$ is an integer from 1 to 2; and $n_3$ is an integer from 0 to 2.

In one embodiment, D-AA-1 is selected from the group consisting of:

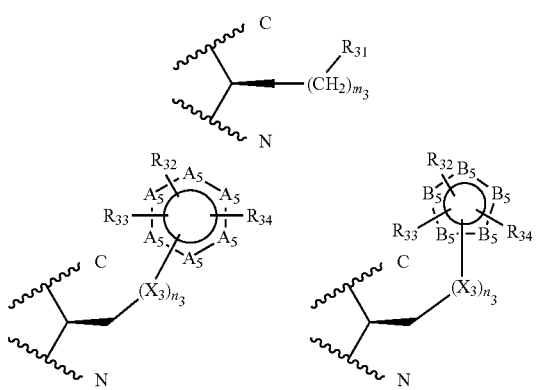

wherein:

$R_{32}$ and $R_{33}$ are separately selected from the group consisting of hydrogen, methyl, ethyl, n-propyl, isopropyl, cyclopropyl, tert-butyl, trifluoromethyl, hydroxyl, hydroxymethyl, methoxyl, trifluoromethoxyl, and halogen;

$R_{34}$ is selected from the group consisting of hydrogen, methyl, ethyl, n-propyl, isopropyl, cyclopropyl, tert-butyl, trifluoromethyl, hydroxyl, hydroxymethyl, methoxyl, trifluoromethoxyl, halogen, —NH$_2$, —CH$_2$NH$_2$, —CH$_2$CH$_2$NH$_2$, —OCH$_2$CH$_2$NH$_2$, —NH—CH(=NH), —CH$_2$NH—CH(=NH), —NH—C(CH$_3$)(=NH), —CH$_2$—NH—C(CH$_3$)(=NH), —C(=NH)NH$_2$, —OCH$_2$C(=NH)NH$_2$, —NH—C(=NH)NH$_2$, and —CH$_2$NH—C(=NH)NH$_2$;

each $A_5$ is separately selected from the group consisting of =CH— and =N—, with the proviso that no more than four $A_5$ are =N—;

each $B_5$ is separately selected from the group consisting of =CH—, =N, —O—, —S—, —NH—, and —N(R$_6$)—, with the proviso that no more than three $B_5$ are heteroatoms;

$R_6$ is selected from the group consisting of hydrogen, $C_{1-6}$ alkyl, and $C_{3-6}$ cycloalkyl; and the wavy line with subscript N indicates point of attachment to the amine group that is attached to D-AA-2 and the wavy line with subscript C indicates point of attachment to the carbonyl group that is attached to D-AA-2.

In some embodiments, CG-1 is selected from the group consisting of hydrogen, optionally substituted $C_{1-6}$ alkyl, and optionally substituted $C_{3-7}$ cycloalkyl and CG-2 is selected from the group consisting of:

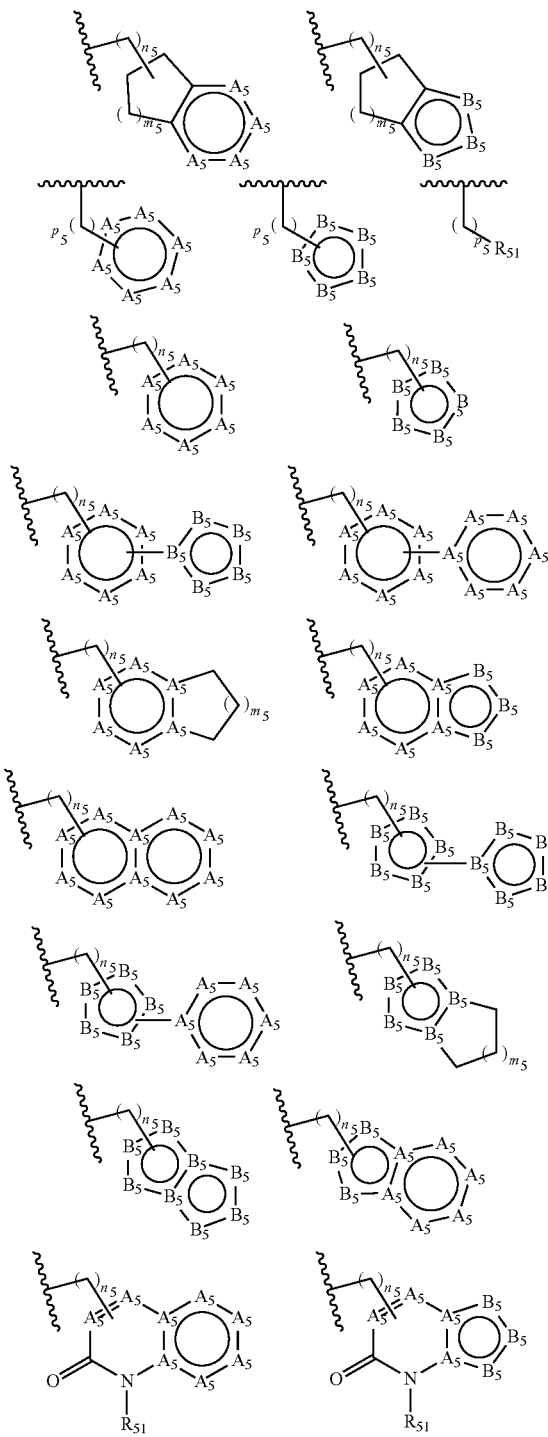

each optionally substituted with methyl, ethyl, n-propyl, isopropyl, cyclopropyl, cyclopentyl, cyclohexyl, tert-butyl, hydroxyl, methoxyl, ethoxyl, hydroxymethyl, trifluoromethyl, trifluoromethoxyl, or halogen moieties;

wherein:
each $A_5$ is separately selected from the group consisting of =CH— and =N—, with the proviso that each $A_5$ containing ring contains no more than four =N— groups;

each $B_5$ is separately selected from the group consisting of —C=, —N=, —O—, —S—, —NH—, and —N($R_6$)—, with the proviso that each $B_5$ containing ring contains no more than three heteroatoms;

$R_6$ is selected from the group consisting of hydrogen, $C_{1-6}$ alkyl, and $C_{3-6}$ cycloalkyl;

$R_{51}$ is selected from the group consisting of hydrogen, methyl, ethyl, and cyclopropyl;

$m_5$ is an integer from 1 to 3;

$n_5$ is an integer from 0 to 2; and $p_5$ is an integer from 0 to 4.

In another embodiment, a compound having the structure of Formula (III), and prodrugs, hydrates, and pharmaceutically acceptable salts thereof is provided:

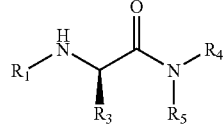

(III)

wherein:
$R_1$ is selected from the group consisting of:

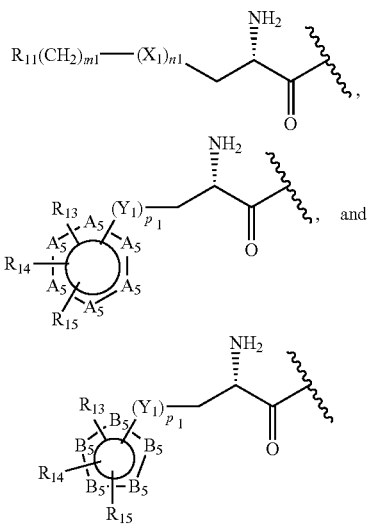

$X_1$ is selected from the group consisting of —O— and —S—;

$m_1$ is an integer from 0 to 4;

$n_1$ is an integer from 0 to 1;

$R_{11}$ is selected from the group consisting of —$NH_2$, —NH—CH(=NH), —NH—C($CH_3$)(=NH), —CH(=NH)$NH_2$, and —NH—C(=NH)$NH_2$;

$R_{13}$ is selected from the group consisting of —$NH_2$, —$CH_2NH_2$, —$CH_2CH_2NH_2$, —$OCH_2CH_2NH_2$, —NH—CH(=NH), —$CH_2$NH—CH(=NH), —NH—C($CH_3$)(=NH), —$CH_2$—NH—C($CH_3$)(=NH), —C(=NH)NH$_2$, —OCH$_2$C(=NH)NH$_2$, —NH—C(=NH)NH$_2$, and —CH$_2$NH—C(=NH)NH$_2$;

R$_{14}$ and R$_{15}$ are separately selected from the group consisting of hydrogen, halogen, methyl, ethyl, hydroxyl, hydroxymethyl, methoxyl, trifluoromethyl, and trifluoromethoxyl;

Y$_1$ is selected from the group consisting of —CH$_2$—, —O—, and —S—;

p$_1$ is an integer from 0 to 1;

R$_3$ is selected from the group consisting of:

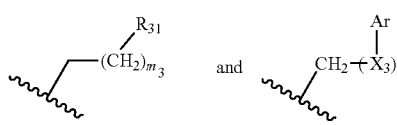

and

Ar is an optionally substituted aryl or heteroaryl;

X$_3$ is selected from the group consisting of —CH$_2$—, —C(CH$_3$)$_2$— —O—, and —S—;

m$_3$ is an integer from 1 to 2;

n$_3$ is an integer from 0 to 2;

R$_{31}$ is selected from the group consisting of optionally substituted C$_{1-10}$ alkyl, C$_{1-10}$ alkenyl, C$_{1-10}$ alkynyl, and C$_{1-10}$ cycloalkyl;

R$_4$ is selected from the group consisting of hydrogen, optionally substituted C$_{1-6}$ alkyl, and optionally substituted C$_{3-7}$ cycloalkyl;

R$_5$ is selected from the group consisting of:

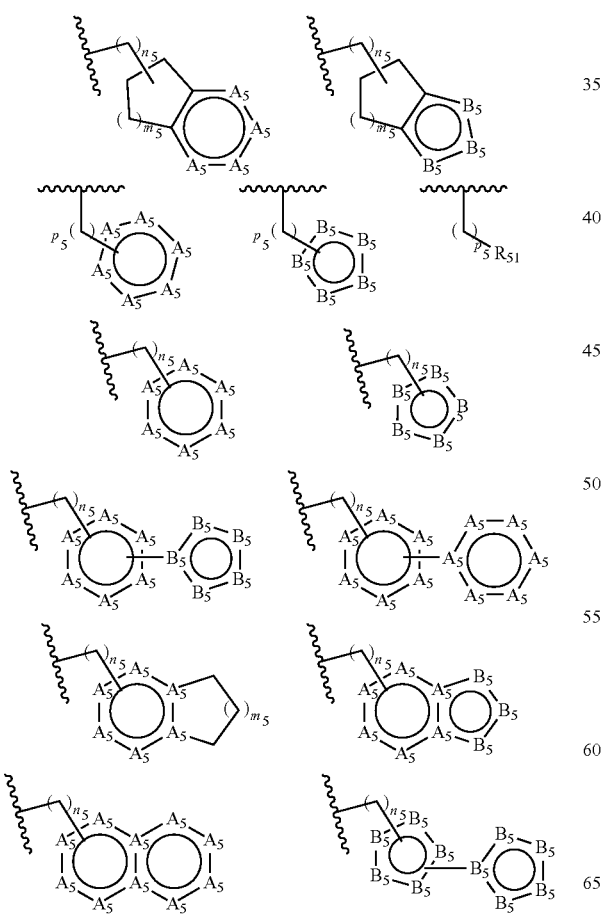

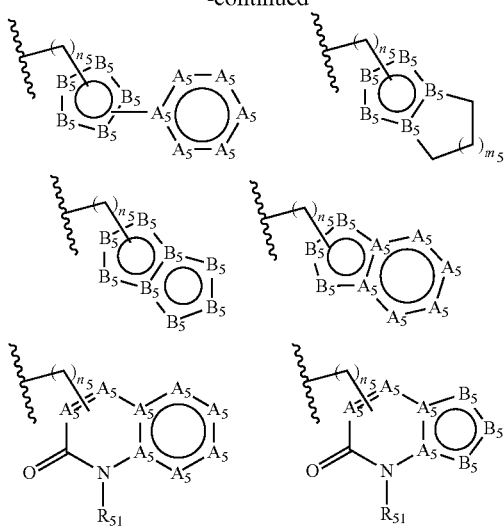

each optionally substituted with methyl, ethyl, n-propyl, isopropyl, cyclopropyl, tert-butyl, hydroxyl, methoxyl, ethoxyl, hydroxymethyl, trifluoromethyl, trifluoromethoxyl, or halogen moieties;

each A$_5$ is separately selected from the group consisting of =CH— and =N—, with the proviso that each A$_5$ containing ring contains no more than four =N— groups;

each B$_5$ is separately selected from the group consisting of —C=, —N=, —O—, —S—, —NH—, and —N(R$_6$)—, with the proviso that each B$_5$ containing ring contains no more than three heteroatoms;

R$_6$ is selected from the group consisting of hydrogen, C$_{1-6}$ alkyl, and C$_{3-6}$ cycloalkyl;

R$_{51}$ is selected from the group consisting of hydrogen, methyl, ethyl, and cyclopropyl;

m$_5$ is an integer from 1 to 3;

n$_5$ is an integer from 0 to 2;

p$_5$ is an integer from 0 to 4;

R$_4$ is optionally bound to R$_5$ to form a five-membered or six-membered heterocyclic ring; and any amino groups are optionally acylated with a natural or artificial amino acid residue having an (S)-configuration;

with the proviso that the compound does not have the formula:

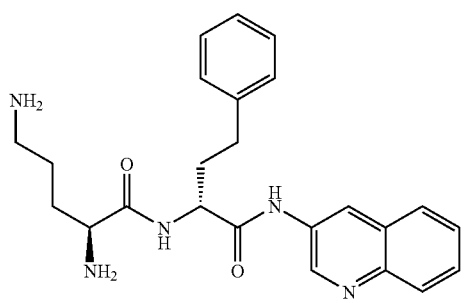

In some embodiments, R₃ is selected from the group consisting of:

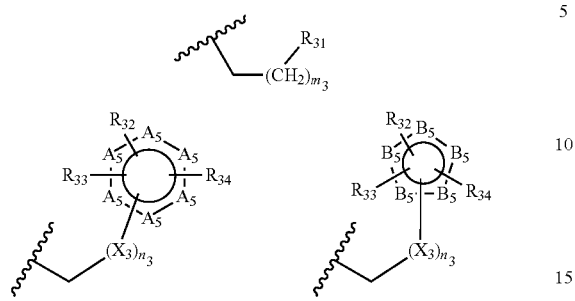

wherein:
- $R_{31}$ is selected from the group consisting of ethyl, propyl, isopropyl, isobutyl, tert-butyl, cyclopropyl, cyclobutyl, cyclopentyl, and cyclohexyl;
- $R_{32}$ and $R_{33}$ are separately selected from the group consisting of hydrogen, methyl, ethyl, n-propyl, isopropyl, cyclopropyl, tert-butyl, trifluoromethyl, hydroxyl, hydroxymethyl, methoxyl, trifluoromethoxyl, and halogen;
- $R_{34}$ is selected from the group consisting of hydrogen, methyl, ethyl, n-propyl, isopropyl, cyclopropyl, tert-butyl, trifluoromethyl, hydroxyl, hydroxymethyl, methoxyl, trifluoromethoxyl, halogen, —NH₂, —CH₂NH₂, —CH₂CH₂NH₂, —OCH₂CH₂NH₂, —NH—CH(=NH), —CH₂NH—CH(=NH), —NH—C(CH₃)(=NH), —CH₂—NH—C(CH₃)(=NH), —C(=NH)NH₂, —OCH₂C(=NH)NH₂, —NH—C(=NH)NH₂, and —CH₂NH—C(=NH)NH₂;
- $X_3$ is selected from the group consisting of —CH₂—, —C(CH₃)₂— —O—, and —S—;
- $m_3$ is an integer from 1 to 2; and
- $n_3$ is an integer from 0 to 2.

In some embodiments, R₄ is bound to R₅ to form a five-membered or six-membered heterocyclic ring and the compound of formula III is selected from the group consisting of:

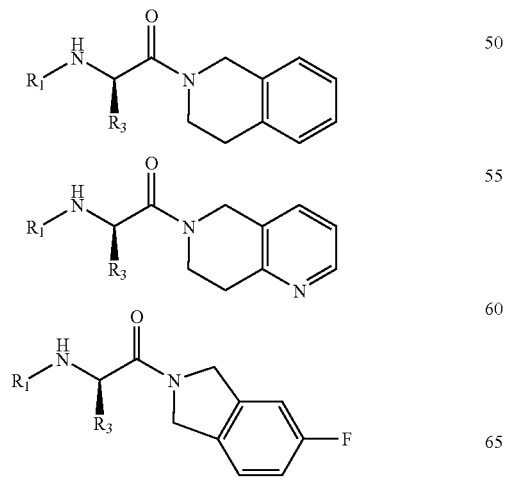

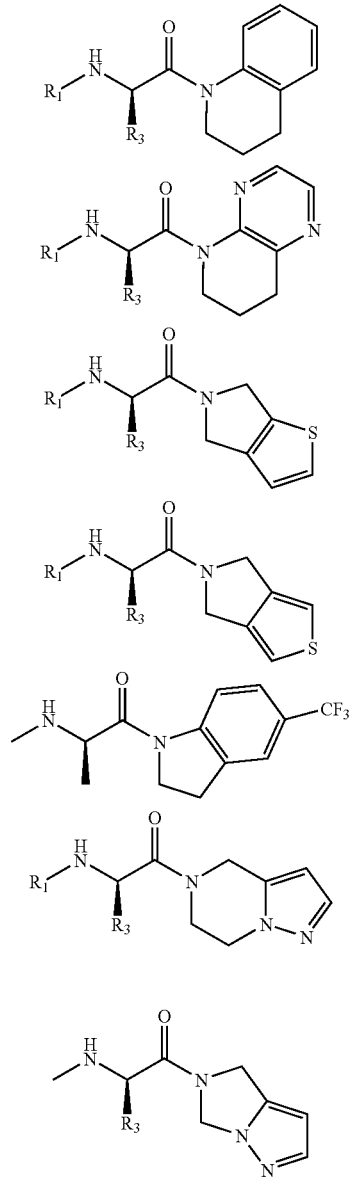

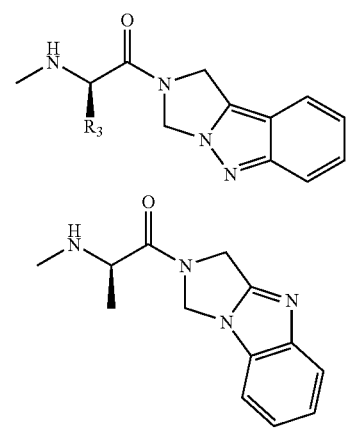

In some embodiments of the compounds of formula II or III, —N(CG-1)(CG-2) or —N(R₄)(R₅) is selected from the group consisting of:
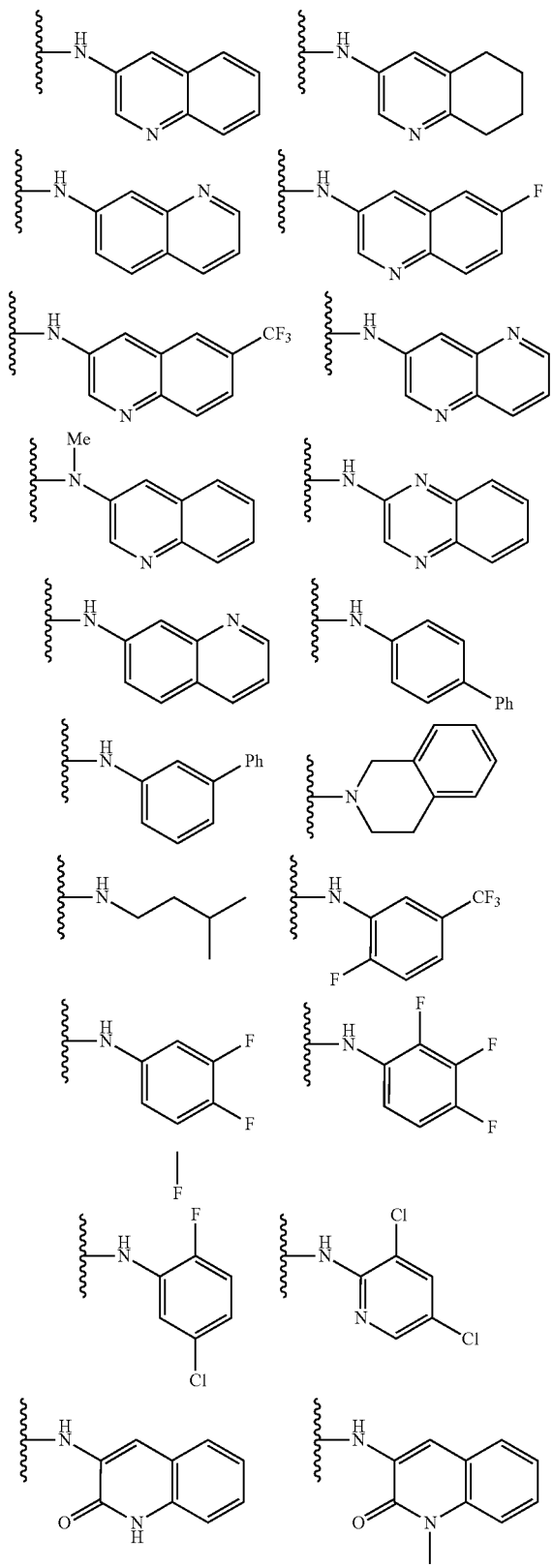
-continued
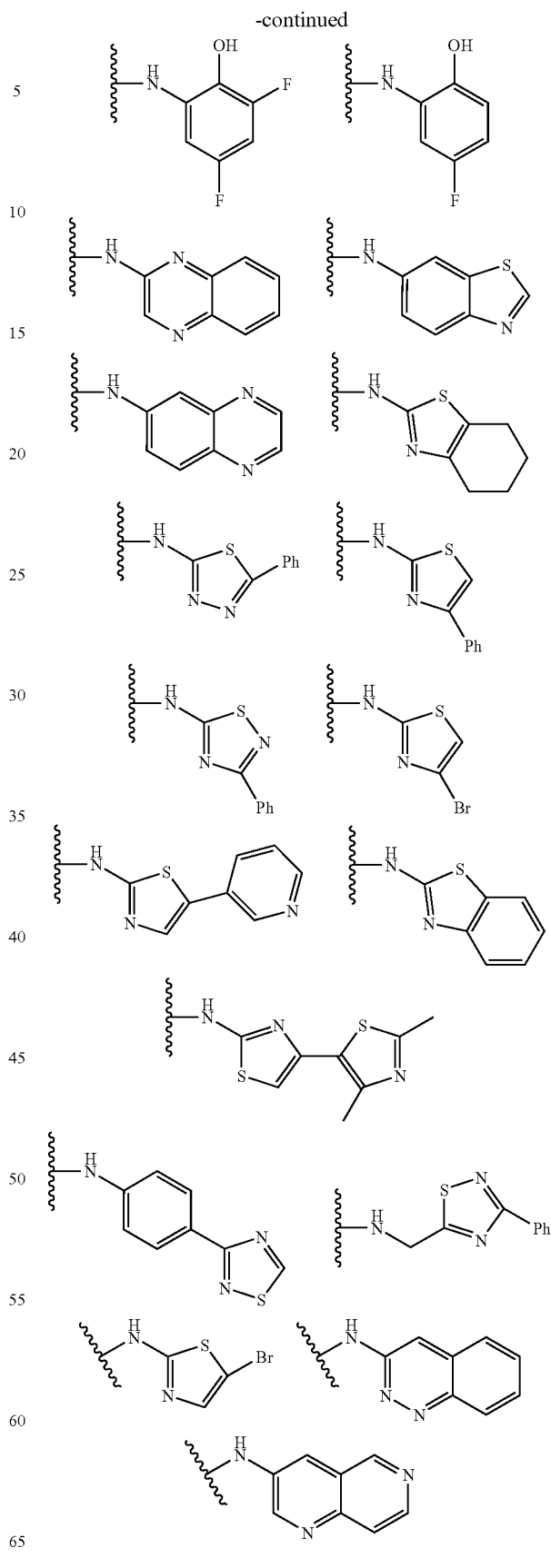

In some of these embodiments, the compound is selected from the group consisting of:
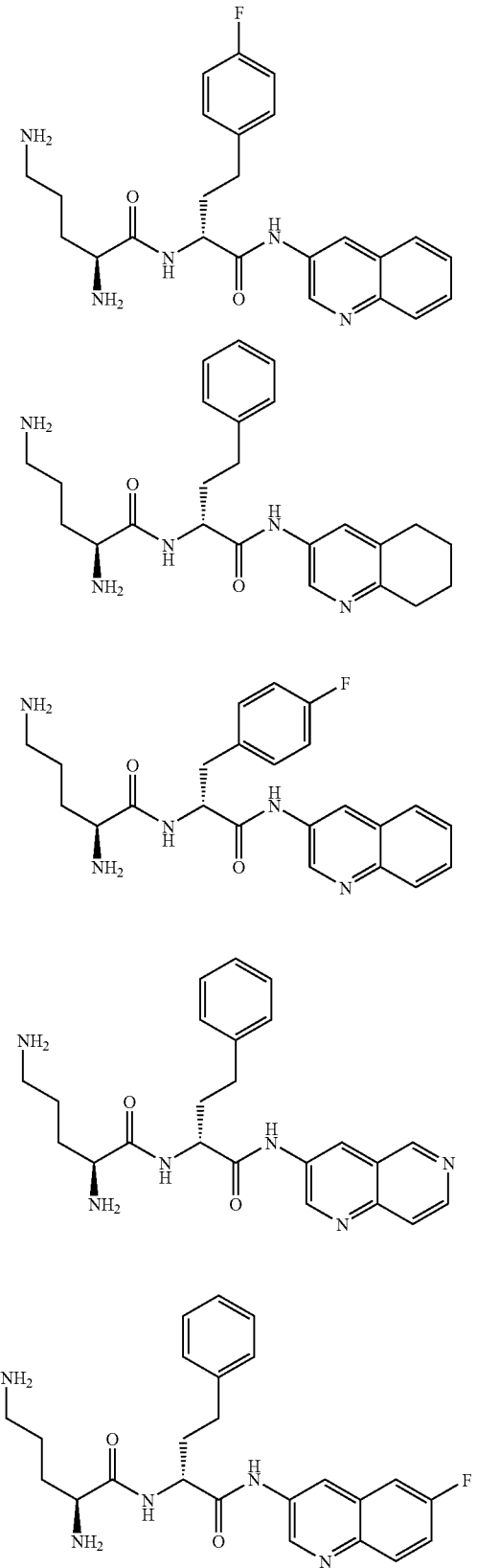
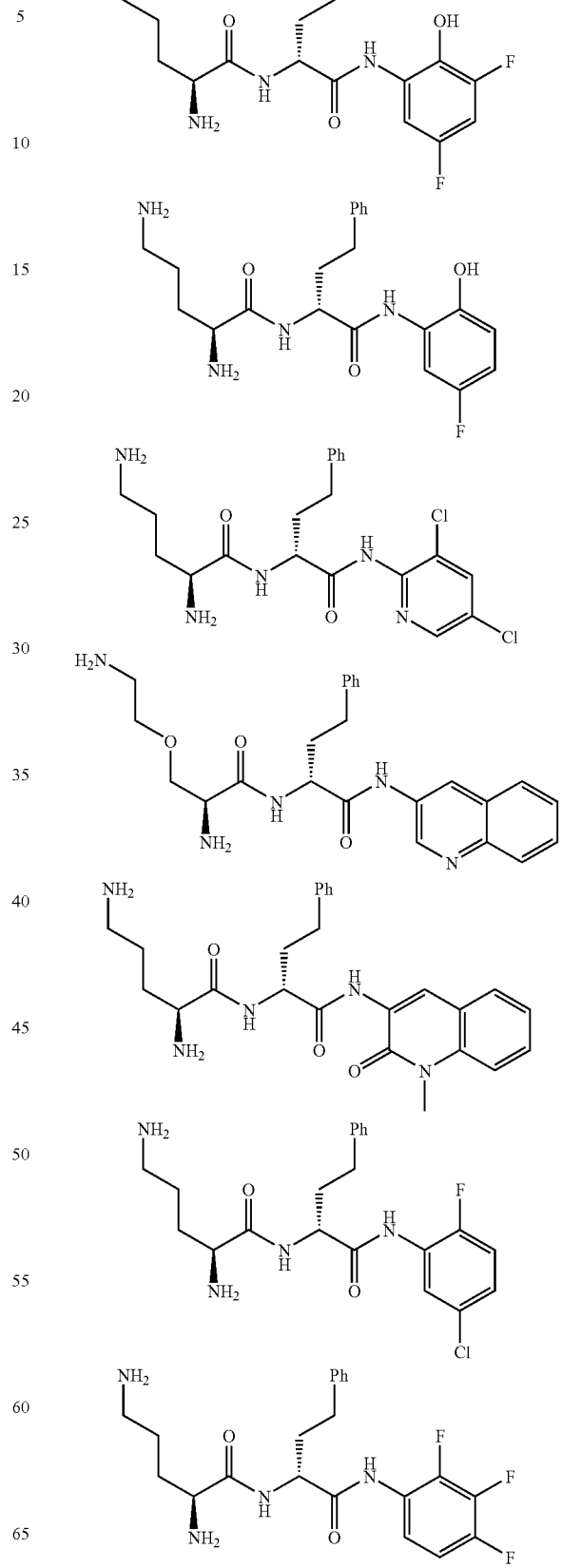

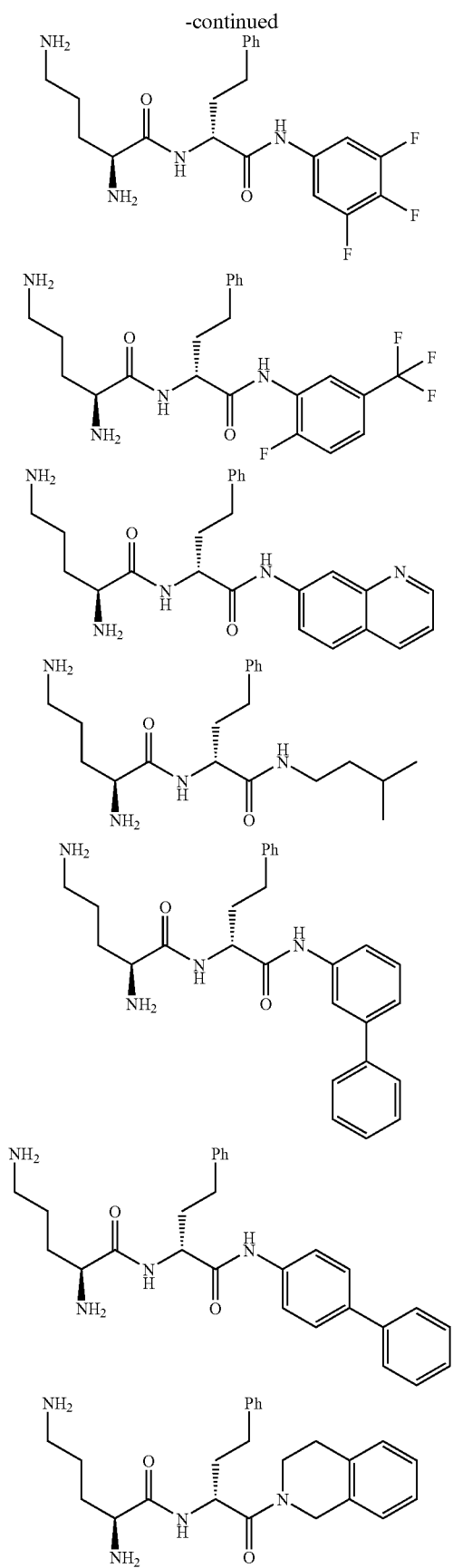

-continued
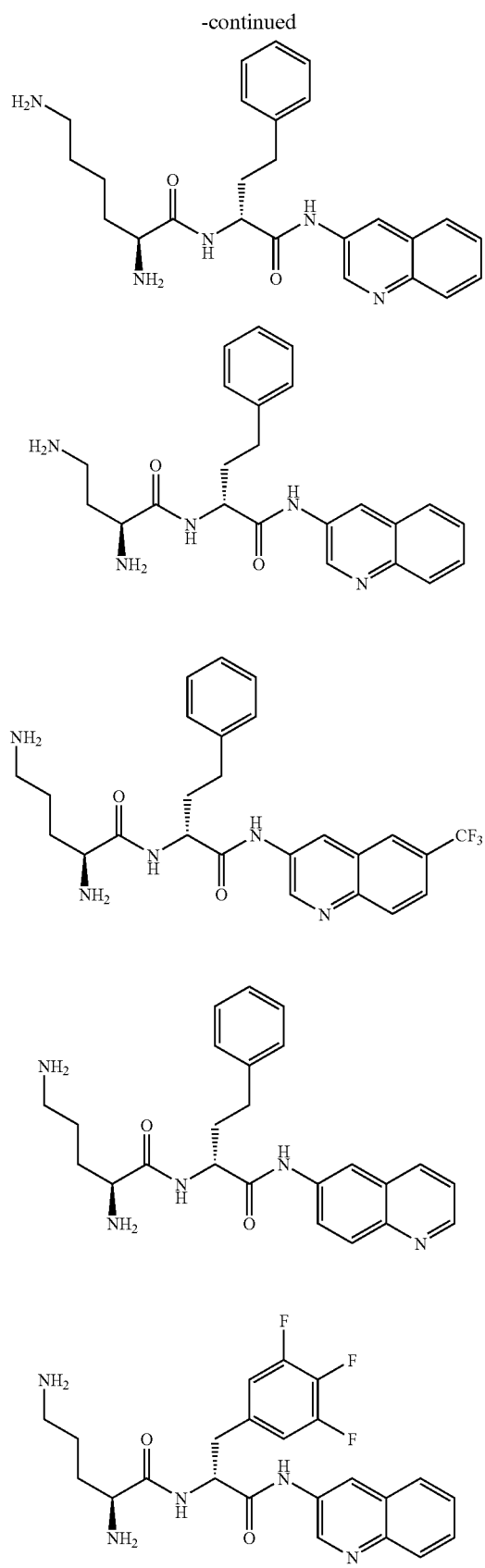
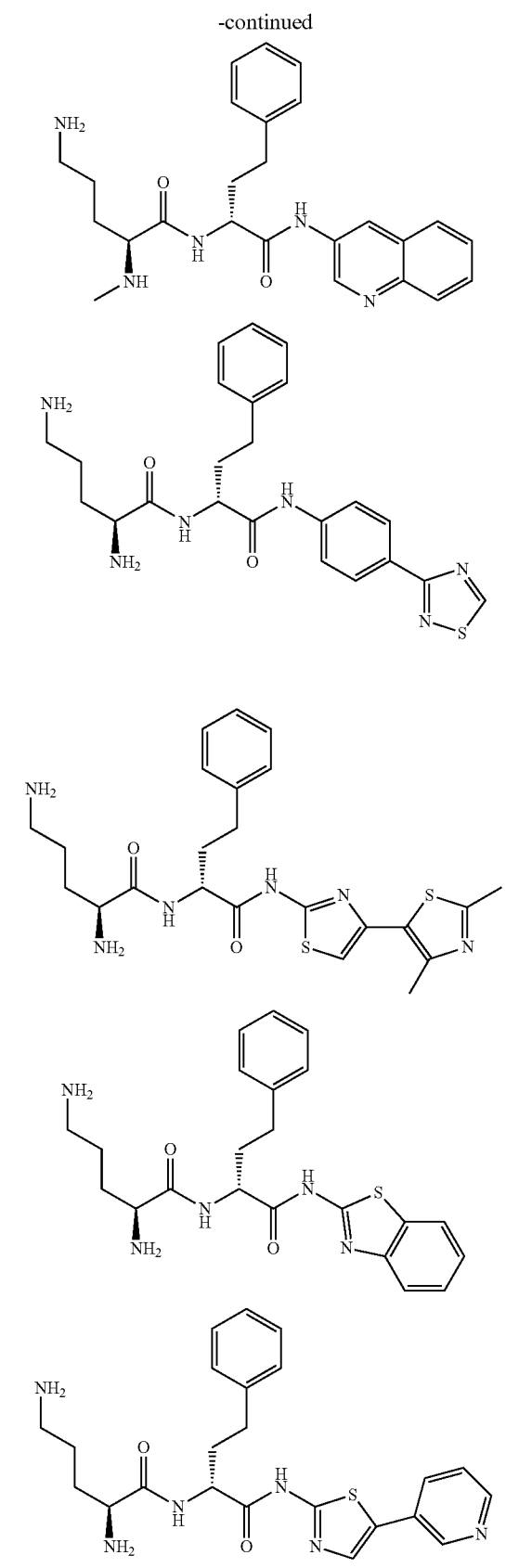

-continued
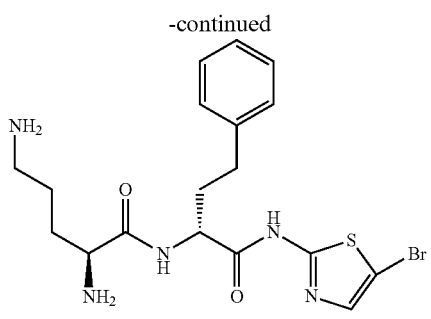
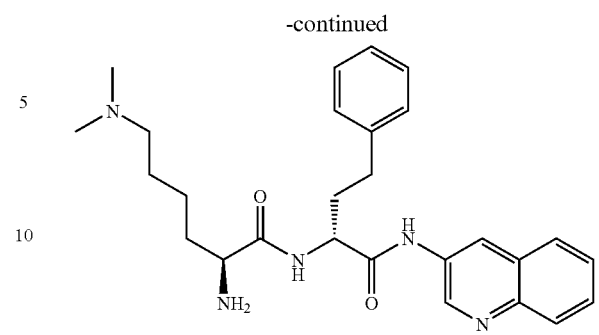
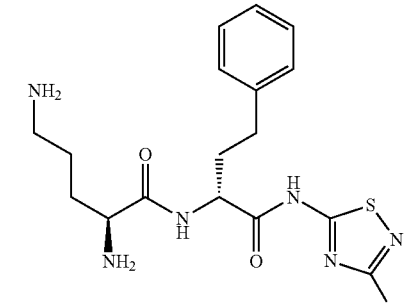
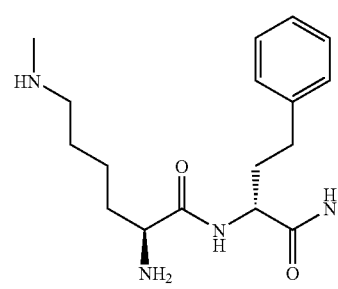
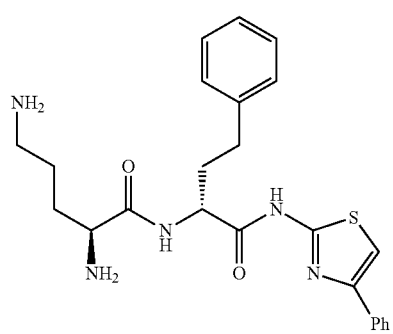
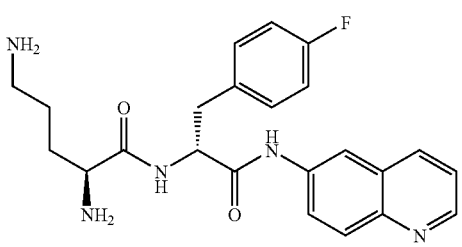
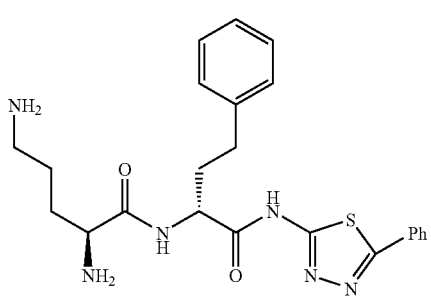
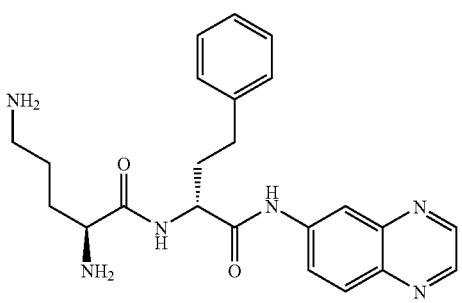
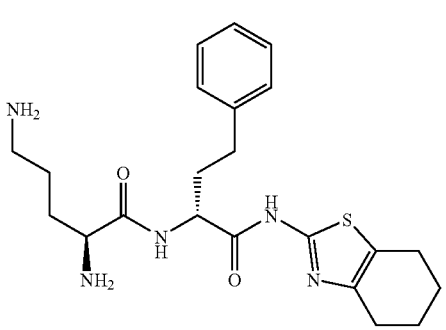
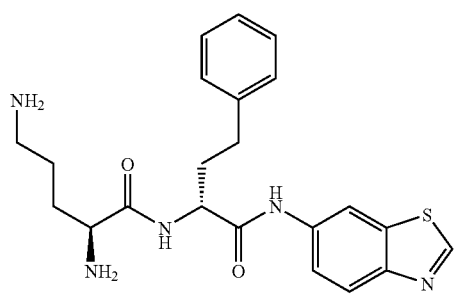

-continued

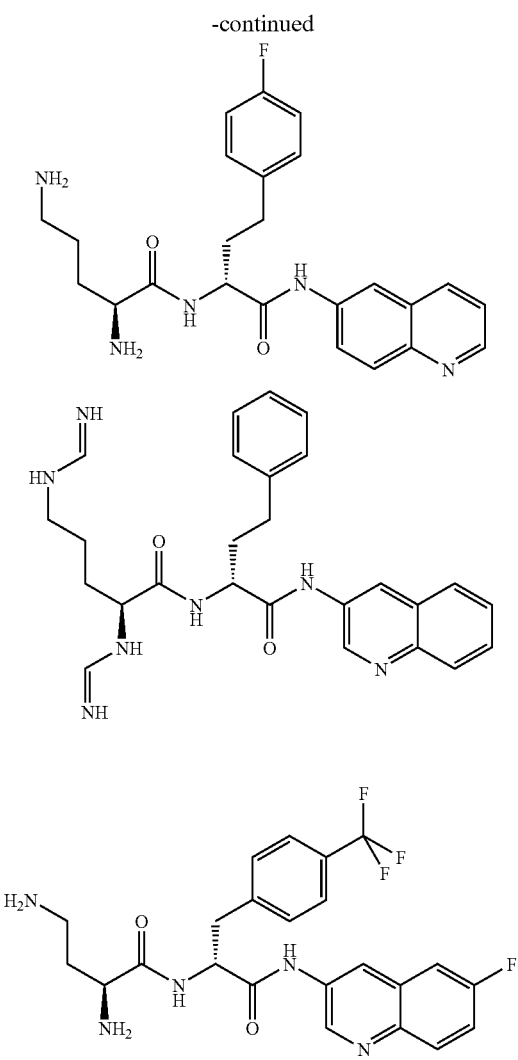

-continued

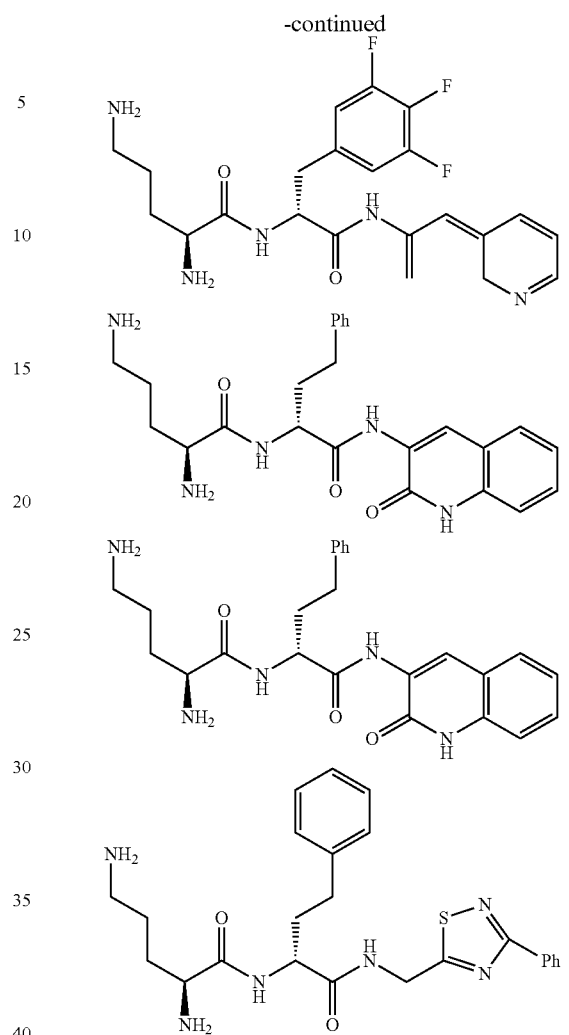

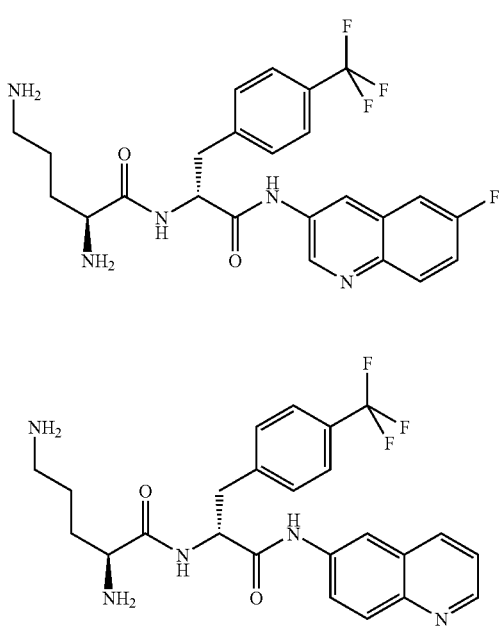

In some embodiments, the compound is selected from the group consisting of:

2-(S)-Amino-N-{4-amino-1-(S)-[3-phenyl-1-(R)-(quinolin-3-ylcarbamoyl)-propylcarbamoyl]-butyl}-succinamic acid;

2-(S),5-Diamino-pentanoic acid [3-phenyl-1-(R)-(5,6,7,8-tetrahydro-quinolin-3-ylcarbamoyl)-propyl]-amide;

2-(S),5-Diamino-pentanoic acid [3-phenyl-1-(R)-(quinolin-6-ylcarbamoyl)-propyl]-amide;

2-(S),5-Diamino-pentanoic acid [3-(4-fluoro-phenyl)-1-(R)-(quinolin-3-ylcarbamoyl)-propyl]-amide;

2-(S),5-Diamino-pentanoic acid [2-(4-fluoro-phenyl)-1-(R)-(quinolin-3-ylcarbamoyl)-ethyl]-amide;

2-(S),5-Diamino-pentanoic acid [1-(R)-(6-fluoro-quinolin-3-ylcarbamoyl)-3-phenyl-propyl]-amide;

2-(S),5-Diamino-pentanoic acid [1-(R)-([1,6]naphthyridin-3-ylcarbamoyl)-3-phenyl-propyl]-amide;

2-(S),5-Diamino-pentanoic acid [1-(R)-(6-trifluoromethyl-quinolin-3-ylcarbamoyl)-3-phenyl-propyl]-amide;

2-(S),4-Diamino-N-[3-phenyl-1-(R)-(quinolin-3-ylcarbamoyl)-propyl]-butyramide;

2-(S),6-Diamino-hexanoic acid [3-phenyl-1-(R)-(quinolin-3-ylcarbamoyl)-propyl]-amide;

2-(S),5-Diamino-pentanoic acid [1-(R)-(methyl-quinolin-3-yl-carbamoyl)-3-phenyl-propyl]-amide;
2-(S),5-Diamino-pentanoic acid [3-phenyl-1-(R)-(quinoxalin-2-ylcarbamoyl)-propyl]-amide;
2-(S),5-Diamino-pentanoic acid [1-(R)-(quinolin-3-ylcarbamoyl)-3-(4-trifluoromethyl-phenyl)-propyl]-amide;
2-(S),5-Diamino-pentanoic acid [1-(R)-(quinolin-3-ylcarbamoyl)-2-(4-trifluoromethyl-phenyl)-ethyl]-amide;
2(R)-(2-(S),5-Diamino-pentanoylamino)-5-methyl-hexanoic acid quinolin-3-ylamide;
2-(S),5-Diamino-pentanoic acid [2-phenyl-1-(R)-(quinolin-3-ylcarbamoyl)-ethyl]-amide;
2-(S),5-Diamino-pentanoic acid [1-(R)-(3,4-dihydro-1H-isoquinoline-2-carbonyl)-3-phenyl-propyl]-amide;
2-(S),5-Diamino-pentanoic acid [1-(R)-(biphenyl-4-ylcarbamoyl)-3-phenyl-propyl]-amide;
2-(S),5-Diamino-pentanoic acid [1-(R)-(biphenyl-3-ylcarbamoyl)-3-phenyl-propyl-amide;
2-(S),5-Diamino-pentanoic acid [1-(R)-(3-methyl-butyl-carbamoyl)-3-phenyl-propyl]-amide;
2-(S),5-Diamino-pentanoic acid [3-phenyl-1-(R)-(quinolin-7-ylcarbamoyl)-propyl]-amide;
2-(S),5-Diamino-pentanoic acid [1-(R)-(2-fluoro-5-trifluoromethyl-phenylcarbamoyl)-3-phenyl-propyl]-amide;
2-(S),5-Diamino-pentanoic acid [3-phenyl-1-(R)-(3,4,5-trifluoro-phenylcarbamoyl)-propyl]-amide;
2-(S),5-Diamino-pentanoic acid [3-phenyl-1-(R)-(2,3,4-trifluoro-phenylcarbamoyl)-propyl]-amide;
2-(S),5-Diamino-pentanoic acid [1-(R)-(5-chloro-2-fluoro-phenylcarbamoyl)-3-phenyl-propyl]-amide;
2-(S),5-Diamino-pentanoic acid [1-(R)-(1-methyl-2-oxo-1,2-dihydro-quinolin-3-ylcarbamoyl)-3-phenyl-propyl]-amide;
3-(S)-Amino-N-{4-(S)-amino-4-[3-phenyl-1-(R)-(quinolin-3-ylcarbamoyl)-propylcarbamoyl]-butyl}-succinamic acid;
2-(R)-[2-(S)-Amino-3-(2-amino-ethoxy)-propionylamino]-4-phenyl-N-quinolin-3-yl-butyramide;
2-(S),5-Diamino-pentanoic acid [1-(R)-(3,5-dichloro-pyridin-2-ylcarbamoyl)-3-phenyl-propyl]-amide;
2-(S),5-Diamino-pentanoic acid [1-(R)-(5-fluoro-2-hydroxy-phenylcarbamoyl)-3-phenyl-propyl]-amide;
2-(S),5-Diamino-pentanoic acid [1-(R)-(3,5-difluoro-2-hydroxy-phenylcarbamoyl)-3-phenyl-propyl]-amide;
2-(S),5-Diamino-pentanoic acid [1-(R)-(cinnolin-3-ylcarbamoyl)-3-phenyl-propyl]-amide;
2-(S),5-Diamino-pentanoic acid [1-(R)-(2-oxo-1,2-dihydro-quinolin-3-ylcarbamoyl)-3-phenyl-propyl]-amide;
2-(S),5-Diamino-pentanoic acid [1-(R)-(quinolin-3-ylcarbamoyl)-2-(3,4,5-trifluoro-phenyl)-ethyl]-amide;
2-(S),5-Diamino-pentanoic acid [1-(R)-(quinolin-6-ylcarbamoyl)-2-(3,4,5-trifluoro-phenyl)-ethyl]-amide;
3-Amino-(S)—N-{4-(S)-(2-(3)-(S)-amino-3-carboxy-propionylamino)-4-[3-phenyl-1-(R)-(quinolin-3-ylcarbamoyl)-propylcarbamoyl]-butyl}-succinamic acid;
2-(S),5-Diamino-pentanoic acid [1-(R)-(quinolin-6-ylcarbamoyl)-2-(4-trifluoromethyl-phenyl)-ethyl]-amide;
5-Amino-2-(S)-methylamino-pentanoic acid [3-phenyl-1-(R)-(quinolin-3-ylcarbamoyl)-propyl]-amide;
2-(S),5-Diamino-pentanoic acid [1-(R)-(6-fluoro-quinolin-3-ylcarbamoyl)-2-(4-trifluoromethyl-phenyl)-ethyl]-amide;
2-(S),4-Diamino-N-[1-(R)-(6-fluoro-quinolin-3-ylcarbamoyl)-2-(4-trifluoromethyl-phenyl)-ethyl]-butyramide;

2-(S),5-Bis-formimidoylamino-pentanoic acid [3-phenyl-1-(R)-(quinolin-3-ylcarbamoyl)-propyl]-amide;
2-(S),5-Diamino-pentanoic acid [3-(4-fluoro-phenyl)-1-(R)-(quinolin-6-ylcarbamoyl)-propyl]-amide;
2-(S),5-Diamino-pentanoic acid [1-(R)-(benzothiazol-6-ylcarbamoyl)-3-phenyl-propyl]-amide;
2-(S),5-Diamino-pentanoic acid [3-phenyl-1-(R)-(quinoxalin-6-ylcarbamoyl)-propyl]-amide;
2-(S),5-Diamino-pentanoic acid [2-(4-fluoro-phenyl)-1-(R)-(quinolin-6-ylcarbamoyl)-ethyl]-amide;
2-(S)-Amino-6-methylamino-hexanoic acid [3-phenyl-1-(R)-(quinolin-3-ylcarbamoyl)-propyl]-amide;
2-(S)-Amino-6-dimethylamino-hexanoic acid [3-phenyl-1-(R)-(quinolin-3-ylcarbamoyl)-propyl]-amide;
2-(S),5-Diamino-pentanoic acid [3-phenyl-1-(R)-(4,5,6,7-tetrahydro-benzothiazol-2-ylcarbamoyl)-propyl]-amide;
2,5-Diamino-pentanoic acid [3-phenyl-1-(R)-(5-phenyl-[1,3,4]thiadiazol-2-ylcarbamoyl)-propyl]-amide;
2-(S),5-Diamino-pentanoic acid [3-phenyl-1-(R)-(4-phenyl-thiazol-2-ylcarbamoyl)-propyl]-amide;
2-(S),5-Diamino-pentanoic acid [3-phenyl-1-(R)-(3-phenyl-[1,2,4]thiadiazol-5-ylcarbamoyl)-propyl]-amide;
2-(S),5-Diamino-pentanoic acid [1-(R)-(5-bromo-thiazol-2-ylcarbamoyl)-3-phenyl-propyl]-amide;
2-(S),5-Diamino-pentanoic acid [3-phenyl-1-(R)-(5-pyridin-3-yl-thiazol-2-ylcarbamoyl)-propyl]-amide;
2-(S),5-Diamino-pentanoic acid [1-(R)-(benzothiazol-2-ylcarbamoyl)-3-phenyl-propyl]-amide;
2-(S),5-Diamino-pentanoic acid [1-(R)-(2',4'-dimethyl-[4,5']bithiazolyl-2-ylcarbamoyl)-3-phenyl-propyl]-amide;
2-(S),5-Diamino-pentanoic acid [3-phenyl-1-(R)-(4-[1,2,4]thiadiazol-3-yl-phenylcarbamoyl)-propyl]-amide;
2-(S),5-Diamino-pentanoic acid {3-phenyl-1-(R)-[(3-phenyl-[1,2,4]thiadiazol-5-ylmethyl)-carbamoyl]-propyl}-amide; and
2-(S),4-Diamino-N-[3-phenyl-1-(R)-(quinolin-6-ylcarbamoyl)-propyl]-butyramide.

In other embodiments of the compounds of formulae II or III, —N(CG-1)(CG-2) or —N(R₄)(R₅) is selected from the group consisting of:

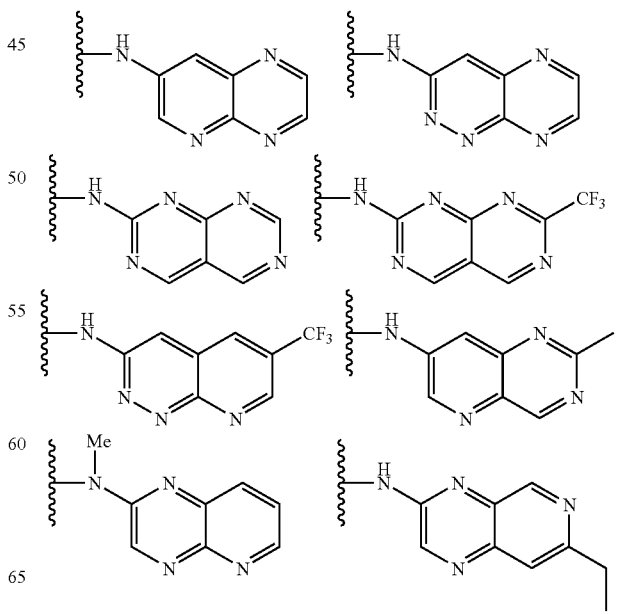

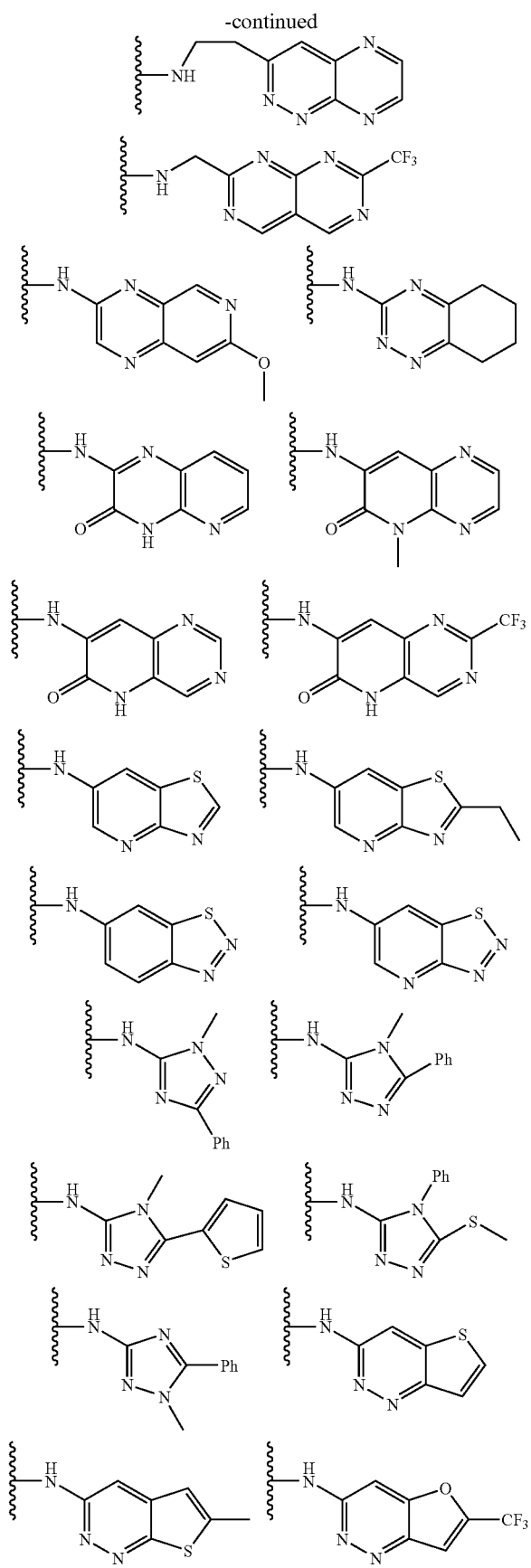
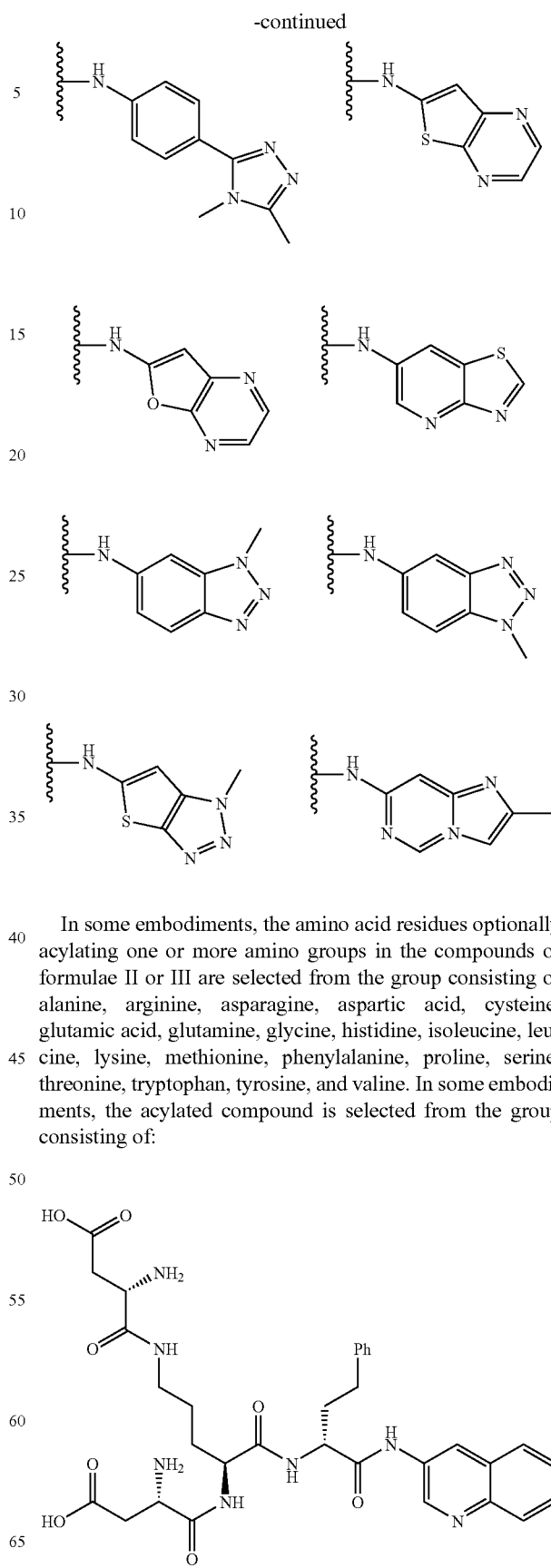

In some embodiments, the amino acid residues optionally acylating one or more amino groups in the compounds of formulae II or III are selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. In some embodiments, the acylated compound is selected from the group consisting of:

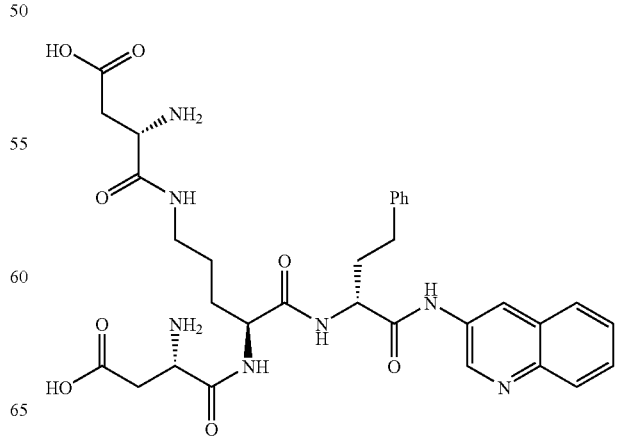

-continued

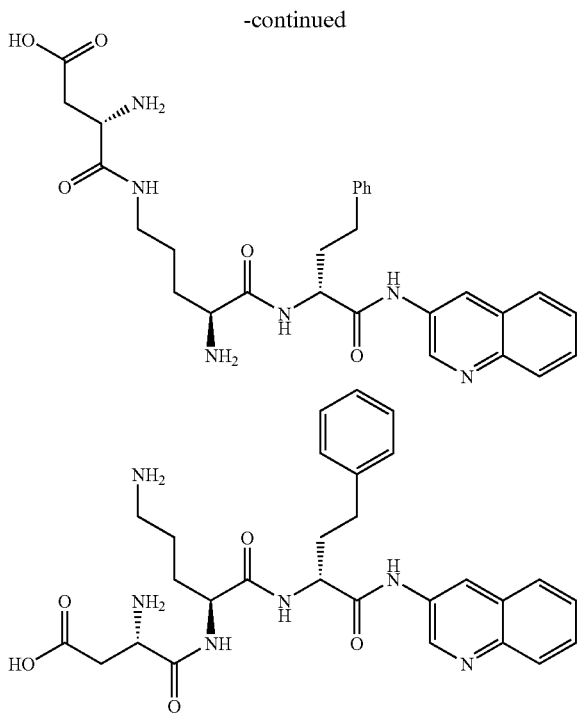

In some embodiments, prodrugs, metabolites, hydrates, and pharmaceutically acceptable salts of the compounds disclosed herein are provided.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded through an amide linkage where the peptide is metabolized to reveal the active moiety. Conventional procedures for the selection and preparation of suitable prodrug derivatives are described, for example, in Design of Prodrugs, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

Metabolites of the compounds disclosed herein include active species that are produced upon introduction of the compounds into the biological milieu.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compounds disclosed herein can be used alone, in combination with other compounds disclosed herein, or in combination with one or more other agents active in the therapeutic areas described herein.

The term "halogen atom," as used herein, means any one of the radio-stable atoms of column 7 of the Periodic Table of the Elements, e.g., fluorine, chlorine, bromine, or iodine, with fluorine and chlorine being preferred.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be a linking amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "alkyl," as used herein, means any unbranched or branched, substituted or unsubstituted, saturated hydrocarbon. The alkyl moiety, may be branched, straight chain, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from substituted or unsubstituted alkyl, substituted or unsubstituted alkenyl, substituted or unsubstituted alkynyl, substituted or unsubstituted cycloalkyl, substituted or unsubstituted cylcloalkenyl, substituted or unsubstituted aryl, substituted or unsubstituted heteroaryl, substituted or unsubstituted heteroaryloxy, heterocyclyl, heterocyclooxy, heteroalicyclyl, hydroxyl, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substituent may be substituted with one of the above substituents.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

An "alkenyl" moiety refers to a group consisting of at least two carbon atoms and at least one carbon-carbon double bond. An alkenyl may be unbranched or branched, substituted or unsubstituted, unsaturated hydrocarbon including polyunsaturated hydrocarbons. In some embodiments, the alkenyl is a $C_1$-$C_6$ unbranched, mono-unsaturated or di-unsaturated, unsubstituted hydrocarbons. The term "cycloalkenyl" refers to any non-aromatic hydrocarbon ring, preferably having five to twelve atoms comprising the ring.

An "alkyne" moiety refers to a group consisting of at least two carbon atoms and at least one carbon-carbon triple bond.

Unless otherwise indicated, the substituent "R" appearing by itself and without a number designation refers to a substituent selected from the group consisting of alkyl, cycloalkyl, aryl, heteroaryl (bonded through a ring carbon) and heteroalicyclyl (bonded through a ring carbon).

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

An "O-carboxy" group refers to a RC(=O)O— group, where R is as defined herein.

A "C-carboxy" group refers to a —C(=O)OR groups where R is as defined herein.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "acylalkyl" refers to a RC(=O)R'— group, with R as defined herein, and R' being a diradical alkylene group. Examples of acylalkyl, without limitation, may include CH$_3$C(=O)CH$_2$—, CH$_3$C(=O)CH$_2$CH$_2$—, CH$_3$CH$_2$C(=O)CH$_2$CH$_2$—, CH$_3$C(=O)CH$_2$CH$_2$CH$_2$—, and the like.

Unless otherwise indicated, when a substituent is deemed to be "optionally substituted," it is meant that the substitutent is a group that may be substituted with one or more group(s) individually and independently selected from alkyl, alkenyl, alkynyl, cycloalkyl, aryl, heteroaryl, heteroalicyclic, hydroxyl, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

The term "heterocyclyl" is intended to mean three-, four-, five-, six-, seven-, and eight- or more membered rings wherein carbon atoms together with from 1 to 3 heteroatoms constitute said ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Binding to the heterocycle can be at the position of a heteroatom or via a carbon atom of the heterocycle, or, for benzo-fused derivatives, via a carbon of the benzenoid ring.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

Methods of Preparation

The compounds disclosed herein may be synthesized by methods described below, or by modification of these methods. Ways of modifying the methodology include, among others, temperature, solvent, reagents etc., and will be obvious to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991, which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety.

In the following schemes P, $P_1$, $P_2$ are used to denote protecting groups compatible with the reaction sequences. Protecting groups P, $P_1$, $P_2$ existing in a specific synthetic scheme may represent different protecting groups but may also represent identical protecting groups if the synthetic strategy does not require protecting group orthogonality. SS— is used to mark covalent attachment of an intermediate to a polymeric solid support. X denotes a leaving group in amide coupling or in carbon-carbon bond formation. $R_L$, $R_D$ and $R_{LD}$ denote substituents in alfa position of homochiral-L, homochiral-D and racemic α-amino acid functionality respectively. Other abbreviations used include: Boc=t-butoxycarbonyl, OBn=benzyl ester, CBz=carbobenzyloxy, and OSu=N-hydroxysuccinimide ester.

In the following schemes, additional steps maybe required for manipulation of substituents $R_L$ and $R_D$. For example hydrogenation in the presence of catalyst can be performed of the cyano group in order to unmask the aminomethyl group.

The general strategies of assembling the peptidic compounds shown below are meant to be illustrative and are not meant to be limiting in any way.

The absolute stereochemistry of the chiral centers is represented in structures with customary wedge-bond representations and the chiral centers of racemic mixtures are represented with customary wavy-line bond representations. Consequently a structure comprising one wedge bond and one wavy-line bond represents a mixture of diastereoisomers.

When the carboxylic acid functionality is activated for the formation of the amide bond the active intermediates can be isolated for the consecutive coupling reaction with the amine or the activation can be performed in situ without the isolation of the active intermediate. The activation of the carboxylic acid functionality can be performed prior to the addition of the amine as well as in the presence of the amine provided that a proper activating reagent is selected.

Different protecting groups, coupling strategies, deprotection reactions shown in the schemes below are typical examples of the methods generally employed in the synthesis of peptidic bonds (*Principles of Peptide Synthesis*, 2$^{nd}$ Ed, M. Bodanszky, Spriner-Verlag, Berlin, 1993) and the methods shown are meant to be illustrative and are not meant to be limiting in any way.

Method A

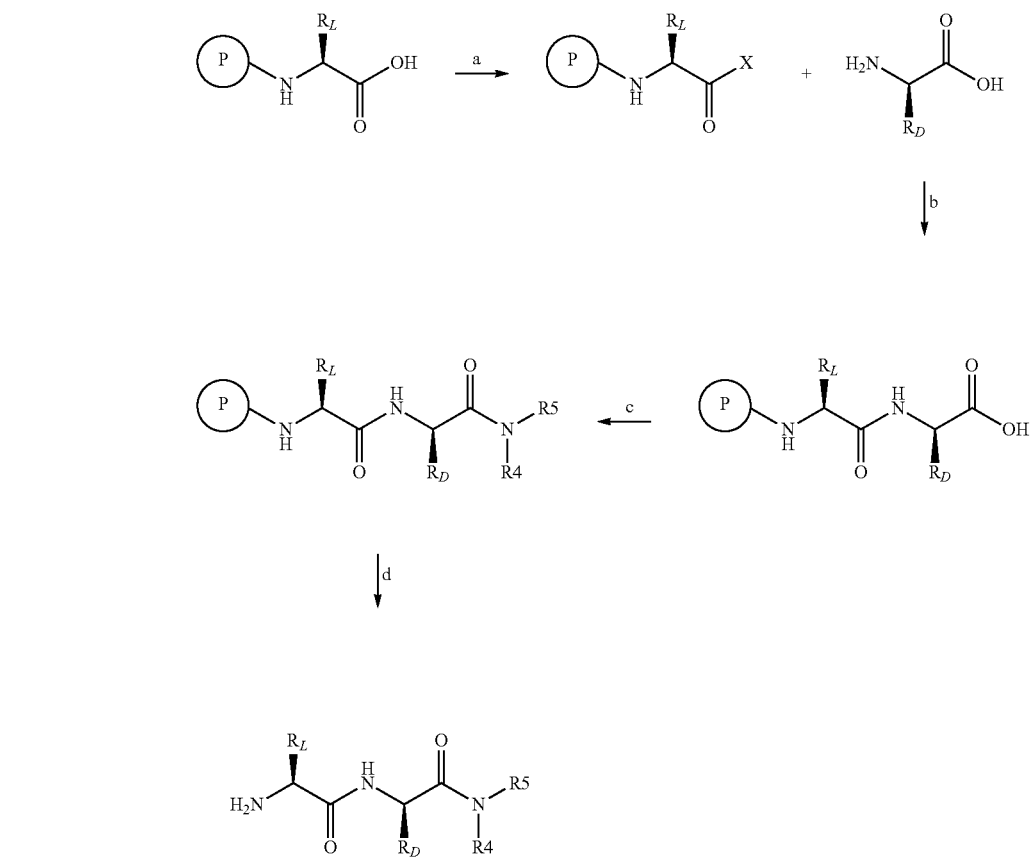

In some embodiments, compounds disclosed herein are synthesized according to method A above. One specific example of a synthesis according to method A is as follows:

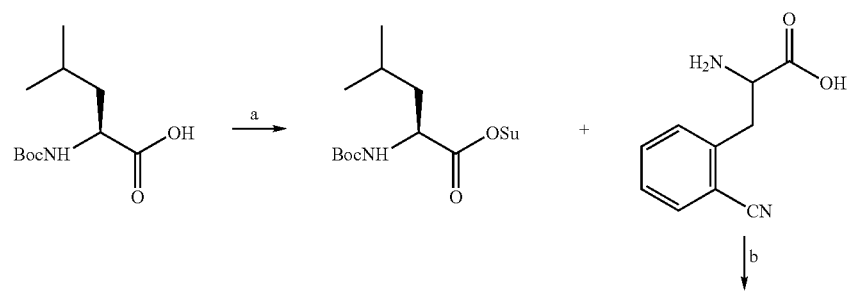

-continued

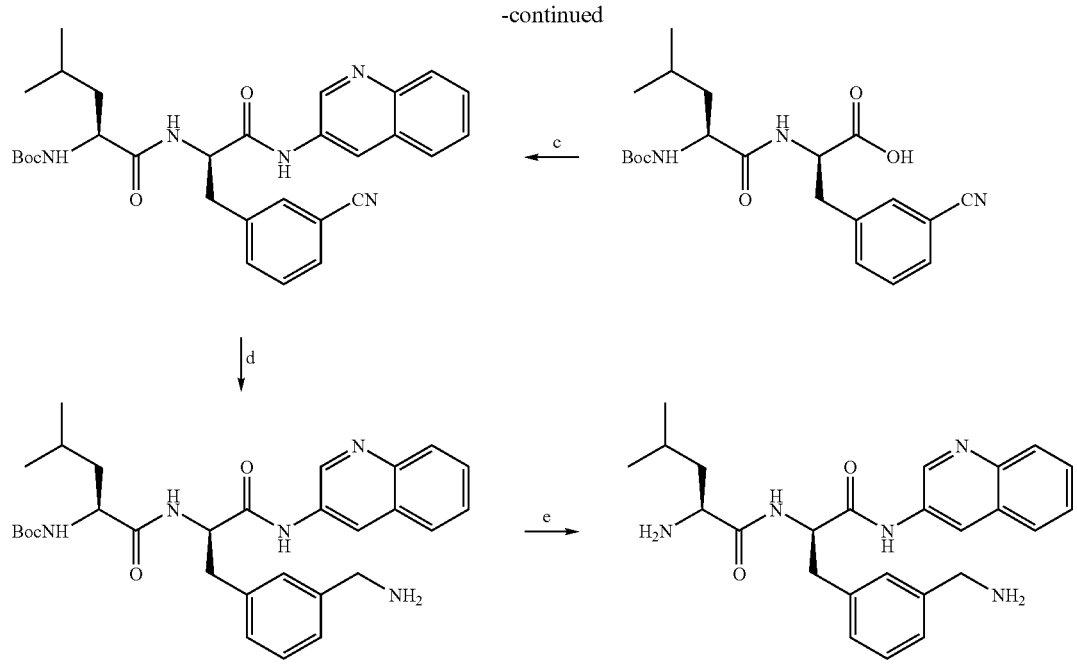

A t-Butoxycarbonyl (Boc) group can be used to protect the amine functionality as shown above, however any other protective group compatible with the reaction sequence can also be used. Activation by formation of N-hydroxysuccinimide ester (step a) is also meant here to be an illustrative example of an activation strategy and any other activation strategy typically employed for the formation of the amide bond can also be used.

Method B

In some embodiments, compounds disclosed herein are synthesized according to Method B above. The aminoacid intermediate containing the $R_D$ substituent can be used in an ester form which may facilitate coupling and purification of the product of step b of Method B. One specific example of a synthesis according to Method B is as follows:

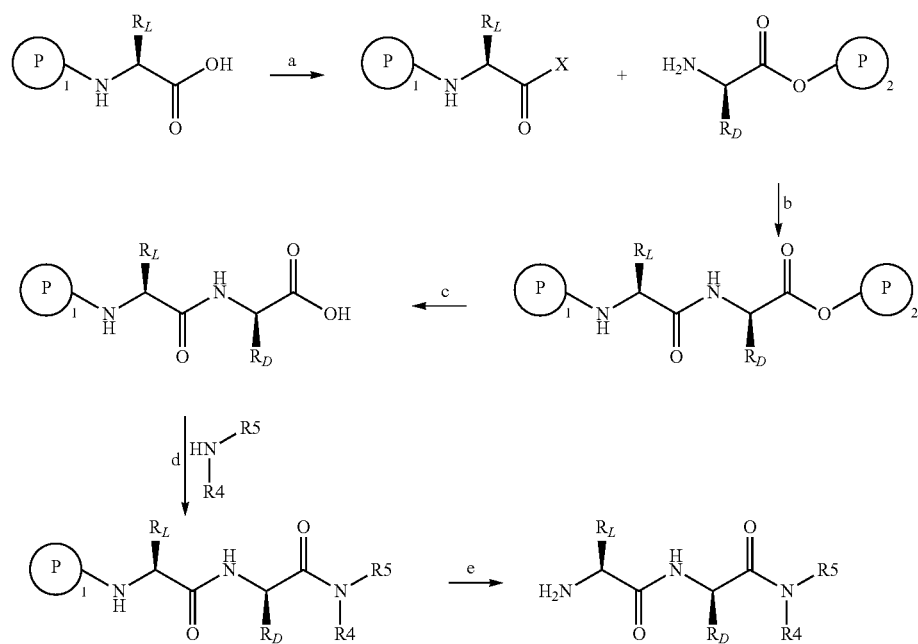

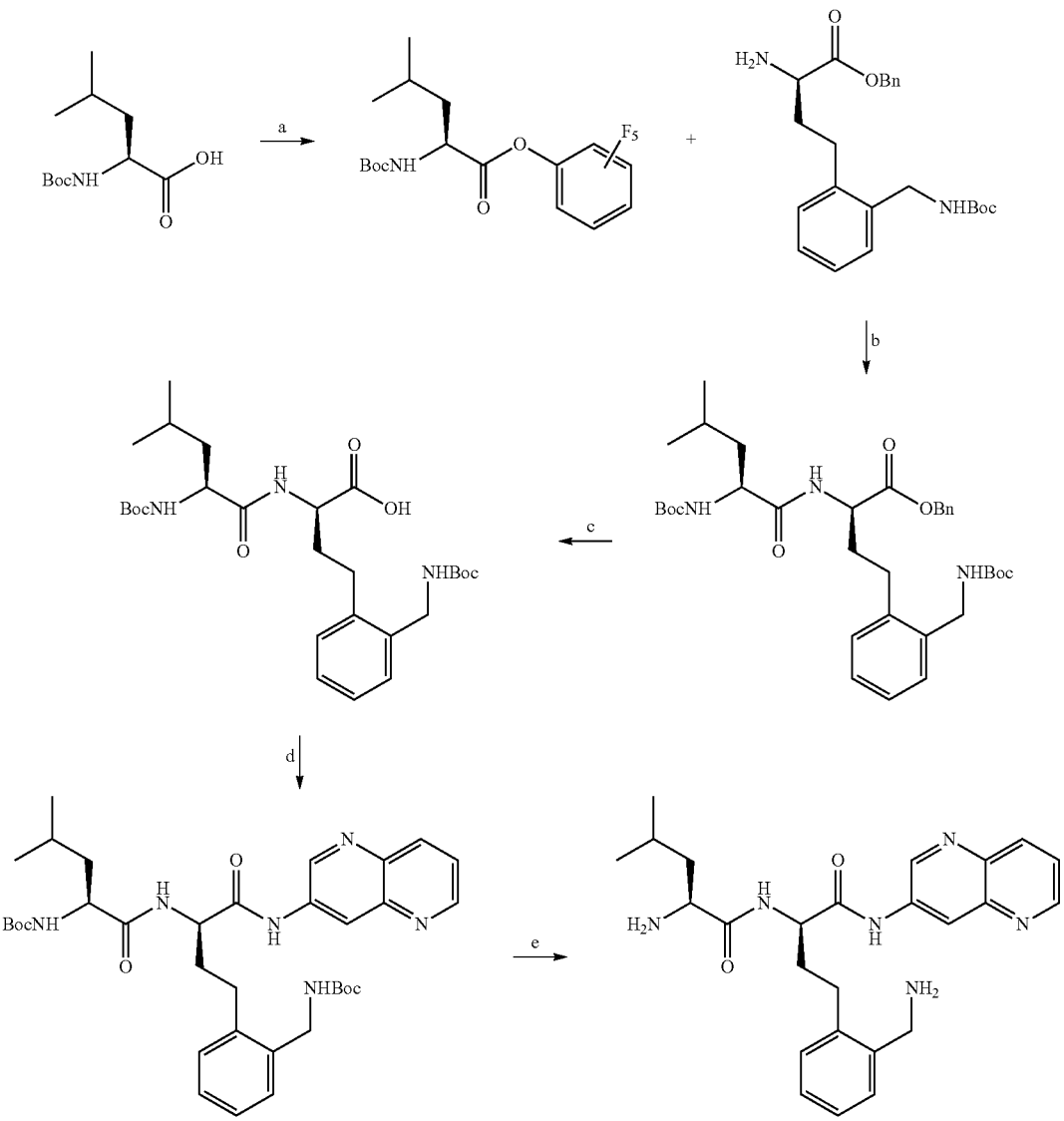
The benzyl ester (Bn) used in the step b of the amide bond formation represents an example of a carboxylic acid protecting group which is compatible with the synthetic sequence. Other ester group compatible with the synthetic sequence can also be employed.
Method C
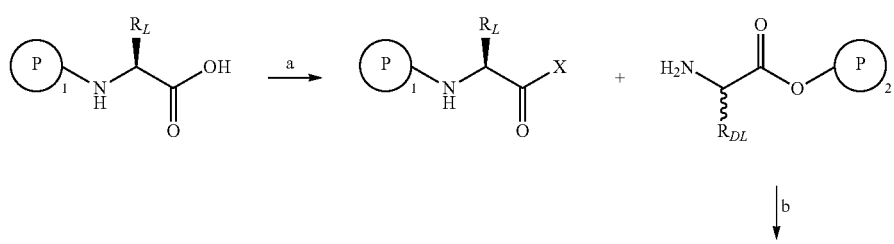

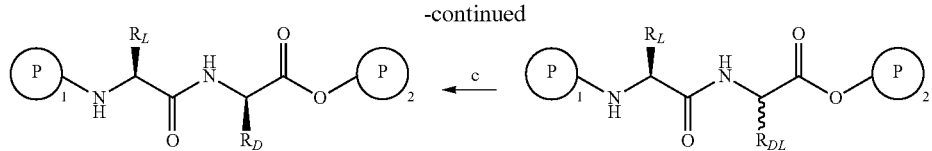

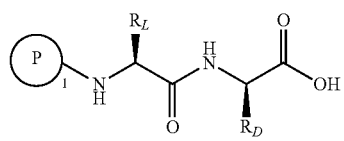

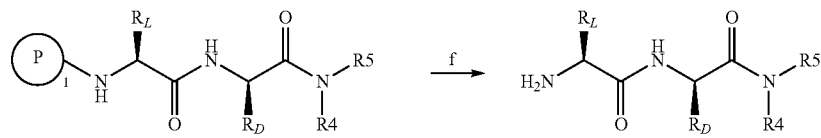

In some embodiments, compounds disclosed herein are synthesized according to Method C above. In cases when the desired aminoacid intermediate of D configuration is not easily available in the homochiral form, the coupling sequence can be preformed using the corresponding racemic intermediate which is then followed by the attachment of the homochiral aminoacid of L configuration. The resulting diastereomeric mixture can be separated by chromatography or by crystallization as shown in step c of the general scheme for Method C and the further steps of the sequence can be performed with the stereochemically uniform material. One specific example of a synthesis according to Method C is as follows:

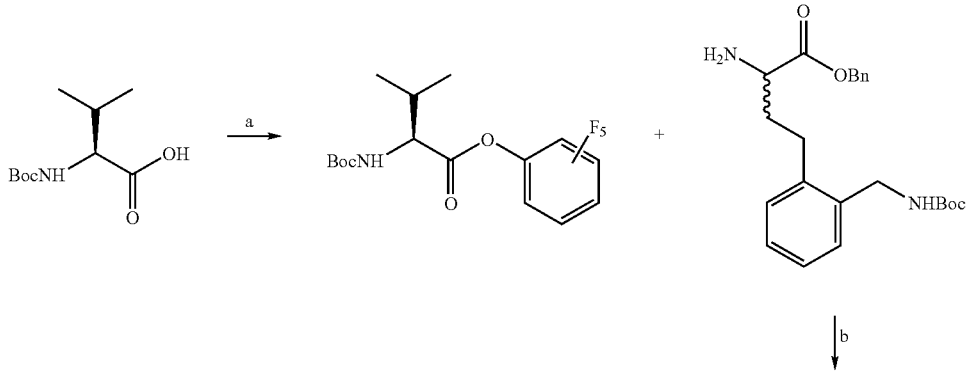

81 82
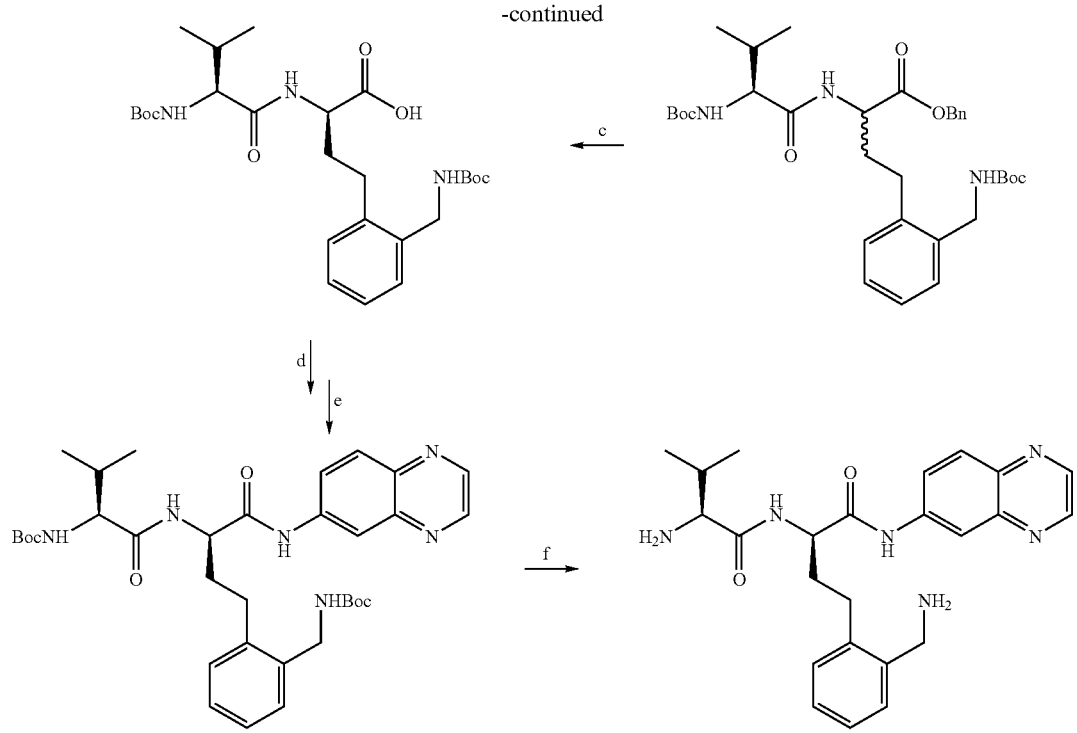
-continued
Method D
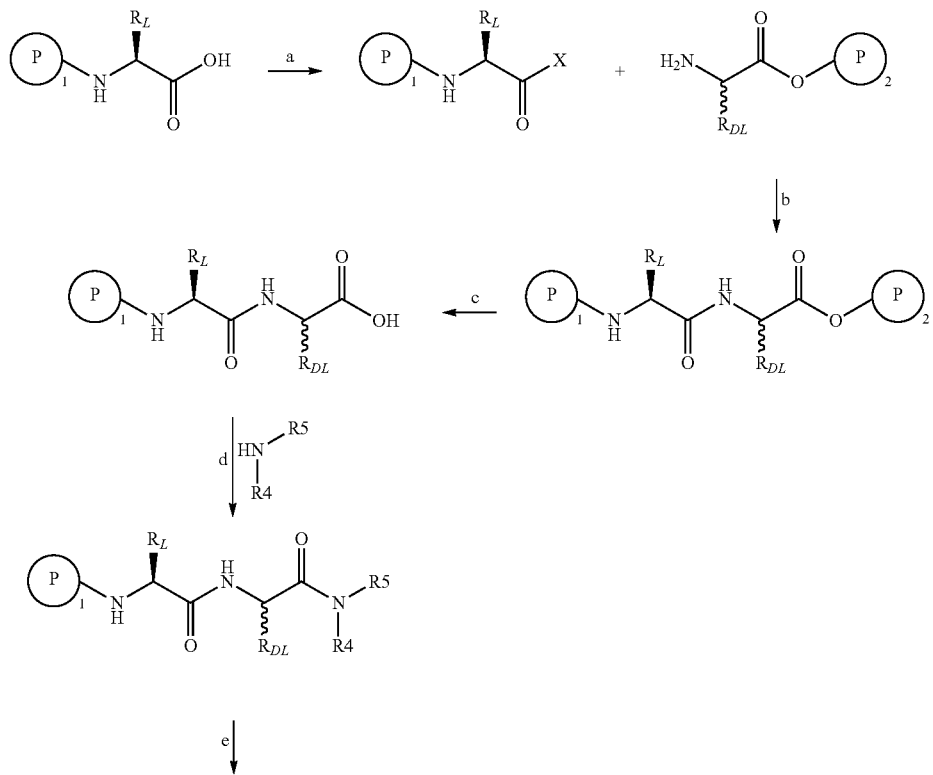

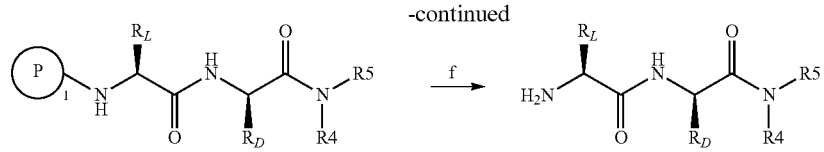

Method D can be used as and alternative to the approach described in Method C for cases when the desired aminoacid intermediate of D configuration is not easily available in the homochiral form. The racemic intermediate containing the sidechain intended to be the sidechain of the D configuration aminoacid of the desired product is coupled to the corresponding protected aminoacid of the L configuration as shown in step b and the resulting diastereoisomeric mixture is used for the next steps of the sequence. The separation of the diastereoisomeric components is performed at a later step where the separation by chromatography or by crystallization can be easily performed. Isolation of the desired diastereoisomer can be performed in step e or even after final removal of protecting groups.

One specific example of a synthesis according to Method D is as follows:

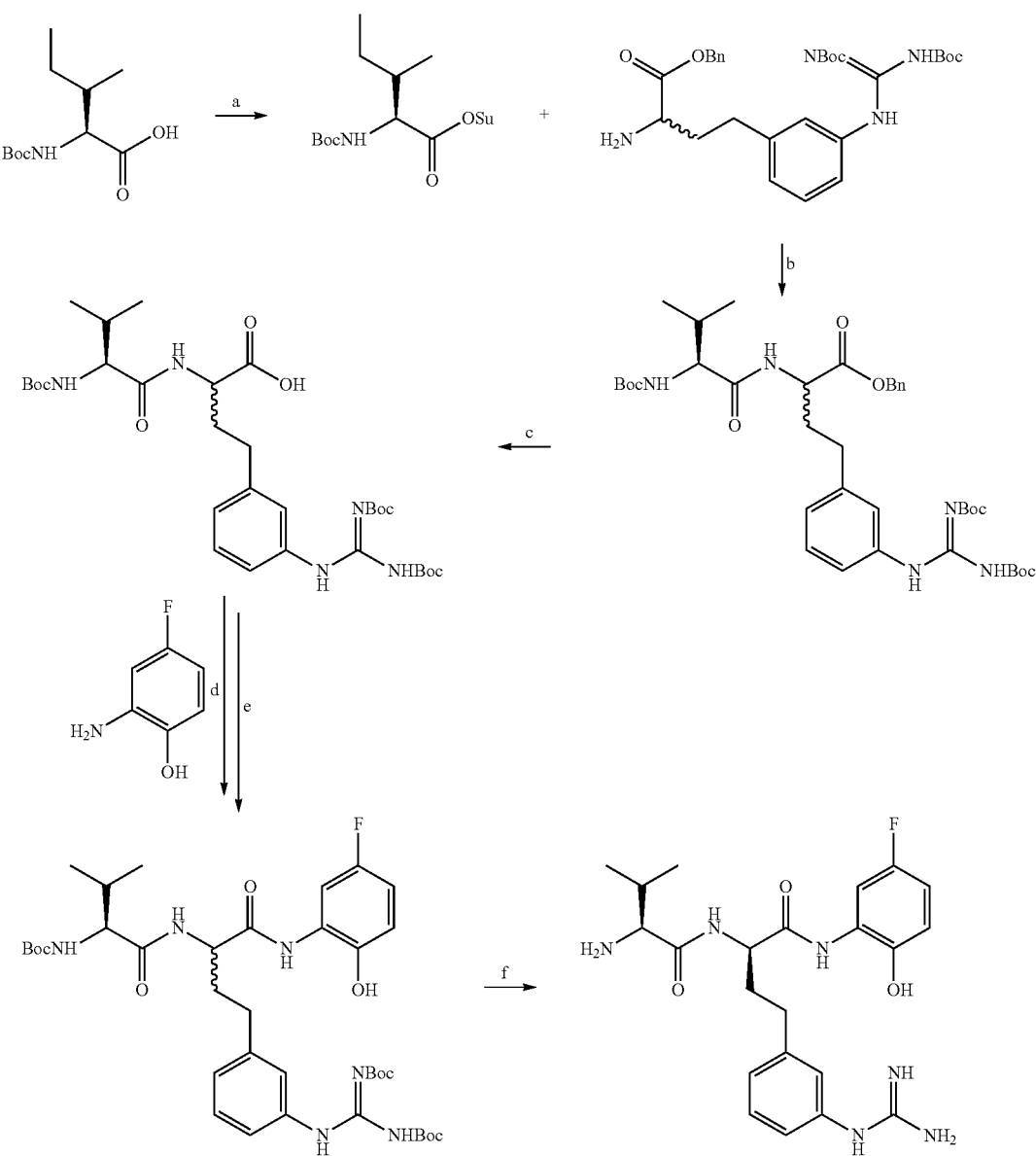

Method E

Preparation of the desired peptidic product may be performed by attaching the protected aminoacid intermediate to the polymeric solid support which can facilitate later coupling reactions and may eliminate the need for the purification of the intermediate products. The amino functionality of the aminoacid of the L configuration can be attached to the solid support material as shown in step a. The following steps of deprotections, activations and amide bond formations can be performed on the intermediates attached to solid support and the release of the product from the solid support can be then performed at the last step of the sequence.

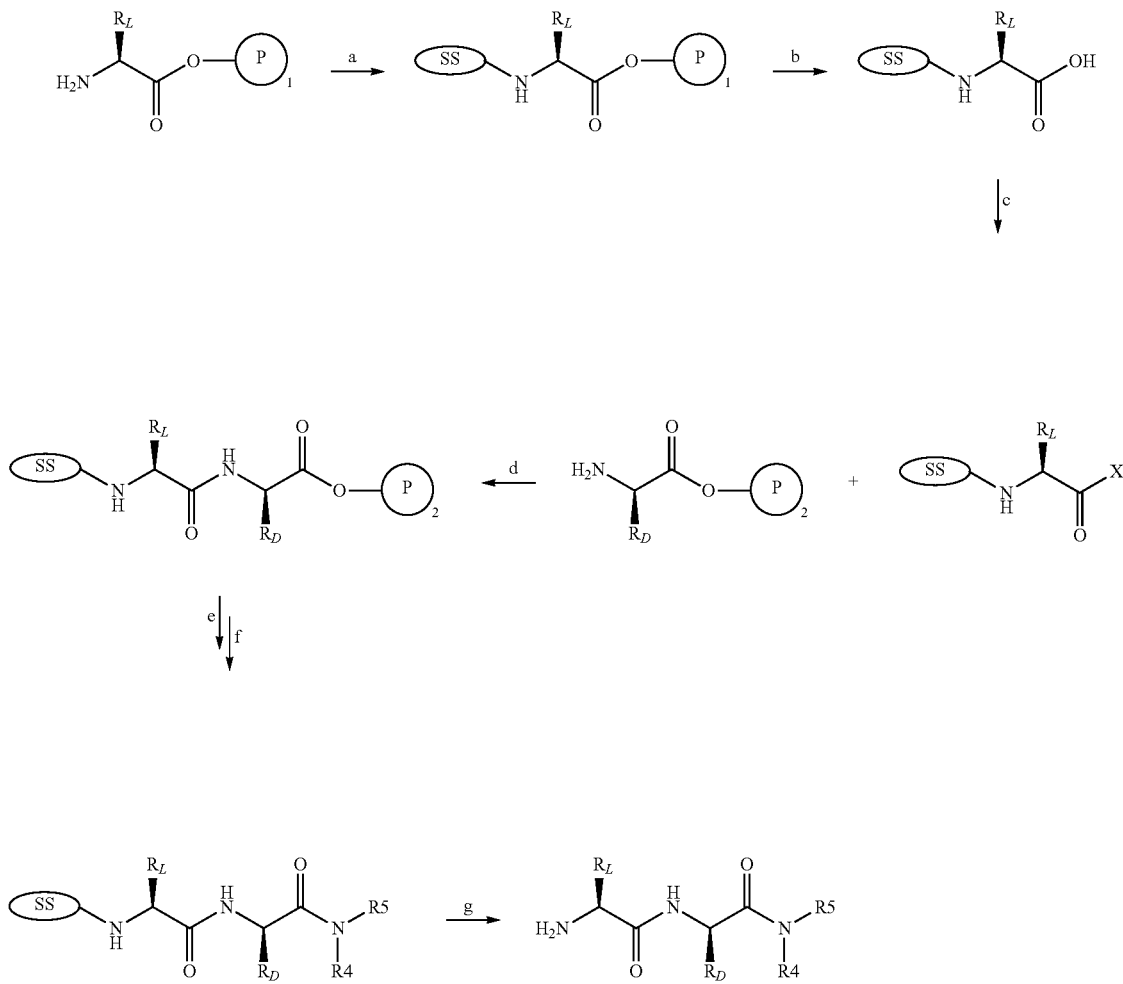

One specific example of a synthesis according to Method E is as follows:

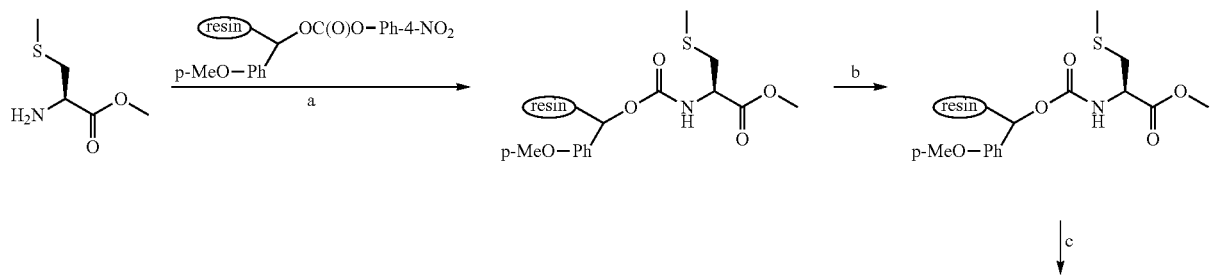

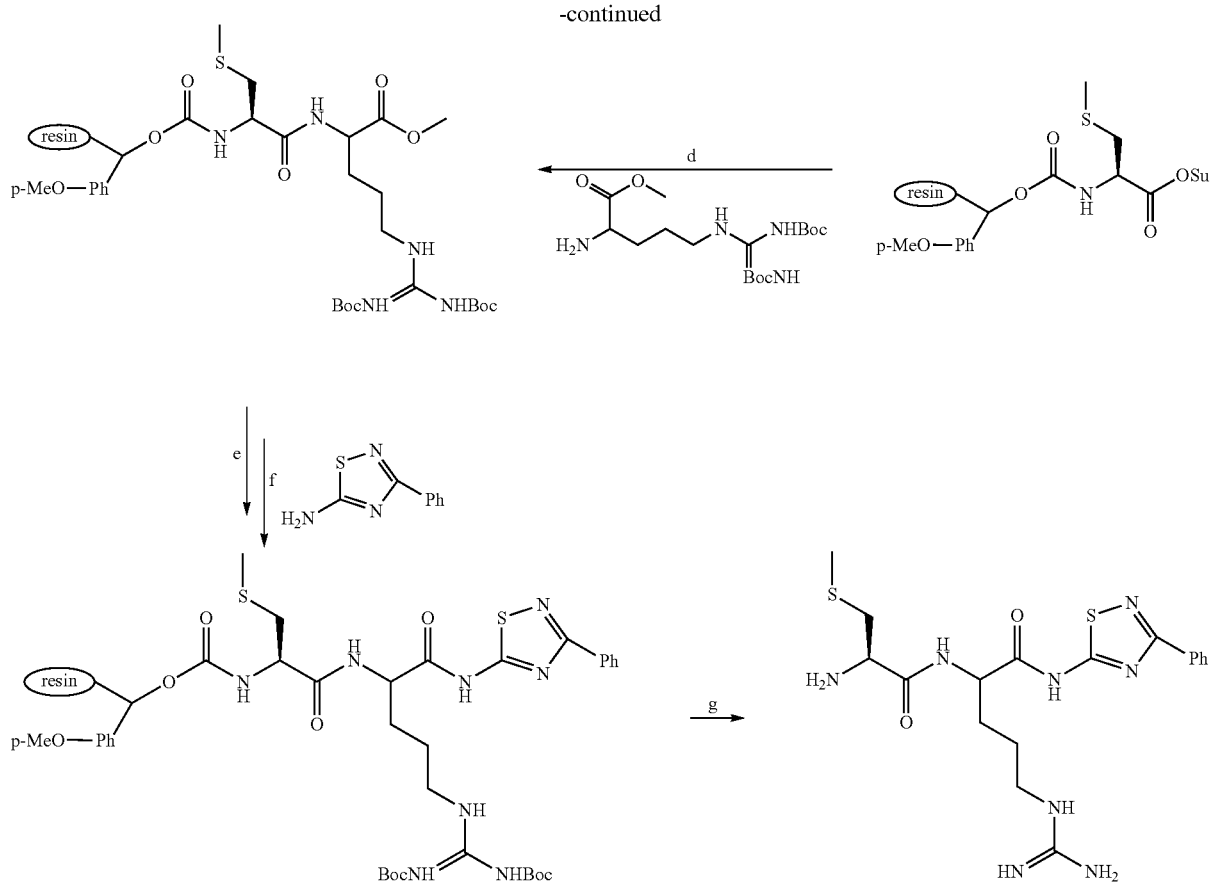

The example above shows a sequence in which the amino functionality of the L aminoacid intermediate can be attached to the solid support through the carbamate linker similar in character to t-butoxycarbonyl protecting group (T. Redman et al., Mol. Diversity, 4: 191-197, (1998)). After the completion of the assembly of the molecule attached to the solid support the final deprotection step can remove all protecting groups present and detach the product from the solid support. Other cleavable linkers attaching the aminoacid to the solid support can be also employed and may require separate steps for removal of protecting groups and detaching the product from the solid support.

Method F

α-Aminoacids employed in the synthetic sequences can have in their sidechains additional amino groups which may also require protection in order to perform the desired coupling reactions. Protecting groups used for these additional amino functionalities maybe identical to the protecting groups employed for protection of the α-amino functionalities abut may also be different.

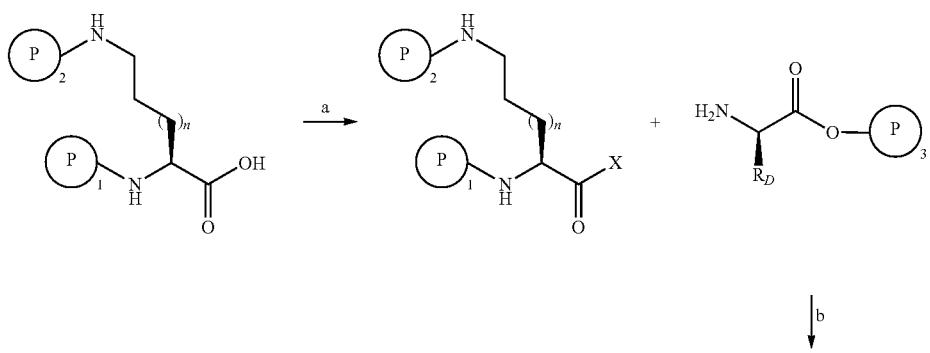

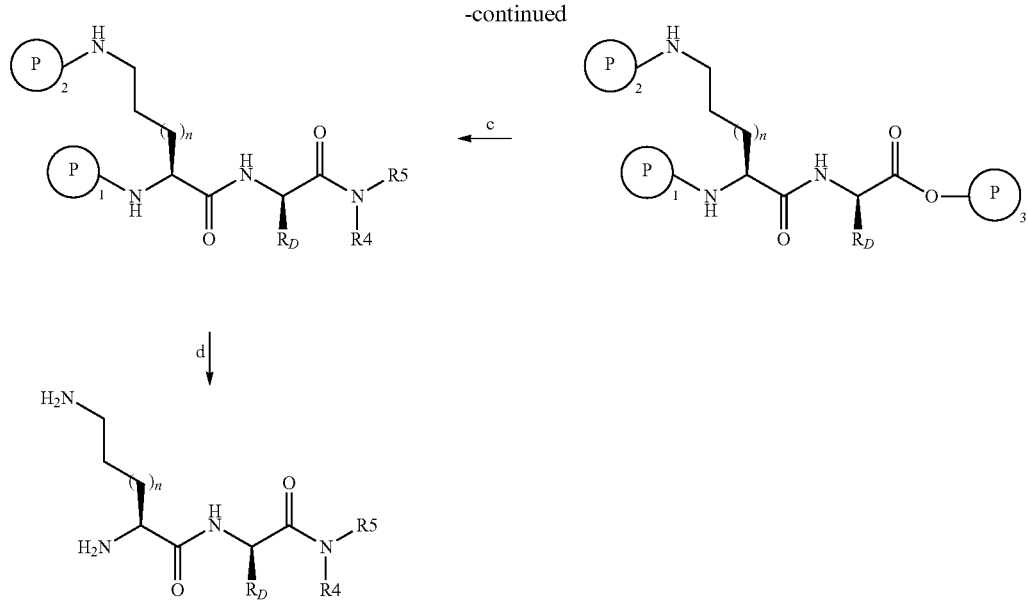
One specific example of a synthesis according to Method F is as follows:
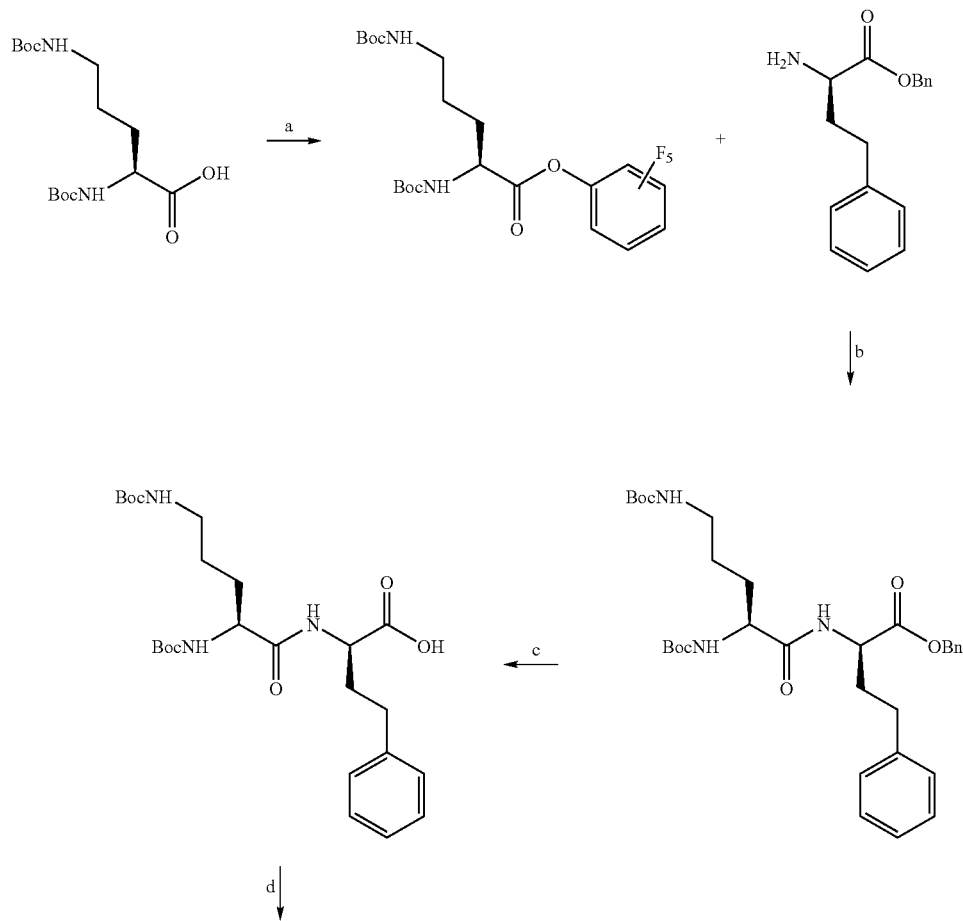

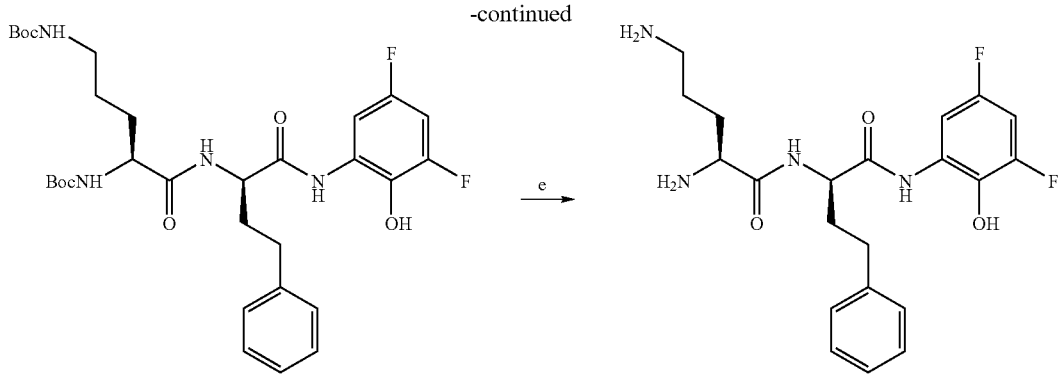

The above example utilizes t-butoxycarbonyl protecting groups for both α- and ω-amines of ornithine which can be activated for coupling in the step a. Deprotection of both amino functionalities can therefore be performed at the same time in step f.

Method G

In case when the L-aminoacid moiety contains two amino groups, one of them can be protected with a typical amino-protecting group while the other one can be used for the attachment to the polymeric solid support which can facilitate later coupling reactions and may eliminate the need for the purification of the intermediate products. The free amino functionality of the monoprotected aminoacid of the L configuration can be attached to the solid support material as shown in step a. The following steps of deprotections, activations and amide bond formations can be performed on the intermediates attached to solid support and the release of the product from the solid support can be then performed at the last step of the sequence.

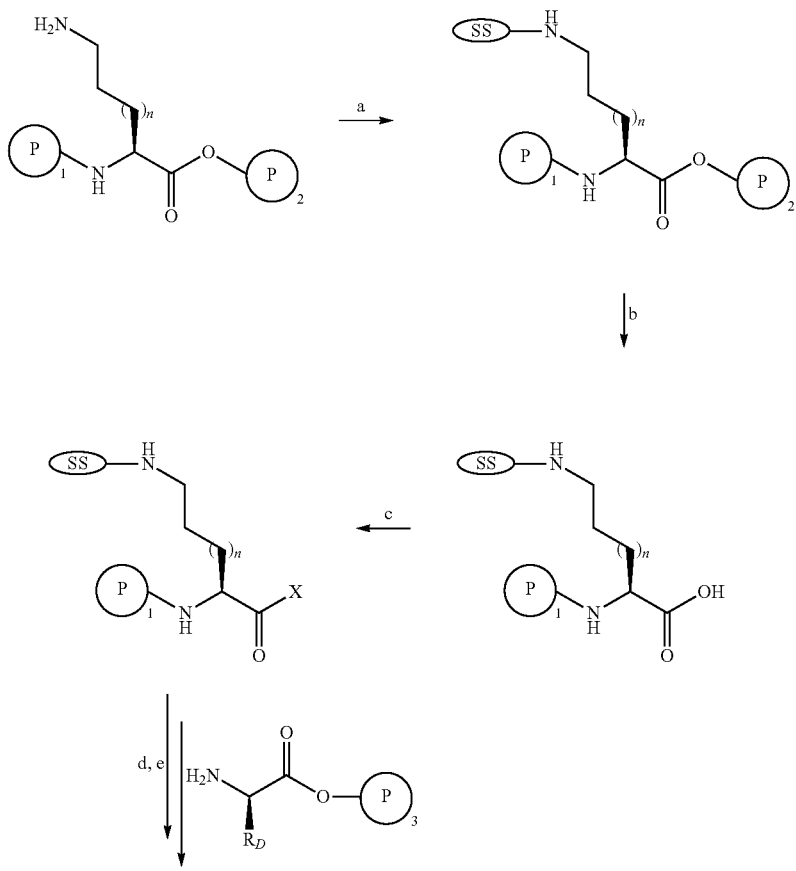

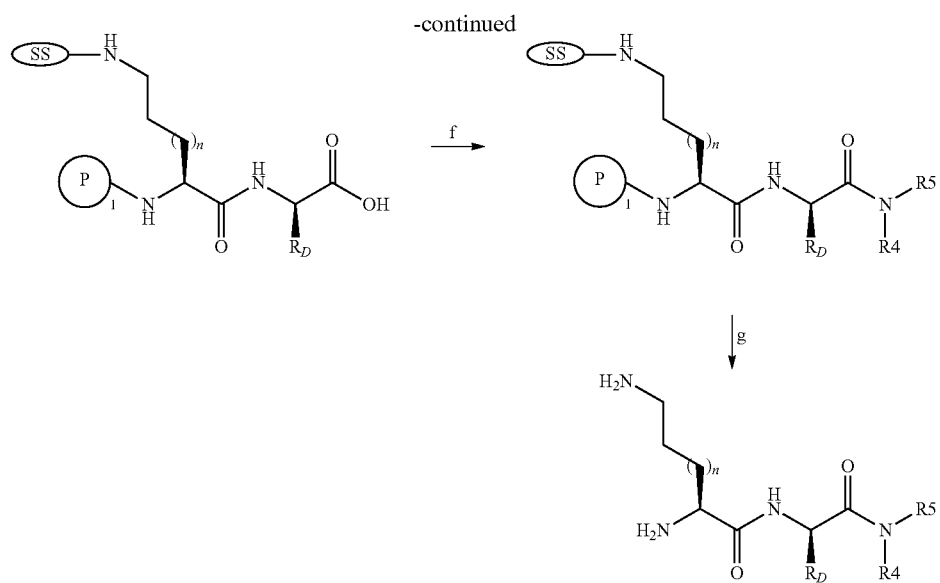
One specific example of a synthesis according to Method G is as follows:
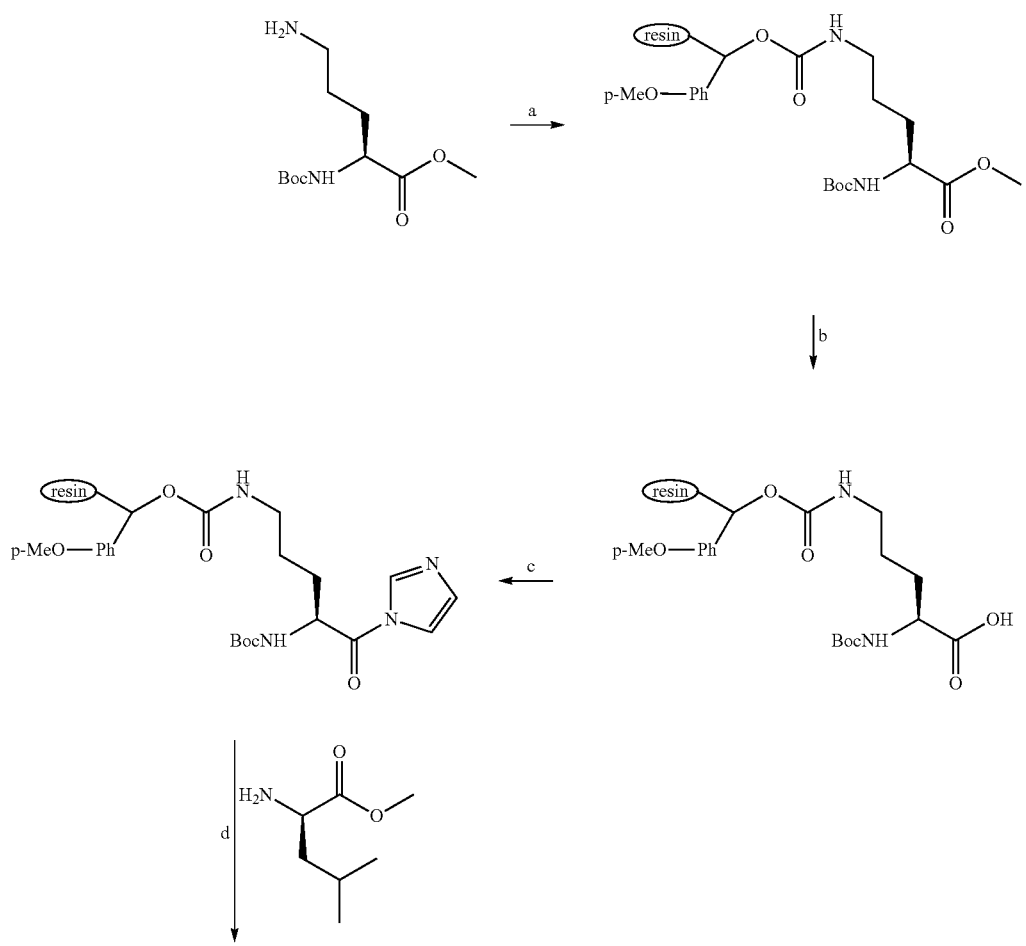

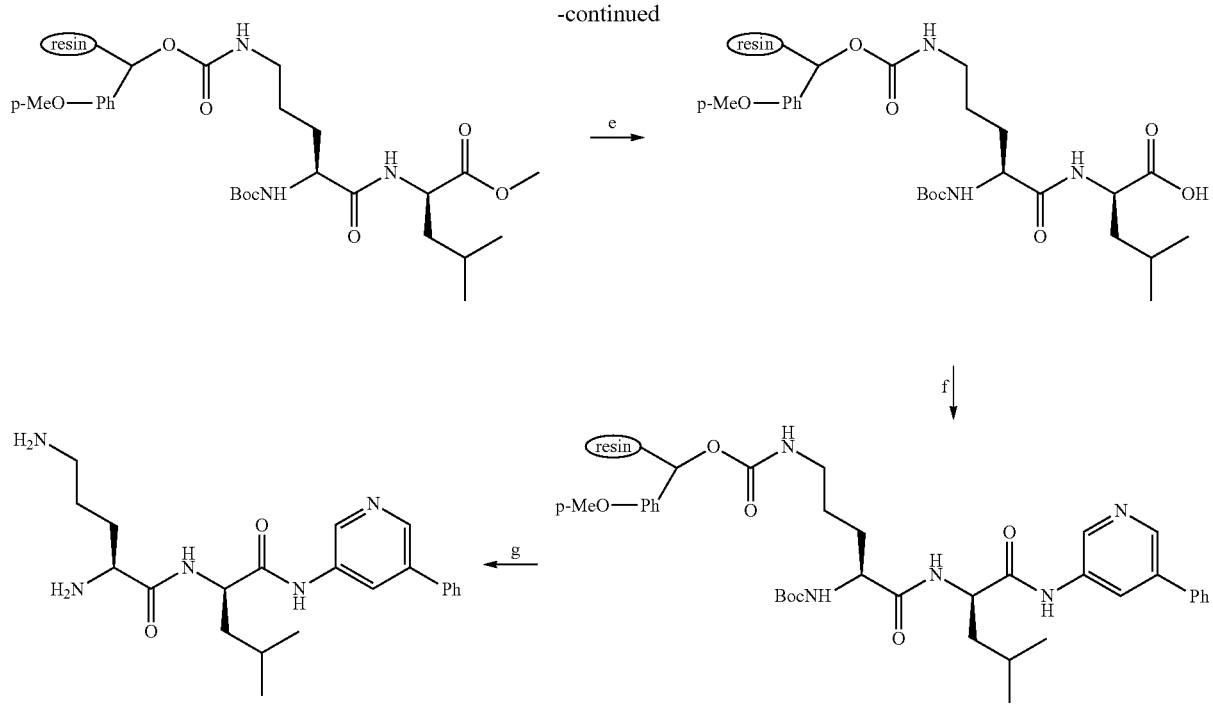

The above example describes the synthetic sequence in which the character of the attachment of the amino functionality is similar in character to the t-butoxycarbonyl group used for the protection of the alfa-amino functionality and the deprotection of the amine can be performed simultaneously with the detachment of the product from the solid support. The character of the linker and the protecting group may also be such that two separate steps maybe required for the deprotection of the amine functionality detachment of the product from the solid support.

Method H

Method H describes a synthetic sequence in which a homochiral N-protected D-α aminoacid intermediate is in the step a converted into the amide. The resulting amide can be then deprotected and coupled with the homochiral N-protected D-α-aminoacid and the resulting intermediate can be than deprotected to provide desired product. An analogous sequence can be also performed with the racemic intermediate containing the sidechain intended to be the sidechain of the D configuration aminoacid of the desired product. This racemic intermediate can be coupled with the corresponding protected aminoacid of the L configuration analogously to step c and the resulting diastereisomeric mixture obtained can be used for next steps of the sequence. The separation of the diastereoisomeric components can be performed immediately following step c or alternatively can be performed at a later step after final removal of protecting groups.

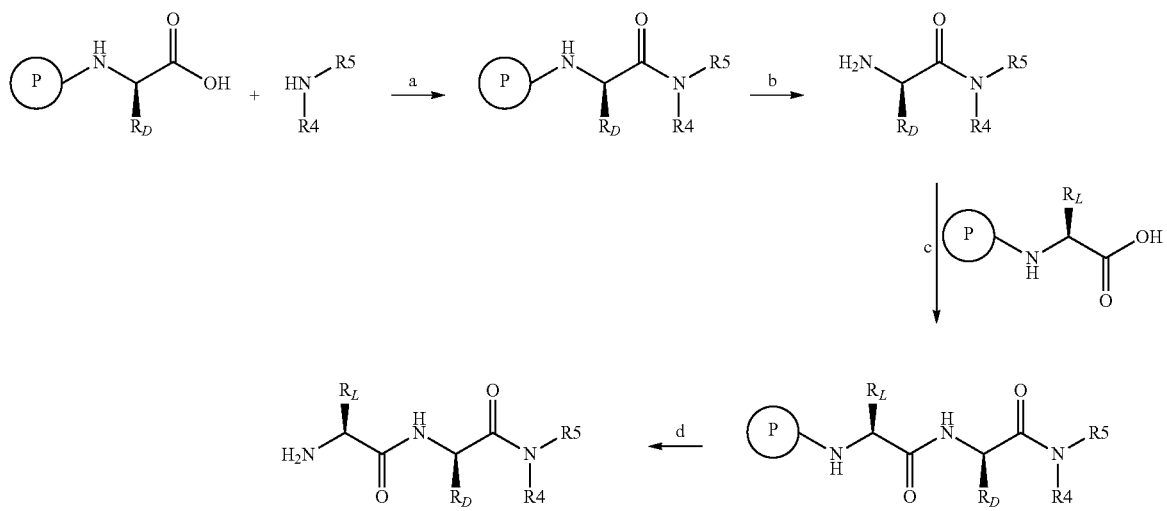

One specific example of a synthesis according to Method H is as follows:

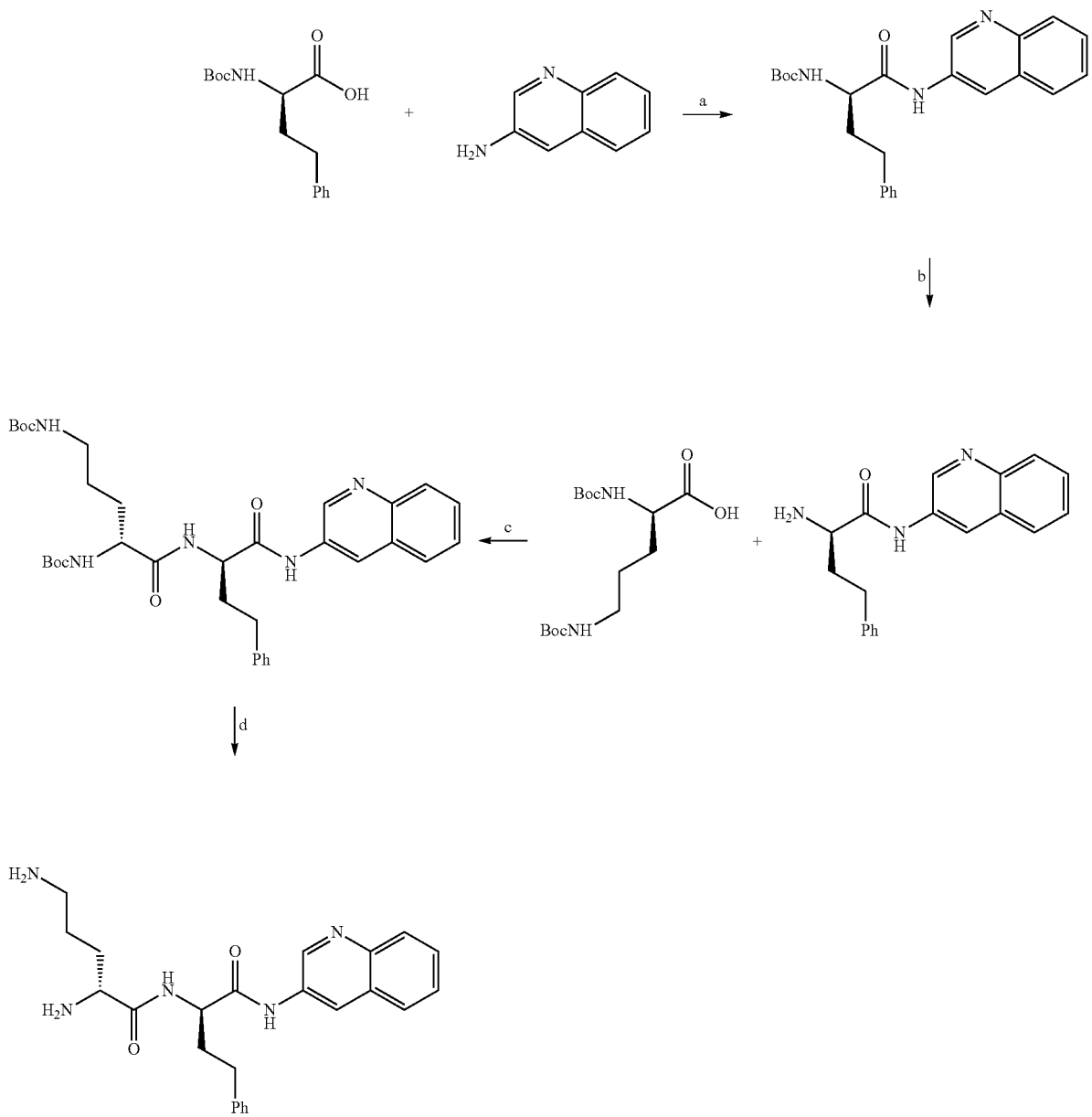

Method I

Homochiral protected aminoacid intermediates necessary for the preparation of the target peptidic compounds which are the subject of this invention can be used when easily available. Homochiral protected aminoacid intermediates necessary for the preparation of the target peptidic can be also prepared by a variety of methods known in the literature using stereoselective reactions or employing known strategies for the separation of enantiomers (*Synthesis of Optically Active α-Amino Acids*, R M Williams, Pergamon, N.Y., 1989). Alternatively, the desired protected aminoacid intermediates can be prepared by a variety of methods in form of a racemic mixture and used as such for coupling with the chomochiral component (e.g. the intermediate containing the aminoacid moiety intended to become a part of the L configuration aminoacid). Method I exemplifies a strategy which can be used for the preparation of racemic protected aminoacid intermediates containing moieties intended to become a part of the D configuration aminoacid.

In step a, the Shiff base of a glycine ester can be alkylated with the appropriate alkylating reagent producing a racemic mixture of the desired protected precursor of the aminoacid of D configuration. In the following steps (b-e) this precursor can be converted into a diastereoisomeric mixture of the final desired product in its protected form which can be separated by chromatography or by crystallization (step f) in order to isolate the material of the L,D configuration. The separation of the desired diastereoisomer can be also performed following the final deprotection step (steps f and g in the reverse order).

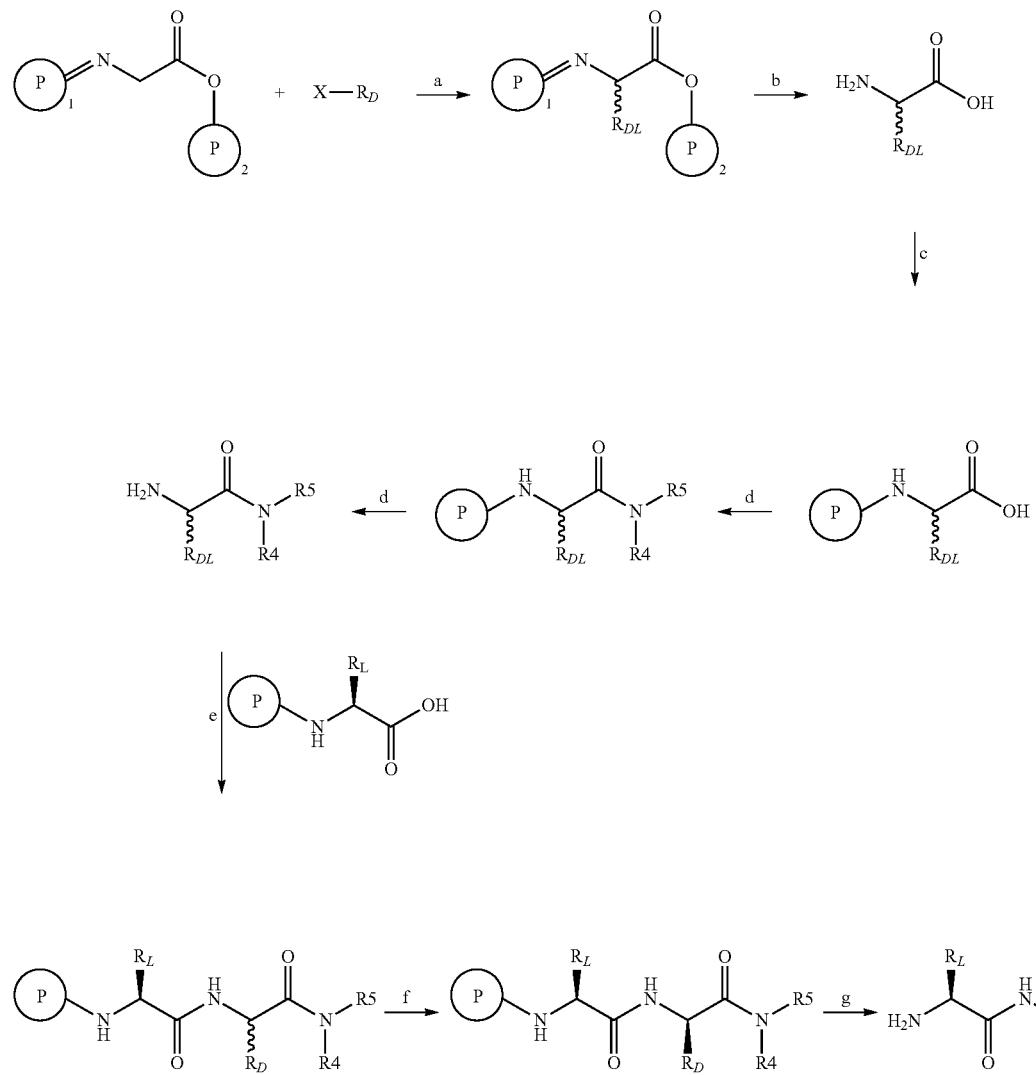
One specific example of a synthesis according to Method I is as follows:
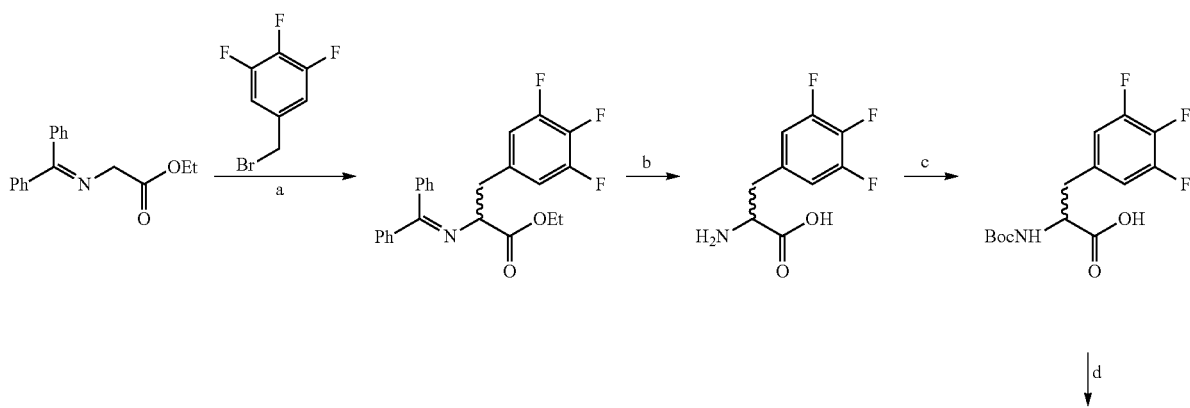

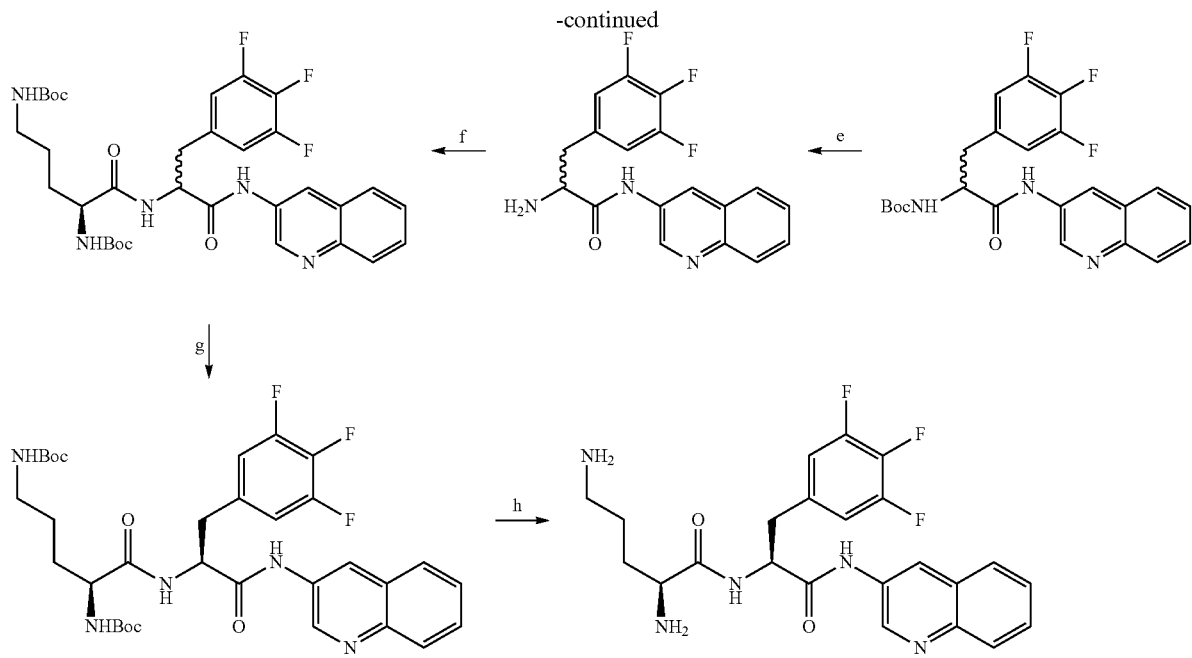

The above example describes the synthetic sequence in which in step a the Shiff base of glycine ethyl ester can be alkylated with a substituted benzyl bromide. By hydrolysis of both protecting groups and protection of the amine (steps b,c) a desired protected aminoacid can be obtained in racemic form. After a series of coupling and deprotection steps (c-e) the diastereoisomeric mixture can be separated by chromatography or crystallization.

Method J

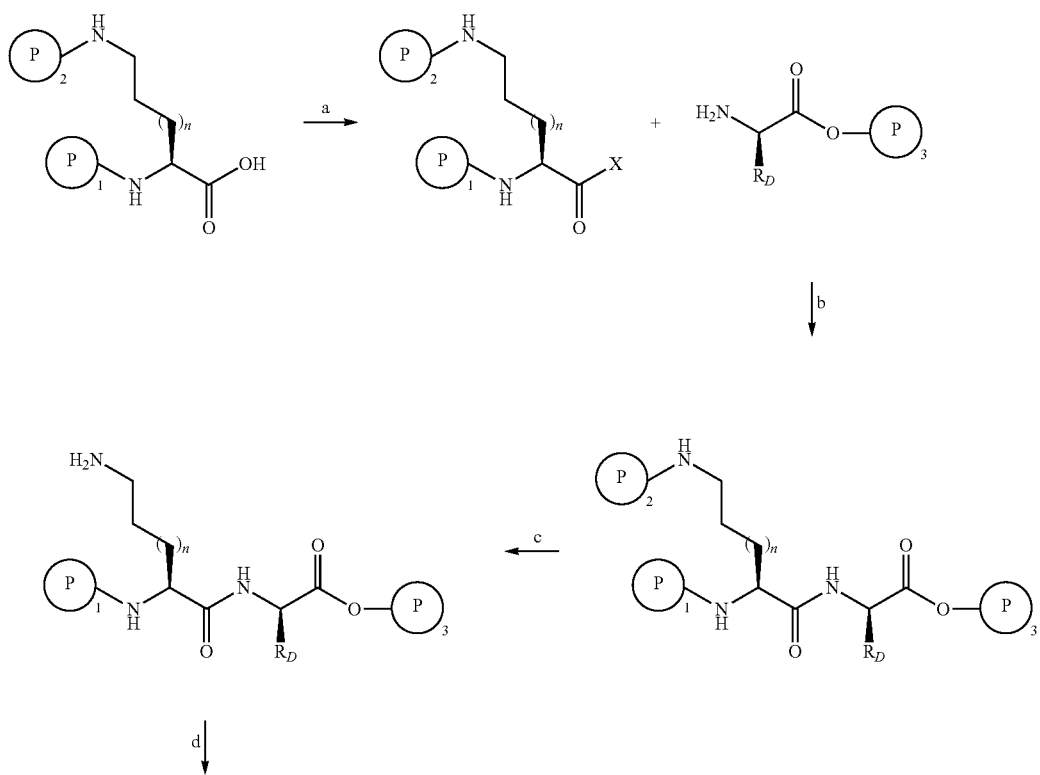

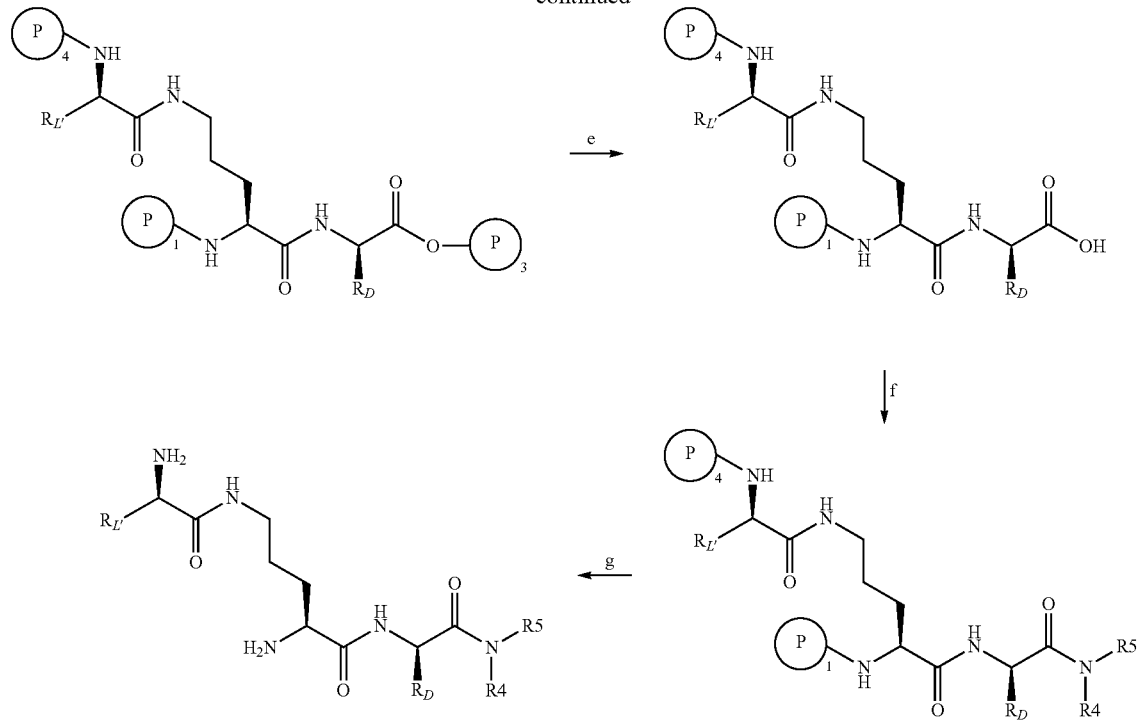

Method J describes a strategy which can be used for the functionalization of the specific amino functionality of the N-terminal dibasic aminoacid. The proper choice of the orthogonal protecting groups $P_1$, $P_2$, $P_3$ and $P_4$ can allow removal of one of the three protecting groups (steps c, e) and attach the additional aminoacid (bearing the L' moiety) to a selected amino group of the dibasic amino acid.

One specific example of a synthesis according to Method J is as follows:

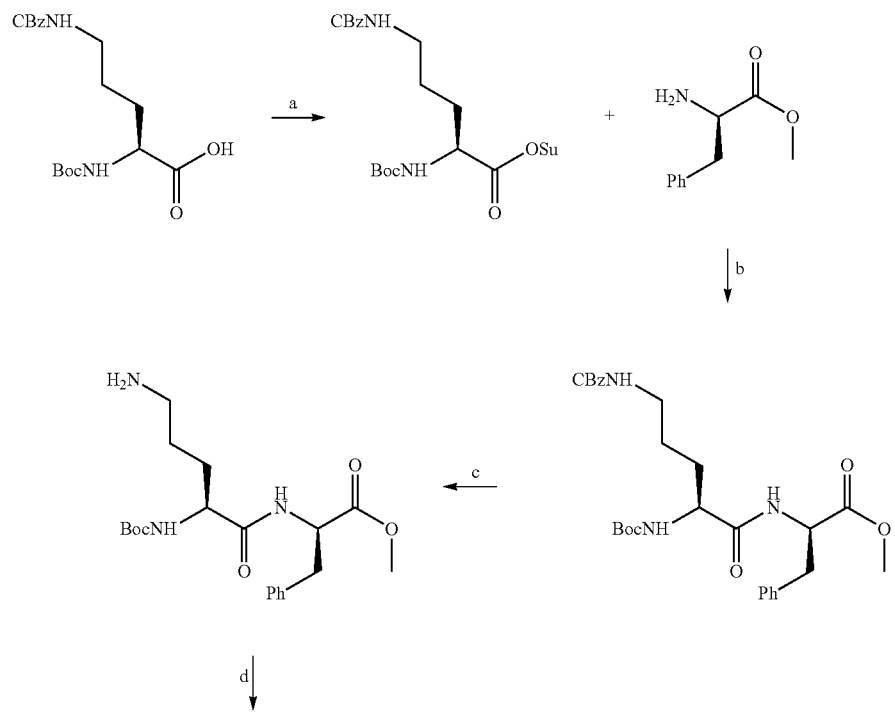

105
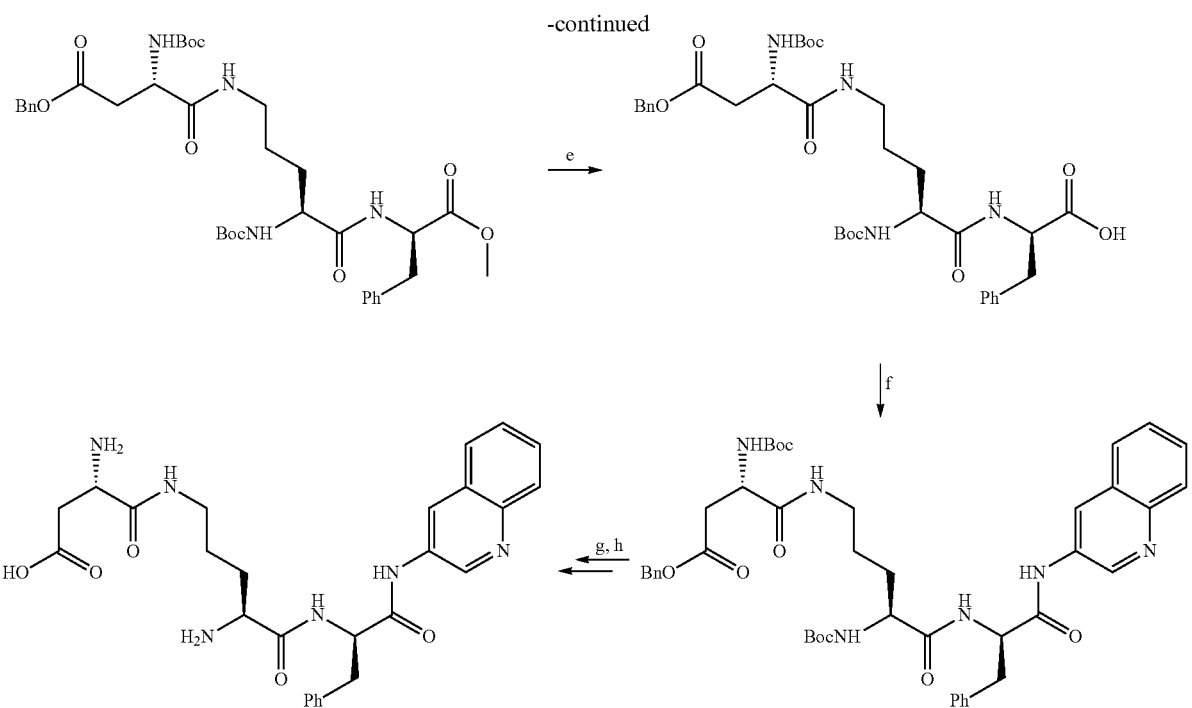
106
Method K
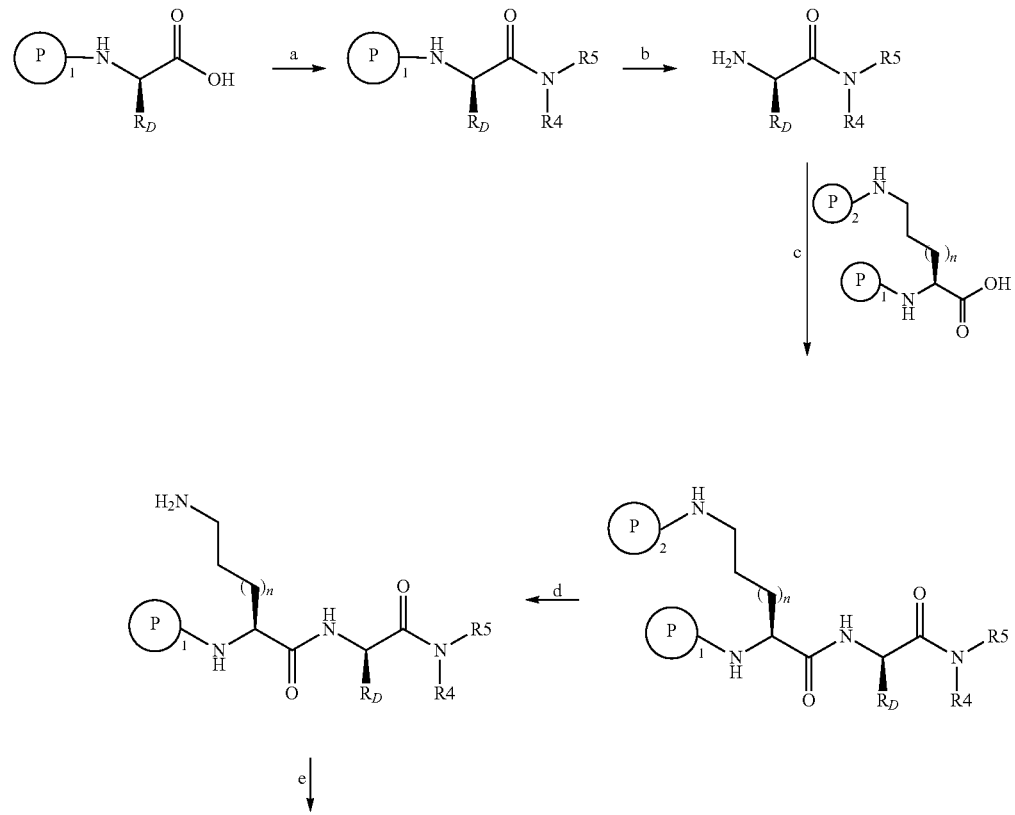

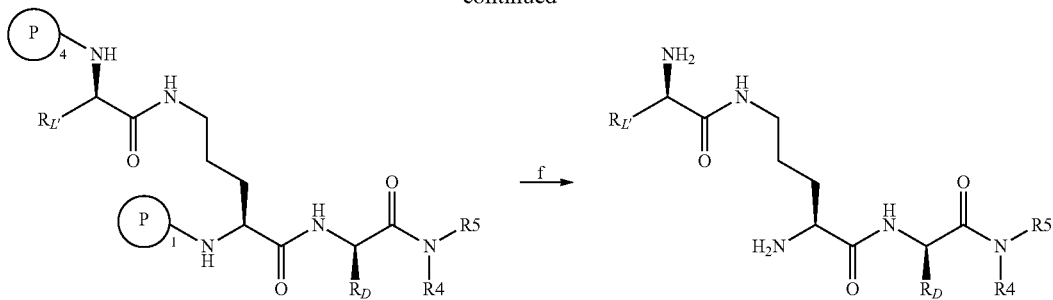

Method K can be used as an alternative strategy leading toward a similar target as described in Method J. Orthogonality of the two protecting groups $P_1$ and $P_2$ is sufficient to allow the introduction of the additional amino acid moiety to a selected amino group of the dibasic aminoacid (steps d and e). Depending on the order of deprotection of the orthogonal protecting groups $P_1$ and $P_2$ introduction of the additional aminoacid moiety can be selectively performed at either of the amino groups of the dibasic aminoacid.

One specific example of a synthesis according to Method K is as follows:

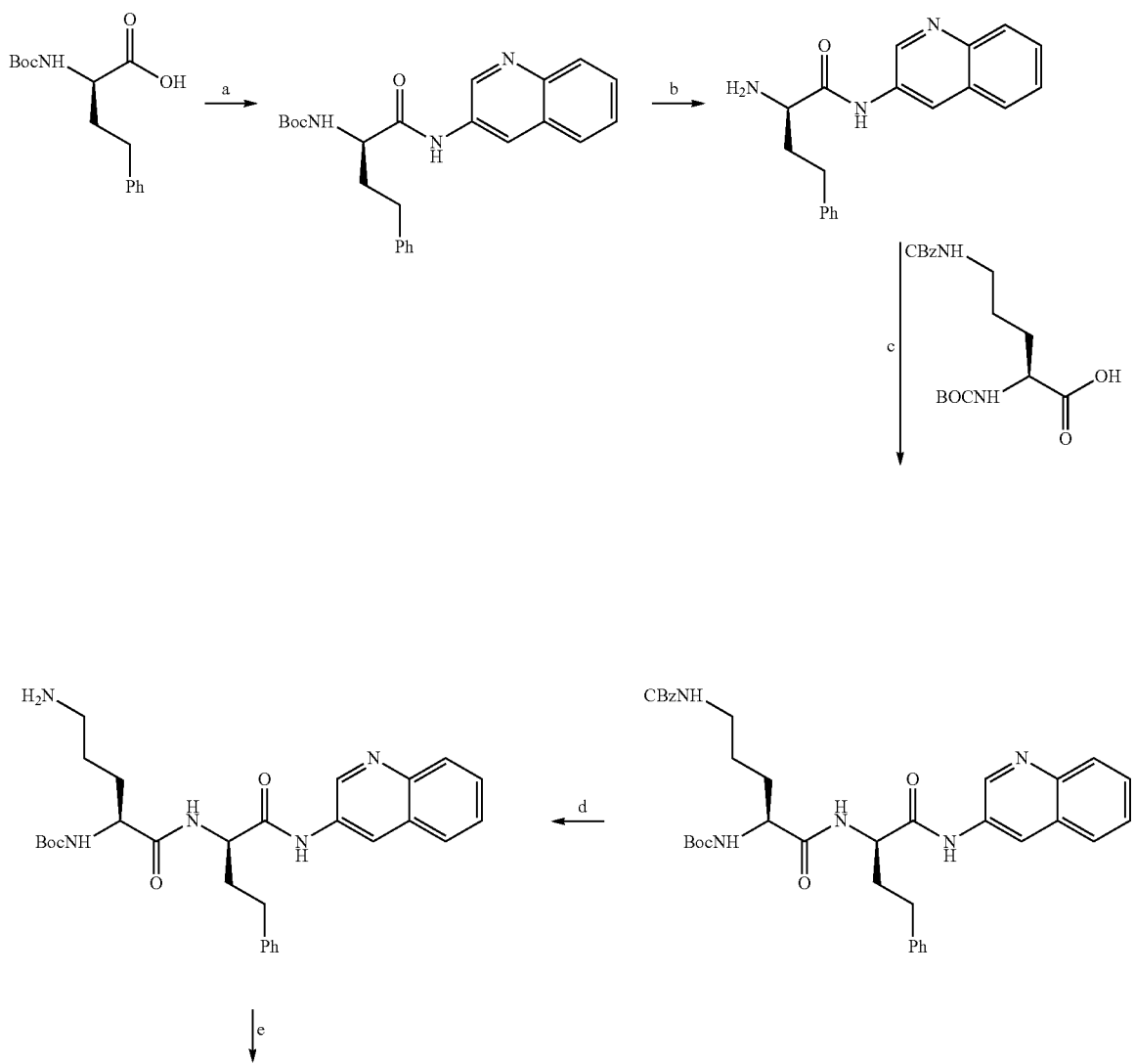

109 110
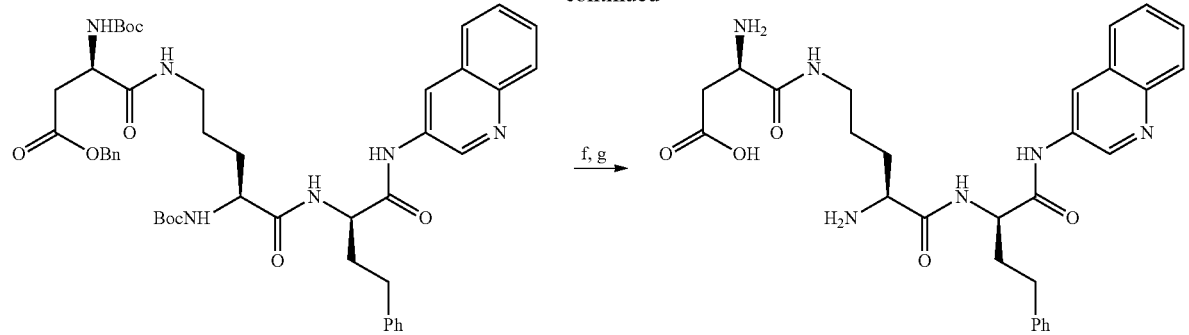
Method L
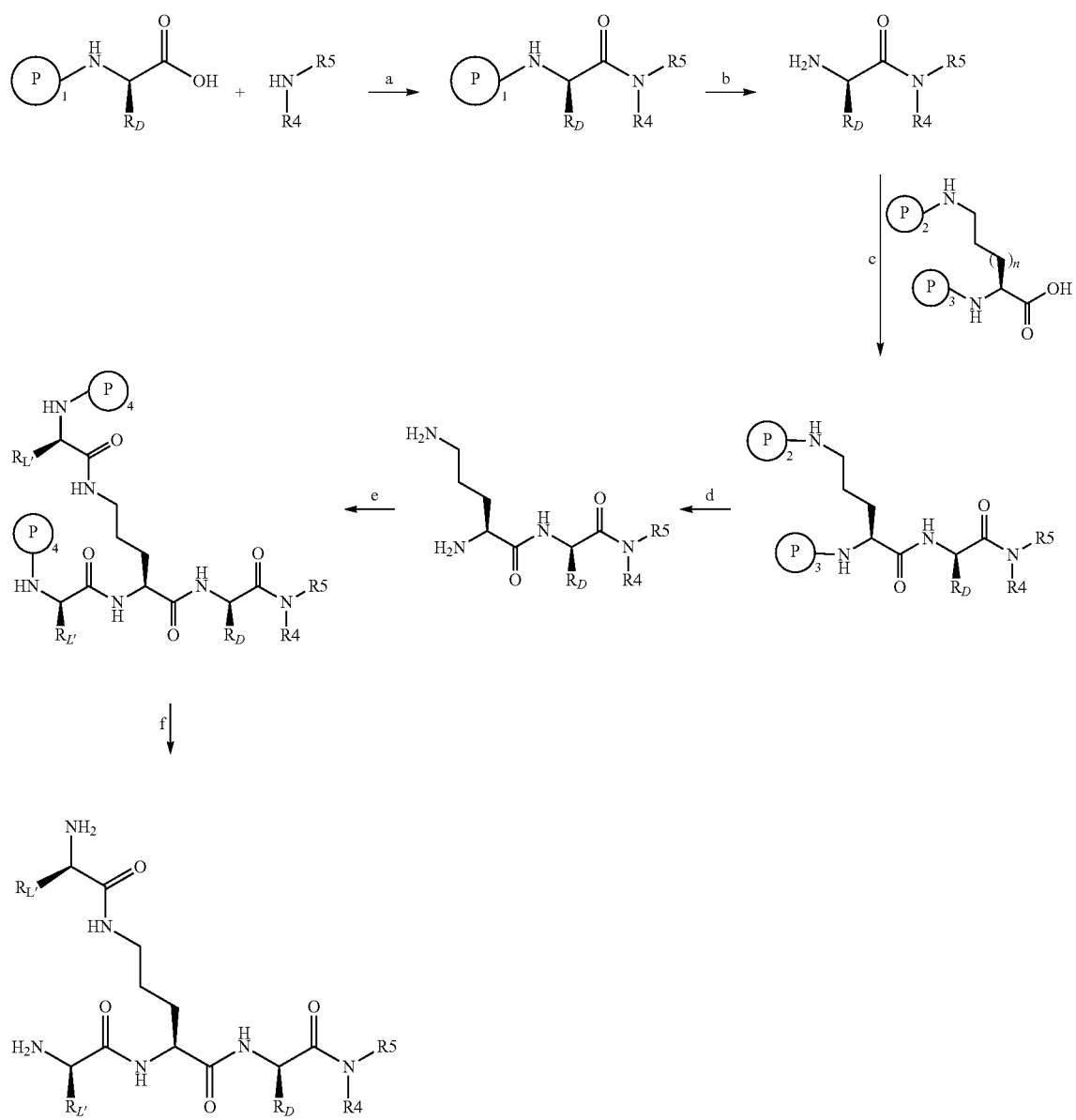

Two non-orthogonal protecting groups can be employed when both amino functionalities of the dibasic aminoacid are intended to be functionalized with two moieties of the same additional aminoacid as exemplified by Method L. Deprotection in step d can unmask both amino groups allowing functionalization of both of them at the same time (step e).

One specific example of a synthesis according to Method L is as follows:

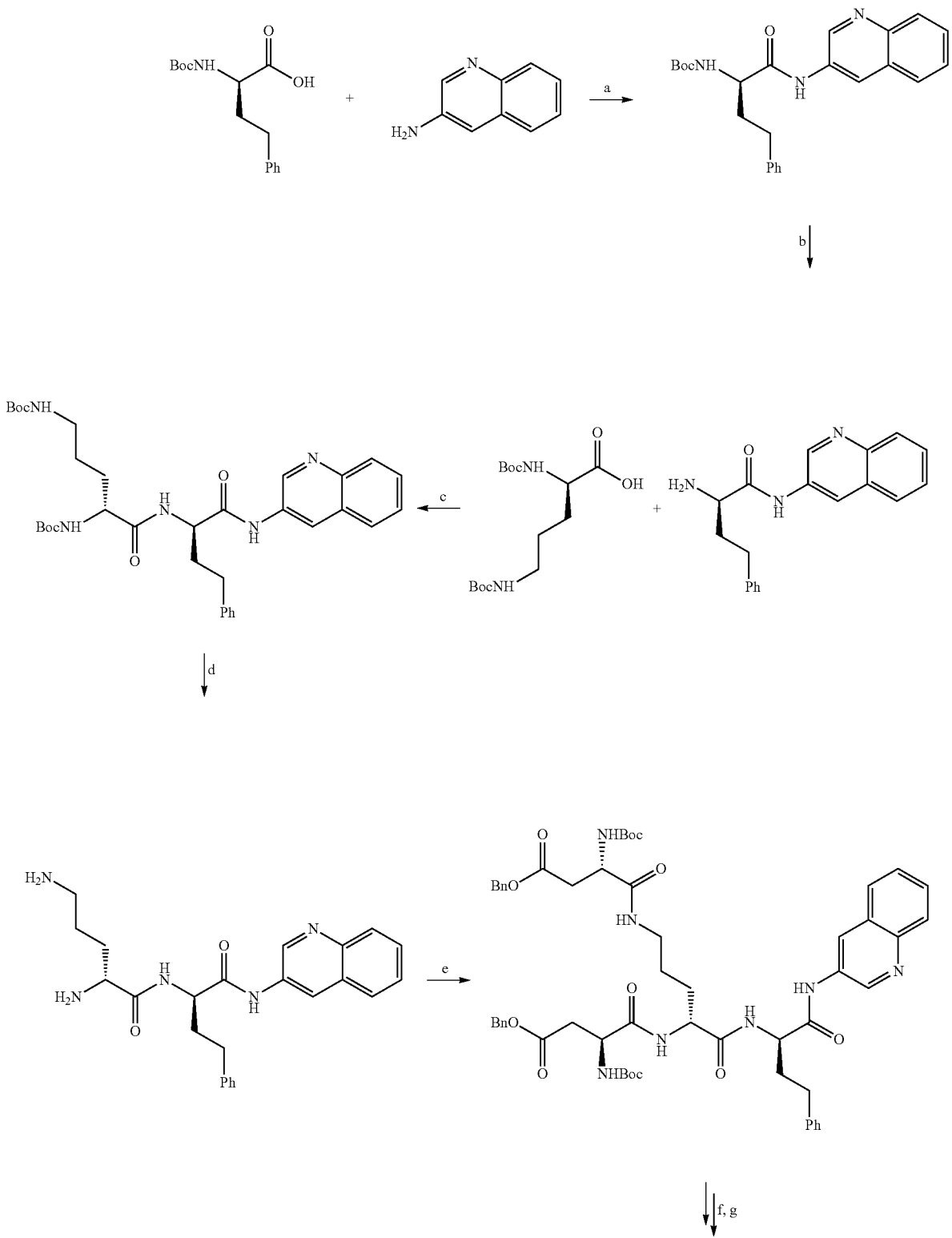

-continued

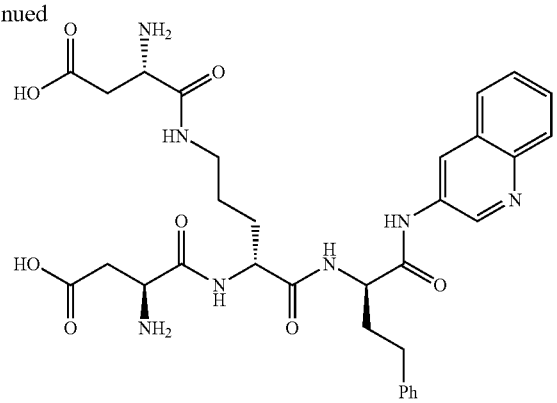

Methods of Use

In some embodiments, a method of treating or preventing a microbial infection is provided, comprising administering to a subject suffering from the microbial infection an amount effective to inhibit an efflux pump of said microbe of a compound described above. In some embodiments, the microbe is a bacteria and exhibits antibiotic resistance through an efflux pump mechanism. In some embodiments, the compound is administered in conjuction with an antibiotic, wherein the compound is selected to reduce or eliminate tissue damage due to tissue accumulation of the compound. In some embodiments, the subject is susceptible to accumulating efflux pump inhibitors in tissue and an improvement over previously disclosed compounds is provided that includes selecting a compound that does not accumulate significantly in tissue.

In some embodiments, a method for treating or preventing growth of antimicrobial-resistant microbes is provided, comprising contacting the microbe with a compound of disclosed above and an antimicrobial agent.

In some embodiments, a method is provided for treating or preventing a microbial infection, comprising identifying a subject that is susceptible to accumulation in tissue of a compound of Formula IIA:

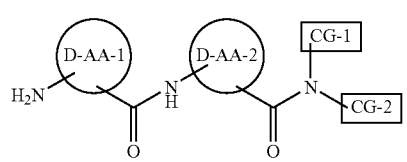
(IIA)

and then administering to the subject a compound of formula II:

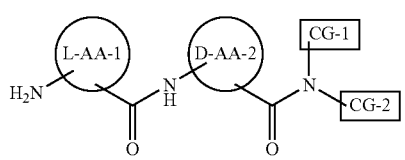
(II)

wherein:
D-AA-1 together with attached amine and carbonyl groups is a first natural or artificial α-amino acid residue having an (R)-configuration;
L-AA-1 together with attached amine and carbonyl groups is the first α-amino acid residue but having an (S)-configuration;
D-AA-2 together with attached amine and carbonyl groups is a second natural or artificial α-amino acid residue having an (R)-configuration;
CG-1 is hydrogen or a carbon-linked capping group; and
CG-2 is a carbon-linked capping group, wherein when CG-1 is a carbon-linked capping group, wherein CG-1 and CG-2 are optionally linked together to form a 5- or 6-membered ring.

In some embodiments, a method if provided for treating a patient by administering an efflux pump inhibitor in conjunction with an antibiotic, wherein the efflux pump inhibitor has the structure:

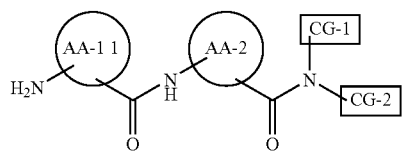

wherein AA-1 and AA-2 together with attached amine and carbonyl groups represent a natural or artificial a-amino acid residue, and wherein the method comprises ascertaining whether reduced cellular accumulation of efflux pump inhibitor in the patient is desirable, and if so, selecting the efflux pump inhibitor from those efflux pump inhibitors having formula II:

(II)

wherein:
L-AA-1 is AA-2 having an (S)-configuration;
D-AA-2 is AA-2 having an (R)-configuration;

CG-1 is hydrogen or a carbon-linked capping group; and

CG-2 is a carbon-linked capping group, wherein when CG-1 is a carbon-linked capping group, wherein CG-1 and CG-2 are optionally linked together to form a 5- or 6-membered ring.

In some embodiments, a method is provided for treating a microbial infection in an animal, specifically including in a mammal, by treating an animal suffering from such an infection with an antimicrobial agent and an efflux pump inhibitor, which increase the susceptibility of the microbe for that antimicrobial agent. Such efflux pump inhibitors can be selected from any of the compounds generically or specifically described herein. In this way a microbe involved in the infection can be treated using the antimicrobial agent in smaller quantities, or can be treated with an antimicrobial agent, which is not therapeutically effective when used in the absence of the efflux pump inhibitor. Thus, this method of treatment is especially appropriate for the treatment of infections involving microbial strains that are difficult to treat using an antimicrobial agent alone due to a need for high dosage levels (which can cause undesirable side effects), or due to lack of any clinically effective antimicrobial agents. However, it is also appropriate for treating infections involving microbes that are susceptible to particular antimicrobial agents as a way to reduce the dosage of those particular agents. This can reduce the risk of side effects. It is also appropriate for treating infections involving microbes that are susceptible to particular antimicrobial agents as a way of reducing the frequency of selection of resistant microbes. In particular embodiments the microbe is a bacterium, which may, for example, be from any of the groups or species indicated above.

In some embodiments, a method is provided for prophylactic treatment of a mammal. In this method, an antimicrobial agent and an efflux pump inhibitor is administered to a mammal at risk of a microbial infection, e.g., a bacterial infection. The efflux pump inhibitor can be selected from any of the compounds generically or specifically described herein.

In some embodiments, a method is provided for enhancing the antimicrobial activity of an antimicrobial agent against a microbe, in which such a microbe is contacted with an efflux pump inhibitor, and an antibacterial agent. The efflux pump inhibitor can be selected from any of the compounds generically or specifically described herein. Thus, this method makes an antimicrobial agent more effective against a cell, which expresses an efflux pump when the cell is treated with the combination of an antimicrobial agent and an efflux pump inhibitor. In particular embodiments the microbe is a bacterium or a fungus, such as any of those indicated above; the antibacterial agent can be selected from a number of structural classes of antibiotics including, e.g., beta-lactams, glycopeptides, aminoglycosides, quinolones, oxazolidinones, tetracyclines, rifamycins, coumermycins, macrolides, and chloramphenicol. In particular embodiments an antibiotic of the above classes can be as stated above.

In other embodiments, a method is provided for suppressing growth of a microbe, e.g., a bacterium, expressing an efflux pump, e.g., a non-tetracycline-specific efflux pump. As illustrated by the case where the microbe is a bacterium, the method involves contacting that bacterium with an efflux pump inhibitor, in the presence of a concentration of antibacterial agent below the MIC of the bacterium. The efflux pump inhibitor can be selected from any of the compounds generically or specifically described herein. This method is useful, for example, to prevent or cure contamination of a cell culture by a bacterium possessing an efflux pump. However, it applies to any situation where such growth suppression is desirable.

In some embodiments, any of the compounds generically or specifically described herein may be administered as an efflux pump inhibitor either alone or, more preferably, in conjunction with another therapeutic agent. In some embodiments, any of the compounds generically or specifically described herein may be administered as an efflux pump inhibitor in conjunction with any of the antibacterial agents specifically or generically described herein, as well as with any other antibacterial agent useful against the species of bacterium to be treated, when such bacteria do not utilize an efflux pump resistance mechanism. In some embodiments, the antibacterial agents are administered at their usual recommended dosages. In other embodiments, the antibacterial agents are administered at reduced dosages, as determined by a physician. For all conventional antibacterials on the market, and many in clinical development, dosage ranges and preferred routes of administration are well established, and those dosages and routes can be used in conjunction with the efflux pump inhibitors of the preferred embodiments. Reduced dosages of the antibacterials are contemplated due to the increased efficacy of the antibacterial when combined with an efflux pump inhibitor.

In some embodiments, a compound disclosed herein is administered along with an antimicrobial agent. The two agents may be administered in a predetermined ratio. For example, the agents may be administered in a 1:1 ratio, 1:2 ratio, 2:1 ratio, etc. The agents may be administered separately, together, simultaneously, or sequentially. The agents may be administered as a combined, fixed dosage form or as separate dosage forms.

In some embodiments, a subject is identified as infected with bacteria that are resistant to an antimicrobial agent. The subject may then be treated with the antimicrobial agent in combination with a compound disclosed herein. A subject may be identified as infected with bacteria that are resistant based on observing an ineffective response of the infection to the antimicrobial. Alternatively, the bacteria may be cultured and identified as a known resistant strain by appropriate microbiological techniques known in the art.

In some embodiments, a subject is identified as a subject that is infected with bacteria that are capable of developing resistance to an antimicrobial. The subject may then be treated with the antimicrobial agent in combination with a compound disclosed herein. A subject may be identified as infected with bacteria that are capable of developing resistance by diagnosing the subject as having symptoms that are characteristic a bacterial infection with a bacteria species known to have resistant strains or a with a bacteria that is a member of group that are known to have resistant strains. Alternatively, the bacteria may be cultured and identified as a species known to have resistant strains or a bacteria that is a member of group that are known to have resistant strains.

In some embodiments, an efflux pump inhibitor is administered at a level sufficient to overcome or suppress the emergence of efflux pump-mediated resistance in bacteria. In some embodiments, this level produces an effective efflux pump inhibitory concentration at the site of infection. In other embodiments, this level produces an effect equivalent to shutting down all efflux pumps in the bacteria.

In some embodiments, a subject is identified as a subject that is at risk of infection with bacteria. The subject may then be prophylactically treated with an efflux pump inhibitor and an antimicrobial agent in order to prevent infection with a resistant bacterial strain. For example, subjects in environments likely to have resistant bacteria, such as a hospital, may be prophylactically treated.

In some embodiments, a subject is treated with an efflux pump inhibitor that is not otherwise generally effective as an antimicrobial. Thus, for example, the MIC of the efflux pump inhibitor may be greater than about 32 µg/ml, 64 µg/ml, 128 µg/ml, or 256 µg/ml.

Microbial Species

The microbial species to be inhibited through the use of efflux pump inhibitors, such as the above-described soft drugs, can be from other bacterial groups or species, such as one of the following: *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

A particularly appropriate example of a microbe appropriate for the use of an efflux pump inhibitor of the preferred embodiments is a pathogenic bacterial species, *Pseudomonas aeruginosa*, which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is administered in conjunction with the efflux pump inhibitor of preferred embodiments, the antibacterial agent, which would otherwise be maintained at a very low intracellular concentration by the export process, can accumulate to a concentration, which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

Antimicrobial Agents

In particular embodiments various antibacterial agents can be used in combination with the efflux pump inhibitors described herein. These include quinolones, tetracyclines, glycopeptides, aminoglycosides, β-lactams, rifamycins, macrolides/ketolides, oxazolidinones, coumermycins, and chloramphenicol. In particular embodiments, an antibiotic of the above classes can be, for example, one of the following.

Beta-Lactam Antibiotics

Beta-lactam antibiotics include, but are not limited to, imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, and LY206763.

Macrolides

Macrolides include, but are not limited to, azithromycin, clarithromycin, erythromycin, oleandomycin, rokitamycin, rosaramicin, roxithromycin, and troleandomycin.

Ketolides

Ketolides include, but are not limited to, telithromycin and cethrimycin.

Quinolones

Quinolones include, but are not limited to, amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, moxifloxacin; gemifloxacin; garenofloxacin; PD131628, PD138312, PD140248, Q-35, AM-1155, NM394, T-3761, rufloxacin, OPC-17116, DU-6859a (see, e.g., Sato, K. et al., 1992, Antimicrob Agents Chemother. 37:1491-98), and DV-7751a (see, e.g., Tanaka, M. et al., 1992, Antimicrob. Agents Chemother. 37:2212-18).

Tetracyclines, Glycylcyclines and Oxazolidinones

Tetracyclines, glycylcyclines, and oxazolidinones include, but are not limited to, chlortetracycline, demeclocycline, doxycycline, lymecycline, methacycline, minocycline, oxytetracycline, tetracycline, tigecycline, linezolide, and eperozolid.

Aminoglycosides

Aminoglycosides include, but are not limited to amikacin, arbekacin, butirosin, dibekacin, fortimicins, gentamicin, kanamycin, meomycin, netilmicin, ribostamycin, sisomicin, spectinomycin, streptomycin, and tobramycin.

Lincosamides

Lincosamides include, but are not limited to, clindamycin and lincomycin.

Screening for Efflux Pump Inhibitors

Potential efflux pump inhibitor compounds can be tested for their ability to inhibit multi-drug resistance efflux pumps of various microbes and to potentiate various antimicrobial agents by using the methods described herein as well as those known in the art. For example, strains of microbes known to overexpress efflux pumps may be treated with the antimicrobial agent with and without the test efflux pump inhibitor compound. A checkerboard assay may be used with varying concentrations of both antimicrobial agent and test compound to determine the relative concentrations at which potentiation is observed.

In one non-limiting example, treatment of *P. aeruginosa* with a test compound allows obtaining one or more of the following biological effects:

pa-301) *P. aeruginosa* strains will become susceptible to antibiotics that could not be used for treatment of pseudomonas infections, or become more susceptible to antibiotics, become more susceptible to antibiotics currently used for treatment of pseudomonas infections.

2) *P. aeruginosa* strains which developed resistance to antibiotics currently used for treatment of pseudomonas infections will become susceptible to these antibiotics.

3) Inhibition of the pump will result in a decreased frequency of resistance development to antibiotic, which is a substrate of the pump.

Obtaining even one of these effects provides a potential therapeutic treatment for infections by this bacterium. Also, similar pumps are found in other microorganisms. Some or all of the above effects can also be obtained with those microbes, and they are therefore also appropriate targets for detecting or using efflux pump inhibitors.

Pharmaceutical Compositions

In another aspect, the present disclosure relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delviery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation.

Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

The following examples serve to more fully describe the preferred embodiments, as well as to set forth the best modes contemplated for carrying out various aspects of the preferred embodiments. It is understood that these examples in no way serve to limit the true scope of this invention, but rather are presented for illustrative purposes. All references cited herein are incorporated by reference in their entirety.

Synthesis of Compounds

The following synthetic methods were used to prepare all compounds described as examples below. Unless otherwise stated all compounds were made in the form of mono methanesulfonate salts and the NMR spectra are that of methanesulfonates of the title compounds. In several cases, the step of converting initially obtained trifluoroacetate salt into methanesulfonate was omitted and the compounds were characterized and tested in trifluoroacetate form. All NMR spectra were recorded in DMSO-$d_6$. The methanesulfonic acid peak 2.34 ppm (3H) was omitted form NMR spectra of methanesulfonates listed below. Unless otherwise indicated, mass spectra were obtained using the electrospray ionization method (MS-ESI). When indicated as MS-EI, electron impact ionization was used.

Example 1

Method F: 2-(S),5-Diamino-pentanoic acid [3-phenyl-1-(R)-(4-phenyl-thiazol-2-ylcarbamoyl)-propyl]-amide mono-methanesulfonate (Compound 59)

(A) D-Homophenylalanine Benzyl ester Tosylate

A solution of D-Homophenylalanine hydrochloride (1.7 g, 7.93 mmol), benzyl alcohol (7.2 mL, 64.0 mmol) and p-toluenesulfonic acid monohydrate (1.8 g, 9.5 mmol) in benzene (30 mL) was heated at reflux in Dean Stark apparatus during 5 hrs, after which time additional benzene (100 mL) was distilled from reaction mixture. The residue was triturated with diethyl ether, the solid was filtered and dried to give title product (2.93 g).

$^1$H NMR (DMSO-$d_6$) 2.00-2.08 (m, 2H), 2.28 (s, 3H), 2.50-2.57 (m, 1H), 2.66-2.74 (m, 1H), 5.25 (dd, J=17 Hz, J=12 Hz, 2H), 7.10-7.49 (m, 9H), 8.42 (brs, 3H)

(B) $N_a N_d$-bis-Boc-L-Ornithyl-D-Homophenylalanine Benzyl ester

D-Homophenylalanine Benzyl ester Tosylate (2.48 g, 5.6 mmol) was suspended in ethyl acetate (25 mL) and a saturated solution of sodium bicarbonate in water was added in portions (25 mL) with stirring at 25° C. The water layer was extracted with ethyl acetate (3×10 mL). The combined organic extract was dried over anhydrous sodium sulfate, filtered and concentrated to dryness to afford D-Homophenylalanine Benzyl ester. The ester was dissolved in acetonitile (25 mL). $N_a N_d$-bis-Boc-L-Ornithine (2.0 g, 6.0 mmol) was then added followed by N-hydroxysuccinimide (50 mg) and dicyclohexylcarbodiimide (1.28 g, 6.2 mmol). The reaction was stirred at 25° C. for 30 hr, filtered and the filtrate concentrated to dryness to afford crude product. It was purified by column chromatography on silica gel (hexane:ethyl acetate=3:1), which gave the title product (2.80 g) as white solid.

$^1$H NMR (DMSO-$d_6$) 1.35 (s, 9H), 1.38 (s, 9H), 1.38-1.74 (m, 4H), 1.87-2.00 (m, 2H), 2.50-2.60 (m, 2H), 2.88 (q, J=6 Hz, 2H), 3.95-4.00 (m, 1H), 4.19-4.24 (m, 1H), 5.25 (dd, J=17 Hz, J=12 Hz, 2H), 6.75-6.80 (m, 2H), 7.24-7.38 (m, 10H), 8.31 (d, J=8 Hz, 1H)

MS (EI) found for $C_{32}H_{43}N_3O_7$ M$^+$=583

(C) $N_a N_d$-bis-Boc-L-Ornithyl-D-Homophenylalanine

A solution of $N_a N_d$-bis-Boc-L-Ornithyl-D-Homophenylalanine Benzyl ester (2.80 g, 4.80 mmol) in methanol (200 mL) was treated with 10% Pd/C catalyst (0:2 g) and stirred in the atmosphere of hydrogen at 25° C. for 3 hr. The catalyst was removed by filtration through Celite pad and the filtrate evaporated to dryness to give the title product (2.48 g).

$^1$H NMR (DMSO-$d_6$) 1.35 (s, 9H), 1.38 (s, 9H), 1.38-1.55 (m, 4H), 1.82-1.92 (m, 1H), 1.93-2.01 (m, 1H), 2.50-2.63 (m, 2H), 2.90 (q, J=6 Hz, 2H), 3.95-4.00 (m, 1H), 4.10-4.16 (m, 1H), 6.77-6.79 (m, 2H), 7.15-7.29 (m, 5H), 8.09 (d, J=8 Hz, 1H)

(D) $N_a N_d$-bis-Boc-L-Ornithyl-D-Homophenylalanine (2-amino-4-phenylthiazole) amide A solution of $N_a N_d$-bis-Boc-L-Ornithyl-D-Homophenylalanine (0.3 g, 0.6 mmol) in methylene chloride (10 mL) was treated with 2-amino-4-phenylthiazole (0.16 g, 0.9 mmol) followed by N-hydroxysuccinimide (10 mg) and dicyclohexylcarbodiimide (0.15 g, 0.7 mmol). The reaction was stirred at 25° C. for 18 hr (HPLC monitoring RP-18, 250×4 mm, water:acetonitrile:triethylamine:acetic acid=500:500:0.6:1 (mL), UV detector, λ=254 nm), filtered and the filtrate washed with 1M hydrochloric acid (25 mL), saturated solution of sodium bicarbonate (25 mL) and water (25 mL). The organic layer was dried over anhydrous sodium sulfate, filtered and concentrated to dryness to afford crude product. The product was purified by column chromatography on silica gel (hexane:ethyl acetate=1:1), which gave the title product (0.37 g) as white solid.

$^1$H NMR (DMSO-$d_6$) 1.35 (s, 9H), 1.38 (s, 9H), 1.42-1.52 (m, 2H), 1.60-1.64 (m, 1H), 1.70-1.74 (m, 1H), 1.90-2.00 (m, 1H), 2.08-2.17 (m, 1H), 2.51-2.60 (m, 1H), 2.63-2.68 (m, 1H), 2.93-2.94 (m, 2H), 4.00 (brs, 1H), 4.53 (brs, 1H), 6.76-6.79 (m, 1H), 6.89-6.95 (m, 1H), 7.16-7.34 (m, 8H), 7.39-7.43 (m, 2H), 7.62 (m, 1H), 7.88-7.91 (m, 2H); MS (EI) found for $C_{34}H_{45}N_5O_6S$ (EI) M$^+$=651

(E) L-Ornithyl-D-Homophenylalanine (2-amino-4-phenylthiazole) amide Mesylate $N_a N_d$-bis-Boc-L-Ornithyl-D-Homophenylalanine (2-amino-4-phenylthiazole) amide was converted into mono-mesylate salt of the title compound according to the procedure described below in detail for compound 3.

Example 2

Method Ha: 2-(S),5-Diamino-pentanoic acid [3-phenyl-1-(R)-(quinolin-3-ylcarbamoyl)-propyl]-amide mono-methanesulfonate (compound 3)

(A) N-Boc-D-Homophenylalanine Quinoline-3-amide

A solution of N-Boc-D-Homophenylalanine (3.0 g, 10.7 mmol) in ethyl acetate (100 mL) was treated with 3-aminoquinoline (3.08 g, 21.4 mmol) followed by dicyclohexylcarbodiimide (2.31 g, 11.2 mmol). The reaction was stirred at 25° C. for 3 hr (HPLC monitoring RP-18, 250×4 mm, water:acetonitrile:triethylamine:acetic acid=500:500:0.6:1 (mL), UV detector, λ=254 nm), filtered and the filtrate washed with 1M hydrochloric acid (25 mL), saturated solution of sodium bicarbonate (25 mL) and water (25 mL). The organic layer was dried over anhydrous sodium sulfate, filtered and concentrated to dryness to afford title compound (4.3 g) as white solid.

$^1$H NMR (DMSO-$d_6$) 1.40 (s, 9H), 1.90-2.05 (m, 2H), 2.58-2.78 (m, 2H), 4.15-4.17 (m, 1H), 7.15-7.33 (m, 6H), 7.54-7.58 (m, 1H), 7.61-7.66 (m, 1H), 7.93 (t, J=9 Hz, 2H), 8.69 (d, J=2 Hz, 1H), 8.92 (d, J=2 Hz, 1H), 10.47 (s, 1H)

MS found for $C_{24}H_{27}N_3O_3$ (M+H)$^+$=406

(B) $N_a N_d$-bis-Boc-L-Ornithyl-D-Homophenylalanine Quinoline-3-amide

A solution of $N_a N_d$-bis-Boc-L-Ornithine (2.79 g, 8.4 mmol), triethylamine (1.29 mL, 9.2 mmol) and methylene chloride (90 mL) was stirred at 25° C. for 10 min, cooled to −10° C. and treated with ethyl chloroformate (0.80 mL, 8.4 mmol). The mixture was stirred at −10° C. for 2 hrs. During this time N-Boc-D-Homophenylalanine Quinoline-3-amide (2.27 g, 5.6 mmol) was treated with trifluoroacetic acid (15 mL) at 25° C. for 1 hr. The solution was concentrated to dryness and treated with diethyl ether (10 mL). The solid was filtered and dried. It was suspended in methylene chloride (40 mL) and neutralized with triethylamine (1.6 mL, 11.2 mmol). The resultant solution was added dropwise to the mixed anhydride and the mixture was allowed to warm up to 25° C. and stirred for an additional 1 hr. Saturated sodium bicarbonate (30 mL) was added, the organic layer was washed with water (30 mL), dried over anhydrous sodium sulfate, filtered and concentrated to dryness to afford crude product. It was purified by column chromatography on silica gel (ethyl acetate: hexane=2:1) to give the title compound (2.55 g) as white solid.

$^1$H NMR (DMSO-$d_6$) 1.35 (s, 9H), 1.36 (s, 9H), 1.40-1.66 (m, 4H) 1.91-1.99 (m, 1H), 2.10-2.18 (m, 1H), 2.56-2.76 (m, 2H), 2.92 (q, J=6 Hz, 2H), 3.97-4.0 (m, 1H) 4.44-4.49 (m, 1H), 6.78 (t, J=5 Hz, 1H), 7.03 (d, J=7 Hz, 1H), 7.15-7.29 (m, 5H), 7.54-7.58 (m, 1H), 7.62-7.66 (m, 1H), 7.88-7.95 (m, 2H), 8.44 (d, J=8 Hz, 1H), 8.69 (d, J=2 Hz, 1H), 8.97 (d, J=2 Hz, 1H), 10.24 (s, 1H)

MS found for $C_{34}H_{45}N_5O_6$ $(M+H)^+=620$ (C) L-Ornithyl-D-Homophenylalanine Quinoline-3-amide Mesylate $N_\alpha N_d$-bis-Boc-L-Ornithyl-D-Homophenylalanine Quinoline-3-amide (3.26 g, 5.3 mmol) was treated with trifluoroacetic acid (25 ml) at 25° C. After 1 hr the reaction was concentrated in vacuo. The residue was dissolved in water (10 mL) and loaded on HP 20 filled column. It was washed with 1.5% sodium bicarbonate solution (600 mL), then water (500 mL), then eluted with water:methanol 2:8 vol (600 mL). Fractions containing organic material (TLC monitoring, ethanol:ammonia=8:2 elution on silica gel plates) were concentrated in vacuo and dried to afford free amine of the title compound. It was suspended in water (50 mL) and methanesulfonic acid (0.32 mL, 5 mmol) was added. Slightly turbulent solution was filtered through Celite pad and the filtrate concentrated to dryness. The residue was triturated with diethyl ether (50 mL), the solid was filtered and dried to give title compound (1.48 g).

$^1$H NMR (DMSO-$d_6$) 1.48-1.57 (m, 1H), 1.62-1.77 (m, 2H), 1.94-2.04 (m, 1H), 2.07-2.16 (m, 1H), 2.60-2.67 (m, 1H), 2.70-2.77 (m, 1H), 2.78-2.84 (m, 2H), 3.39 (brs, 1H), 4.55 (brs, 1H), 6.03 (brs, 4H), 7.16-7.30 (m, 5H), 7.55-7.60 (m, 1H), 7.63-7.67 (m, 1H), 7.94 (dd, J=14 Hz, J=8 Hz, 2H), 8.50 (brs, 1H), 8.68 (d, J=2 Hz 1H), 8.95 (d, J=2 Hz, 1H), 10.61 (s, 1H)

MS found for $C_{24}H_{29}N_5O_2$ $(M+H)^+=420$

Example 3

Method IIb: 4-(S)-Aminomethyl-pyrrolidine-2-(S)-carboxylic acid [3-phenyl-1-(R)-(quinolin-3-ylcarbamoyl)-propyl]-amide mono-methanesulfonate (compound 15)

(A) D-Homophenylalanine Quinoline-3-amide

N-Boc-D-homophenylalanine Quinoline-3-amide (2.6 g, 6.42 mmol, procedure 1A) was treated with trifluoroacetic acid (15 mL) at 25° C. for 1 hr. The solution was concentrated to dryness and treated with diethyl ether (10 mL). The solid was filtered and dried. It was dissolved in water (180 mL) and neutralized to pH=7.5 with saturated solution of sodium bicarbonate. The mixture was stirred for 1 hr and the solid was filtered and dried giving the title compound (1.30 g) as white solid.

$^1$H NMR (DMSO-$d_6$) 1.76-1.85 (m, 1H), 1.99-2.08 (m, 1H), 2.65-2.81 (m, 2H), 3.44 (dd, J=8 Hz, J=5 Hz, 1H), 7.15-7.31 (m, 6H), 7.54-7.58 (m, 1H), 7.62-7.66 (m, 1H), 7.91-7.96 (m, 2H), 8.75 (d, J=2 Hz, 1H), 8.99 (d, J=2 Hz, 1H)

(B) N-Boc trans-4-(N-Boc aminomethyl)-L-Prolinyl D-Homophenylalanine Quinoline-3 amide A solution of N-Boc-trans-4-(N-Boc aminomethyl)-L-Proline (0.15 g, 0.44 mmol, U.S. Pat. No. 6,399,629) and D-Homophenylalanine Quinoline-3-amide (0.23 g, 0.66 mmol) in ethyl acetate (10 mL) was treated with dicyclohexylcarbodiimide (0.12 g, 0.60 mmol). The reaction was stirred at 25° C. for 3 hr (HPLC monitoring RP-18, 250×4 mm, water: acetonitrile:triethylamine:acetic acid=500:500:0.6:1 (mL), UV detector, λ=254 nm), filtered and the filtrate washed with 1M hydrochloric acid (25 mL), saturated solution of sodium bicarbonate (25 mL) and water (25 mL). The organic layer was dried over anhydrous sodium sulfate, filtered and concentrated to dryness to afford crude compound. It was purified by column chromatography on silica gel (hexane:ethyl acetate=1:3) to afford the title compound (0.22 g) as white solid.

$^1$H NMR (DMSO-$d_6$) (two rotamers) 1.36 (s, 18H), 1.38 (s, 18H), 1.88-1.92 (m, 2H), 2.00-2.20 (m, 2H), 2.32-2.45 (m, 4H), 2.55-2.70 (m, 4H), 2.89-2.98 (m, 5H), 3.05-3.09 (m, 1H) 3.30-3.34 (m, 2H), 3.46-3.51 (m, 2H), 4.22-4.28 (m, 2H), 4.40-4.45 (m, 1H) 4.52-4.56 (m, 1H), 6.98-7.03 (m, 2H), 7.16-7.30 (m, 10H), 7.55-7.66 (m, 4H), 7.90 (d, J=9 Hz, 2H), 7.93-7.96 (dd, J=8 Hz, J=4 Hz, 2H), 8.36 (d, J=8 Hz, 1H), 8.54 (d, J=8 Hz, 1H), 8.68 (dd, J=15 Hz, J=2 Hz, 1H), 8.94 (d, J=2 Hz, 1H), 8.99 (d, J=2 Hz, 1H), 10.06 (s, 1H), 10.62 (s, 1H)

(C) Amino-trans-4-aminomethyl-L-Prolinyl D-Homophenylalanine Quinoline-3 amide Mesylate N-Boc trans-4-(N-Boc aminomethyl)-L-Prolinyl D-Homophenylalanine Quinoline-3 amide was converted into mono-mesylate salt of the tile product according to the procedure described for compound 3 to give the title compound (0.11 g) as off white solid.

Example 4

Method I: 2-(S),5-Diamino-pentanoic acid [1-(R)-(quinolin-3-ylcarbamoyl)-2-(3,4,5-trifluoro-phenyl)-ethyl]-amide (Compound 41)

(A) N-(Diphenylmethylene) (3,4,5-trifluoro)-D,L-Phenylalanine ethyl ester

A solution of N-(Diphenylmethylene)glycine ethyl ester (1.10 g, 4.1 mmol) and 3,4,5-trifluorobenzylbromide (0.91 g, 4.0 mmol) in dimethylformamide (10 mL) was treated with anhydrous potassium carbonate (2.83 g, 20.5 mmol) and stirred for 18 hrs at 25° C. The mixture was filtered and the filtrate was evaporated to dryness to give crude product. It was purified by column chromatography on silica gel (hexane: ethyl acetate=4:1) to give title compound (1.2 g).

$^1$H NMR (DMSO-$d_6$) 1.17 (t, J=7 Hz, 3H), 3.05-3.19 (m, 2H), 4.06-4.18 (m, 3H), 6.96-7.03 (m, 2H), 7.36-7.47 (m, 10H)

MS (EI) found for $C_{24}H_{20}NO_2F_3$ $M^+=411$

(B) (3,4,5-trifluoro)-D,L-Phenylalanine hydrochloride

N-(Diphenylmethylene) (3,4,5-trifluoro)-D,L-Phenylalanine ethyl ester (1.33 g, 3.2 mmol) was suspended in water (15 mL) at 25° C. and treated with conc. hydrochloric acid (5 mL). The mixture was heated at reflux for 4 hrs and evaporated to dryness. The residue was triturated with diethyl ether (4×20 mL). The solid was filtered and dried to afford title compound (0.72 g)

$^1$H NMR (DMSO-d$_6$) 3.09-3.25 (m, 2H), 4.24 (t, J=7 Hz, 1H), 7.28-7.34 (m, 2H), 8.50 (brs, 3H)

(C) N-Boc-(3,4,5-trifluoro)-D,L-Phenylalanine (3,4,5-trifluoro)-D,L-Phenylalanine hydrochloride (0.72 g, 2.8 mmol) was suspended in methylene chloride (20 mL), cooled to 0° C. and treated with triethylamine (2.0 mL, 14 mmol) and di-tert-butyl dicarbonate (0.68 g, 3.1 mmol). The mixture was allowed to warm up to 25° C., stirred for 18 hrs and evaporated to dryness. The residue was dissolved in water (50 mL) and extracted with diethyl ether (2×20 mL). Water layer was cooled to 0° C. and acidified with 1M hydrochloric acid to pH=2. The mixture was extracted with ethyl acetate (2×20 mL). Organic extract was dried over sodium sulfate, filtered and concentrated to give title compound (0.82 g).

$^1$H NMR (DMSO-d$_6$) 1.31 (s, 9H), 2.78 (dd, J=14 Hz, J=11 Hz, 1H), 3.04 (dd, J=14 Hz, J=4 Hz, 1H) 4.09-4.15 (m, 1H), 7.13-7.23 (m, 3H)

(D) (3,4,5-trifluoro)-D,L-phenylalanine Quinoline-3-amide Trifluoroacetate

A solution of N-Boc-(3,4,5-trifluoro)-D,L-phenylalanine (0.81 g, 2.5 mmol) and in dimethylformamide (10 mL) was treated with 3-aminoquinoline (0.55 g, 3.8 mmol) followed by dicyclohexylcarbodiimide (0.52 g, 2.5 mmol). The reaction was stirred at 25° C. for 18 hr (HPLC monitoring RP-18, 250×4 mm, water:acetonitrile:triethylamineacetic acid=500: 500:0.6:1 (mL), UV detector, λ=254 nm), filtered and the filtrate evaporated to dryness. The residue was dissolved in methylene chloride (30 mL) and washed with 1M hydrochloric acid (25 mL), saturated solution of sodium bicarbonate (25 mL) and water (25 mL). The organic layer was dried over anhydrous sodium sulfate, filtered and concentrated to dryness to afford Boc protected title compound (1.1 g) as white solid. It was treated with trifluoroacetic acid (10 mL) at 25° C. for 1 hr. The solution was concentrated to dryness and treated with diethyl ether (10 mL). The solid was filtered and dried to give the title compound (1.31 g)

$^1$H NMR (DMSO-d$_6$) 3.13 (dd, J=14 Hz, J=8 Hz, 1H), 3.27 (dd, J=14 Hz, J=6 Hz, 1H) 4.31 (brs, 1H), 7.23-7.31 (m, 2H), 7.61-7.64 (m, 1H), 7.69-7.73 (m, 1H), 8.00 (d, J=8 Hz, 2H), 8.64 (d, J=2 Hz, 1H), 8.91 (d, J=2 Hz, 1H), 11.04 (s, 1H)

MS (EI) found for $C_{23}H_{22}N_3O_3F_3$ M$^+$=445

(E) $N_aN_{d}$-Bis-Boc-L-Ornithyl-(3,4,5-trifluoro)-D-Phenylalanine Quinoline-3-amide A solution of $N_aN_{d}$-bis-Boc-L-Ornithine (1.25 g, 3.7 mmol), triethylamine (0.57 mL, 4.1 mmol) and methylene chloride (60 mL) was stirred at 25° C. for 10 min, cooled to −10° C. and treated with ethyl chloroformate (0.36 mL, 3.7 mmol). The mixture was stirred at −10° C. for 2 hrs. (3,4,5-trifluoro)-D,L-phenylalanine Quinoline-3-amide Trifluoroacetate (1.31 g) was suspended in methylene chloride (20 mL) and neutralized with triethylamine (0.70 mL, 5.0 mmol). The resultant solution was added dropwise to the mixed anhydride and the mixture was allowed to warm up to 25° C. and stirred for an additional 1 hr. Saturated sodium bicarbonate (30 mL) was added, the organic layer was washed with water (30 mL), dried over anhydrous sodium sulfate, filtered and concentrated to dryness to afford crude product. TLC (silica gel Merck plates, diethyl ether:ethyl acetate=1:1) revealed the presence of two diastereoisomers. They were separated by column chromatography on silica gel with diethyl ether:ethyl acetate=3:1 to give the title compound (0.25 g) as white solid.

$^1$H NMR (DMSO-d$_6$) 1.10-1.23 (m, 4H), 1.34 (s, 9H), 1.37 (s, 9H), 2.78-2.83 (m, 2H), 2.88-2.94 (m, 1H), 3.20-3.25 (, 1H), 3.87-4.90 (m, 1H) 4.75-4.78 (m, 1H), 6.70 (brs, 1H), 6.95 (d, J=7 Hz, 1H), 7.23 (dd, J=9 Hz, J=7 Hz, 2H), 7.57-7.61 (m, 1H), 7.64-7.69 (m, 1H), 7.92-7.98 (m, 2H), 8.50 (d, J=8 Hz, 1H), 8.70 (d, J=2 Hz, 1H), 8.97 (d, J=2 Hz, 1H), 10.36 (s, 1H)

MS found for $C_{33}H_{40}N_5O_6F_3$ (M+H)$^+$=660

(F) L-ornithyl-(3,4,5-trifluoro)-D-phenylalanine Quinoline-3-amide Mesylate $N_aN_{d}$-bis-Boc-L-ornithyl-(3,4,5-trifluoro)-D-Phenylalanine Quinoline-3-amide was converted into mono-mesylate salt of the tile product according to the procedure described for compound 3 to give the title product (0.15 g) as off white solid.

Example 5

Method K: 3-(S)-Amino-N-{4-(S)-amino-4-[3-phenyl-1-(R)-(quinolin-3-ylcarbamoyl)-propylcarbamoyl]-butyl}-succinamic acid mono-mesylate salt (compound 34)

(A) $N_a$-Boc, $N_d$-Cbz-L-Ornithyl-D-Homophenylalanine Quinoline-3-amide

The title compound was prepared as in step (B) of Method Ha (compound 3) except that $N_a$-Boc, $N_d$-Cbz-L-Ornithine was used.

$^1$H NMR (DMSO-d$_6$) 1.35 (s, 9H), 1.40-1.71 (m, 4H) 1.90-1.99 (m, 1H), 2.10-2.18 (m, 1H), 2.53-2.76 (m, 2H), 3.01 (q, J=6 Hz, 2H), 3.98-4.04 (m, 1H), 4.44-4.49 (m, 1H), 4.98 (s, 2H), 7.08 (d, J=7 Hz, 1H), 7.15-7.35 (m, 12H), 7.55-7.59 (m, 1H), 7.63-7.66 (m, 1H), 7.90-7.97 (m, 2H), 8.45 (d, J=8 Hz, 1H), 8.70 (d, J=2 Hz, 1H), 8.98 (d, J=2 Hz, 1H), 10.27 (s, 1H)

MS (EI) found for $C_{37}H_{43}N_5O_6$ M$^+$=653

(B) $N_a$-Boc-L-Ornithyl-D-Homophenylalanine Quinoline-3-amide

A solution of $N_a$-Boc, $N_d$-Cbz-L-Ornithyl-D-Homophenylalanine Quinoline-3-amide (2.0 g, 3.06 mmol) in methanol (220 mL) was treated with 10% Pd/C catalyst (0.1 g) and stirred in the atmosphere of hydrogen at 40° C. for 3 hr. Catalyst was filtered through Celite pad and the filtrate evaporated to dryness to give the title product (1.64 g)

$^1$H NMR (DMSO-d$_6$) 1.36 (s, 9H), 1.38-1.48 (m, 2H) 1.56-1.72 (m, 2H), 1.92-2.02 (m, 1H), 2.10-2.18 (m, 1H), 2.55-2.76 (m, 4H), 3.98-4.02 (m, 1H), 4.44-4.49 (m, 1H), 4.98 (s, 2H), 7.13 (d, J=7 Hz, 1H), 7.15-7.30 (m, 5H), 7.55-7.59 (m, 1H), 7.63-7.66 (m, 1H), 7.90-7.96 (m, 2H), 8.52 (d, J=8 Hz, 1H), 8.70 (d, J=2 Hz, 1H), 8.98 (d, J=2 Hz, 1H), 10.31 (s, 1H)

MS found for $C_{29}H_{37}N_5O_4$ (M+H)$^+$=520

(C) N-Boc-β-benzyl-L-Aspartyl N$_a$-Boc-L-Ornithyl-D-Homophenylalanine Quinoline-3-amide A solution of N$_a$-Boc-L-Ornithyl-D-Homophenylalanine Quinoline-3-amide (0.8 g, 1.54 mmol) in methylene chloride (10 mL) was treated with N-Boc-β-benzyl-L-Aspartic acid N-hydroxysuccinimide ester (0.67 g, 1.60 mmol) and stirred at 25° C. for 18 hr. The mixture was filtered and the filtrate was concentrated to dryness. The residue was chromatographed on silica gel (hexane:ethyl acetate=1:2) to give the title product (1.15 g).

$^1$H NMR (DMSO-d$_6$) 1.36 (s, 18H), 1.40-1.64 (m, 4H) 1.85-1.89 (m, 1H), 2.08-2.18 (m, 1H), 2.55-2.76 (m, 4H), 3.02-3.13 (m, 2H), 3.98-4.02 (m, 1H), 4.29-4.33 (m, 1H), 4.45-4.49 (m, 1H), 5.06 (s, 2H), 7.06-7.09 (m, 1H), 7.15-7.35 (m, 1H), 7.55-7.59 (m, 1H), 7.63-7.66 (m, 1H), 7.87-7.96 (m, 3H), 8.40 (d, J=8 Hz, 1H), 8.70 (d, J=2 Hz, 1H), 8.98 (d, J=2 Hz, 1H), 10.31 (s, 1H)

(D) N$_d$-L-aspartyl-L-Ornithyl-D-Homophenylalanine Quinoline-3-amide

A solution of N-Boc-β-benzyl-L-aspartyl N$_a$-Boc-L-Ornithyl-D-Homophenylalanine Quinoline-3-amide (1.1 g, 1.33 mmol) in methanol (200 mL) was treated with 10% Pd/C catalyst (0.1 g) and stirred in the atmosphere of hydrogen at 40° C. for 3 hr. Catalyst was filtered through Celite pad and the filtrate evaporated to dryness. The residue was converted into mono-mesylate salt of the tile product according to the procedure described for compound 3 to give the title compound.

Example 6

2-(R),5-Diamino-pentanoic acid [3-phenyl-1-(R)-(quinolin-3-ylcarbamoyl)-propyl]-amide (Compound 1)

2-(R),5-Diamino-pentanoic acid [3-phenyl-1-(R)-(quinolin-3-ylcarbamoyl)-propyl]-amide was obtained according to Method Ha.

1H NMR 1.47-1.55 (m, 1H), 1.61-1.78 (m, 3H), 1.94-2.04 (m, 1H), 2.08-2.17 (m, 1H), 2.60-2.68 (m, 1H), 2.71-2.84 (m, 3H), 3.39 (brs, 1H), 4.56 (brs, 1H), 6.07 (brs, 4H), 7.16-7.31 (m, 5H), 7.55-7.60 (m, 1H), 7.63-7.67 (m, 1H), 7.94 (dd, J=15 Hz, J=8 Hz, 2H), 8.46 (brs, 1H), 8.68 (d, J=2 Hz, 1H) 8.94 (d, J=2 Hz, 1H), 10.62 (s, 1H)

MS C$_{24}$H$_{29}$N$_5$O$_2$ (M+H)$^+$=420

Example 7

2-(S),5-Diamino-pentanoic acid [3-phenyl-1-(S)-(quinolin-3-ylcarbamoyl)-propyl]-amide (Compound 2)

2-(S),5-Diamino-pentanoic acid [3-phenyl-1-(S)-(quinolin-3-ylcarbamoyl)-propyl]-amide was obtained according to Method Ha.

1H NMR 1.57-1.68 (m, 3H), 1.73-1.79 (m, 1H), 1.94-2.04 (m, 1H), 2.08-2.17 (m, 1H), 2.59-2.67 (m, 1H), 2.70-2.76 (m, 1H), 2.80-2.85 (m, 2H), 3.56 (brs, 1H), 4.57 (brs, 1H), 6.71 (brs, 4H), 7.16-7.31 (m, 5H), 7.56-7.60 (m, 1H), 7.64-7.68 (m, 1H), 7.94 (dd, J=14 Hz, J=8 Hz, 2H), 8.65 (brs, 1H), 8.67 (d, J=2 Hz 1H), 8.94 (d, J=2 Hz, 1H), 10.64 (s, 1H)

MS C$_{24}$H$_{29}$N$_5$O$_2$ (M+H)$^+$=420

Example 8

2-(S),5-Diamino-pentanoic acid [3-phenyl-1-(R)-(quinolin-3-ylcarbamoyl)-propyl]-amide (Compound 3)

2-(S),5-Diamino-pentanoic acid [3-phenyl-1-(R)-(quinolin-3-ylcarbamoyl)-propyl]-amide was obtained according to Method Ha.

1H NMR 1.48-1.57 (m, 1H), 1.62-1.77 (m, 2H), 1.94-2.04 (m, 1H), 2.07-2.16 (m, 1H), 2.60-2.67 (m, 1H), 2.70-2.77 (m, 1H), 2.78-2.84 (m, 2H), 3.39 (brs, 1H), 4.55 (brs, 1H), 6.03 (brs, 4H), 7.16-7.30 (m, 5H), 7.55-7.60 (m, 1H), 7.63-7.67 (m, 1H), 7.94 (dd, J=14 Hz, J=8 Hz, 2H), 8.50 (brs, 1H), 8.68 (d, J=2 Hz 1H), 8.95 (d, J=2 Hz, 1H), 10.61 (s, 1H)

MS C$_{24}$H$_{29}$N$_5$O$_2$ (M+H)$^+$=420

Example 9

2-(R),5-Diamino-pentanoic acid [3-phenyl-1-(S)-(quinolin-3-ylcarbamoyl)-propyl]-amide (Compound 4)

2-(R),5-Diamino-pentanoic acid [3-phenyl-1-(S)-(quinolin-3-ylcarbamoyl)-propyl]-amide was obtained according to Method Ha.

1H NMR 1.46-1.53 (m, 1H), 1.62-1.76 (m, 3H), 1.94-2.03 (m, 1H), 2.07-2.16 (m, 1H), 2.60-2.68 (m, 1H), 2.70-2.84 (m, 3H), 3.37 (brs, 1H), 4.56 (brs, 1H), 5.93 (brs, 4H), 7.16-7.31 (m, 5H), 7.55-7.61 (m, 1H), 7.63-7.67 (m, 1H), 7.94 (dd, J=15 Hz, J=8 Hz, 2H), 8.43 (brs, 1H), 8.68 (d, J=2 Hz, 1H), 8.94 (d, J=2 Hz, 1H), 10.61 (s, 1H)

MS C$_{24}$H$_{29}$N$_5$O$_2$ (M+H)$^+$=420

Example 10

2-(S)-Amino-N-{4-amino-1-(S)-[3-phenyl-1-(R)-(quinolin-3-ylcarbamoyl)-propylcarbamoyl]-butyl}-succinamic acid (Compound 5)

2-(S)-Amino-N-{4-amino-1-(S)-[3-phenyl-1-(R)-(quinolin-3-ylcarbamoyl)-propylcarbamoyl]-butyl}-succinamic acid was obtained according to Method K.

1H NMR 1.43-1.53 (m, 1H), 1.55-1.70 (m, 2H), 1.80-1.90 (m, 1H), 1.92-2.04 (m, 1H), 2.06-2.12 (m, 1H), 2.50-2.83 (m, 4H), 2.76-2.83 (m, 2H), 4.06 (brs, 1H), 4.42 (brs, 1H), 4.52 (brs, 1H), 7.16-7.32 (m, 5H), 7.55-7.60 (m, 1H), 7.62-7.66 (m, 1H), 7.88-7.95 (m, 2H), 8.65 (brs, 1H), 8.70 (d, J=2 Hz 1H), 8.99 (d, J=2 Hz, 1H), 9.02 (d, J=2 Hz, 1H), 10.74 (s, 1H)

MS C$_{28}$H$_{34}$N$_6$O$_5$ (M+H)$^+$=535

Example 11

2-(S),5-Diamino-pentanoic acid [3-phenyl-1-(R)-(5,6,7,8-tetrahydro-quinolin-3-ylcarbamoyl)-propyl]-amide (Compound 6)

2-(S),5-Diamino-pentanoic acid [3-phenyl-1-(R)-(5,6,7,8-tetrahydro-quinolin-3-ylcarbamoyl)-propyl]-amide was obtained according to Method Ha.

1H NMR 1.50-1.57 (m, 1H), 1.61-1.83 (m, 7H), 1.88-1.98 (m, 1H), 2.00-2.09 (m, 1H), 2.55-2.61 (m, 1H), 2.64-2.75 (m, 5H), 2.78-2.84 (m, 2H), 3.44 (brs, 1H), 4.47 (brs, 1H), 6.00 (brs, 4H), 7.17-7.30 (m, 5H), 7.72 (d, J=2 Hz, 1H), 8.46 (d, J=2 Hz, 1H), 8.50 (brs, 1H), 10.18 (s, 1H)

MS C$_{24}$H$_{33}$N$_5$O$_2$ (M+H)$^+$=424

Example 12

2-(S),5-Diamino-pentanoic acid [3-phenyl-1-(R)-(quinolin-6-ylcarbamoyl)-propyl]-amide (Compound 7)

2-(S),5-Diamino-pentanoic acid [3-phenyl-1-(R)-(quinolin-6-ylcarbamoyl)-propyl]-amide was obtained according to Method Ha.

1H NMR 1.51-1.60 (m, 1H), 1.60-1.69 (m, 2H), 1.71-1.79 (m, 1H), 1.93-2.03 (m, 1H), 2.06-2.15 (m, 1H), 2.58-2.64 (m, 1H), 2.68-2.74 (m, 1H), 2.78-2.85 (m, 2H), 3.43-3.47 (m, 1H), 4.54-4.57 (m, 1H), 6.19 (brs, 4H) 7.17-7.31 (m, 5H), 7.49 (dd, J=8 Hz, J=4 Hz, 1H), 7.85 (dd, J=9 Hz, J=2 Hz, 1H), 7.98 (d, J=9 Hz, 1H), 8.28 (d, J=8 Hz, 1H), 8.36 (d, J=2 Hz, 1H), 8.55 (brs, 1H), 8.79 (dd, J=4 Hz, J=1.5 Hz, 1H), 10.48 (s, 1H)

MS $C_{24}H_{29}N_5O_2$ (EI) $M^+$=419

Example 13

2-(S),5-Diamino-pentanoic acid [3-(4-fluoro-phenyl)-1-(R)-(quinolin-3-ylcarbamoyl)-propyl]-amide (Compound 8)

2-(S),5-Diamino-pentanoic acid [3-(4-fluoro-phenyl)-1-(R)-(quinolin-3-ylcarbamoyl)-propyl]-amide was obtained according to Method I.

1H NMR 1.57-1.79 (m, 4H), 1.93-2.03 (m, 1H), 2.07-2.15 (m, 1H), 2.58-2.64 (m, 1H), 2.67-2.74 (m, 1H), 2.78-2.85 (m, 2H), 3.51 (brs, 1H), 4.53 (brs, 1H), 7.08-7.12 (m, 2H), 7.23-7.29 (m, 2H) 7.56-7.60 (m, 1H), 7.63-7.67 (m, 1H), 7.91-7.96 (m, 2H), 8.60 (brs, 1H), 8.67 (d, J=2 Hz, 1H), 8.94 (d, J=2 Hz, 1H), 10.62 (s, 1H)

MS $C_{24}H_{28}N_5O_2F$ $(M+H)^+$=438

Example 14

2-(S),5-Diamino-pentanoic acid [3-(4-fluoro-phenyl)-1-(S)-(quinolin-3-ylcarbamoyl)-propyl]-amide (Compound 9)

2-(S),5-Diamino-pentanoic acid [3-(4-fluoro-phenyl)-1-(S)-(quinolin-3-ylcarbamoyl)-propyl]-amide was obtained according to Method I.

1H NMR 1.51-1.57 (m, 1H), 1.62-1.75 (m, 3H), 1.93-2.03 (m, 1H), 2.06-2.16 (m, 1H), 2.33 (s, 3H) 2.59-2.67 (m, 1H), 2.69-2.74 (m, 1H), 2.78-2.85 (m, 2H), 3.43 (brs, 1H), 4.53 (brs, 1H), 7.07-7.12 (m, 2H), 7.24-7.29 (m, 2H), 7.55-7.59 (m, 1H), 7.63-7.67 (m, 1H), 7.89-7.96 (m, 2H), 8.48 (brs, 1H), 8.66 (d, J=2 Hz, 1H), 8.93 (d, J=2 Hz, 1H), 10.60 (s, 1H)

MS $C_{24}H_{28}N_5O_2F$ $(M+H)^+$=438

Example 15

2-(S),5-Diamino-pentanoic acid [2-(4-fluoro-phenyl)-1-(R)-(quinolin-3-ylcarbamoyl)-ethyl]-amide (Compound 11)

2-(S),5-Diamino-pentanoic acid [2-(4-fluoro-phenyl)-1-(R)-(quinolin-3-ylcarbamoyl)-ethyl]-amide was obtained according to Method Ha.

1H NMR 1.32-1.37 (m, 1H), 1.44-1.55 (m, 3H), 2.67-2.75 (m, 2H), 2.94 (dd, J=13 Hz, J=9 Hz, 1H), 3.15 (dd, J=13 Hz, J=5 Hz, 1H), 3.32 (brs, 1H), 4.79 (brs, 1H), 7.13 (t, J=9 Hz, 2H), 7.33 (dd, J=9 Hz, J=5 Hz, 2H), 7.57-7.61 (m, 1H), 7.65-7.69 (m, 1H), 7.95 (t, J=9 Hz, 2H), 8.50 (brs, 1H), 8.66 (d, J=2 Hz, 1H), 8.91 (d, J=2 Hz, 1H), 10.67 (s, 1H)

MS $C_{23}H_{26}N_5O_2F$ $(M+H)^+$=424

Example 16

2-(S),5-Diamino-pentanoic acid [1-(R)-(6-fluoro-quinolin-3-ylcarbamoyl)-3-phenyl-propyl]-amide (Compound 11)

2-(S),5-Diamino-pentanoic acid [1-(R)-(6-fluoro-quinolin-3-ylcarbamoyl)-3-phenyl-propyl]-amide was obtained according to Method Ha.

1H NMR 1.54-1.60 (m, 1H), 1.62-1.69 (m, 2H), 1.71-1.76 (m, 1H), 1.96-2.04 (m, 1H), 2.08-2.17 (m, 1H), 2.59-2.76 (m, 2H), 2.79-2.85 (m, 2H), 3.47 (brs, 1H), 4.55 (brs, 1H), 7.17-7.31 (m, 5H), 7.52-7.58 (m, 1H), 7.78 (dd, J=9 Hz, J=2 Hz, 1H), 8.02 (dd, J=9 Hz, J=5 Hz, 1H), 8.58 (brs, 1H), 8.70 (d, J=2 Hz, 1H), 8.93 (d, J=2 Hz, 1H), 10.68 (s, 1H)

MS $C_{24}H_{28}N_5O_2F$ $(M+H)^+$=438

Example 17

2-(S),5-Diamino-pentanoic acid [1-(R)-(6-trifluoromethyl-quinolin-3-ylcarbamoyl)-3-phenyl-propyl]-amide (Compound 13)

2-(S),5-Diamino-pentanoic acid [1-(R)-(6-trifluoromethyl-quinolin-3-ylcarbamoyl)-3-phenyl-propyl]-amide was obtained according to Method Ha.

1H NMR 1.56-1.69 (m, 3H), 1.72-1.78 (m, 1H), 1.96-2.05 (m, 1H), 2.09-2.18 (m, 1H), 2.59-2.67 (m, 1H), 2.70-2.76 (m, 1H), 2.78-2.85 (m, 2H), 3.54 (brs, 1H), 4.58 (brs, 1H), 7.16-7.31 (m, 5H), 7.89 (dd, J=9 Hz, J=2 Hz, 1H), 8.16 (d, J=9 Hz, 1H), 8.49 (s, 1H), 8.65 (brs 1H), 8.87 (d, J=2 Hz, 1H), 9.11 (d, J=2 Hz, 1H), 10.80 (s, 1H)

MS $C_{25}H_{28}N_5O_2F_3$ $(M+H)^+$=488

Example 18

4-(R)-Aminomethyl-pyrrolidine-2-(S)-carboxylic acid [3-phenyl-1-(R)-(quinolin-3-ylcarbamoyl)-propyl]-amide (Compound 14)

4-(R)-Aminomethyl-pyrrolidine-2-(S)-carboxylic acid [3-phenyl-1-(R)-(quinolin-3-ylcarbamoyl)-propyl]-amide was obtained according to Method Hb.

1H NMR 1.48-1.52 (m, 1H), 1.99-2.03 (m, 1H), 2.10-2.18 (m, 1H), 2.58-2.73 (m, 4H), 2.83-2.86 (m, 3H), 3.17 (brs, 1H), 3.88 (brs, 1H), 4.54-4.59 (m, 1H), 7.17-7.30 (m, 5H), 7.56-7.68 (m, 2H), 7.94 (dd, J=14 Hz, J=8 Hz, 2H), 8.60 (brs, 1H), 8.68 (s 1H), 8.94 (d, J=2 Hz, 1H), 10.66 (s, 1H)

MS $C_{25}H_{29}N_5O_2$ $(M+H)^+$=432

Example 19

4-(S)-Aminomethyl-pyrrolidine-2-(S)-carboxylic acid [3-phenyl-1-(R)-(quinolin-3-ylcarbamoyl)-propyl]-amide (Compound 15)

4-(S)-Aminomethyl-pyrrolidine-2-(S)-carboxylic acid [3-phenyl-1-(R)-(quinolin-3-ylcarbamoyl)-propyl]-amide was obtained according to Method Hb.

1H NMR 1.85-1.93 (m, 1H), 1.94-2.04 (m, 2H), 2.09-2.18 (m, 1H), 2.58-2.78 (m, 4H), 2.81-2.85 (m, 2H), 3.12 (brs, 1H), 3.90 (brs, 1H), 4.54-4.59 (m, 1H), 7.16-7.30 (m, 5H), 7.56-7.68 (m, 2H), 7.94 (dd, J=14 Hz, J=8 Hz, 2H), 8.57 (brs, 1H), 8.68 (d, J=2 Hz 1H), 8.93 (d, J=2 Hz, 1H), 10.66 (s, 1H)
MS $C_{25}H_{29}N_5O_2$ (M+H)$^+$=432

Example 20

2-(S),4-Diamino-N-[3-phenyl-1-(R)-(quinolin-3-ylcarbamoyl)-propyl]-butyramide (Compound 16)

2-(S),4-Diamino-N-[3-phenyl-1-(R)-(quinolin-3-ylcarbamoyl)-propyl]-butyramide was obtained according to Method Ha.

1H NMR 1.71-1.80 (m, 1H), 1.92-2.05 (m, 2H), 2.08-2.16 (m, 1H), 2.59-2.67 (m, 1H), 2.69-2.77 (m, 1H), 2.93 (t, J=7 Hz, 2H), 3.57 (brs, 1H), 4.53-4.57 (m, 1H), 7.16-7.31 (m, 5H), 7.55-7.59 (m, 1H), 7.63-7.67 (m, 1H), 7.90-7.96 (m, 2H), 8.60 (brs, 1H), 8.67 (d, J=2 Hz, 1H), 8.94 (d, J=2 Hz, 1H), 10.63 (s, 1H)

MS $C_{23}H_{27}N_5O_2$ (M+H)$^+$=406

Example 21

2-(S),6-Diamino-hexanoic acid [3-phenyl-1-(R)-(quinolin-3-ylcarbamoyl)-propyl]-amide (Compound 17)

2-(S),6-Diamino-hexanoic acid [3-phenyl-1-(R)-(quinolin-3-ylcarbamoyl)-propyl]-amide was obtained according to Method Ha.

1H NMR 1.35-1.46 (m, 2H), 1.52-1.58 (m, 3H), 1.67-1.74 (m, 1H), 1.96-2.05 (m, 1H), 2.09-2.16 (m, 1H), 2.59-2.67 (m, 1H), 2.69-2.74 (m, 1H), 2.77 (t, J=7 Hz, 2H), 3.52 (t, J=7 Hz, 1H), 4.54 (brs, 1H), 7.17-7.31 (m, 5H), 7.56-7.60 (m, 1H), 7.63-7.68 (m, 1H), 7.91-7.97 (m, 2H), 8.61 (brs, 1H), 8.68 (d, J=2 Hz, 1H), 8.95 (d, J=2 Hz, 1H), 10.61 (s, 1H)

MS $C_{25}H_{31}N_5O_2$ (EI) M$^+$=433

Example 22

2-(S),5-Diamino-pentanoic acid [1-(R)-(methyl-quinolin-3-yl-carbamoyl)-3-phenyl-propyl]-amide (Compound 18)

2-(S),5-Diamino-pentanoic acid [1-(R)-(methyl-quinolin-3-yl-carbamoyl)-3-phenyl-propyl]-amide was obtained according to Method Ha.

1H NMR 1.45-1.48 (m, 1H), 1.58-1.65 (m, 3H), 1.78-1.88 (m, 2H), 2.27 (brs 1H), 2.48 (brs, 1H) 2.76-2.82 (m, 2H), 3.26 (s, 3H) 3.35 (brs, 1H), 4.16 (brs, 1H), 5.90 (brs, 4H), 6.78-6.82 (m, 5H), 7.69 (t J=7 Hz, 1H), 7.84 (t, J=7 Hz, 1H), 7.94 (d, J=8 Hz, 1H), 8.05 (d, J=8 Hz, 1H), 8.34 (s, 1H), (8.41 (brs, 1H), 8.86 (s, 1H)

MS $C_{25}H_{31}N_5O_2$ (M+H)$^+$=434

Example 23

2-(S),5-Diamino-pentanoic acid [3-phenyl-1-(R)-(quinoxalin-2-ylcarbamoyl)-propyl]-amide tris trifluoroacetate salt (Compound 19)

2-(S),5-Diamino-pentanoic acid [3-phenyl-1-(R)-(quinoxalin-2-ylcarbamoyl)-propyl]-amide tris trifluoroacetate salt was obtained according to Method Ha.

1H NMR 1.62-1.69 (m, 2H), 1.76-1.89 (m, 2H), 1.95-2.05 (m, 1H), 2.11-2.19 (m, 1H), 2.62-2.79 (m, 2H), 2.83-2.89 (m, 2H), 3.97 (brs, 1H), 4.75 (brs, 1H), 7.16-7.30 (m, 5H), 7.73-7.77 (m, 1H), 7.81-7.85 (m, 1H), 7.89 (brs 2H) 7.90-7.92 (m, 1H), 8.05-8.07 (m, 1H), 8.28 (brs, 2H), 9.07 (d, J=7 Hz, 1H), 9.60 (s, 1H), 11.45 (s, 1H)

MS $C_{25}H_{31}N_5O_2$ (M+H)$^+$=434

Example 24

2-(S),5-Diamino-pentanoic acid [1-(R)-(quinolin-3-ylcarbamoyl)-3-(4-trifluoromethyl-phenyl)-propyl]-amide tris trifluoroacetate salt (Compound 20)

2-(S),5-Diamino-pentanoic acid [1-(R)-(quinolin-3-ylcarbamoyl)-3-(4-trifluoromethyl-phenyl)-propyl]-amide tris trifluoroacetate salt was obtained according to Method Ha.

1H NMR 1.61-1.68 (m, 2H), 1.74-1.83 (m, 2H), 1.98-2.08 (m, 1H), 2.15-2.23 (m, 1H), 2.73-2.91 (m, 4H), 3.93-4.01 (m, 1H), 4.57-4.63 (m, 1H), 7.45-7.48 (m, 2H), 7.56-7.60 (m, 1H), 7.63-7.68 (m, 3H), 7.78 (brs 3H), 7.89-7.96 (m, 2H), 8.27 (brs, m 3H), 8.64 (d, J=2 Hz, 1H), 8.93-8.97 (m, 3H), 10.73 (s, 1H)

Example 25

2-(S),5-Diamino-pentanoic acid [1-(R)-(quinolin-3-ylcarbamoyl)-2-(4-trifluoromethyl-phenyl)-ethyl]-amide (Compound 21)

2-(S),5-Diamino-pentanoic acid [1-(R)-(quinolin-3-ylcarbamoyl)-2-(4-trifluoromethyl-phenyl)-ethyl]-amide was obtained according to Method Ha.

1H NMR 1.28-1.35 (m, 1H), 1.44-1.52 (m, 3H), 2.65-2.74 (m, 2H), 3.06 (dd, J=13 Hz, J=9 Hz, 1H), 3.27 (dd, J=13 Hz, J=5 Hz, 1H), 3.34 (brs, 1H), 4.86 (brs, 1H), 7.52-7.69 (m, 6H), 8.54 (brs, 1H), 8.66 (d, J=2 Hz, 1H), 8.92 (d, J=2 Hz, 1H), 10.72 (s, 1H)

MS $C_{24}H_{26}N_5O_2F_3$ (M+H)$^+$=474

Example 26

2(R)-(2-(S),5-Diamino-pentanoylamino)-5-methyl-hexanoic acid quinolin-3-ylamide (Compound 22)

2(R)-(2-(S),5-Diamino-pentanoylamino)-5-methyl-hexanoic acid quinolin-3-ylamide was obtained according to Method I.

1H NMR 0.87 (dd, J=7 Hz, J=2 Hz, 6H), 1.16-1.32 (m, 2H), 1.51-1.74 (m, 6H), 1.77-1.86 (m, 1H), 2.75-2.86 (m, 2H), 3.50 (brs, 1H), 4.48-4.55 (m, 1H), 6.51 (brs, 4H), 7.56-7.68 (m, 2H), 7.92-7.97 (m, 2H), 8.50 (brs 1H), 8.69 (d, J=2 Hz, 1H), 8.96 (d, J=2 Hz, 1H), 10.63 (s, 1H)

MS $C_{21}H_{31}N_5O_2$ (M+H)$^+$=386

Example 27

2-(S),5-Diamino-pentanoic acid [2-phenyl-1-(R)-(quinolin-3-ylcarbamoyl)-ethyl]-amide (Compound 23)

2-(S),5-Diamino-pentanoic acid [2-phenyl-1-(R)-(quinolin-3-ylcarbamoyl)-ethyl]-amide was obtained according to Method Ha.

1H NMR 1.31-1.38 (m, 1H), 1.42-1.55 (m, 3H), 2.63-2.75 (m, 2H), 2.95 (dd, J=13 Hz, J=9 Hz, 1H), 3.17 (dd, J=13 Hz, J=5 Hz, 1H), 3.37 (brs, 1H), 4.81 (brs, 1H), 7.18-7.31 (m, 5H), 7.56-7.60 (m, 1H), 7.63-7.69 (m, 1H), 7.91-7.97 (m, 2H), 8.53 (brs, 1H), 8.65 (d, J=2 Hz, 1H), 8.90 (d, J=2 Hz, 1H), 10.65 (s, 1H)

MS $C_{23}H_{27}N_5O_2$ (M+H)$^+$=406

Example 28

2-(S),5-Diamino-pentanoic acid [1-(R)-(3,4-dihydro-1H-isoquinoline-2-carbonyl)-3-phenyl-propyl]-amide (Compound 24)

2-(S),5-Diamino-pentanoic acid [1-(R)-(3,4-dihydro-1H-isoquinoline-2-carbonyl)-3-phenyl-propyl]-amide was obtained according to Method Ha.

1H NMR 1.41-1.48 (m, 1H), 1.62-1.68 (m, 3H), 1.80-1.96 (m, 2H), 2.53-2.64 (m, 2H), 2.74-2.81 (m, 2H), 3.25-3.28 (m, 1H), 3.52-3.74 (m, 3H), 4.50-4.56 (m, 3H), 4.80-4.85 (m, 1H), 7.13-7.30 (m, 9H), 8.30-8.35 (m, 2H)

MS $C_{24}H_{32}N_4O_2$ $(M+H)^+=409$

Example 29

2-(S),5-Diamino-pentanoic acid [1-(R)-(biphenyl-4-ylcarbamoyl)-3-phenyl-propyl]-amide (Compound 25)

2-(S),5-Diamino-pentanoic acid [1-(R)-(biphenyl-4-ylcarbamoyl)-3-phenyl-propyl]-amide was obtained according to Method Ha.

1H NMR 1.60-1.68 (m, 2H), 1.72-1.87 (m, 2H), 1.94-2.00 (m, 1H), 2.05-2.12 (m, 1H), 2.55-2.73 (m, 2H), 2.82-2.88 (m, 2H), 3.85-3.89 (m, 1H), 4.56-4.62 (m, 1H), 7.20-7.74 (m, 14H), 9.00 (d, J=8 Hz, 1H), 10.36 (s, 1H)

MS $C_{27}H_{32}N_4O_2$ $(M+H)^+=445$

Example 30

2-(S),5-Diamino-pentanoic acid [1-(R)-(biphenyl-3-ylcarbamoyl)-3-phenyl-propyl-amide (Compound 26)

2-(S),5-Diamino-pentanoic acid [1-(R)-(biphenyl-3-ylcarbamoyl)-3-phenyl-propyl-amide was obtained according to Method Ha.

1H NMR 1.60-1.66 (m, 2H), 1.73-1.82 (m, 2H), 1.92-2.00 (m, 1H), 2.05-2.14 (m, 1H), 2.56-2.72 (m, 2H), 2.84 (t, J=7 Hz, 2H), 3.86 (brs, 1H), 4.54-4.60 (m, 1H), 7.18-7.72 (m, 13H), 7.93 (s, 1H), 8.90 (d, J=8 Hz, 1H), 10.33 (s, 1H)

MS $C_{27}H_{32}N_4O_2$ $(M+H)^+=445$

Example 31

2-(S),5-Diamino-pentanoic acid [3-phenyl-1-(R)-(quinolin-7-ylcarbamoyl)-propyl]-amide (Compound 28)

2-(S),5-Diamino-pentanoic acid [3-phenyl-1-(R)-(quinolin-7-ylcarbamoyl)-propyl]-amide was obtained according to Method Ha.

1H NMR 1.51-1.59 (m, 1H), 1.62-1.69 (m, 2H), 1.70-1.77 (m, 1H), 1.93-2.03 (m, 1H), 2.06-2.13 (m, 1H), 2.57-2.65 (m, 1H), 2.67-2.76 (m, 1H), 2.77-2.85 (m, 2H), 3.46 (brs, 1H), 4.58 (brs, 1H), 7.19-7.30 (m, 5H), 7.42 (dd, J=8 Hz, J=4 Hz, 1H), 7.73 (dd, J=9 Hz, J=2 Hz, 1H), 7.93 (d, J=9 Hz, 1H), 8.27 (d, J=8 Hz, 1H), 8.45 (d, J=2 Hz, 1H), 8.55 (brs, 1H), 8.84 (dd, J=4 Hz, J=1.5 Hz, 1H), 10.51 (s, 1H)

MS $C_{24}H_{29}N_5O_2$ $(M+H)^+=420$

Example 32

2-(S),5-Diamino-pentanoic acid [1-(R)-(2-fluoro-5-trifluoromethyl-phenylcarbamoyl)-3-phenyl-propyl]-amide (Compound 29)

2-(S),5-Diamino-pentanoic acid [1-(R)-(2-fluoro-5-trifluoromethyl-phenylcarbamoyl)-3-phenyl-propyl]-amide was obtained according to Method Ha.

1H NMR 1.62-1.72 (m, 2H), 1.76-1.90 (m, 2H), 1.94-2.02 (m, 1H), 2.04-2.12 (m, 1H), 2.59-2.74 (m, 2H), 2.80-2.87 (m, 2H), 3.95 (brs, 1H), 4.68 (brs, 1H), 7.17-7.33 (m, 6H), 7.51-7.60 (m, 2H), 7.90 (brs, 2H, NH), 8.28 (brs, 2H, NH) 9.10 (d, J=7 Hz, 1H), 10.34 (s, 1H)

MS $C_{22}H_{26}N_4O_2F_4$ $(M+H)^+=455$

Example 33

2-(S),5-Diamino-pentanoic acid [3-phenyl-1-(R)-(3,4,5-trifluoro-phenylcarbamoyl)-propyl]-amide (Compound 30)

2-(S),5-Diamino-pentanoic acid [3-phenyl-1-(R)-(3,4,5-trifluoro-phenylcarbamoyl)-propyl]-amide was obtained according to Method Ha.

1H NMR 1.52-1.75 (m, 4H), 1.88-1.97 (m, 1H), 1.99-2.07 (m, 1H), 2.53-2.61 (m, 1H), 2.64-2.71 (m, 1H), 2.76-2.84 (m, 2H), 3.47 (brs, 1H), 4.41 (brs, 1H), 7.16-7.29 (m, 5H), 7.53 (dd, J=10 Hz, J=6 Hz, 2H), 8.56 (brs, 1H), 10.52 (s, 1H)

MS $C_{21}H_{25}N_4O_2F_3$ $(M+H)^+=423$

Example 34

2-(S),5-Diamino-pentanoic acid [3-phenyl-1-(R)-(2,3,4-trifluoro-phenylcarbamoyl)-propyl]-amide (Compound 31)

2-(S),5-Diamino-pentanoic acid [3-phenyl-1-(R)-(2,3,4-trifluoro-phenylcarbamoyl)-propyl]-amide was obtained according to Method Ha.

1H NMR 1.55-1.75 (m, 4H), 1.90-1.98 (m, 1H), 2.01-2.09 (m, 1H), 2.56-2.72 (m, 2H), 2.76-2.82 (m, 2H), 3.48 (brs, 1H), 4.59 (brs, 1H), 7.17-7.33 (m, 6H), 7.47-7.53 (m, 1H), 8.56 (brs, 1H), 10.52 (s, 1H)

MS $C_{21}H_{25}N_4O_2F_3$ $(M+H)^+=423$

Example 35

2-(S),5-Diamino-pentanoic acid [1-(R)-(5-chloro-2-fluoro-phenylcarbamoyl)-3-phenyl-propyl]-amide (Compound 32)

2-(S),5-Diamino-pentanoic acid [1-(R)-(5-chloro-2-fluoro-phenylcarbamoyl)-3-phenyl-propyl]-amide was obtained according to Method Ha.

1H NMR 1.58-1.75 (m, 4H), 1.87-1.97 (m, 1H), 2.01-2.10 (m, 1H), 2.58-2.72 (m, 2H), 2.76-2.82 (m, 2H), 3.54 (brs, 1H), 4.65 (brs, 1H), 7.17-7.36 (m, 7H), 7.97 (dd, J=7 Hz, J=2 Hz, 1H), 8.60 (brs, 1H), 10.12 (s, 1H)

MS $C_{21}H_{26}N_4O_2F^{35}Cl$ $(M+H)^+=421$

Example 36

2-(S),5-Diamino-pentanoic acid [1-(R)-(1-methyl-2-oxo-1,2-dihydro-quinolin-3-ylcarbamoyl)-3-phenyl-propyl]-amide (Compound 33)

2-(S),5-Diamino-pentanoic acid [1-(R)-(1-methyl-2-oxo-1,2-dihydro-quinolin-3-ylcarbamoyl)-3-phenyl-propyl]-amide was obtained according to Method Ha.

1H NMR 1.54-1.77 (m, 4H), 1.90-2.01 (m, 1H), 2.07-2.17 (m, 1H), 2.58-2.76 (m, 2H), 2.78-2.85 (m, 2H), 3.57 (brs, 1H), 3.73 (s, 3H), 4.52-4.56 (m, 1H), 5.95 (brs, 4H), 7.16-7.31 (m, 7H), 7.55-7.58 (m, 2H), 7.71 (d, J=8 Hz, 1H), 8.62 (s, 1H), 9.55 (s, 1H)

MS $C_{25}H_{31}N_5O_3$ $(M+H)^+=450$

Example 37

3-(S)-Amino-N-{4-(S)-amino-4-[3-phenyl-1-(R)-(quinolin-3-ylcarbamoyl)-propylcarbamoyl]-butyl}-succinamic acid acid (Compound 34)

3-(S)-Amino-N-{4-(S)-amino-4-[3-phenyl-1-(R)-(quinolin-3-ylcarbamoyl)-propylcarbamoyl]-butyl}-succinamic acid acid was obtained according to Method K.

1H NMR 1.48-1.56 (m, 1H), 1.60-1.70 (m, 2H), 1.82-1.90 (m, 1H), 2.07-2.17 (m, 2H), 2.49-2.55 (m, 2H), 2.60-2.67 (m, 1H), 2.70-2.77 (m, 1H), 2.99-3.05 (m, 1H), 3.33-3.40 (m, 1H), 3.77-3.82 (m, 2H), 4.43-4.48 (m, 1H), 7.16-7.32 (m, 5H), 7.55-7.60 (m, 1H), 7.62-7.66 (m, 1H), 7.90-7.96 (m, 2H), 8.50 (brs, 1H), 8.70 (d, J=2 Hz 1H), 9.00 (d, J=2 Hz, 1H), 9.61 (d, J=7 Hz, 1H), 11.02 (s, 1H)

MS $C_{28}H_{34}N_6O_5$ $(M+H)^+=535$

Example 38

2-(R)-[2-(S)-Amino-3-(2-amino-ethoxy)-propionylamino]-4-phenyl-N-quinolin-3-yl-butyramide (Compound 35)

2-(R)-[2-(S)-Amino-3-(2-amino-ethoxy)-propionylamino]-4-phenyl-N-quinolin-3-yl-butyramide was obtained according to Method Hb.

1H NMR 1.96-2.05 (m, 1H), 2.08-2.17 (m, 1H), 2.58-2.79 (m, 2H), 2.95 (t, J=5 Hz, 2H), 3.50-3.65 (m, 4H), 3.74 (brs, 1H), 4.55 (brs, 1H), 7.16-7.31 (m, 7H), 7.55-7.58 (m, 2H), 7.90-7.96 (m, 12H), 8.40 (brs 1H) 8.67 (d, J=2 Hz, 1H), 8.93 (d, J=2 Hz, 1H), 10.61 (s, 1H)

MS $C_{24}H_{29}N_5O_3$ $(M+H)^+=436$

Example 39

2-(S),5-Diamino-pentanoic acid [1-(R)-(3,5-dichloro-pyridin-2-ylcarbamoyl)-3-phenyl-propyl]-amide (Compound 36)

2-(S),5-Diamino-pentanoic acid [1-(R)-(3,5-dichloro-pyridin-2-ylcarbamoyl)-3-phenyl-propyl]-amide was obtained according to Method Hb.

1H NMR 1.58-1.76 (m, 4H), 1.90-2.00 (m, 1H), 2.02-2.13 (m, 1H), 2.60-2.83 (m, 4H), 3.63 (brs, 1H), 4.62 (brs, 1H), 7.18-7.30 (m, 5H), 8.31 (d, J=2 Hz, 1H), 8.49 (d, J=2 Hz, 1H), 8.67 (brs, 1H), 10.58 (brs, 1H)

MS $C_{20}H_{25}N_5O_2$ 35Cl2 $(M+H)^+=438$

Example 40

2-(S),5-Diamino-pentanoic acid [1-(R)-(5-fluoro-2-hydroxy-phenylcarbamoyl)-3-phenyl-propyl]-amide (Compound 37

2-(S),5-Diamino-pentanoic acid [1-(R)-(5-fluoro-2-hydroxy-phenylcarbamoyl)-3-phenyl-propyl]-amide was obtained according to Method Hb.

1H NMR 1.48-1.72 (m, 4H), 1.87-1.97 (m, 1H), 2.02-2.11 (m, 1H), 2.55-2.72 (m, 2H), 2.76-2.82 (m, 2H), 3.50 (brs, 1H), 4.57 (brs, 1H), 6.72-6.77 (m, 1H), 6.81-6.85 (m, 1H), 7.16-7.30 (m, 5H), 7.80 (dd, J=11 Hz, J=3 Hz, 1H), 8.46 (brs, 1H), 9.31 (brs, 1H)

MS $C_{21}H_{27}N_4O_3F$ $(M+H)^+=403$

Example 41

2-(S),5-Diamino-pentanoic acid [1-(R)-(cinnolin-3-ylcarbamoyl)-3-phenyl-propyl]amide tris trifluoroacetate salt (Compound 39)

2-(S),5-Diamino-pentanoic acid [1-(R)-(cinnolin-3-ylcarbamoyl)-3-phenyl-propyl]-amide tris trifluoroacetate salt was obtained according to Method Ha.

1H NMR 1.60-1.69 (m, 2H), 1.77-1.87 (m, 2H), 1.95-2.05 (m, 1H), 2.11-2.19 (m, 1H), 2.61-2.79 (m, 2H), 2.83-2.89 (m, 2H), 3.95 (brs, 1H), 4.78-4.83 (m, 1H), 7.16-7.30 (m, 5H), 7.82-7.84 (m, 4H), 8.03-8.07 (m, 1H), 8.25 (brs, 2H), 8.38-8.42 (m, 1H), 8.71 (s, 1H), 9.05 (d, J=8 Hz, 1H), 11.71 (s, 1H)

MS $C_{23}H_{28}N_6O_2$ $(M+H)^+=421$

Example 42

2-(S),5-Diamino-pentanoic acid [1-(R)-(2-oxo-1,2-dihydro-quinolin-3-ylcarbamoyl)-3-phenyl-propyl]-amide (Compound 40)

2-(S),5-Diamino-pentanoic acid [1-(R)-(2-oxo-1,2-dihydro-quinolin-3-ylcarbamoyl)-3-phenyl-propyl]-amide was obtained according to Method Ha.

1H NMR 1.54-1.74 (m, 4H), 1.92-2.00 (m, 1H), 2.06-2.15 (m, 1H), 2.58-2.74 (m, 2H), 2.79-2.83 (m, 2H), 3.39 (brs, 1H), 4.57 (brs, 1H), 7.17-7.32 (m, 7H), 7.41-7.44 (m, 1H), 7.64 (d, J=8 Hz, 1H), 8.62 (s, 1H), 9.52 (s, 1H), 12.32 (brs, 1H)

MS $C_{24}H_{29}N_5O_3$ $(M+H)^+=436$

Example 43

2-(S),5-Diamino-pentanoic acid [1-(R)-(quinolin-3-ylcarbamoyl)-2-(3,4,5-trifluoro-phenyl)-ethyl]-amide (Compound 41)

2-(S),5-Diamino-pentanoic acid [1-(R)-(quinolin-3-ylcarbamoyl)-2-(3,4,5-trifluoro-phenyl)-ethyl]-amide was obtained according to Method I.

1H NMR 1.27-1.36 (m, 1H), 1.46-1.53 (m, 3H), 2.66-2.76 (m, 2H), 2.96 (dd, J=13 Hz, J=9 Hz, 1H), 3.16 (dd, J=13 Hz, J=4 Hz, 1H), 3.24 (brs, 1H), 4.76-4.80 (m, 1H), 7.26 (dd, J=9 Hz, J=7 Hz, 2H), 7.57-7.61 (m, 1H), 7.65-7.69 (m, 1H), 7.93-7.98 (m, 2H), 8.47 (brs, 1), 8.66 (d, J=2 Hz, 1H), 8.93 (d, J=2 Hz, 1H), 10.65 (s, 1H)

MS $C_{23}H_{24}N_5O_2F_3$ $(M+H)^+=460$

Example 44

-Amino-(S)—N-{4-(S)-(2-(3)-(S)-amino-3-carboxy-propionylamino)-4-[3-phenyl-1-(R)-(quinolin-3-ylcarbamoyl)-propylcarbamoyl]-butyl}-succinamic acid tris methanesulfonate (Compound 43)

3-Amino-(S)—N-{4-(S)-(2-(3)-(S)-amino-3-carboxy-propionylamino)-4-[3-phenyl-1-(R)-(quinolin-3-ylcarbamoyl)-propylcarbamoyl]-butyl}-succinamic acid tris methanesulfonate was obtained according to Method L.

1H NMR 1.44-1.64 (m, 3H), 1.74-1.82 (m, 1H), 1.93-2.03 (m, 1H), 2.07-2.16 (m, 1H), 2.53-2.94 (m, 6H), 3.09-3.21 (m, 1H), 3.46-3.58 (m, 1H), 4.02 (brs, 1H), 4.17 (brs, 1H), 4.39-4.44 (m, 1H), 4.47-4.53 (m, 1H), 7.16-7.32 (m, 5H), 7.55-7.60 (m, 1H), 7.62-7.66 (m, 1H), 7.90-7.96 (m, 2H), 8.15 (brs, 4H), 8.44 (t, J=6 Hz, 1H), 8.51 (d, J=8 Hz, 1H), 8.69 (d, J=2 Hz 1H), 8.97 (d, J=2 Hz, 1H), 10.53 (s, 1H), 12.95 (brs, 2H)

MS $C_{32}H_{39}N_7O_8$ (M+H)$^+$=650

Example 45

5-Amino-2-(S)-methylamino-pentanoic acid [3-phenyl-1-(R)-(quinolin-3-ylcarbamoyl)-propyl]-amide (Compound 45)

5-Amino-2-(S)-methylamino-pentanoic acid [3-phenyl-1-(R)-(quinolin-3-ylcarbamoyl)-propyl]-amide was obtained according to Method Hb.

1H NMR 1.57-1.61 (m, 2H), 1.70-1.79 (m, 2H), 2.03-2.07 (m, 1H), 2.10-2.15 (m, 1H), 2.55 (s, 3H), 2.65-2.75 (m, 2H), 2.84-2.88 (m, 2H), 3.86 (brs, 1H), 4.56 (brs, 1H), 7.20-7.32 (m, 5H), 7.56-7.68 (m, 2H), 7.65 (brs, 1H), 8.66 (d, J=2 Hz 1H), 8.95 (d, J=2 Hz, 1H), 10.73 (s, 1H)

MS $C_{25}H_{31}N_5O_2$ (M+H)$^+$=434

Example 46

2-(S),5-Diamino-pentanoic acid [1-(R)-(6-fluoro-quinolin-3-ylcarbamoyl)-2-(4 trifluoromethyl-phenyl)-ethyl]-amide (Compound 46)

2-(S),5-Diamino-pentanoic acid [1-(R)-(6-fluoro-quinolin-3-ylcarbamoyl)-2-(4-trifluoromethyl-phenyl)-ethyl]-amide was obtained according to Method Ha.

1H NMR 1.27-1.34 (m, 1H), 1.42-1.50 (m, 3H), 2.62-2.75 (m, 2H), 3.05 (dd, J=13 Hz, J=9 Hz, 1H), 3.26 (dd, J=13 Hz, J=5 Hz, 1H), 3.34 (brs, 1H), 4.84-4.88 (m, 1H), 7.52-7.58 (m, 3H), 7.67 (d, J=8 Hz, 2H), 7.79 (dd, J=10 Hz, J=3 Hz, 1H), 8.02 (dd, J=9 Hz, J=5 Hz, 1H), 8.54 (brs, 1H), 8.68 (d, J=2 Hz, 1H), 8.90 (d, J=2 Hz, 1H), 10.79 (s, 1H)

MS $C_{24}H_{25}N_5O_2F_4$ (M+H)$^+$=492

Example 47

2-(S),5-Diamino-pentanoic acid [1-(R)-(benzothiazol-6-ylcarbamoyl)-3-phenyl-propyl]-amide (Compound 50)

2-(S),5-Diamino-pentanoic acid [1-(R)-(benzothiazol-6-ylcarbamoyl)-3-phenyl-propyl]-amide was obtained according to Method Ha.

1H NMR 1.54-1.75 (m, 4H), 1.90-2.00 (m, 1H), 2.03-2.12 (m, 1H), 2.56-2.73 (m, 2H), 2.79-2.85 (m, 2H), 3.50 (brs, 1H), 4.55 (brs, 1H), 6.41 (brs, 4H), 7.16-7.31 (m, 5H), 7.65 (dd, J=9 Hz, J=2 Hz, 1H), 8.02 (d, J=9 Hz, 1H), 8.52 (d, J=2 Hz, 1H), 8.55 (brs, 1H), 9.27 (s, 1H), 10.43 (s, 1H)

MS $C_{22}H_{27}N_5O_2S$ (M+H)$^+$=426

Example 48

4-(R)-Aminomethyl-pyrrolidine-2-(S)-carboxylic acid [3-phenyl-1-(R)-(quinolin-6-ylcarbamoyl)-propyl]-amide tris trifluoroacetate salt (Compound 52)

4-(R)-Aminomethyl-pyrrolidine-2-(S)-carboxylic acid [3-phenyl-1-(R)-(quinolin-6-ylcarbamoyl)-propyl]-amide tris trifluoroacetate salt was obtained according to Method Hb.

1H NMR 1.60-1.68 (m, 1H), 1.94-2.04 (m, 1H), 2.09-2.18 (m, 1H), 2.52-2.74 (m, 4H), 2.92-3.04 (m, 3H), 3.43 (brs, 1H), 4.30-4.37 (m, 1H), 4.56-4.61 (m, 1H), 7.18-7.32 (m, 5H), 7.57 (dd, J=8 Hz, J=4 Hz, 1H), 7.86-8.02 (m, 5H), 8.38-8.42 (m, 2H), 8.74 (brs, 1H), 8.86 (dd, J=4 Hz, J=2 Hz 1H), 9.13 (d, J=8 Hz, 1H), 9.52 (brs 1H), 10.65 (s, 1H)

MS $C_{25}H_{29}N_5O_2$ (M+H)$^+$=432

Example 49

4-(S)-Aminomethyl-pyrrolidine-2-(S)-carboxylic acid [3-phenyl-1-(R)-(quinolin-6-ylcarbamoyl)-propyl]-amide tris trifluoroacetate salt (Compound 53)

4-(S)-Aminomethyl-pyrrolidine-2-(S)-carboxylic acid [3-phenyl-1-(R)-(quinolin-6-ylcarbamoyl)-propyl]-amide tris trifluoroacetate salt was obtained according to Method Hb.

1H NMR 1.94-2.03 (m, 1H), 2.09-2.22 (m, 3H), 2.52-2.76 (m, 3H), 2.96 (t, J=6 Hz, 2H), 3.05 (brs, 1H), 3.51 (brs, 1H), 4.46 (brs 1H), 4.54-4.60 (m, 1H), 7.18-7.32 (m, 5H), 7.59 (dd, J=8 Hz, J=4 Hz, 1H), 7.89-8.05 (m, 5H), 8.41-8.44 (m, 2H), 8.77 (brs, 1H), 8.87 (dd, J=4 Hz, J=2 Hz 1H), 9.16 (d, J=8 Hz, 1H), 9.78 (brs 1H), 10.66 (s, 1H)

MS $C_{25}H_{29}N_5O_2$ (M+H)$^+$=432

Example 50

2-(S)-Amino-6-methylamino-hexanoic acid [3-phenyl-1-(R)-(quinolin-3-ylcarbamoyl)-propyl]-amide (Compound 55)

2-(S)-Amino-6-methylamino-hexanoic acid [3-phenyl-1-(R)-(quinolin-3-ylcarbamoyl)-propyl]-amide was obtained according to Method Hb.

1H NMR 1.34-1.43 (m, 2H), 1.50-1.58 (m, 3H), 1.65-1.73 (m, 1H), 1.96-2.04 (m, 1H), 2.09-2.16 (m, 1H), 2.58-2.76 (m, 2H), 2.81 (t, J=7 Hz, 2H), 3.25-3.40 (m, 3H), 3.43 (brs, 1H), 4.54 (brs, 1H), 7.17-7.31 (m, 5H), 7.56-7.60 (m, 1H), 7.63-7.68 (m, 1H), 7.91-7.97 (m, 2H), 8.58 (brs, 1H), 8.68 (d, J=2 Hz, 1H), 8.95 (d, J=2 Hz, 1H), 10.61 (s, 1H)

MS $C_{26}H_{33}N_5O_3$ (M+H)$^+$=448

Example 51

2,5-Diamino-pentanoic acid [3-phenyl-1-(R)-(5-phenyl-[1,3,4]thiadiazol-2-ylcarbamoyl)-propyl]-amide (Compound 58)

2,5-Diamino-pentanoic acid [3-phenyl-1-(R)-(5-phenyl-[1,3,4]thiadiazol-2-ylcarbamoyl)-propyl]-amide was obtained according to Method Ha.

1H NMR 1.58-1.77 (m, 4H), 1.93-2.02 (m, 1H), 2.04-2.14 (m, 1H), 2.56-2.73 (m, 2H), 2.82 (t, J=7 Hz, 2H), 3.54 (brs, 1H), 4.56 (brs, 1H), 7.1.6-7.30 (m, 6H), 7.51-7.54 (m, 3H), 7.90-7.93 (m, 2H), 8.63 (brs, 1H)

MS $C_{23}H_{28}N_6O_2S$ (M+H)$^+$=453

Example 52

2-(S),5-Diamino-pentanoic acid [3-phenyl-1-(R)-(4-phenyl-thiazol-2-ylcarbamoyl)-propyl]-amide (Compound 59)

2-(S),5-Diamino-pentanoic acid [3-phenyl-1-(R)-(4-phenyl-thiazol-2-ylcarbamoyl)-propyl]-amide was obtained according to Method F.

1H NMR 1.47-1.55 (m, 1H), 1.63-1.75 (m, 3H), 1.92-2.02 (m, 1H), 2.08-2.17 (m, 1H), 2.55-2.62 (m, 1H), 2.76-2.84 (m, 2H), 3.40 (brs, 1H), 4.59 (brs, 1H), 6.27 (brs, 4H), 7.16-7.34 (m, 8H), 7.41-7.44 (m, 2H), 7.63 (m, 1H), 7.88 (d, J=1 Hz, 1H), 7.81 (d, J=2 Hz, 1H)

MS $C_{24}H_{29}N_5O_2S$ (M+H)$^+$=452

Example 53

2-(S),5-Diamino-pentanoic acid [1-(R)-(5-bromo-thiazol-2-ylcarbamoyl)-3-phenyl-propyl]-amide (Compound 61)

2-(S),5-Diamino-pentanoic acid [1-(R)-(5-bromo-thiazol-2-ylcarbamoyl)-3-phenyl-propyl]-amide was obtained according to Method F.

1H NMR 1.50-1.74 (m, 4H), 1.92-2.09 (m, 2H), 2.53-2.70 (m, 2H), 2.76-2.84 (m, 2H), 3.48 (brs, 1H), 4.54 (brs, 1H), 7.16-7.29 (m, 6H), 7.56 (s, 1H), 8.62 (brs, 1H)

MS $C_{18}H_{24}NO_2S^{78}Br$ (M+H)$^+$=454

Example 54

2-(S),5-Diamino-pentanoic acid [1-(R)-(benzothiazol-2-ylcarbamoyl)-3-phenyl-propyl]-amide (Compound 63)

2-(S),5-Diamino-pentanoic acid [1-(R)-(benzothiazol-2-ylcarbamoyl)-3-phenyl-propyl]-amide was obtained according to Method F.

1H NMR 1.49-1.56 (m, 1H), 1.61-1.73 (m, 3H), 1.93-2.03 (m, 1H), 2.05-2.15 (m, 1H), 2.56-2.63 (m, 1H), 2.66-2.73 (m, 1H), 2.77-2.83 (m, 2H), 3.34 (brs, 1H), 4.56-4.60 (m, 1H), 6.15 (brs, 4H), 7.16-7.32 (m, 7H), 7.40-7.45 (m, 1H), 7.71-7.75 (m, 1H), 7.93-7.97 (m, 1H), 8.46 (brs, 1H)

MS $C_{22}H_{27}N_5O_2S$ (M+H)$^+$=426

Example 55

2-(S)-Amino-4-phenyl-N-quinolin-3-yl-butyramide (Compound 67)

2-(S)-Amino-4-phenyl-N-quinolin-3-yl-butyramide was obtained according to Method Ha.

$^1$H NMR 1.76-1.85 (m, 1H), 1.99-2.08 (m, 1H), 2.65-2.81 (m, 2H), 3.44 (dd, J=8 Hz, J=5 Hz, 1H), 7.15-7.31 (m, 6H), 7.54-7.58 (m, 1H), 7.62-7.66 (m, 1H), 7.91-7.96 (m, 2H), 8.75 (d, J=2 Hz, 1H), 8.99 (d, J=2 Hz, 1H)

MS $C_{19}H_{19}N_3O$ (EI) M$^+$=305

Example 56

2-(S),4-Diamino-N-[3-phenyl-1-(R)-(quinolin-6-ylcarbamoyl)-propyl]-butyramide (Compound 68)

2-(S),4-Diamino-N-[3-phenyl-1-(R)-(quinolin-6-ylcarbamoyl)-propyl]-butyramide was obtained according to Method Ha.

1H NMR 1.76-1.78 (m, 1H), 1.94-2.04 (m, 2H), 2.06-2.17 (m, 1H), 2.58-2.75 (m, 2H), 2.93 (t, J=8 Hz, 2H), 3.61 (brs, 1H), 4.56 (brs, 1H), 6.20 (brs, 4H), 7.17-7.31 (m, 5H), 7.49 (dd J=8 Hz, J=4 Hz, 1H), 7.84 (dd, J=9 Hz, J=2 Hz, 1H), 7.98 (d, J=9 Hz, 1H), 8.61 (brs, 1H), 8.79 (dd, J=6 Hz, J=2 Hz 1H), 10.51 (s, 1H)

MS $C_{23}H_{27}N_5O_2$ (M+H)$^+$=406

Biological Data

Example 57

Effect of Stereochemistry on EPI Activity

This example shows the initial microbiological evaluation of the efflux pump inhibitory (EPI) activity of four stereoisomeric compounds (1 through 4).

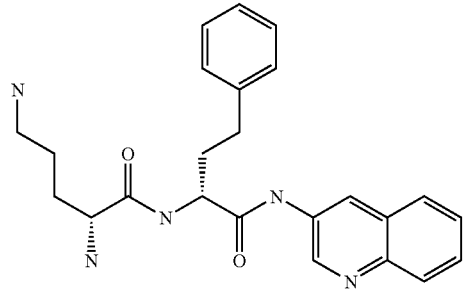

1

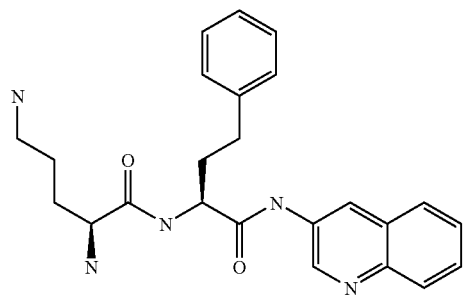

2

-continued

3

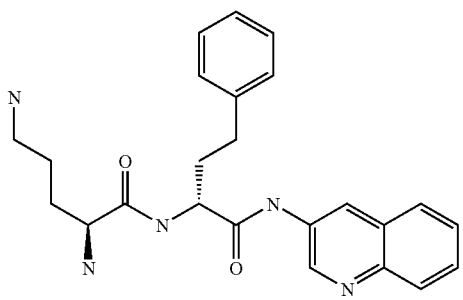

4

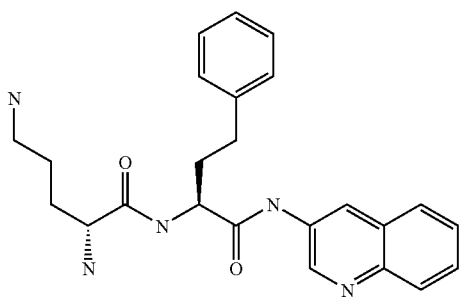

EPI activity was recorded as concentration of an EPI compound that is necessary to increase susceptibility to levofloxacin of the strain of P. aeruginosa, PAM1723, overexpressing the MexAB-OprM efflux pump eight-fold. The levofloxacin potentiating activity of the test compounds was assessed by the checkerboard assay (Antimicrobial Combinations, *Antibiotics in Laboratory Medicine*, Ed. Victor Lorian, M.D., Fourth edition, 1996, pp 333-338, which is incorporated herein by reference in its entirety) using a broth microdilution method performed as recommended by the NCCLS (National Committee for Clinical Laboratory Standards (NCCLS), 1997, *Methods for Dilution of Antimicrobial Susceptibility Tests for Bacteria That Grow Aerobically*, Fourth Edition; Approved Standard. NCCLS Document M7-A4, Vol 17 No. 2, which is incorporated herein by reference in its entirety). In this assay, multiple dilutions of two drugs, namely an EPI and levofloxacin, were tested, alone and in combination, at concentrations equal to, above and below their respective minimal inhibitory concentrations (MICs). All EPI compounds were readily soluble in water and stock solutions were prepared at a final concentration of 10 mg/ml. Stock solutions were further diluted, according to the needs of the particular assay, in Mueller Hinton Broth (MHB). Stock solution was stored at −80° C.

The checkerboard assay was performed in microtiter plates. Levofloxacin was diluted in the x axis, each column containing a single concentration of levofloxacin. EPIs were diluted in the y axis, each row containing an equal concentration of an EPI. The result of these manipulations was that each well of the microtiter plate contains a unique combination of concentrations of the two agents. The assay was performed in MHB with a final bacterial inoculum of 5×105 CFU/ml (from an early-log phase culture). Microtiter plates were incubated during 20 h at 35° C. and were read using a microtiterplate reader (Molecular Devices) at 650 nm as well as visual observation using a microtiter plate-reading mirror. The MIC was defined as the lowest concentration of antibiotics, within the combination, at which the visible growth of the organism was completely inhibited.

TABLE 1

| | Levofloxacin potentiation by the EPI compounds | | | | | | | | |
|---|---|---|---|---|---|---|---|---|---|
| | Antibiotic MIC (µg/l) in the presence of EPI (µg/ml) | | | | | | | | |
| Compound | 0 | 0.625 | 1.25 | 2.5 | 5 | 10 | 20 | 40 | 80 | $MPC_8$ (µg/l) |
| 1 | 2 | | 2 | 1 | 0.5 | 0.06 | 0.03 | 0.015 | 0.008 | 10 |
| 2 | 2 | | 2 | 2 | 2 | 1 | 0.125 | 0.06 | 0.03 | 20 |
| 3 | 2 | | 2 | 1 | 0.25 | 0.03 | 0.015 | 0.015 | 0.015 | 10 |
| 4 | 2 | | 2 | 2 | 2 | 0.5 | 0.06 | 0.06 | 0.03 | 20 |

The experiment depected in Table 1 demonstrates that all four compounds have similar levofloxacin potentiating activity ($MPC_8$ of 10 to 20 µg/ml) against the MexAB-OprM over-producing strain of P. aeruginosa.

The following examples describe in vitro stability of compound 3 in comparison with its three stereoisomer analogs.

Example 58

In Vitro Stability

To test the stability of the compounds in vitro, samples were prepared and analyzed by LC/MS/MS according to the following procedure.

Homogenization: A chunk of fresh tissue was weighed and mixed with saline at 1:1 ratio (w/v) in a 12×75 mm polypropylene round bottom tube. The mixture was homogenized with a Polytron homogenizer (on ice, 3×10 seconds with 10 second intervals at the setting of 7).

Incubation and TCA-precipitation: An appropriate amount of a tissue homogenate was pre-warmed at 37° C. for 2 minutes in an Eppendorf tube. The compound to be tested was added to the tube to a final concentration of 2 μg/ml, mixed, and a 60 μl aliquot was immediately taken (as 0 hour sample) and mixed with 120 μl of 4% TCA (trichloroacetic acid) in an Eppendorf tube. The temperature of the tube containing the rest of the tissue sample was returned to 37° C. for incubation. Later, samples were taken as scheduled and mixed with TCA as described above. Plasma and lavage samples were directly incubated with the compounds without addition of saline and homogenization.

LC/MS/MS sample vial preparation: TCA-precipitated sample tubes were vortexed for 30 seconds, centrifuged in a microfuge at top speed (13.2 k rpm) for 5 minutes. The supernatant was collected. The pH was neutralized to about 3.5 with ammonium acetate buffer. The sample (45 μl) was transferred to a glass LC/MS/MS vial (Kimble, 11 mm, 1.5 ml) and 5 μl of an internal standard was added to a final concentration of 500 ng/ml. LC/MS/MS analysis was performed in Chemistry Department of San Diego State University.

LC/MS/MS protocol: Thermo-Finnigan TSQ Quantum triple sector mass spectrometer with electrospray (ESI) ionization was used to analyze the samples. The operation conditions were: Mobile phase of pH 3.00 water/formic acid: acetonitrile-methanol (45%:5%:50% by volume); Thermo-Keystone Betabasic C-18 column (2.1 mm×50 mm) operated at 0.100 mL/min.

Stability in Rat Serum and Tissue Homogenates.

As demonstrated by the data depicted in FIG. 1A, compound 1 was highly stable in all of the tissues tests. After 16 hrs of incubation, there was still 70-80% of the compound left in the reaction tubes.

Figure 1B:
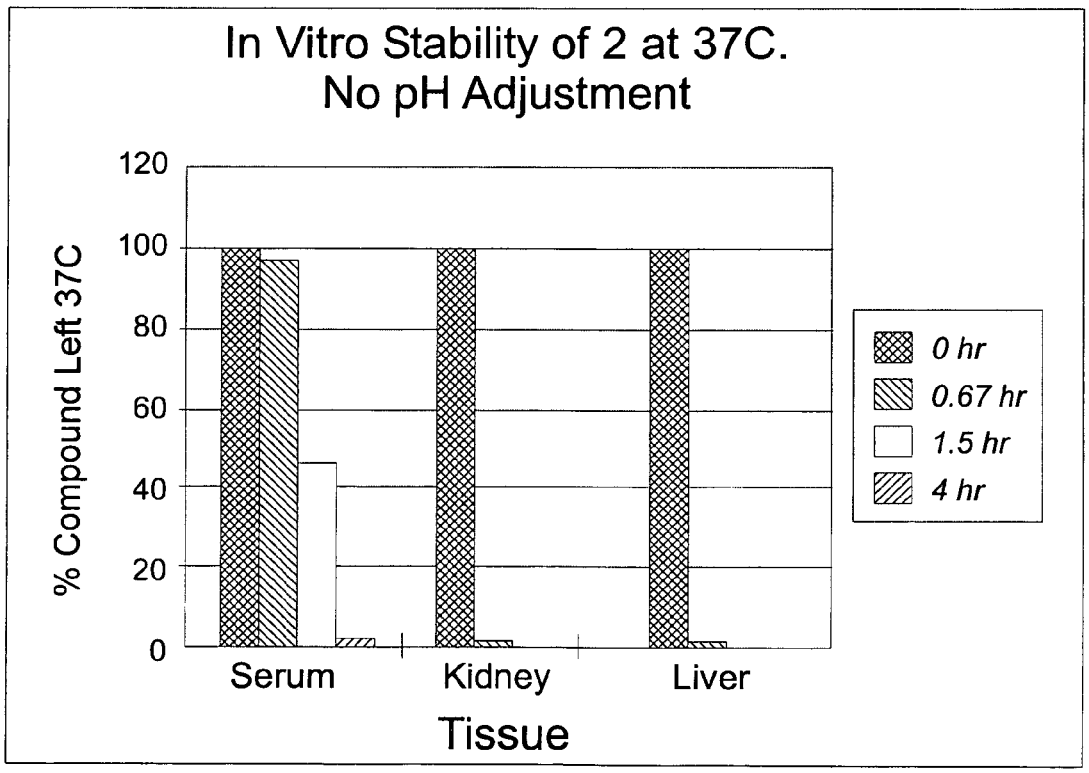

As demonstrated by the data depicted in FIG. 1B, compound 2 in serum was intermediately stable. After 1.5 hr of incubation there was still about half of the compound left, but the compound was almost all gone after 4 hr. This compound was, however very unstable in kidney and liver. Hardly any was left after the first 40 minutes of incubation.

Figure 1C:
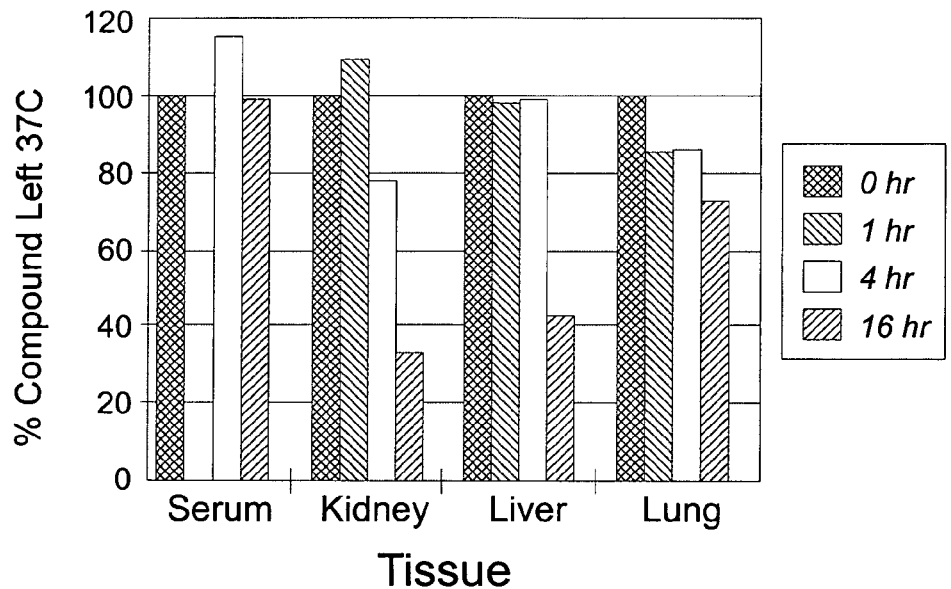

As demonstrated by the data depicted in FIG. 1C, compound 3 was at least as stable as 1 in rat serum. However, this compound appeared to be more unstable than 1 in kidney and liver.

Example 59

Stability in Tissues at Different pH

Figure 2:
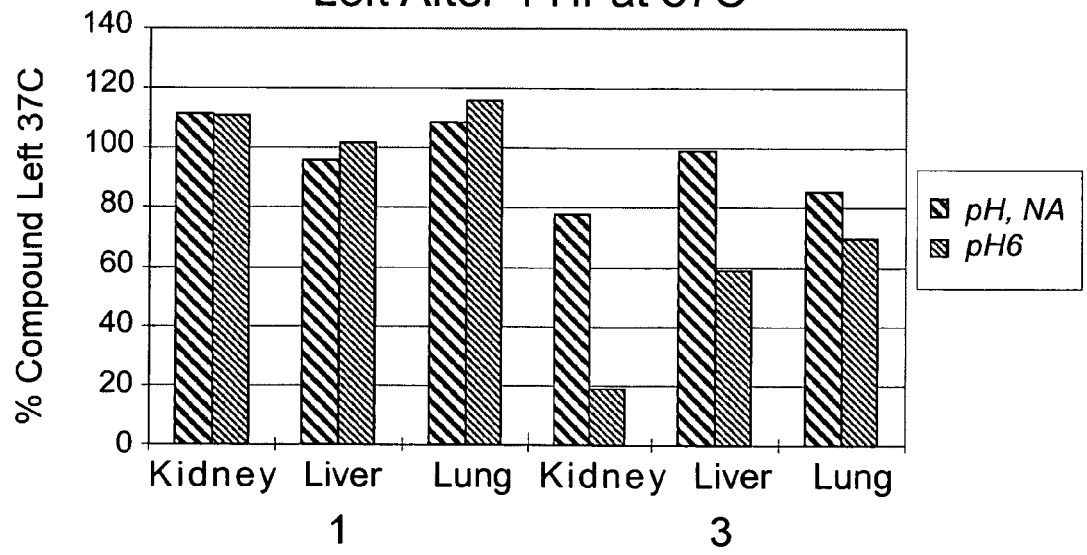
FIG. 2 is a bar graph depicting in vitro stability of two stereoisomers of an EPI compound in tissue homogenates at different pHs.

Many proteases responsible for degrading EPI compounds are located in lysozymes. Lysozymes typically have an acidic pH (about 4.8-5), whereas the pH in tissue homogenates that were prepared was higher (kidney, pH 6.8; liver, pH 6.6; and lung, pH 7.5). To test the effect of tissue homogenates closer to physiological conditions, the pH was lowered to about 6 by adding acetic acid to the tissue homogenates and compound stability was tested. FIG. 2 depicts the stability of compounds 1 and 3 at different pH. The data demonstrate that, while stability of compound 1 in different tissues was essentially unchanged, that of compound 3 exhibited significant differences. At pH 6, compound 3 was degraded faster than at no pH change. The pH-dependent degradation of compound 3 was especially evident in kidney homogenates.

Figure 3:
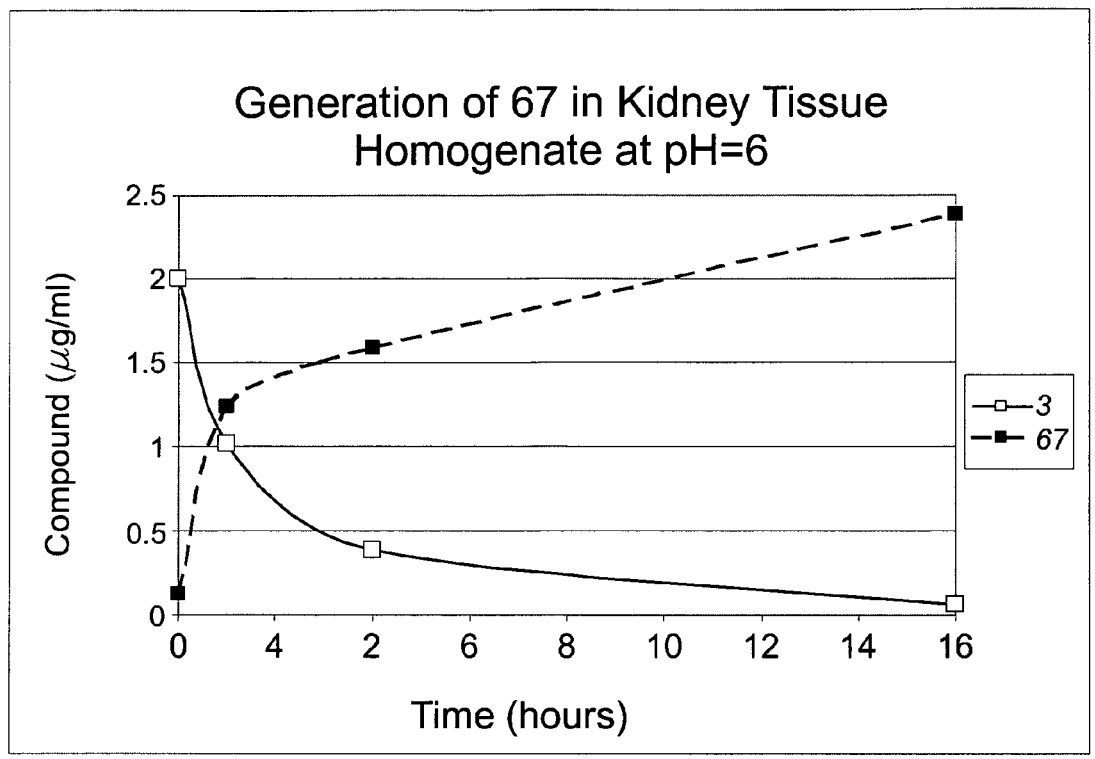
FIG. 3 is a graph depicting the disappearance of an EPI compound and the concomitant appearance of its degradation product.

FIG. 3 depicts the level of compound 3 and the expected degradation product of compound 3 (compound 67) as a function of time. Concomitant with the disappearance of compound 3, the degradation product 67 increased in rat kidney homogenates.

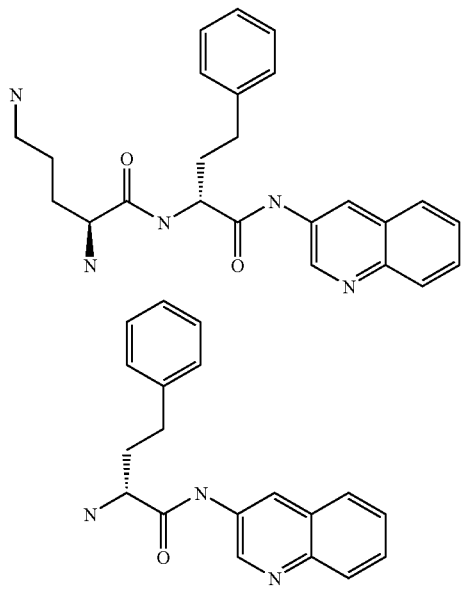

Example 60

Stability in Tissue Homogenate Supernatant

Figure 4:
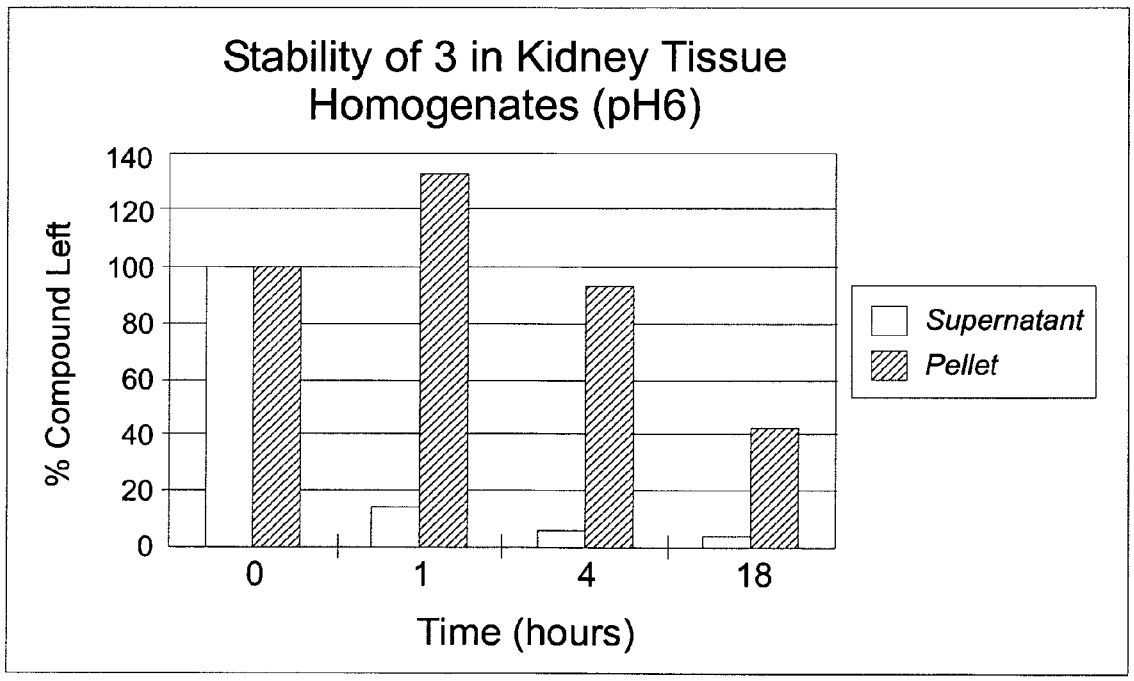
FIG. 4 is a bar graph comparing the stability of an EPI compound in supernatant and pellet of kidney tissue homogenates.

FIG. 4 is a bar graph depicting the stability of compound 3 in the supernatant and pellet of kidney tissue homogenates. Greater instability of compound 3 was observed in the supernatant of the kidney tissue homogenates obtained after 5 min. centrifugation in the microcentrifuge. This result indicates that enzymes which are responsible for the degradation of 3 are soluble as opposed to membrane bound.

Figure 5:
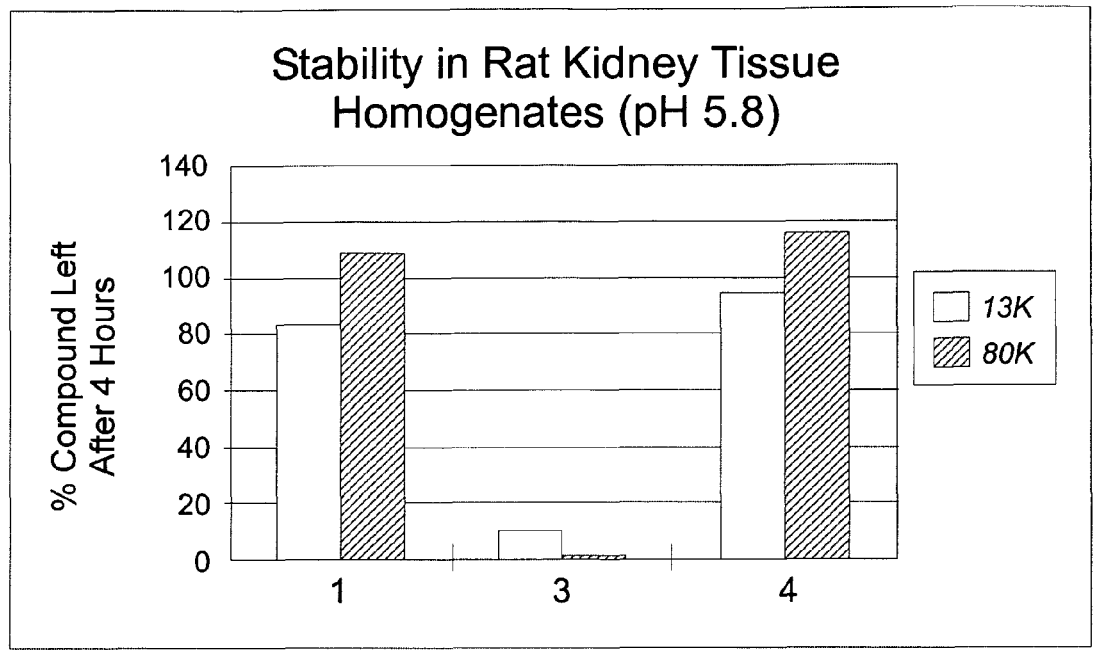
FIG. 5 is a bar graph comparing the stability of three stereroisomers of an EPI compound in the supernatant of rat kidney tissue homgenates.

FIG. 5 compares the stability of compounds 1, 3, and 4 in rat kidney tissue homogenates. The supernatant instability was selective to compound 3: neither compound 1 nor compound 4 show any instability at the same conditions.

Moreover, it appears that the level of degradation observed in the presence of high-speed supernatant (80K) was much higher that one observed in the presence of the non-fractionated homogenate. This result supports that membranes might contain inhibitors of peptidases involved in selective degradation of compound 3.

Example 61

Stability of Compound 3 in Rabbit Tissue Homogenates

Figure 6:
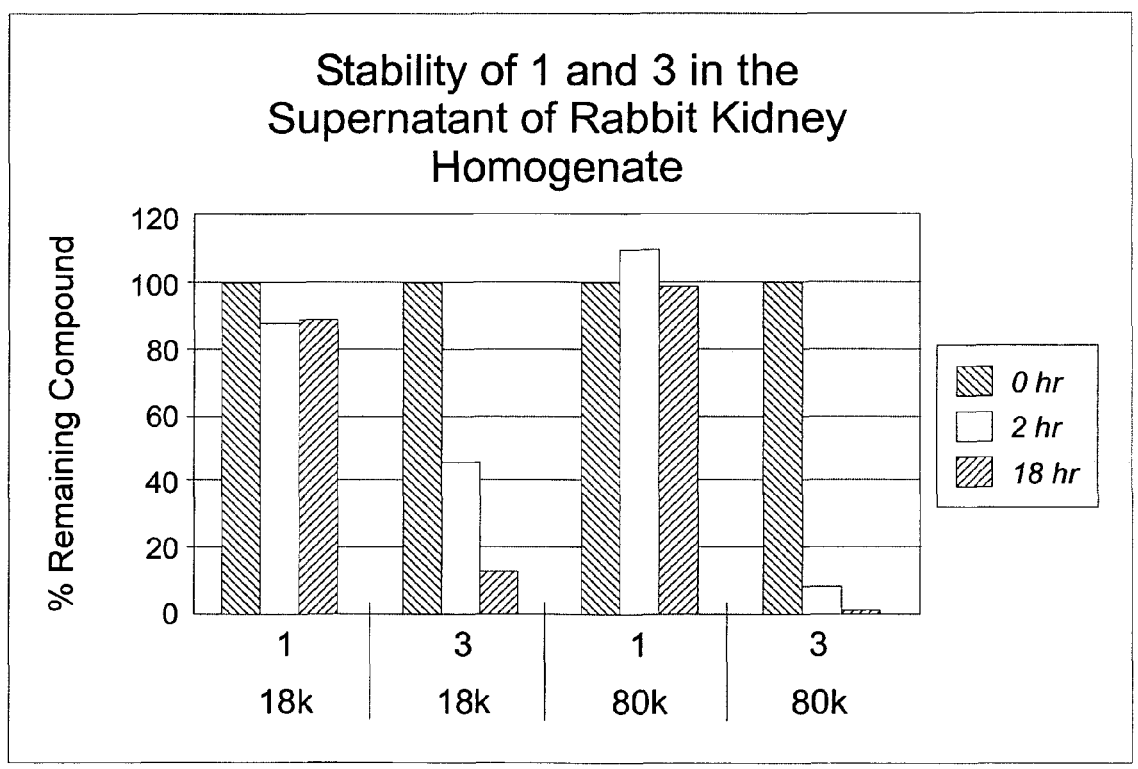
FIG. 6 is a bar graph comparing the stability of two stereroisomers of an EPI compound in the supernatant of rabbit kidney tissue homgenates.

FIG. 6 compares the stability of compounds 1 and 3 in fractionated rabbit kidney tissue homogenates. Similar instability of compound 3 as compared to compound 1 was observed in the supernatant of rabbit kidney homogenates.

Greater instability is observed in the 80K supernatant as compared to 18K supernatant.

Example 62

Time Dependence of EPI Activity

Stability of compounds was also evaluated using a bioassay. The test compound at 320 µg/ml was treated with rabbit kidney supernatant for 0, 0.5, 1 and 2 hours. 120 µl was taken at designated times, heated at 80° C. to inactivate the enzyme, centrifuged and used in levofloxacin potentiation assay to determine whether or not their levofloxacin potentiation activity is reduced after the treatment. Levofloxacin potentiation activity was defined as the amount of a test compound, which is essential to decrease MIC of the strain PAM1723 of *P. aeruginosa* eight-fold ($MPC_8$). In order to establish $MPC_8$, the MIC of the test compound for PAM1723 (MIC=2 µg/ml) grown in the presence of 0.25 µg/ml of levofloxacin was determined.

TABLE 2

Evaluation of tissue instability of EPIs using bioassay.

| Compound | Saline (2 hours) | $EPI\ MPC_8$ after incubation (h) with rabbit kidney supernatant at 37° C. | | | |
|---|---|---|---|---|---|
| | | 0 | 0.5 | 1 | 2 |
| 1 | 5 | 10 | 10 | 10 | 10 |
| 3 | 5 | 20 | 40 | 81 | 81 |

81 means that activity is >80 µg/ml

The bioassay indicated that compound 3 but not compound 1 demonstrates time-dependent reduction of the EPI activity after treatment with supernatant of rabbit kidney homogenate (Table 2).

Example 63

Stability of Compound 3 in Human Serum and Tissue Homogenates

Figure 7:
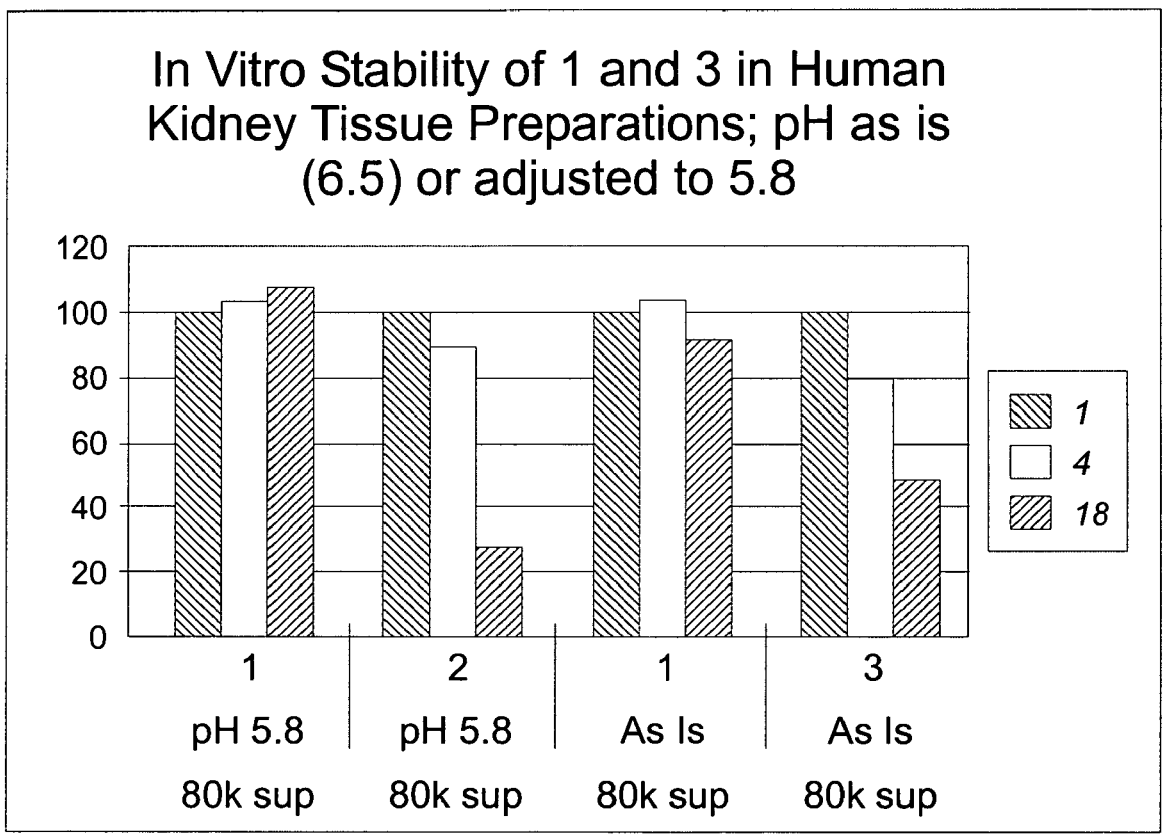
FIG. 7 is a bar graph comparing the stability of two stereroisomers of an EPI compound in human kidney tissue.

The pattern of in vitro stability of compound 3 (stable in serum but unstable in tissues) observed in rodents was also reproduced using human kidney tissues or serum. FIG. 7 compares the in vitro stability of compounds 1 and 3 in human kidney tissue preparations. Time-dependent degradation of compound 3 but not compound 1 was demonstrated when either compound was treated with homogenates prepared from frozen cadaverous kidney. Moreover, the degradation of compound 3 was stronger at lower pH, indicating that the acidic pH is essential for optimal hydrolytic activity.

Figure 8:
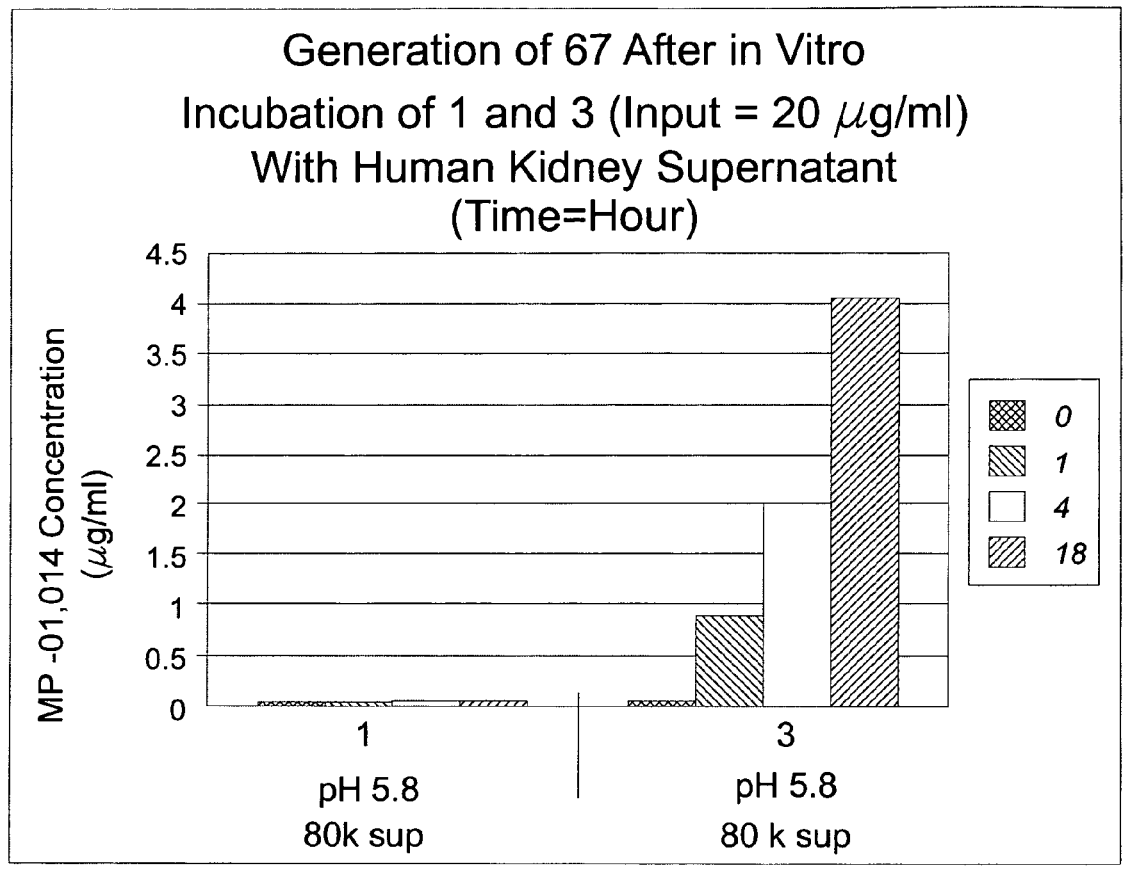
FIG. 8 is a bar graph depicting the formation of a metabolite of an EPI compound in human kidney tissue.

FIG. 8 depicts formation of the metabolite, compound 67, in human kidney tissue. Concomitant with the disappearance of compound 3, generation of the expected metabolite of the presumed intralysosomal degradation, compound 67, was detected using human kidney.

Example 64

Stability of Compound 3 in Human Serum

Figure 9:
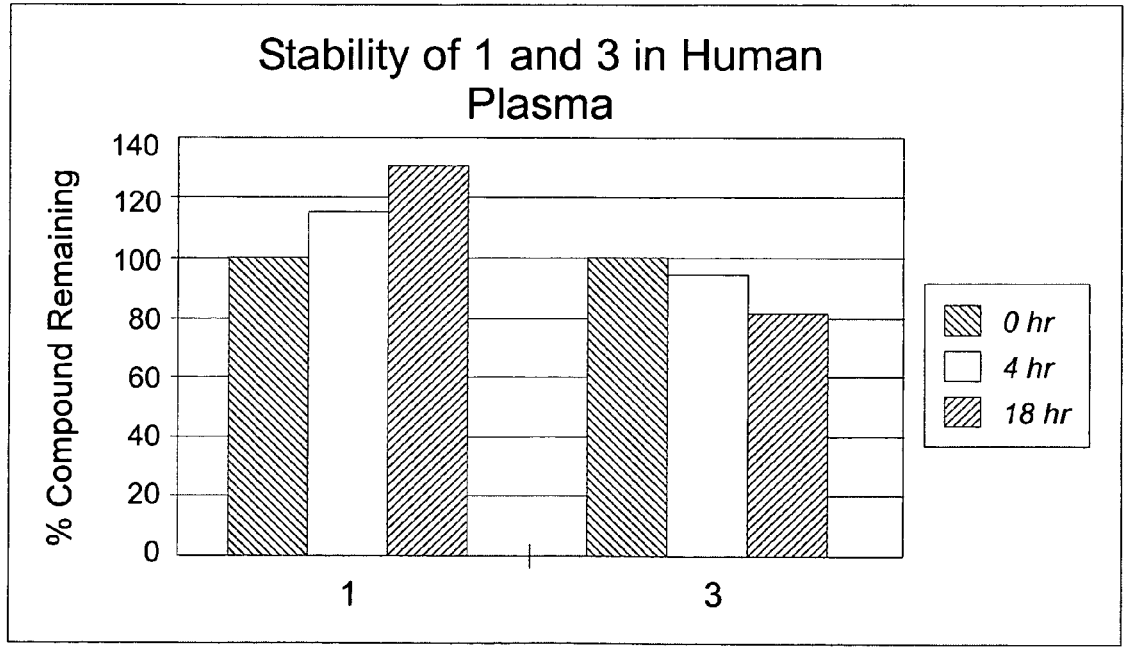
FIG. 9 is a bar graph comparing the stability of two stereoisomers of an EPI compound in human serum as a function of time.

FIG. 9 compares the stability of compounds 1 and 3 in human serum as a function of time. Both compound 1 and compound 3 were stable after 18 hours of incubation with human serum. This result supports that the degradation of compound 3 is selective for the intracellular enzymes with low pH being optimum, such as those found in lysosomes.

Example 65

Stability Bioassay

Stability in rat and human serum was also evaluated using a bioassay. 320 µg/ml of the test compound was treated with 50% serum for 4 hours. Next, the MIC of a test compound for PAM1723 (MIC=2 µg/ml) grown in the presence of 0.25 µg/ml of levofloxacin was determined (MPC8), and compared with that of a compound treated with saline for 4 hours. Compound MC-207110 (L-phenylalanine-L-ornithine-a-naphtylamide) which is unstable in both rat and human serum, was used as a positive control (Table 3).

TABLE 3

Evaluation of serum stability of EPIs using bioassay.

| Compound | Saline | $EPI\ MPC_8$ after 4 hours at 37° C. | |
|---|---|---|---|
| | | Frozen Rat serum | Frosen Human serum |
| MC-207110 | 2.5 | >80 | >80 |
| 3 | 5 | 5 | 5 |

Example 66

Stability in *P. aeruginosa*

Figure 10:
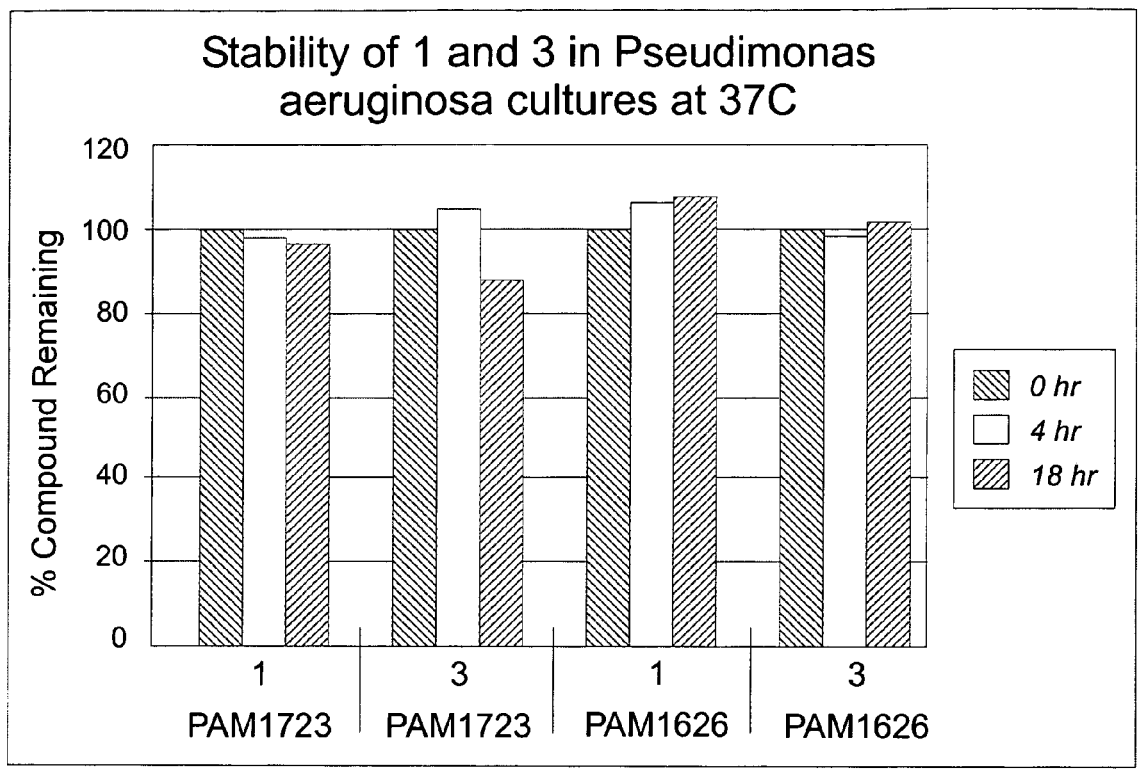
FIG. 10 is a bar graph depicting the stability of two stereoisomers of an EPI compound in Pseudomonas aeruginosa.

Overnight cultures of two different strains of *P. aeruginosa* overexpressing (strain PAM1723) or lacking (PAM1626) efflux pumps were incubated with compounds 1 or 3 at 50 µg/ml for various times. Compounds were extracted using 4% TCA and analysed by LC/MC/MC. The results presented on FIG. 10 demonstrated that both compounds 1 and 3 are stable in cultures of tested bacterial strains. This data supports that EPI compounds with hydrolytic instability are not degraded by bacterial cells.

Example 67

Bioassays of Several EPI Compounds

Bioassays as described in Example 62 and Example 65 were used to evaluate the stability of various compounds in serum and rabbit kidney homogenates. Decreased levofloxacin potentiation activity after the treatments is indicative of enzymatic instability of compounds (Table 4).

TABLE 4

EPI Activity and Stability of Representative Compounds in Serum and Kidney Tissues Evaluated Using Bioassay.

| Compound # | EPI MPC$_8$ (μg/ml) after 4 hours at 37° C. | | | EPI MPC$_8$ (μg/ml) after incubation (h) with rabbit kidney supernatant at 37° C. | | | | |
|---|---|---|---|---|---|---|---|---|
| | Saline | Frozen Rat serum | Frosen Human serum | Saline (2 hours) | 0 | 0.5 | 1 | 2 |
| 1 | 5 | 5 | 5 | 5 | 10 | 10 | 10 | 10 |
| 3 | 5 | 5 | 5 | 5 | 20 | 40 | >80 | >80 |
| 6 | 2.5 | 2.5 | 2.5 | 5 | 10 | 20 | 40 | >80 |
| 7 | 10 | 10 | 10 | 10 | 40 | 80 | >80 | >80 |
| 8 | 2.5 | 2.5 | 2.5 | 2.5 | 10 | 20 | 80 | >80 |
| 9 | 5 | >80 | 5 | 5 | 40 | >80 | >80 | >80 |
| 10 | 5 | 10 | 5 | 5 | 20 | 20 | 80 | >80 |
| 11 | 2.5 | 2.5 | 2.5 | 2.5 | 10 | 20 | >80 | >80 |
| 13 | <2.5 | <2.5 | <2.5 | <2.5 | 40 | >40 | >40 | >40 |
| 16 | 10 | 10 | 20 | 10 | 40 | 80 | >80 | >80 |
| 17 | 5 | 5 | 5 | 5 | 10 | >80 | >80 | >80 |
| 18 | 80 | >80 | >80 | 80 | >80 | >80 | >80 | >80 |
| 19 | 40 | >80 | >80 | 80 | >80 | >80 | >80 | >80 |
| 21 | <1.25 | <1.25 | <1.25 | <1.25 | 5 | 10 | 20 | 80 |
| 23 | 10 | 10 | 20 | 10 | 40 | 40 | >80 | >80 |
| 25 | 2.5 | 10 | 10 | 5 | 80 | >80 | >80 | >80 |
| 26 | 2.5 | 2.5 | 2.5 | 2.5 | 80 | >80 | >80 | >80 |
| 28 | 5 | >40 | 10 | 5 | >40 | >40 | >40 | >40 |
| 29 | 10 | 20 | 10 | 10 | 40 | 40 | >80 | >80 |
| 30 | 5 | 5 | 40 | 5 | 20 | 20 | 80 | >80 |
| 31 | 10 | 10 | 10 | 10 | 20 | 40 | >80 | >80 |
| 32 | 5 | 10 | 10 | 10 | 20 | 80 | >80 | >80 |
| 34 | 40 | >80 | >80 | 40 | >80 | >80 | >80 | >80 |
| 36 | 10 | >80 | 20 | 10 | >80 | >80 | >80 | >80 |
| 37 | 10 | 10 | 10 | 10 | 20 | 80 | >80 | >80 |
| 39 | 10 | >40 | 20 | 10 | >40 | >40 | >40 | >40 |
| 40 | 2.5 | 10 | 2.5 | 5 | 20 | 40 | >80 | >80 |
| 41 | 2.5 | 2.5 | 2.5 | 2.5 | 10 | 20 | 40 | >40 |
| 46 | 1.25 | 1.25 | 1.25 | 1.25 | 20 | 40 | >40 | >40 |

These compounds demonstrate serum stability but instability in the supernatant of rabbit kidney homogenates. Several compounds, which are unstable in rat kidney homogenates are also unstable in rat serum (e.g., compounds 9, 18, 19, 28, 34, 36, and 39).

Several examples below provide in vivo characterization of the selected EPI compounds.

Example 68

Rat Serum Pharmacokinetics After 1 min IV Bolus Administration

Figure 11:
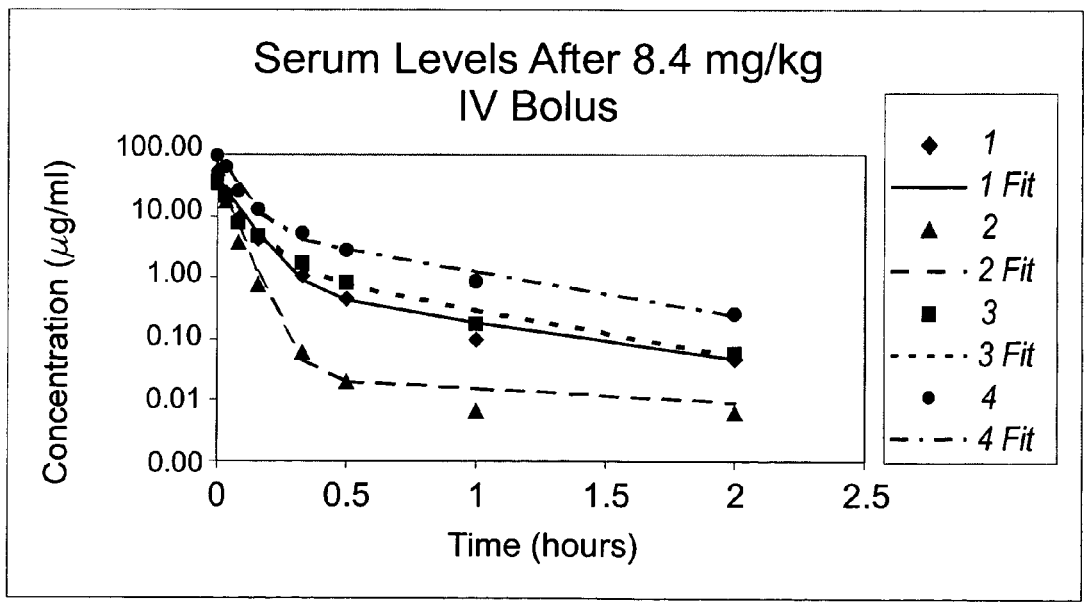
FIG. 11 is a graph depicting the pharmacokinetics of four stereoisomers of an EPI compound after IV bolus administration in rats.

Rat serum pharmacokinetics of compounds 1, 2, 3 and 4 was evaluated after IV bolus administration (FIG. 1). FIG. 11 depicts the serum concentrations as a function of time. The PK profiles of compounds 1, 2 and 4 were very similar while the compound 2 levels decreased more rapidly faster. These data support the instability of compound 2 in serum as compared with serum stability of compounds 1, 2 and 4.

Example 69

Rat Serum Pharmacokinetics After 2-hour IV Infusion

Figure 12:
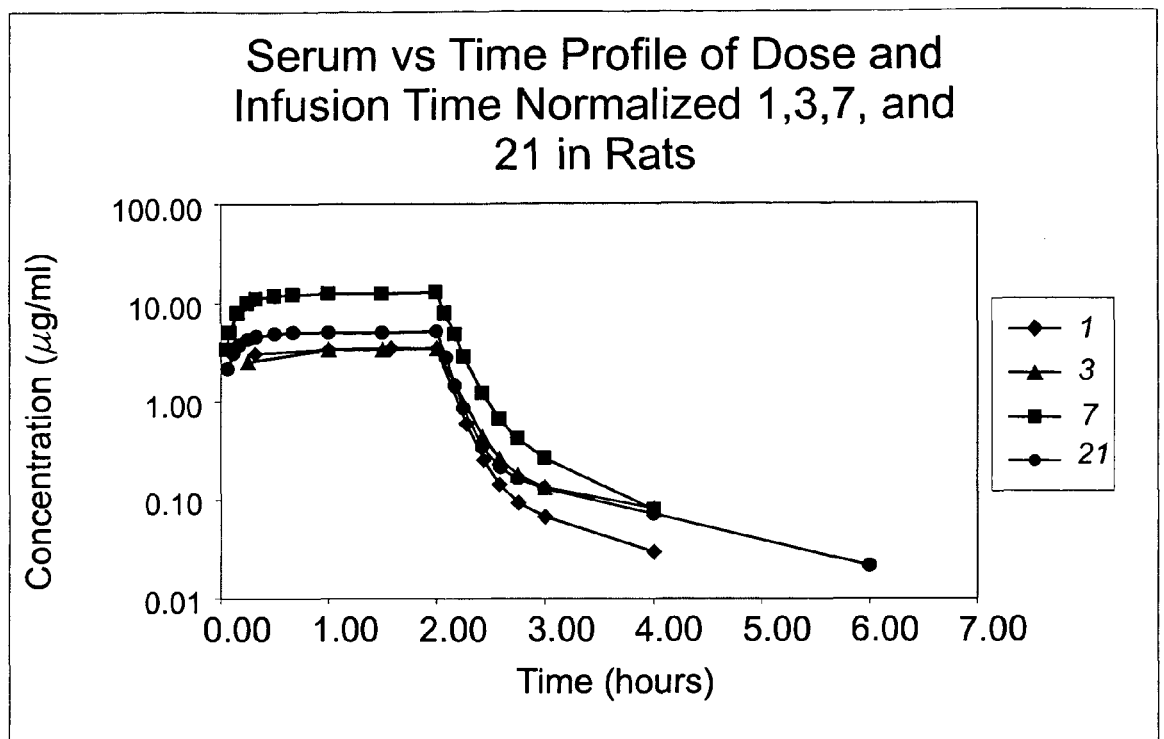
FIG. 12 is a graph depicting the pharmacokinetics of four EPI compounds after IV infusion administration in rats.

Rat serum pharmacokinetics of compounds 1, 3, 7, and 21 was evaluated after 2-hour IV infusion of 1 mg/ml EPI solution in 0.9% saline. Total infused dose was 10 mg/kg. FIG. 12 depicts the serum concentrations as a function of time. A two-compartment model was used to fit the data and calculate PK parameters. All compounds, regardless of their stability in tissue homogenates, showed a similar PK profile: rapid alpha-elimination with a longer beta-phase. Compound 7, which was unstable in tissue homogenates, had the best serum PK profile.

TABLE 5

Pharmacokinetics after IV infusion.

| Compound | CL (L/hr/kg) |
|---|---|
| 1 | 1.44 |
| 3 | 1.4 |
| 7 | 0.39 |
| 21 | 0.97 |

Example 70

Tissue Levels of 1, 2, 3 and 4 After IV Bolus Administration

Figure 13:
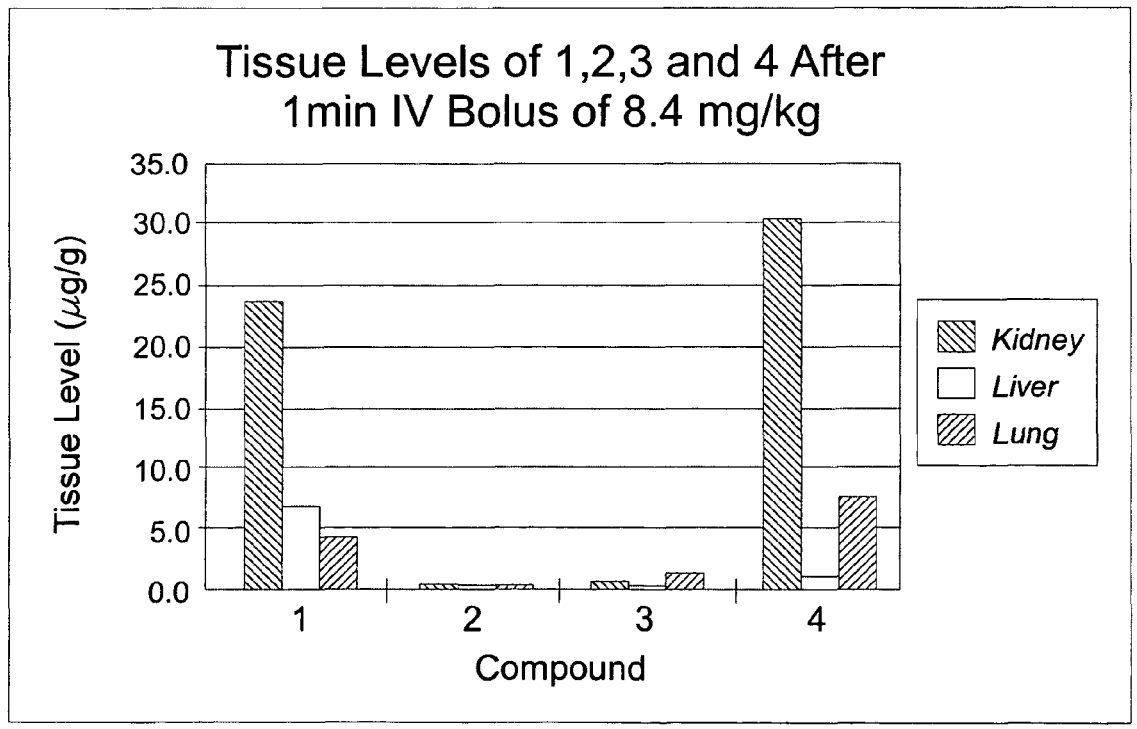
FIG. 13 is a graph depicting the pharmacokinetics of four stereoisomers of an EPI compound in tissue after IV bolus administration in rats.

Tissue levels of compounds 1, 2, 3 and 4 were evaluated in kidney, liver and lung six-hours after 8.4 mg/kg IV bolus administration. FIG. 13 depicts the levels as a function of time. At 6 hours after IV injection, compound 2 levels fell below the detectable level in all the tissues tested and compound 3 was also present at very low level. On the other hand, compounds 1 and 4 were present at relatively high levels, especially in kidney.

This experiment indicated that there is a correlation between the instability in tissue homogenates and tissue levels of the test compounds: 1 and 4 were shown to be stable in tissue homogenates and the same compounds are found in tissues at much higher levels than the unstable compounds 2 and 3.

Example 71

Tissue Levels of Selected EPIs After Two-Hour IV Infusion

Levels of EPIs in various tissues were evaluated after 2-hour IV infusion in rats. The rats received 10 mg/kg IV infusion through FVC. Animals were divided into 2 groups: group 1 was sacrificed immediately after the end of infusion and group 2, 2h or 4h after the end of infusion. Tissues from each animal were collected, homogenized and compounds were extracted. Tissues were mixed with saline at 1:1 ratio (v/w) in 12×75 mm polypropylene round bottom tubes. The mixtures were homogenized with a Polytron homogenizer (on ice, 3×10-15 seconds with 30 seconds intervals at the setting of 7). 50 µl of homogenized tissue were immediately transferred to an Eppendorf tube and 2-volumes of 4% TCA were added. After vortexing for 30 seconds, the tubes were centrifuged in a microfuge at top speed (13.2 k rpm) for minutes. The supernatant was collected, and 45 µl of the supernatant was transferred to a glass LC/MS/MS vial (Kimble, 11 mm, 1.5 ml) for analysis, which allowed determination of tissue levels of EPIs at the end of the infusion and 2h or 4h later.

TABLE 5

Tisue Levels of compound 1 after 2-hour Infusion in Rat

| Tissue | Concentration (µg/ml) at 2 h | Concentration (µg/ml) at 4 h | 2 h/4 h Ratio |
|---|---|---|---|
| Kidney | 49.31 | 29.64 | 1.66 |
| Liver | 10.55 | 10.62 | 0.99 |
| Lung | 6.50 | 4.18 | 1.55 |
| Muscle | 4.54 | 2.86 | 1.59 |
| Brain | 0.18 | 0.13 | 1.34 |
| Pancreas | 5.40 | 4.05 | 1.34 |
| Thymus | 3.41 | 2.76 | 1.23 |
| Spleen | 5.01 | 3.71 | 1.35 |
| Heart | 2.18 | 2.34 | 0.93 |
| Testicles | 0.58 | 0.28 | 2.04 |

High levels of compound 1 was observed in several tissues including kidney, liver, and lung. No significant changes in the level of compound 1 were observed two-hours after the end of infusion (Table 5).

TABLE 6

Tisue Levels of compound 3 after 2-hour Infusion in Rat

| Tissue | Concentration (µg/ml) at 2 h | Concentration (µg/ml) at 4 h | 2 h/4 h Ratio |
|---|---|---|---|
| Kidney | 12.21 | 1.68 | 7.28 |
| Liver | 1.33 | 0.83 | 1.60 |
| Lung | 4.27 | 1.91 | 2.23 |
| Muscle | 2.18 | 1.14 | 1.91 |
| Brain | 0.07 | 0.21 | 0.35 |
| Pancreas | 1.11 | 0.38 | 2.91 |
| Thymus | 2.46 | 1.46 | 1.69 |
| Spleen | 4.41 | 0.72 | 6.16 |
| Heart | 2.26 | 0.47 | 4.82 |
| Testicles | 0.32 | 0.06 | 5.14 |

Lower levels of compound 3 as compared to 1 were observed in several tissues including kidney, liver and lung. Significant changes in the level of compound 3 were observed two-hours after the end of infusion (Table 6).

TABLE 7

Tisue Levels of 7 after 2-hour Infusion in Rat

| Tissue | Concentration (µg/ml) at 2 h | Concentration (µg/ml) at 6 h | 2 h/4 h Ratio |
|---|---|---|---|
| Kidney | 55.36 | 0.96 | 57.37 |
| Liver | 7.96 | 0.27 | 29.85 |
| Lung | 13.04 | 3.17 | 4.11 |

While relatively high levels of compound 7 were observed in tissues at the end of 2-hour infusion, this compound cleared from tissues relatively fast, presumably due to selective intralysosomal degradation (Table 7).

TABLE 8

Tisue Levels of 21 after 2-hour Infusion in Rat

| Tissue | Concentration (µg/ml) at 2 h | Concentration (µg/ml) at 4 h | Concentration (µg/ml) at 6 h | 2 h/6 h Ratio |
|---|---|---|---|---|
| Kidney | 58.71 | 20.76 | 2.92 | 20.10 |
| Liver | 5.95 | 2.32 | 0.20 | 30.21 |
| Lung | 13.39 | NA | 3.90 | 3.43 |
| Muscle | 4.75 | 1.36 | 1.21 | 3.94 |
| Brain | 0.49 | 0.47 | 0.03 | 16.37 |
| Pancreas | 9.71 | 1.58 | 0.47 | 20.73 |
| Thymus | 7.25 | 6.00 | 3.59 | 2.02 |
| Spleen | 7.66 | 4.44 | 2.21 | 3.46 |
| Heart | 5.25 | 1.76 | 0.72 | 7.33 |
| Testicles | 0.70 | 0.33 | 0.08 | 8.32 |

Slower clearance of compound 21 was observed 2 hours after the end of the infusion. Significantly less compound was detected in tissues 2 hours later, indicating tissue-specific degradation of compound 21 (Table 8).

Example 72

Tissue Levels of Compound 3 After 5 Day Repeated Dosing in Rat

Figure 14:
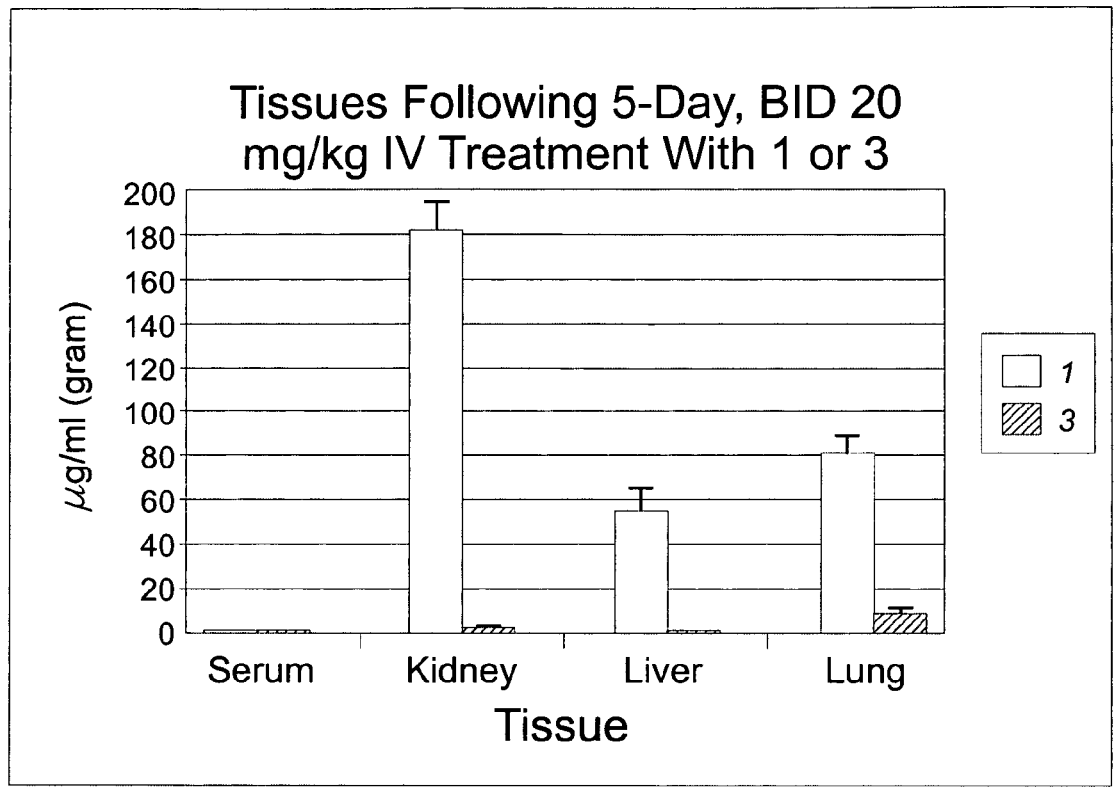
FIG. 14 is a bar graph depicting tissue levels of two stereoisomers of an EPI compound after 5-day repeated dosing in rats.

The decreased tissue accumulation of compound 3 vis-a-vis 1 was confirmed in a multi-dose experiment. Rats received 20 mg/kg of either compound twice daily for 5 days. Animal were sacrifised 6 hours after the last dose and levels of compounds in kidneys, liver and lung were determined. FIG. 14 depicts the measured tissue levels. Approximately 100-fold, 60-fold, and 10-fold less compound 3 accumulated in kidney, liver and lung respectively, as compared to compound 1.

Example 73

Tissue Levels of Compound 67 After IV Administration in Rats

Compound 67, which is the expected metabolite of proteolytic intracellular degradation of compound 3, was detected in rat tissues after IV infusion, confirming the tissue-specific degradation of compound 3 (Tables 9A, B).

TABLE 9A

Tissue levels of 67 after 6-Hours or 5 Day Repeated Dosing in Rats.

|  | Level of 67 | | |
|---|---|---|---|
| 6-hour after IV (8.4 mg/kg) | Kidneys | Liver | Lung |
| Average (mg/kg) | 0.28 | 0.09 | 1.09 |
| stand'd dev. | 0.03 | 0.04 | 0.05 |

TABLE 9A

Tissue levels of 67 after 6-Hours or 5 Day Repeated Dosing in Rats.

| 6-hour after 5-day IV | Level of 67 | | |
|---|---|---|---|
| (20 mg/kg/BID) | kidney | liver | lung |
| Average (mg/kg) | 0.11 | 0.04 | 0.34 |
| stand'd dev. | 0.00 |  | 0.06 |

Example 74

Tissue Levels of Compounds 1 and 3 After IP Administration in Mice

Figure 15:
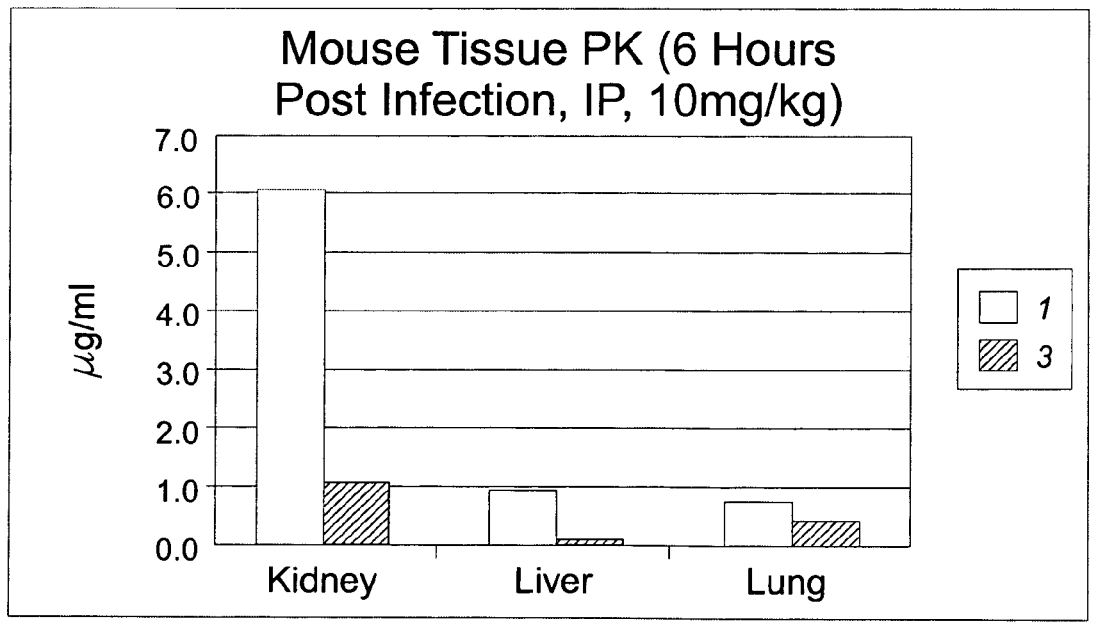
FIG. 15 is a bar graph depicting tissue levels of an EPI compound in mice after IP bolus administration.

Levels of compounds 1 and 3 were evaluated in kidney, liver and lung six-hours after 10 mg/kg IP bolus administration in mice. FIG. 15 depicts the resulting tissue levels. The results show that the presumed intracellular hydrolytic degradation also occurs in mice. Thus, compound 3 and other compounds can be used in mouse efficacy models of *P. aeruginosa* infection.

Example 75

Tissue levels of Compound 3 After Administration of Acylated Forms

Figure 16:
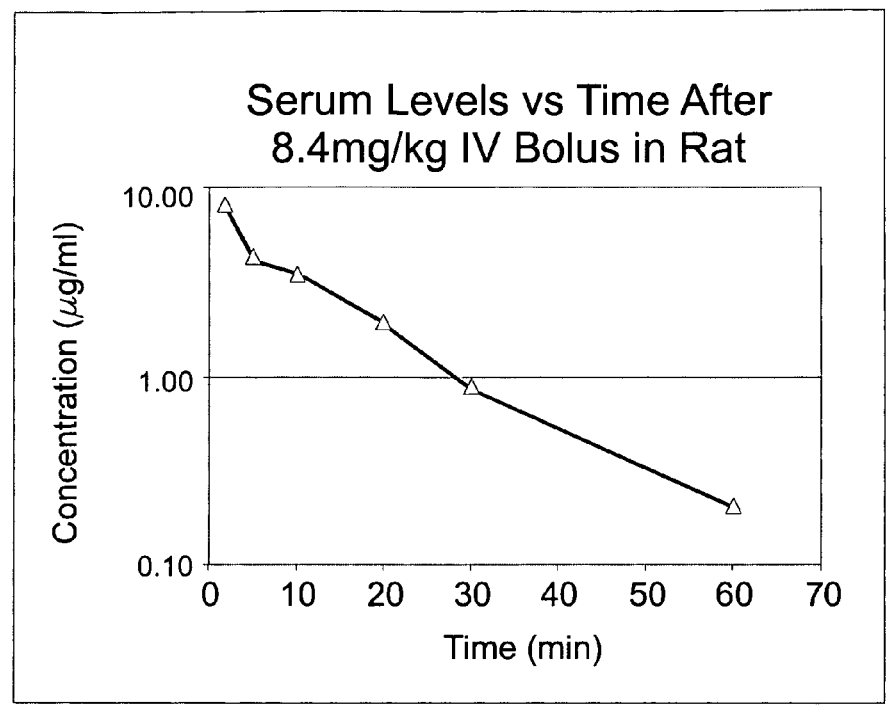
FIG. 16 is a graph depicting serum levels of an EPI compound after administration of a prodrug of the compound.

The present example indicates that compound 5, in which compound 3 was acylated at its alfa-$NH_2$, was readily metabolized in serum to produce compound 3.Rats were injected with compound 5 (8.4 mg/kg) and serum levels of the parent compound 3 were evaluated after extraction. The serum levels as a function of time are depicted in FIG. 16.

Figure 17:
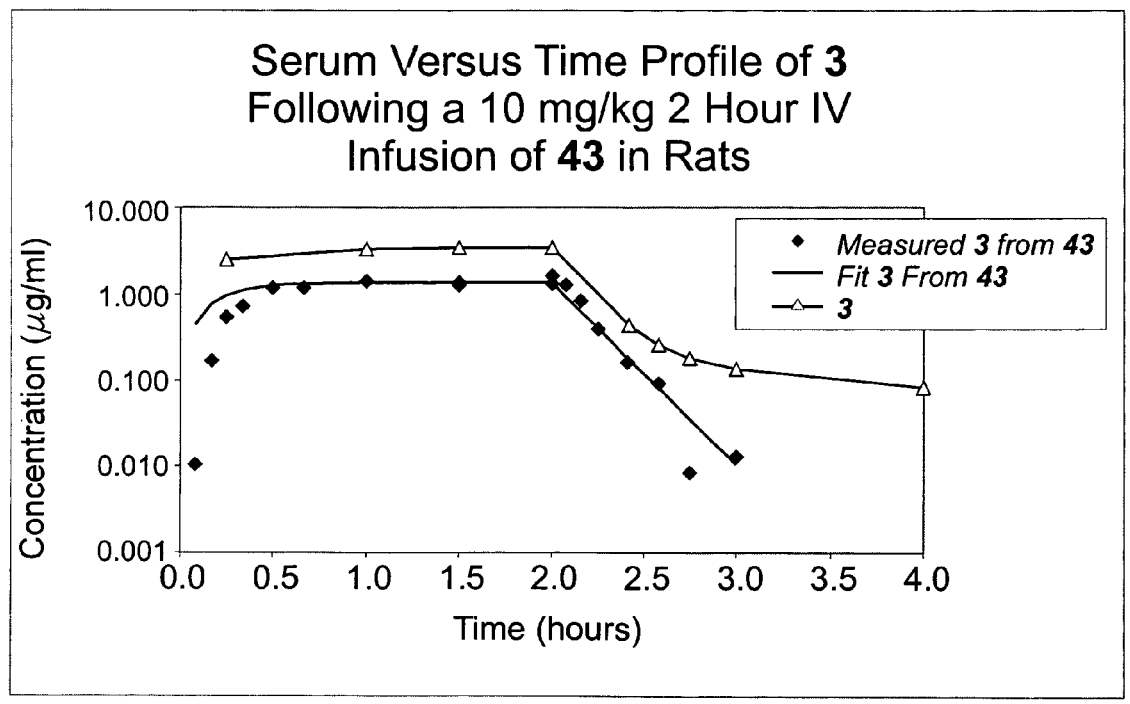
FIG. 17 is a graph depicting serum levels of an EPI compound after administration of a prodrug of the compound.

Compound 43, in which compound 3 was acylated at both of its free amine functionalities is also readily metabolized in serum to produce compound 3. Rats were infused for two hours with compound 43 at 10 mg/kg and serum levels of the parent compound 3 were evaluated after extraction. FIG. 17 depicts the serum levels of compound 3 as a function of time.

Example 76

Acute Toxicity of Acylated Compound 3

The present example demonstrates that the substitution of a single or both free amines functionalities of compound 3 with the acyl group reduced 2 to 8-fold acute toxicity of the parent compound. Acute toxicity was measured as minimal lethal dose (MLD). MLD is defined as a minimal concentration of a compound that has lethal effect for at least one mouse from the group of three mice after IV bolus injection into the mouse tail vein. Compounds 5, 34, and 43 did not have levofloxacin potentiating activity in vitro at concentrations up to 80 μg/ml.

TABLE 10

Minimal lethal doses of selected compounds after bolus administration in mice

| Compound | MLD (mg/kg) |
|---|---|
| 3 | 25 |
| 5 | 75 |
| 34 | 50 |
| 43 | 150 |

Several examples below demonstrate efficacy of selected EPI compounds. 6-8 week old Swiss Webster male mice were used for the efficacy experiments.

Example 77

Efficacy of Compound 1 in Mouse Sepsis Models of PA Infection Inoculum Preparation

*P. aeruginosa* strain PAM1032 overexpressing MexAB-OprM efflux pump was grown overnight in Mueller-Hinton Broth (MHB). The next day, the overnight culture was diluted in fresh MHV and was allowed to re-grow to ~$10^8$ CFU/mL (OD600~0.3). The culture was spun down, washed twice with phosphate buffered saline (PBS) and re-suspend in PBS to ~$1.2 \times 10^7$ CFU/mL (OD=0.12). Next, this culture was mixed 1:1 with 14% hog-gastric mucin in PBS to give a final inoculum of $6 \times 10^6$ CFU/mL.

Infection and Treatment

Each group of animals was infected with 0.5 mL of inoculum via the intraperitoneal (IP) route and then was immediately treated with 0.2 mL of levofloxacin or PBS via the subcutaneous (SQ) route, and next with 0.2 mL EPI via the IP route. Two hours after the first treatment, the animals were treated again with 0.2 mL of levofloxacin or PBS via the SQ route and 0.2 mL of EPI via the IP route. After 24 hours, the proportion of surviving animals in each treatment group was calculated and ED50 was determined.

Treatment Groups to Determine $ED_{50}$

Twelve groups of 5 mice were used to determine the effect of each fixed concentration of EPI compound on ED50 of levofloxacin. The effect of the EPI at 50 mg/kg was determined according to the following experimental design:

| | |
|---|---|
| 1 | Levofloxacin 200 mg/kg (100 mg/kg × 2) |
| 2 | Levofloxacin 200 mg/kg plus EPI 50 mg/kg (100 and 25 mg/kg × 2 respectively) |
| 3 | Levofloxacin 100 mg/kg (50 mg/kg × 2) |
| 4 | Levofloxacin 100 mg/kg plus EPI 50 mg/kg (50 and 25 mg/kg × 2 respectively) |
| 5 | Levofloxacin 50 mg/kg (25 mg/kg × 2) |
| 6 | Levofloxacin 50 mg/kg plus EPI 50 mg/kg (25 and 25 mg/kg × 2 respectively) |
| 7 | Levofloxacin 25 mg/kg (12.5 mg/kg × 2) |
| 8 | Levofloxacin 25 mg/kg plus EPI 50 mg/kg (12.5 and 25 mg/kg × 2 respectively) |
| 9 | Levofloxacin 12.5 mg/kg (6.25 mg/kg × 2) |
| 10 | Levofloxacin 12.5 mg/kg plus EPI 50 mg/kg (6.25 and 25 mg/kg × 2 respectively) |
| 11 | PBS plus EPI 50 mg/kg (6.25 and 25 mg/kg × 2 respectively) |
| 12 | Virulence control (PBS treatment) |

Figure 18:
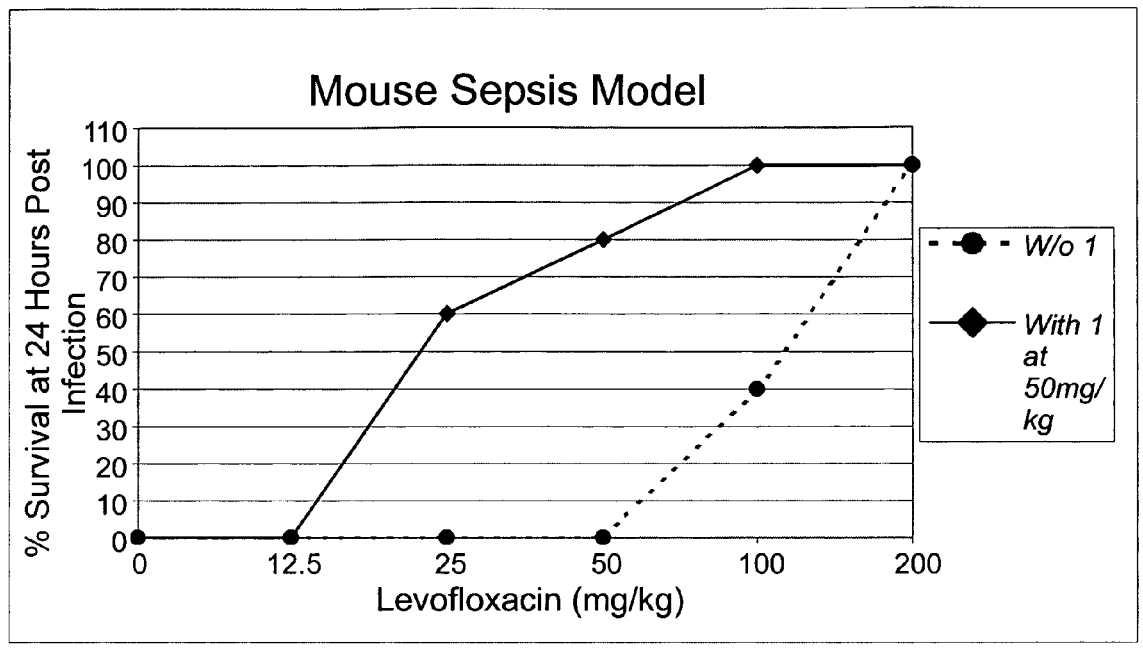
FIG. 18 is a graph depicting mouse survival rates after administration of an EPI compound with various concentrations of levofloxacin.

The percent survival at 24 hours post infection for levofloxacin doses of 0, 12.5, 25, 50, 100, and 200 mg/kg alone, and for levofloxacin doses of 0, 12.5, 25, 50, 100, and 200 mg/kg with 50 mg/kg of MP-001,001 are plotted in FIG. 18, In this study, 4-fold decrease of $ED_{50}$ of levofloxacin was observed in the presence of compound 1 at 50 mg/kg.

Efficacy of 3 in Mouse Sepsis Model of PA Infection.

Figure 19:
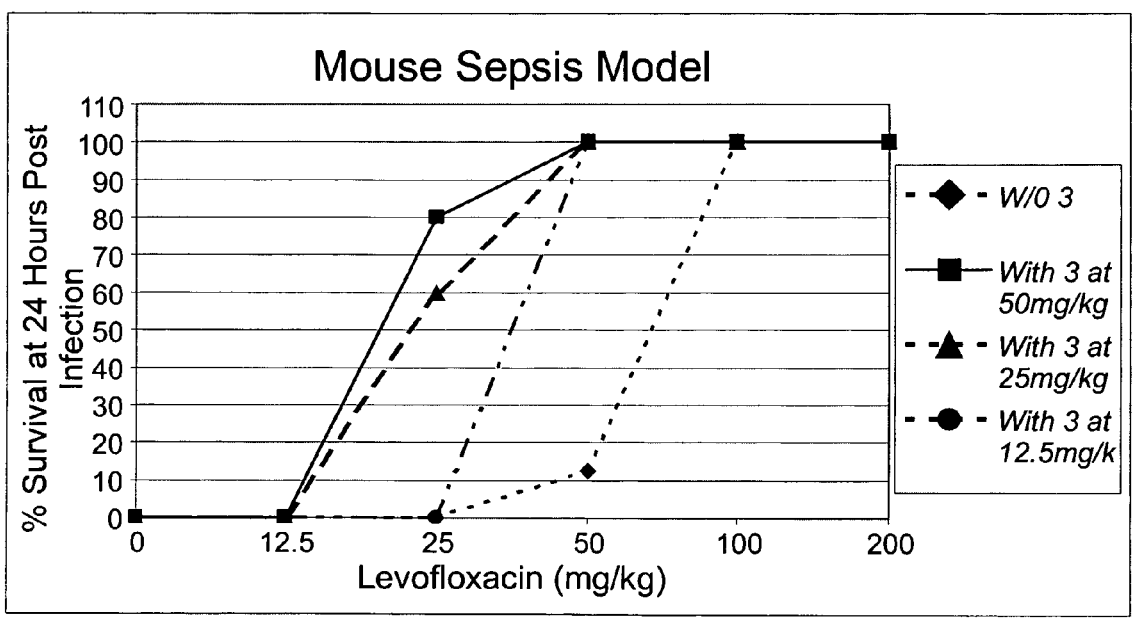
FIG. 19 is a graph depicting mouse survival rates after administration of an EPI compound with various concentrations of levofloxacin.

Efficacy of compound 3 in the Mouse Sepsis Model was evaluated as in for compound 1. Several concentrations of compound 3 were used to determine their effect on the $ED_{50}$ of levofloxacin. In these studies, a dose-dependent decrease in $ED_{50}$ (up to 4-fold) was observed in the presence of increasing concentrations of compound 3. The survival rates are in FIG. 19.

Example 78

Efficacy EPIs in Neutropenic Mice Lung Model of PA Infection

Figure 20:
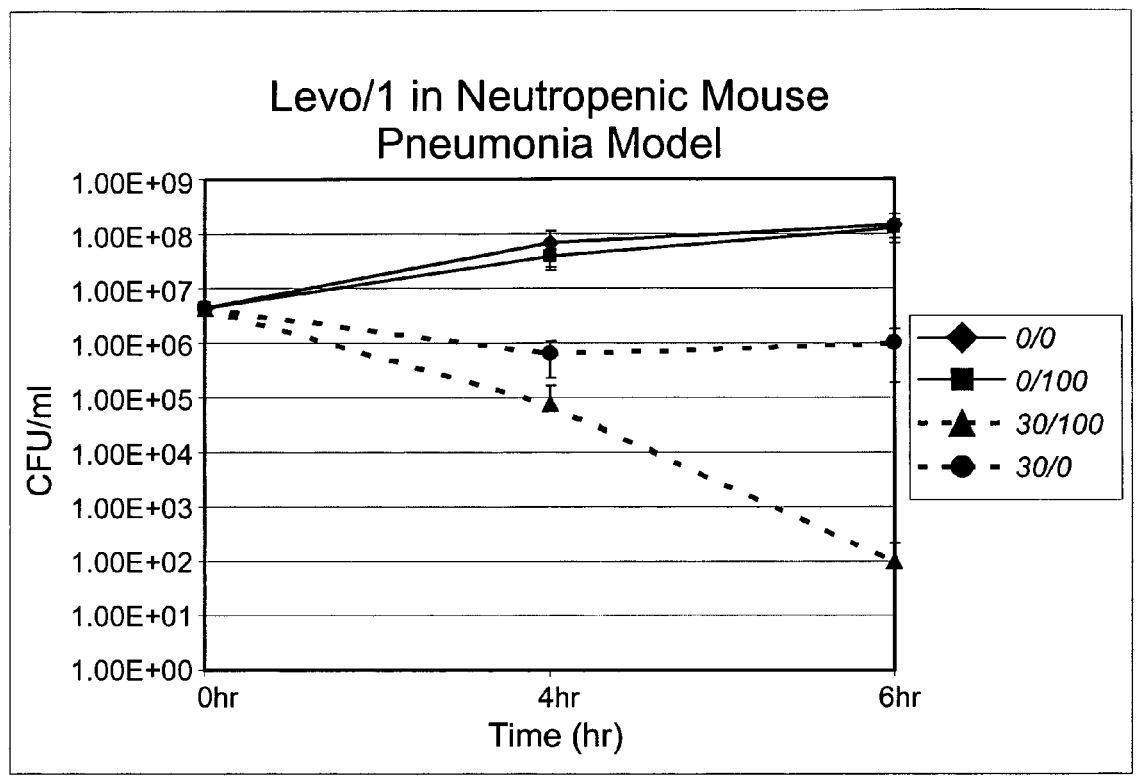
FIG. 20 is a graph depicting P. aeruginosa growth in a mouse model of lung infection after administration of an EPI compound with levofloxacin.

Neutropenia was induced by cyclophosphamide 100 mg/kg IP on days 3 and 1 prior to infection. The strain 29A2 of *P. aeruginosa* overexpressing MexAB-OprM efflux pump was grown overnight in Mueller-Hinton Broth (MHB). The next day overnight culture was diluted in fresh MHB and was allowed to re-grow to ~$10^8$ CFU/mL (OD600~0.3). The culture was spun down, washed twice with phosphate buffered saline (PBS) and re-suspended in PBS to ~$4×10^7$ CFU/mL. 50 μl of inoculum was used for intratracheal instillation of mice, which were anesthetized with sevoflourane/oxygen. Mice were treated with Levofloxacin SQ (Total dose is 30 mg/kg) and/or EPI IP (Total dose was 100 mg/kg) at 0 and 2 hours post infection. Four mice from each treatment group were euthanized at various times after the start of treatment. The lungs were removed aseptically, homogenized in saline, and immediately plated to determine bacterial load (CFU/ml) in infected lungs. *P. aeruginosa* is plotted as a function of time in FIG. 20. No difference in growth of *P. aeruginosa* was observed with either no addition (0/0) or with 100 mg/kg of compound 1 alone (0/100). Levofloxacin at 30 mg/kg (30/0) had static effect while addition of compound 1 to levo significantly decreased bacterial load in the infected lungs (30/100) indicating potentiating effect in vivo.

Figure 21A:
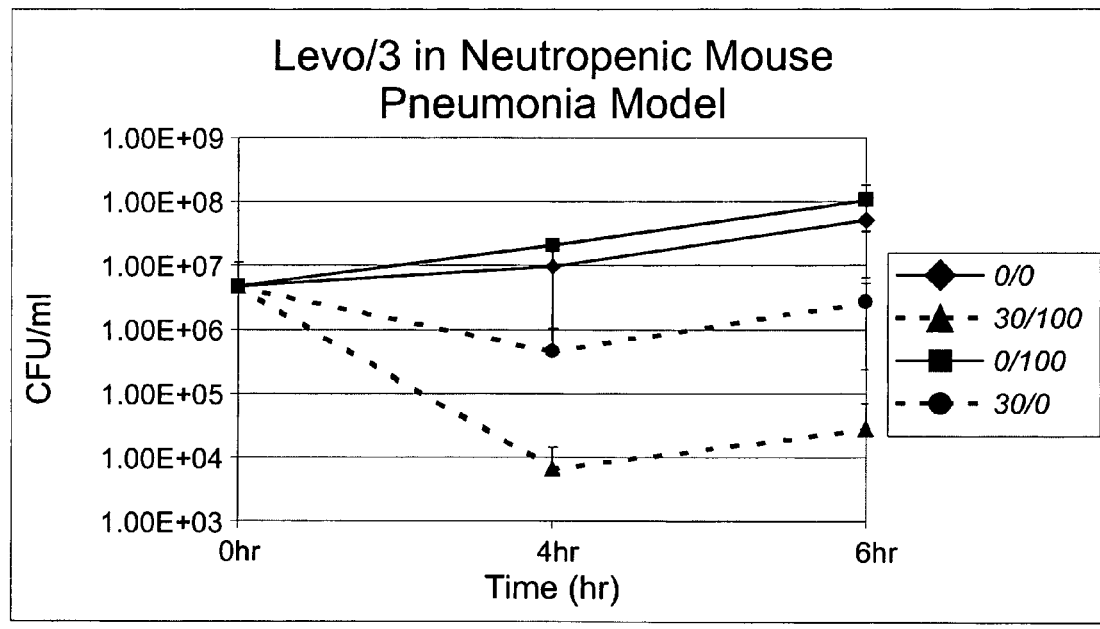
FIGS. 21A and 21B are graphs depicting P. aeruginosa growth in a mouse model of lung infection after administration of an EPI compound with and without levofloxacin.
Figure 21B:
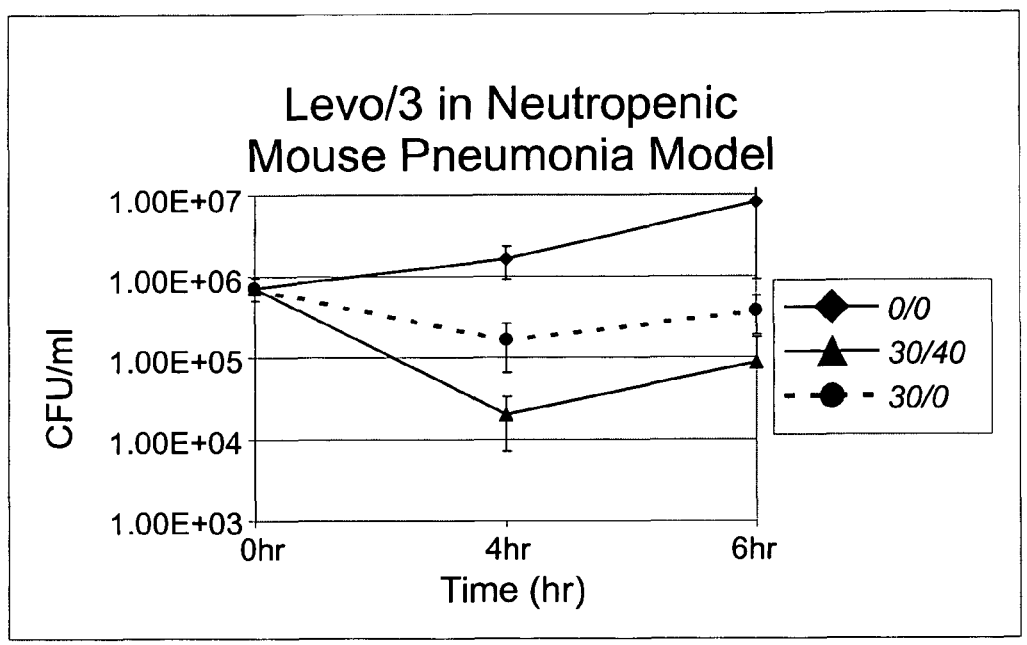

The effect of compound 3 in the same mouse model was also studied. *P. aeruginosa* levels were plotted after administration of compound 3 at 100 mg/kg (FIG. 21A) and 40 mg/kg (FIG. 21B). Compound 3, which was more unstable than compound 1 in lung tissue homogenates, still had the dose-dependent efficacy in levofloxacin potentiation.

In summary, both compounds 1 and 3 had similar efficacy in a pneumonia model of *P. aeruginosa* infection despite their differential stability in lung cells.

Efficacy of Compound 5 in Neutrapenic Mice Lung Model of PA Infection.

Figure 22:
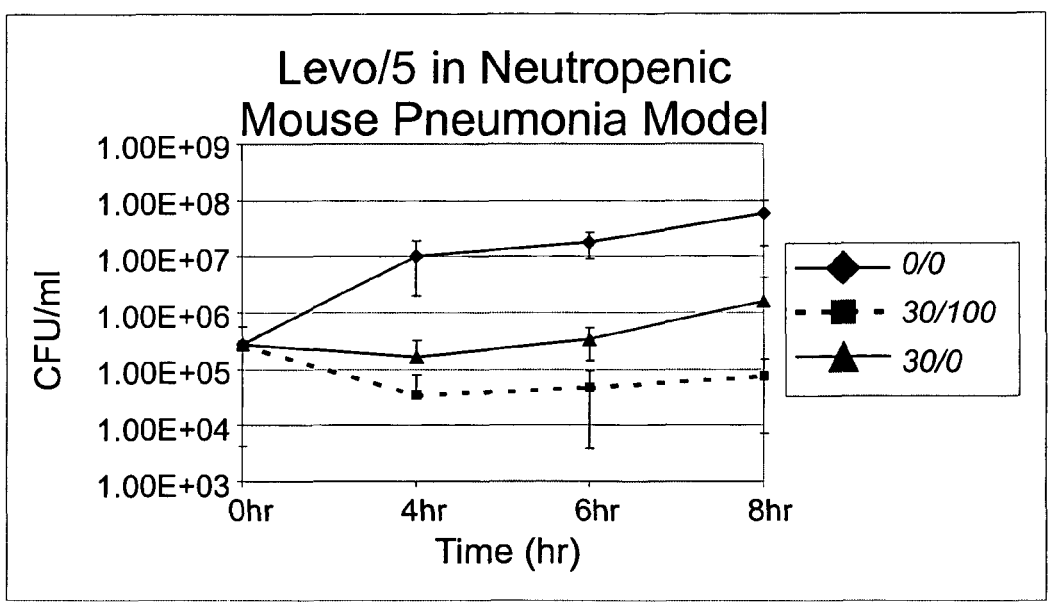
FIG. 22 is a graph depicting P. aeruginosa growth in a mouse model of lung infection after administration of a prodrug of an EPI compound with levofloxacin.

The effect of compound 3 in the same mouse model was also studied. FIG. 22 is a graph of *P. aeruginosa* levels after administration of compound 5. Since compound 5 appears to be readily converted to compound 3 in serum, it was, as expected, efficacious in animal models of *P. aeruginosa* infection. Compound 5 (which is devoid of levofloxacin potentiating activity) was efficacious in a Neutropenic Mice Lung Model of *P. aeruginosa* Infection.

Example 79

Efficacy of EPIs in Neutrapenic Mice Thigh Model of PA Infection

Efficacy of the EPIs was evaluated in a Neutrapenic Mice Thigh Model of *P. aeruginosa* Infection. Neutropenia was induced by cyclophosphamide 100 mg/kg IP on days 3 and 1 prior to infection. *P. aeruginosa* strain PAM1723 overexpressing MexAB-OprM efflux pump was grown overnight in Mueller-Hinton Broth (MHB). The next day, the overnight culture was diluted in fresh MHB and was allowed to re-grow to ~$10^8$ CFU/mL (OD600~0.3). The culture was spun down, washed twice with phosphate buffered saline (PBS) and re-suspend in PBS to ~$4×10^6$ CFU/mL. Next, this culture was mixed 1:1 with 14% hog-gastric mucin in PBS to give a final inoculum of $2×10^6$ CFU/mL. Infection was initiated with injection of 0.1 mL of inoculum (~$2×10^5$ CFU/thigh) directly into both thighs of each mouse. Two mice from each treatment group were euthanized at various times after the start of treatment. The thighs were removed aseptically, homogenized in saline, and immediately plated to determine bacterial load (CFU/ml). Treatment was initiated 2 hours post infection. Levofloxacin (30 mg/kg) and EPIs (60 mg/kg) were given SQ and IP, respectively in 0.2 ml of saline.

Figure 23:
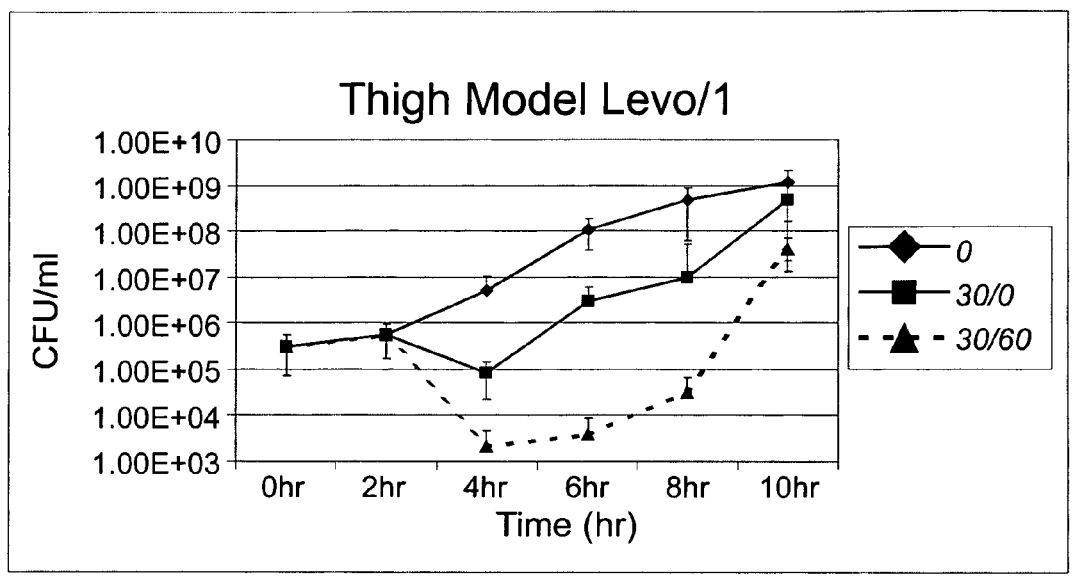
FIG. 23 is a graph depicting P. aeruginosa growth in a mouse thigh model of P. aeruginosa infection after administration of an EPI compound with levofloxacin.

In the first experiment, levofloxacin was given at 30 mg/kg and compound 1 was given at 60 mg/kg 2 hours post-infection. FIG. 23 depicts the bacterial load as a function of time. Compound 1 significantly enhanced activity of levofloxacin as evident by the decreased load of bacteria at the site of infection in the presence of the EPI as compared to levofloxacin alone.

Figure 24:
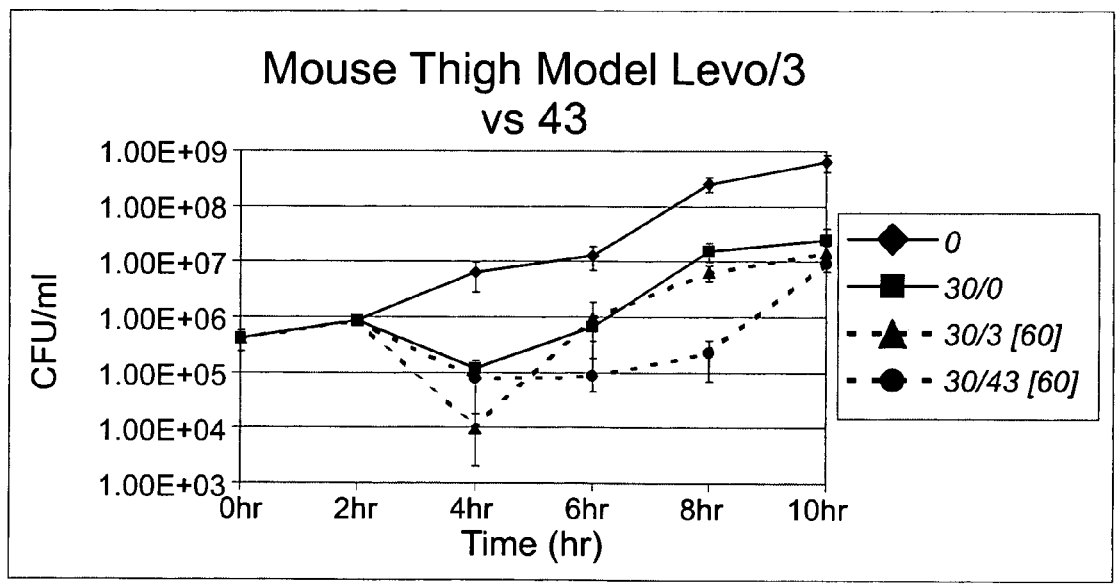
FIG. 24 is a graph depicting P. aeruginosa growth in a mouse thigh model of P. aeruginosa infection after administration of an EPI compound and its prodrug levofloxacin.

In the second experiment, levofloxacin was given at 30 mg/kg and compound 3 or compound 43 was given at 60 mg/kg 2 hours post-infection. Compound 43 is a derivative of compound 3 in which both primary amines are converted into L-aspartatamines. FIG. 24 depicts the bacterial load as a function of time. Compound 43 did not have in vitro levofloxacin potentiating activity. However, both compounds 3 and 43 potentiated levofloxacin in vivo as demonstrated in neutropenic mouse thigh model of infection.

Efficacy of Compound 21 in Neutrapenic Mice Thigh Model of PA Infection.

Figure 25:
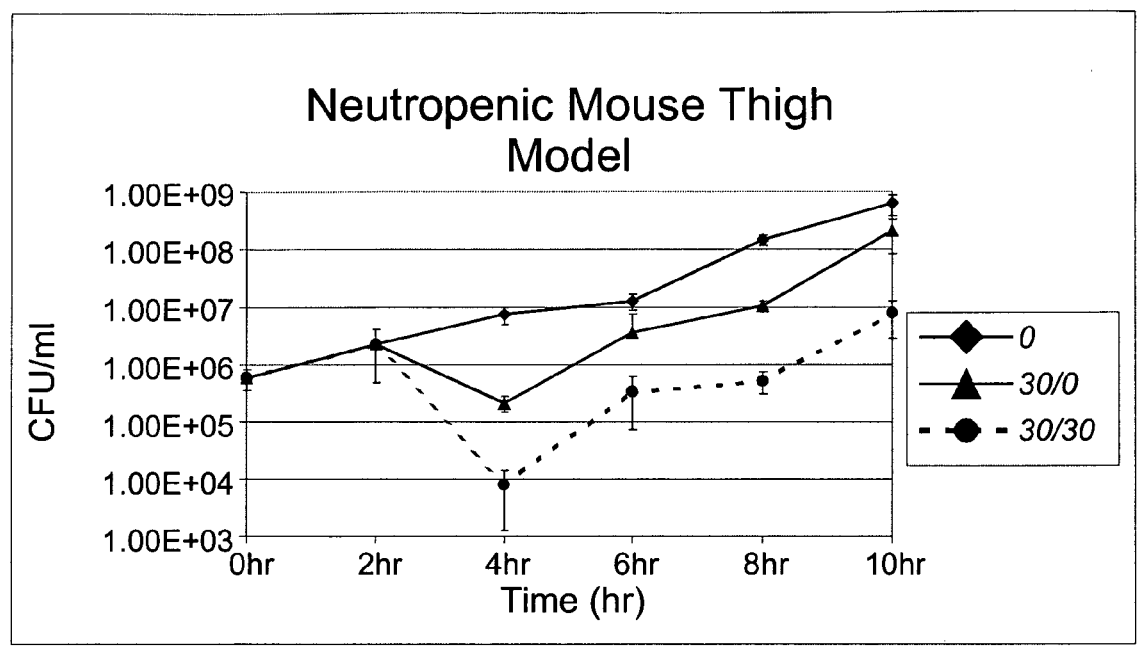
FIG. 25 is a graph depicting P. aeruginosa growth in a mouse thigh model of P. aeruginosa infection after administration of an EPI compound with levofloxacin.

Compound 21 (a potent compound that was unstable in tissue homogenates and does not accumulate in rat tissues), was also tested in the thigh model as above. FIG. 25 depicts the resulting bacterial load as a function of time. Compound 21 significantly enhanced activity of levofloxacin as evident by the decreased load of bacteria at the site of infection in the presence of the EPI as compared to levofloxacin alone.

All references cited herein are incorporated herein by reference in their entirety. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only.

What is claimed is:

1. A compound having the structure of Formula (III):

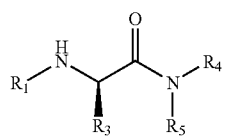
(III)

wherein:
R$_1$ is:

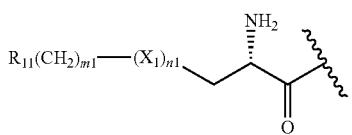

X$_1$ is selected from the group consisting of —O— and —S—;
m$_1$ is an integer from 0 to 4;
n$_1$ is an integer from 0 to 1;
R$_{11}$ is selected from the group consisting of —NH$_2$, —NH—CH(=NH), —NH—C(CH$_3$)(=NH), —CH(=NH)NH$_2$, and —NH—C(=NH)NH$_2$;
R$_3$ is selected from the group consisting of:

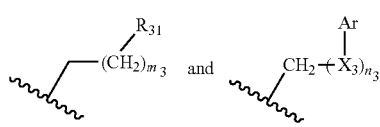

X$_3$ is selected from the group consisting of —CH$_2$—, —C(CH$_3$)$_2$—, —O—, and —S—;
m$_3$ is an integer from 1 to 2;
n$_3$ is an integer from 0 to 2;
R$_{31}$ is selected from the group consisting of C$_{1-10}$ alkyl, C$_{1-10}$ alkenyl, C$_{1-10}$ alkynyl, and C$_{1-10}$ cycloalkyl;

R$_4$ is selected from the group consisting of hydrogen, optionally substituted C$_{1-6}$ alkyl, and optionally substituted C$_{3-7}$ cycloalkyl;
Ar is an optionally substituted phenyl,
R$_5$ is selected from the group consisting of:

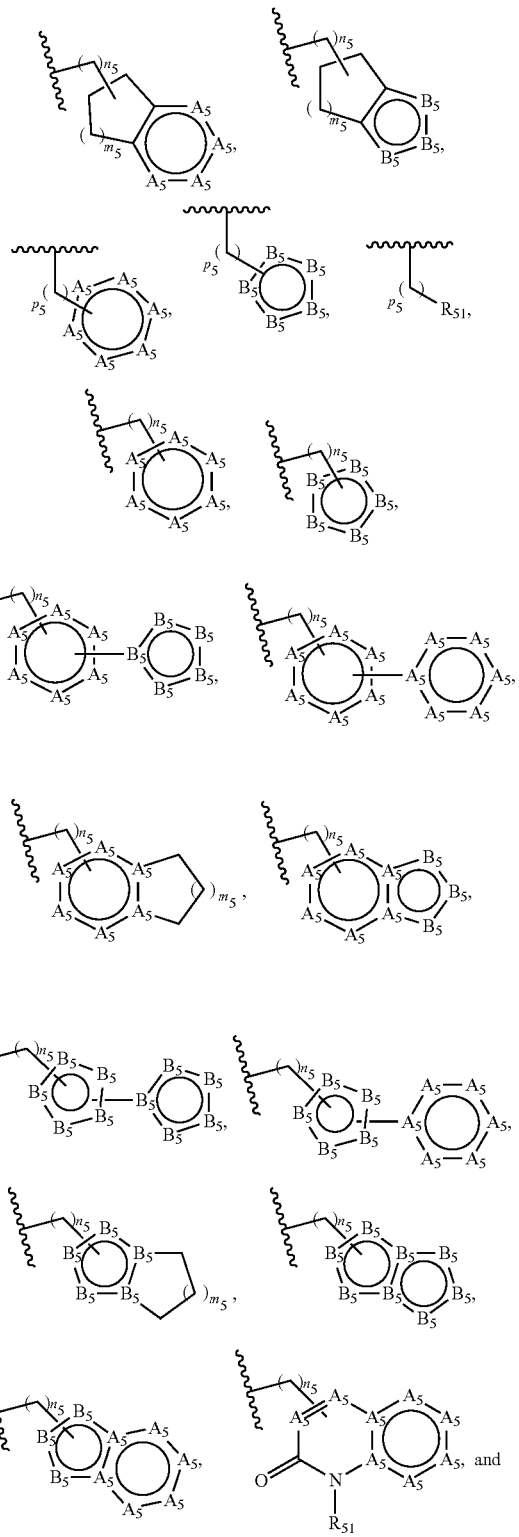

-continued

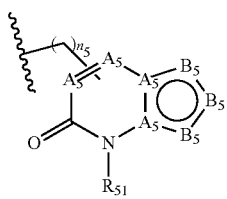

each optionally substituted with methyl, ethyl, n-propyl, isopropyl, cyclopropyl, tert-butyl, hydroxyl, methoxyl, ethoxyl, hydroxymethyl, trifluoromethyl, trifluoromethoxyl, or halogen moieties, and

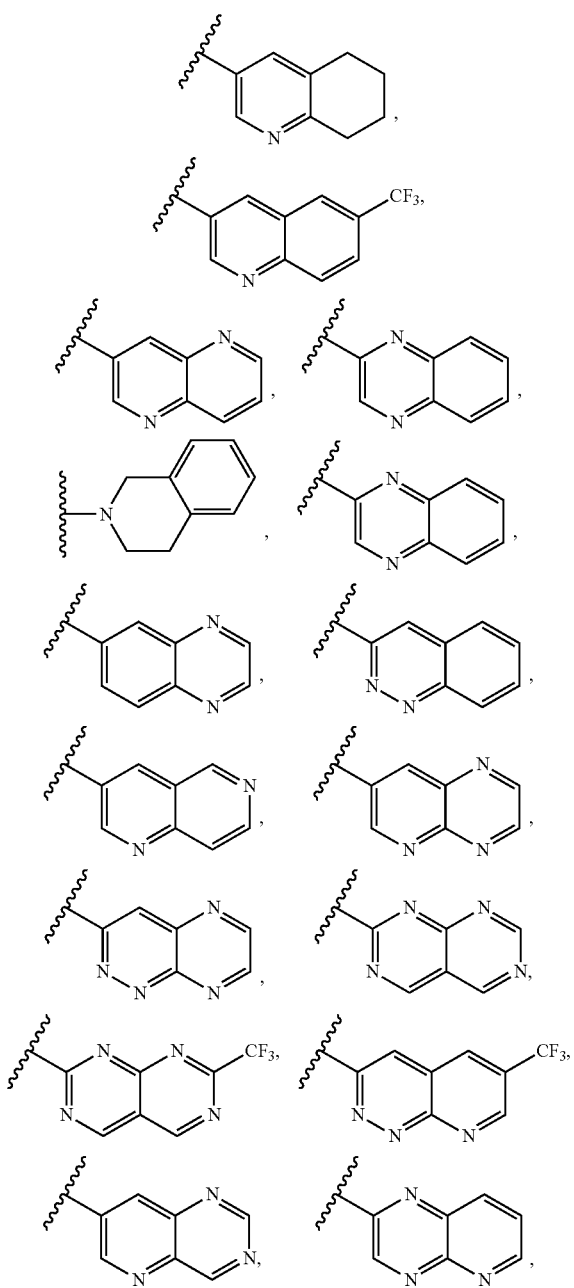

-continued

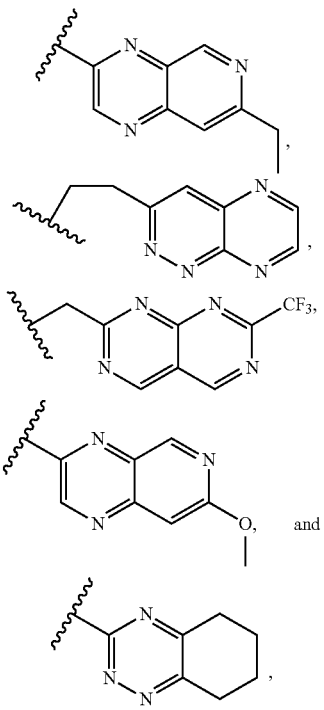

wherein:
each $A_5$ is separately selected from the group consisting of =CH— and =N—, with the proviso that each $A_5$ containing ring contains no more than four =N— groups;

each $B_5$ is separately selected from the group consisting of —C=, —N=, —O—, —S—, —NH—, and —N($R_6$)—, with the proviso that each $B_5$ containing ring contains no more than three heteroatoms;

$R_6$ is selected from the group consisting of hydrogen, $C_{1-6}$ alkyl, and $C_{3-6}$ cycloalkyl;

$R_{51}$ is selected from the group consisting of hydrogen, methyl, ethyl, and cyclopropyl;

$m_5$ is an integer from 1 to 3;

$n_5$ is an integer from 0 to 2;

$p_5$ is an integer from 0 to 4; and any amino groups present in $R_1$ are optionally acylated with an amino acid having an (S)-configuration selected from aspartic acid and glutamic acid.

2. The compound of claim 1, wherein $R_3$ is selected from the group consisting of:

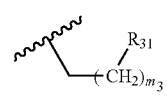

wherein:
$R_{31}$ is selected from the group consisting of ethyl, propyl, isopropyl, isobutyl, tert-butyl, cyclopropyl, cyclobutyl, cyclopentyl, and cyclohexyl; and $m_3$ is an integer from 1 to 2.

3. The compound of claim 1, wherein —N(R₄)(R₅) is selected from the group consisting of:
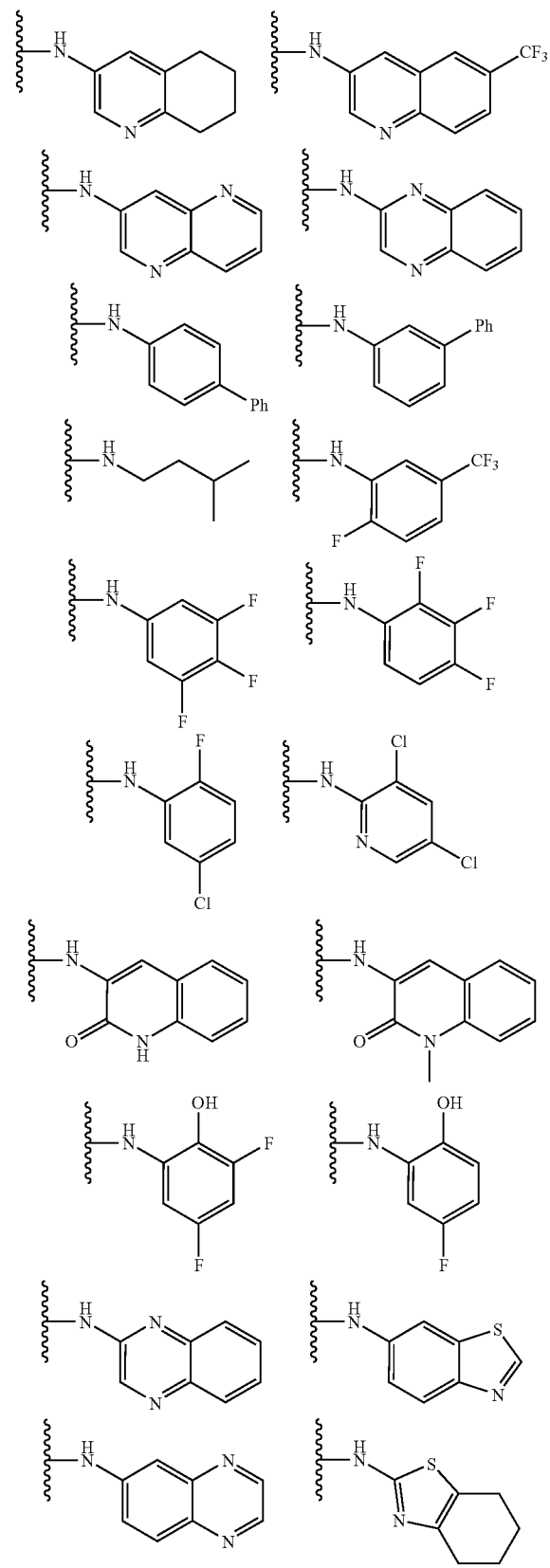
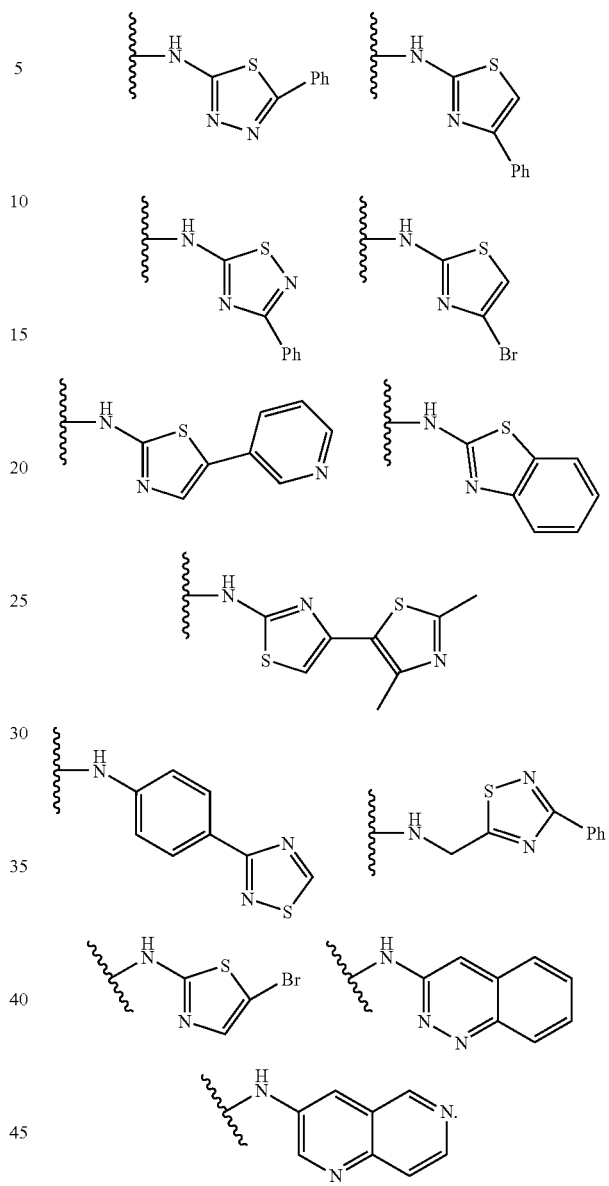
4. The compound of claim 3, selected from the group consisting of:
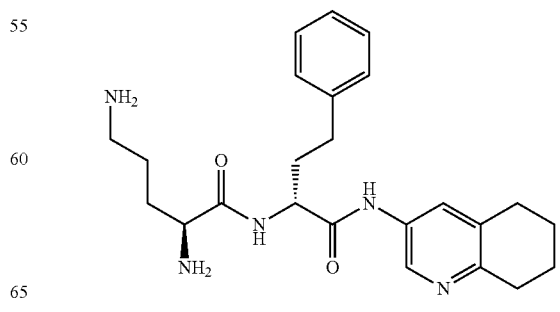

-continued
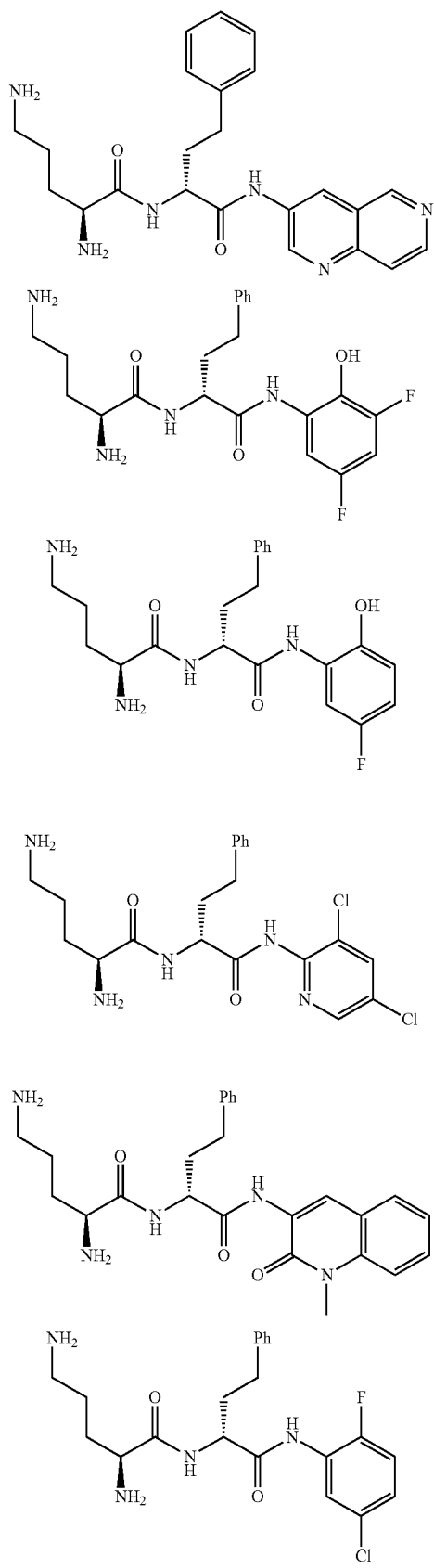
-continued
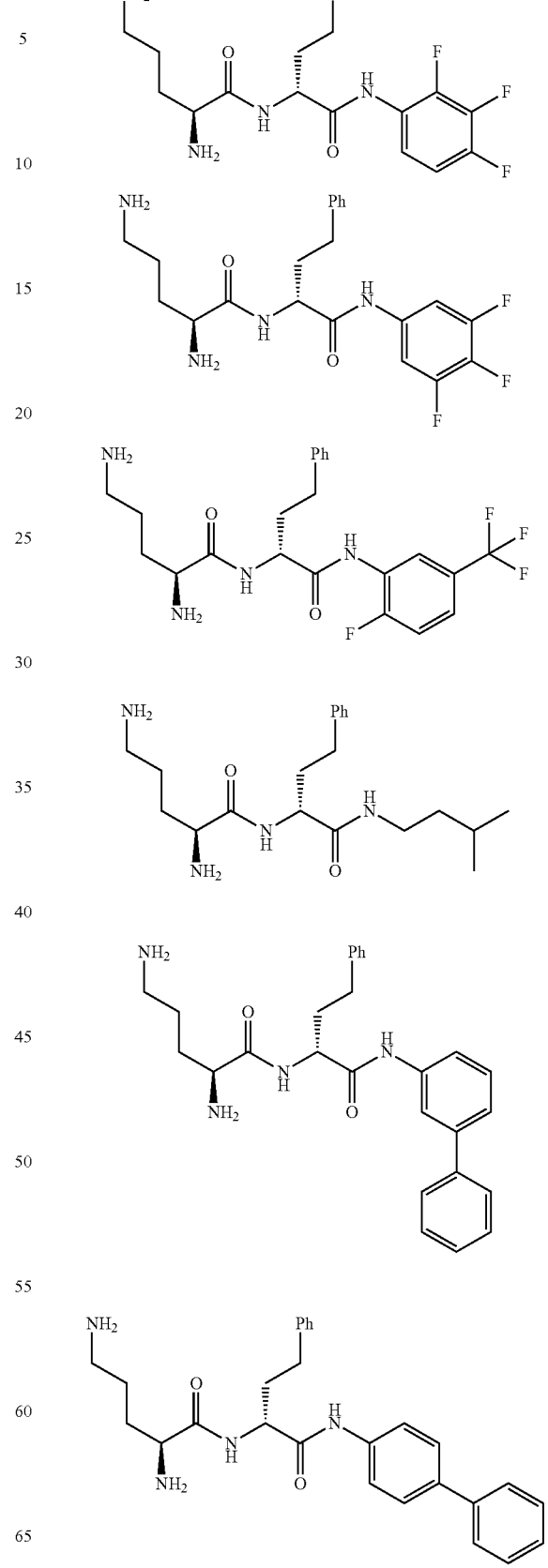

169
-continued
170
-continued
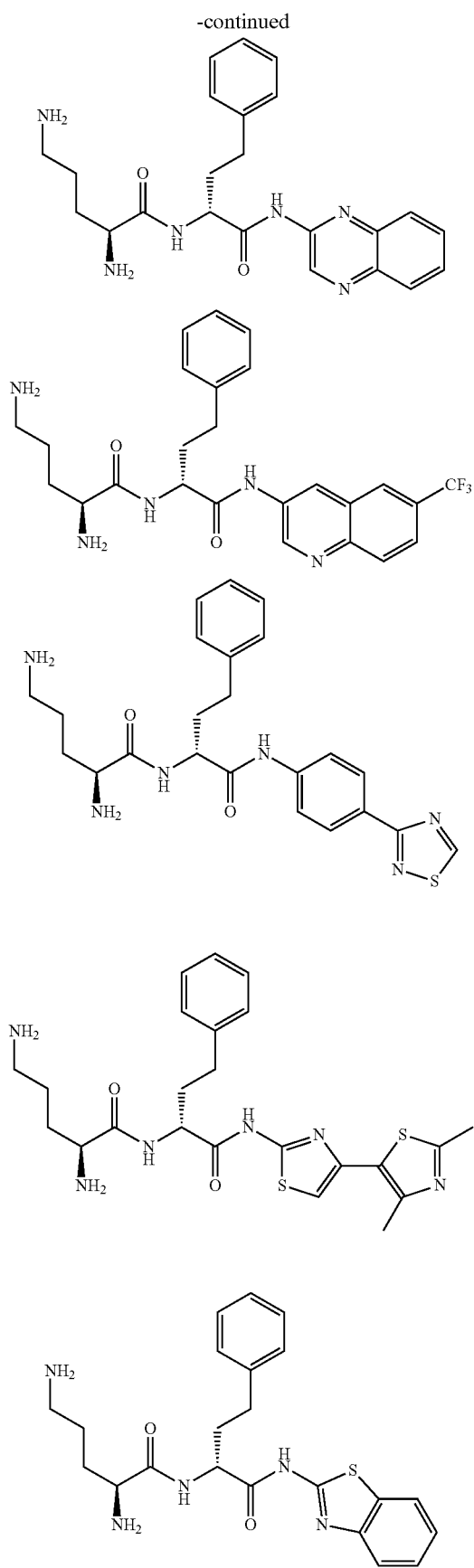
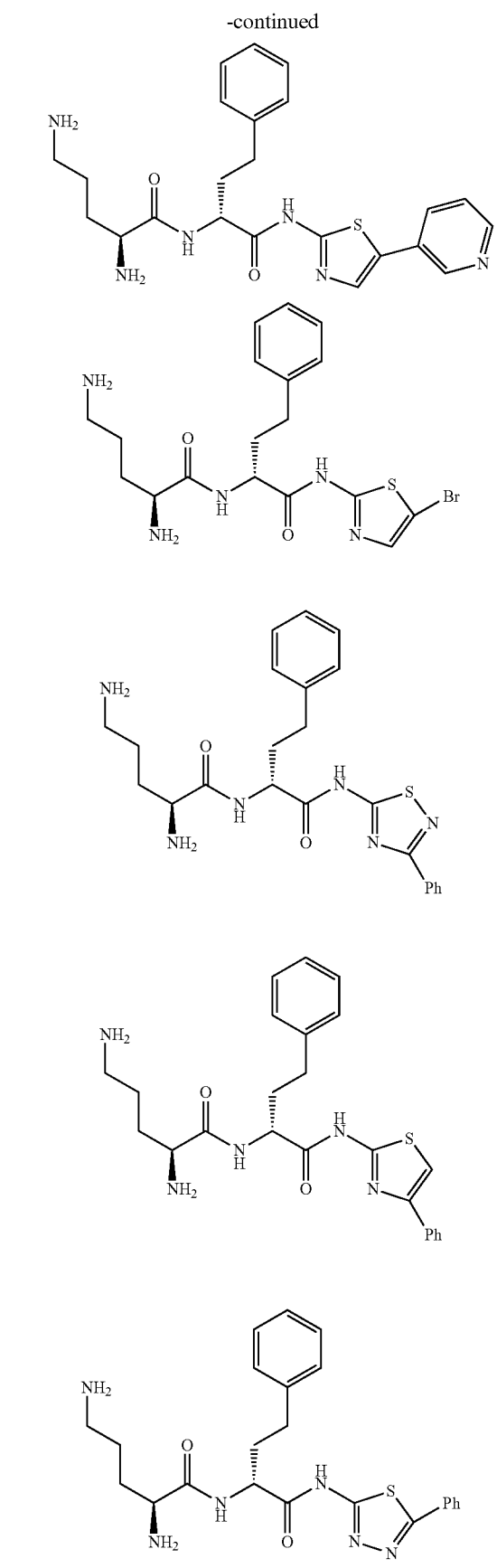

-continued

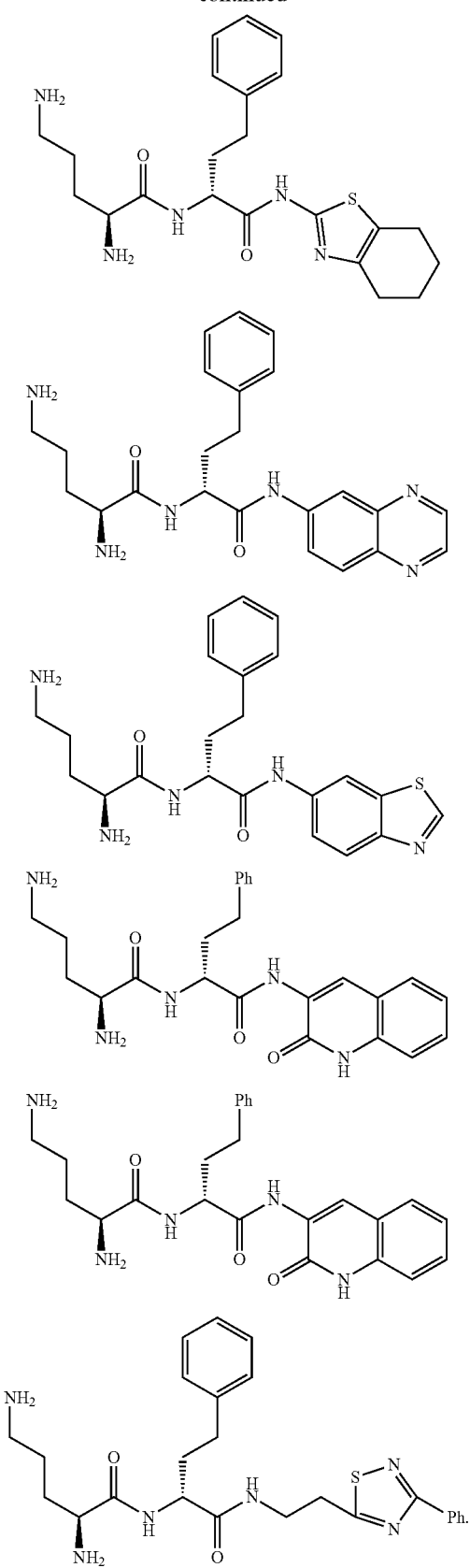

5. A pharmaceutical composition, comprising a compound of 1 in an amount effective to inhibit an efflux pump of a microbe.

6. A pharmaceutical composition, comprising a compound of 1 in combination with an antimicrobial agent.

7. The compound of claim 1, wherein:

n1 is 0;

m1 is an integer from 2 to 4; and $R_{11}$ is —$NH_2$.

8. The compound of claim 1, wherein:

$R_{31}$ is selected from the group consisting of $C_{1-10}$ alkyl and $C_{3-10}$ cycloalkyl;

$X_3$ is —$CH_2$—; and n3 is an integer from 0 to 1.

9. The compound of claim 3, wherein:

n1 is 0;

m1 is an integer from 2 to 4;

$R_{11}$ is —$NH_2$;

$R_{31}$ is selected from the group consisting of $C_{1-10}$ alkyl and $C_{3-10}$ cycloalkyl;

$X_3$ is —$CH_2$—; and n3 is an integer from 0 to 1.

10. The compound of claim 9, wherein $R_3$ is

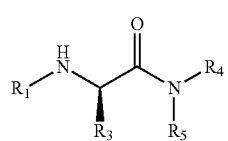

11. A compound having the structure of Formula (III):

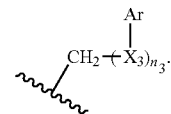

(III)

wherein:

$R_1$ is:

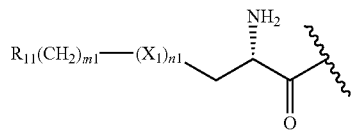

$X_1$ is selected from the group consisting of —O— and —S—;

$m_1$ is an integer from 0 to 4;

$n_1$ is an integer from 0 to 1;

$R_{11}$ is selected from the group consisting of —$NH_2$, —NH—CH(=NH), —NH—C($CH_3$)(=NH), —CH(=NH)$NH_2$, and —NH—C(=NH)$NH_2$;

R₃ is selected from the group consisting of:

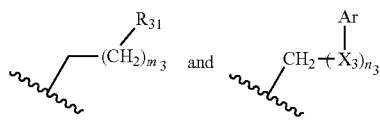

X₃ is selected from the group consisting of —CH₂—, —C(CH₃)₂— —O—, and —S—;
m₃ is an integer from 1 to 2;
n₃ is an integer from 0 to 2;
R₃₁ is selected from the group consisting of $C_{1-10}$ alkyl, $C_{1-10}$ alkenyl, $C_{1-10}$ alkynyl, and $C_{1-10}$ cycloalkyl;
R₄ is selected from the group consisting of hydrogen, optionally substituted $C_{1-6}$ alkyl, and optionally substituted $C_{3-7}$ cycloalkyl;
Ar is phenyl substituted with one or more groups independently selected from the group consisting of heterocyclyl, heteroaryl, chlorine, bromine, iodine, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl, and
R₅ is

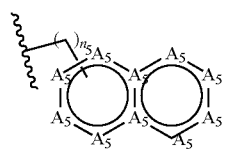

optionally substituted with methyl, ethyl, n-propyl, isopropyl, cyclopropyl, tert-butyl, hydroxyl, methoxyl, ethoxyl, hydroxymethyl, trifluoromethyl, trifluoromethoxyl, or halogen moieties;
each A₅ is separately selected from the group consisting of =CH— and =N—, with the proviso that each A₅ containing ring contains no more than four =N— groups;
n₅ is an integer from 0 to 2; and
any amino groups present in R₁ are optionally acylated with an amino acid having an (S)-configuration selected from aspartic acid and glutamic acid.

12. The compound of claim 11, selected from the group consisting of:

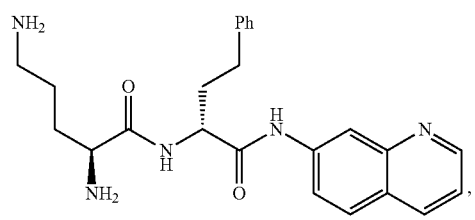

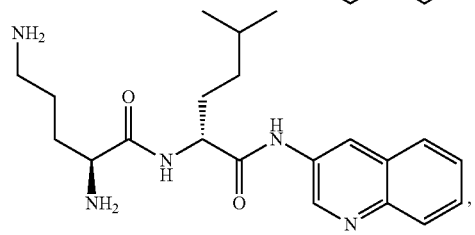

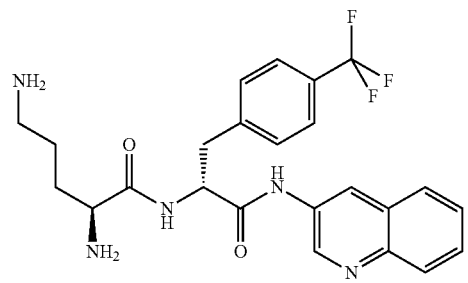

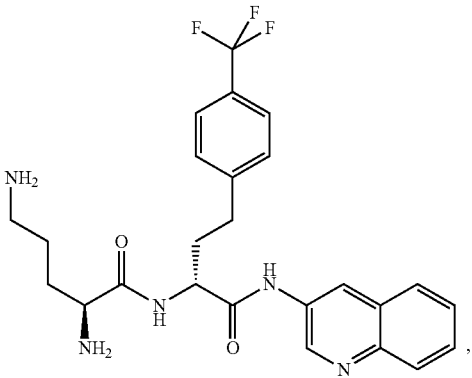

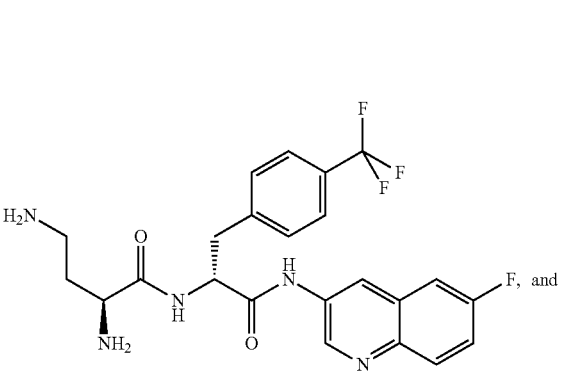

F, and

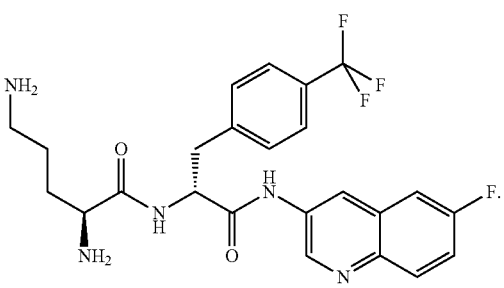

F.

13. The compound of claim 11, selected from the group consisting of:

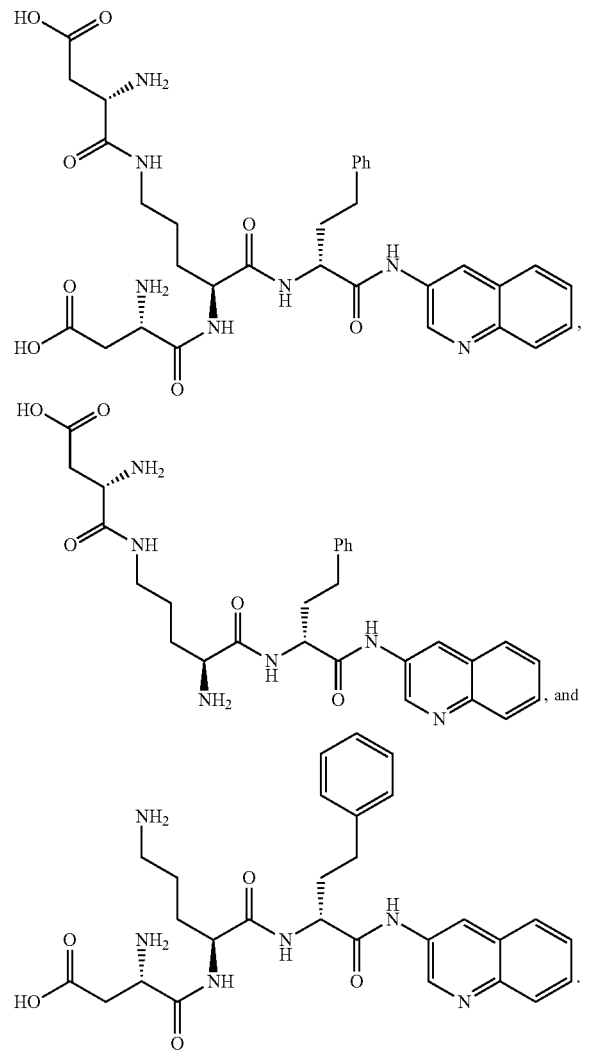

, and

14. The compound of claim 1, wherein $R_4$ is hydrogen.

15. A compound having the structure of Formula (III):

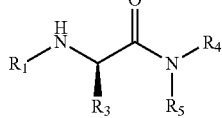 (III)

wherein:

$R_1$ is:

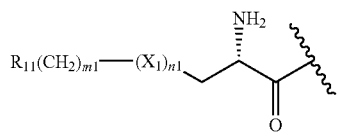

$X_1$ is selected from the group consisting of —O— and —S—;

$m_1$ is an integer from 0 to 4;

$n_1$ is an integer from 0 to 1;

$R_{11}$ is selected from the group consisting of —NH$_2$, —NH—CH(=NH), —NH—C(CH$_3$)(=NH), —CH(=NH)NH$_2$, and —NH—C(=NH)NH$_2$;

$R_3$ is selected from the group consisting of:

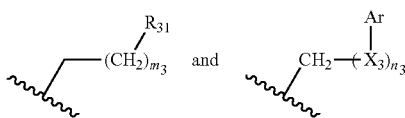

$X_3$ is selected from the group consisting of —CH$_2$—, —C(CH$_3$)$_2$— —O—, and —S—;

$m_3$ is an integer from 1 to 2;

$n_3$ is an integer from 0 to 2;

$R_{31}$ is selected from the group consisting of $C_{1-10}$ alkyl, $C_{1-10}$ alkenyl, $C_{1-10}$ alkynyl, and $C_{1-10}$ cycloalkyl;

Ar is an optionally substituted phenyl, $R_4$ is bound to $R_5$ to form a five-membered or six-membered heterocyclic ring selected from the group consisting of:

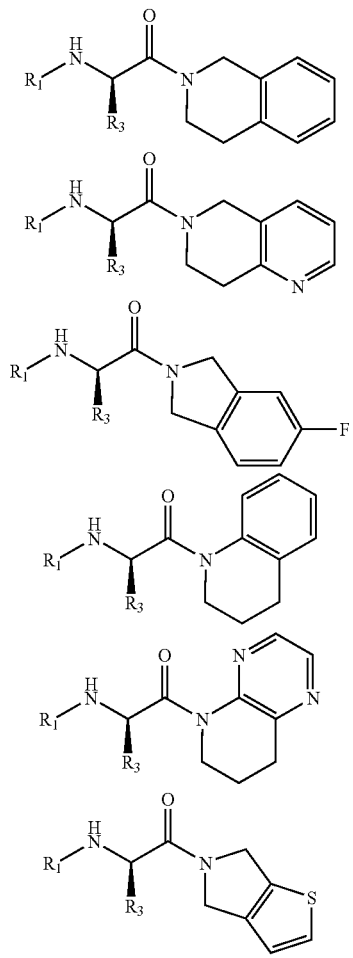

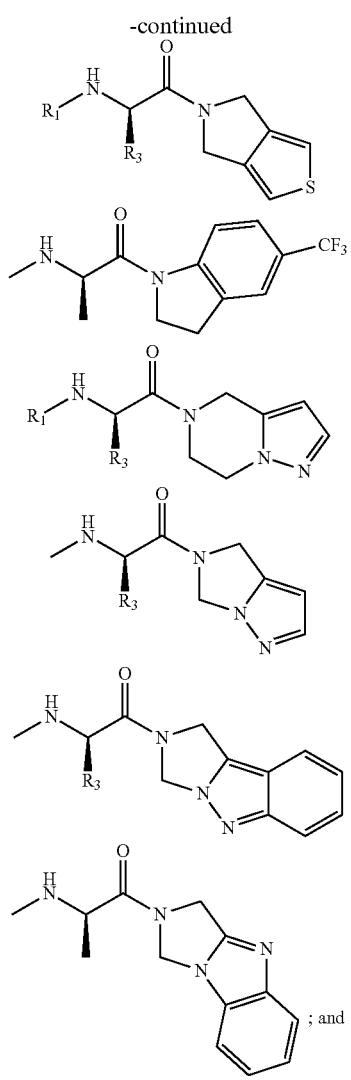

any amino groups present in $R_1$ are optionally acylated with an amino acid having an (S)-configuration selected from aspartic acid and glutamic acid.

16. A method of treating a bacterial infection, comprising administering to a subject suffering from said bacterial infection an amount effective to inhibit an efflux pump of said bacteria of a compound of claim 1 or 11.

17. The method of claim 16, wherein the subject is a human.

18. The method of claim 16, wherein the bacteria is selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella bronchiseptica, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii,* and *Bacteroides splanchnicus*.

19. A method for inhibiting growth of antibacterial-resistant bacteria, comprising contacting the bacteria with a compound of claim 1 or 11 and an antibacterial agent.

20. The method of claim 19, wherein the antibacterial agent is selected from the group consisting of a quinolone, aminoglycoside, beta-lactam, coumermycin, chloramphenical, lipopeptide, glycopeptide, glycylcycline, ketolide, macrolide, oxazolidonone, rifamycin, streptogramin, and tetracycline.

21. The method of claim 20, wherein the antibacterial agent is selected from the group consisting of ciprofloxacin, levofloxacin, moxifloxacin, ofloxacin, gatifloxacin, cinoxacin, gemifloxacin, norfloxacin, lomofloxacin, pefloxacin, garenoxacin, sitafloxacin, and DX-619.

22. A method for treating a bacterial infection in a subject, wherein the bacteria causing the infection exhibit antibiotic resistance through an efflux pump mechanism, comprising:
  administering to a subject an antibiotic to which said bacteria are resistant; and
  administering to said subject a compound of claim 1 or 11 in conjunction with said antibiotic.

23. The method of claim 22, wherein the antibiotic is selected from the group consisting of a quinolone, aminoglycoside, beta-lactam, coumermycin, chloramphenical, lipopeptide, glycopeptide, glycylcycline, ketolide, macrolide, oxazolidonone, rifamycin, streptogramin, and tetracycline.

24. The method of claim 23, wherein the antibiotic is selected from the group consisting of ciprofloxacin, levofloxacin, moxifloxacin, ofloxacin, gatifloxacin, cinoxacin, gemifloxacin, norfloxacin, lomofloxacin, pefloxacin, garenoxacin, sitafloxacin, and DX-619.

25. The compound of claim 11, having the structure:

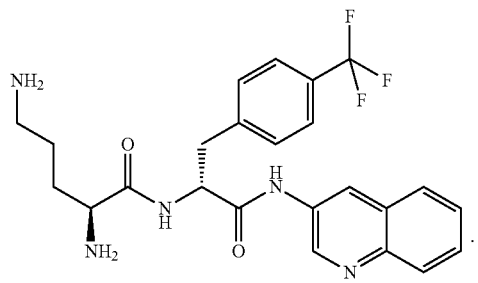

* * * * *

UNITED STATES PATENT AND TRADEMARK OFFICE
CERTIFICATE OF CORRECTION

PATENT NO.        : 7,893,020 B2
APPLICATION NO.   : 11/134147
DATED             : February 22, 2011
INVENTOR(S)       : Glinka et al.

It is certified that error appears in the above-identified patent and that said Letters Patent is hereby corrected as shown below:

At column 5, line 29, please delete "—NH—C(=O—NH)NH$_2$;" and insert therefore -- —NH—C(=NH)NH$_2$--.

At column 13, line 21, please delete "—C(CH$_3$)$_2$— —O—," and insert therefore -- —C(CH$_3$)$_2$—, —O—,--.

At column 13, line 28, please delete "C$_{1-10}$" and insert therefore --C$_{1-6}$--.

At column 15, line 40, please delete "—C(CH$_3$)$_2$— —O—," and insert therefore -- —C(CH$_3$)$_2$—, —O—,--.

At column 44, line 18, please delete "—C(CH$_3$)$_2$— —O—," and insert therefore -- —C(CH$_3$)$_2$—, —O—,--.

At column 47, line 21, please delete "—C(CH$_3$)$_2$— —O—," and insert therefore -- —C(CH$_3$)$_2$—, —O—,--.

At column 49, line 40, please delete "—C(CH$_3$)$_2$— —O—," and insert therefore -- —C(CH$_3$)$_2$—, —O—,--.

At column 62, line 5, please delete " 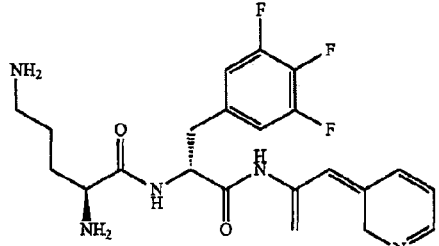 " and insert therefore

Signed and Sealed this
Nineteenth Day of February, 2013

Teresa Stanek Rea
*Acting Director of the United States Patent and Trademark Office*

CERTIFICATE OF CORRECTION (continued)
U.S. Pat. No. 7,893,020 B2

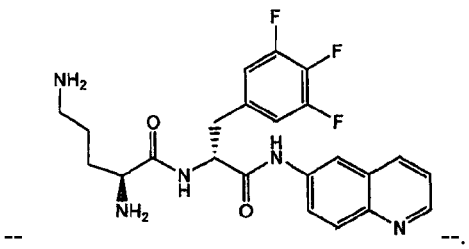

-- -- .

At column 135, line 59, please delete "11" and insert therefore --10--.

At column 142, line 65, please delete "brs, 1" and insert therefore --brs, 1H--.

At column 145, line 1, please delete "7.1.6-7.30" and insert therefore --7.16-7.30--.

At column 145, line 36, please delete "$C_{18}H_{24}NO_2S^{78}Br$" and insert therefore --$C_{18}H_{24}N_5O_2S^{78}Br$--.

At column 153, line 52, please delete "FIG. 1" and insert therefore --FIG. 11--.

At column 155, line 1, please delete "indicated" and insert therefore --indicates--.

At column 155, line 28, please delete "minutes." and insert therefore --5 minutes.--.

At column 155, line 36, please delete "Tisue" and insert therefore --Tissue--.

At column 155, line 56, please delete "Tisue" and insert therefore --Tissue--.

At column 156, line 5, please delete "Tisue" and insert therefore --Tissue--.

At column 156, line 21, please delete "Tisue" and insert therefore --Tissue--.

At column 156, line 36, please delete "Tisue" and insert therefore --Tissue--.

At column 158, line 44, please delete "MHV" and insert therefore --MHB--.

At column 172, line 2 in Claim 5, please delete "of" and insert therefore --of claim--.

At column 172, line 5 in Claim 6, please delete "of" and insert therefore --of claim--.

At column 173, line 11 in Claim 11, please delete "—C(CH₃)₂— —O—," and insert therefore -- —C(CH₃)₂—, —O—,--.

At column 176, line 19 in Claim 15, please delete "—C(CH₃)₂— —O—," and insert therefore -- —C(CH₃)₂—, —O—,--.